United States Patent
Kim et al.

(10) Patent No.: US 11,858,947 B2
(45) Date of Patent: Jan. 2, 2024

(54) HETEROCYCLIC COMPOUND AND ORGANIC LIGHT EMITTING DEVICE INCLUDING THE SAME

(71) Applicant: LG CHEM, LTD., Seoul (KR)

(72) Inventors: Minjun Kim, Daejeon (KR); Jin Joo Kim, Daejeon (KR); Wanpyo Hong, Daejeon (KR); Dong Hoon Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 501 days.

(21) Appl. No.: 16/973,516

(22) PCT Filed: Jul. 12, 2019

(86) PCT No.: PCT/KR2019/008638
§ 371 (c)(1),
(2) Date: Dec. 9, 2020

(87) PCT Pub. No.: WO2020/013657
PCT Pub. Date: Jan. 16, 2020

(65) Prior Publication Data
US 2021/0340159 A1    Nov. 4, 2021

(30) Foreign Application Priority Data

Jul. 13, 2018  (KR) .......................... 10-2018-0081632

(51) Int. Cl.
*C07D 519/00*    (2006.01)
*H01L 51/00*    (2006.01)
(Continued)

(52) U.S. Cl.
CPC ......... *C07D 519/00* (2013.01); *H10K 85/615* (2023.02); *H10K 85/6572* (2023.02); *H10K 85/6574* (2023.02); *H10K 85/6576* (2023.02)

(58) Field of Classification Search
None
See application file for complete search history.

(56) References Cited

U.S. PATENT DOCUMENTS

2004/0251816 A1   12/2004   Leo et al.
2016/0013427 A1   1/2016   Kim et al.
(Continued)

FOREIGN PATENT DOCUMENTS

EP     3263555 A1      1/2018
JP     2013-544759     12/2013
(Continued)

OTHER PUBLICATIONS

Computer-generated English-language translation of KR-20170057850-A.*
(Continued)

*Primary Examiner* — Vu A Nguyen
(74) *Attorney, Agent, or Firm* — Bryan Cave Leighton Paisner LLP

(57) ABSTRACT

Provided is a heterocyclic compound of Chemical Formula 1:
(Continued)

US 11,858,947 B2
Page 2

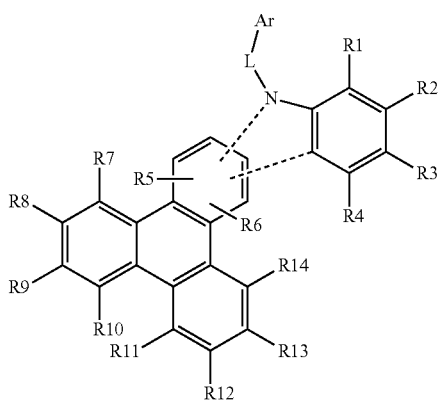

wherein:

L is a substituted or unsubstituted tricyclic or higher divalent heterocyclic group including two or more heteroatoms selected from among N, O and S;

Ar is a substituted or unsubstituted alkyl group, a substituted or unsubstituted aryl group, or a substituted or unsubstituted heteroaryl group; and R1 to R14 are the same as or different from each other, and each independently is hydrogen, a nitrile group, a halogen group, a substituted or unsubstituted alkyl group, a substituted or unsubstituted aryl group, or a substituted or unsubstituted heteroaryl group, or bond to adjacent groups to form at least one substituted or unsubstituted aromatic ring;

and an organic light emitting device including the same.

10 Claims, 1 Drawing Sheet

(51) Int. Cl.
  *H01L 51/50* (2006.01)
  *H10K 85/60* (2023.01)

(56) References Cited

U.S. PATENT DOCUMENTS

| | | |
|---|---|---|
| 2016/0133844 A1 | 5/2016 | Kim et al. |
| 2018/0083202 A1 | 3/2018 | Kim et al. |
| 2018/0155325 A1* | 6/2018 | Lee .............. H10K 85/657 |

FOREIGN PATENT DOCUMENTS

| | | | | |
|---|---|---|---|---|
| KR | 10-2016-0007967 | | 1/2016 | |
| KR | 10-2016-0131963 | | 11/2016 | |
| KR | 10-2017-0057850 | | 5/2017 | |
| KR | 20170057850 A | * | 5/2017 | ........... C07D 209/56 |
| KR | 10-2017-0077806 | | 7/2017 | |
| KR | 20170077806 A | * | 7/2017 | ........... C07D 487/04 |
| KR | 10-2017-0113334 | | 10/2017 | |
| KR | 10-2018-0032021 | | 3/2018 | |
| KR | 20180032021 A | * | 3/2018 | ............. C09K 11/06 |
| KR | 10-2018-0063651 | | 6/2018 | |
| KR | 10-2018-0071880 | | 6/2018 | |
| KR | 20180071880 A | * | 6/2018 | ........... C07D 487/04 |
| WO | 2013-009095 | | 1/2013 | |

OTHER PUBLICATIONS

Computer-generated English-language translation of KR-20180071880-A.*

* cited by examiner

【FIG. 1】

| |
|---|
| 4 |
| 3 |
| 2 |
| 1 |

【FIG. 2】

| |
|---|
| 4 |
| 10 |
| 9 |
| 8 |
| 7 |
| 6 |
| 5 |
| 2 |
| 1 |

HETEROCYCLIC COMPOUND AND ORGANIC LIGHT EMITTING DEVICE INCLUDING THE SAME

CROSS-REFERENCE TO RELATED APPLICATIONS

This application is a National Stage Application of International Application No. PCT/KR2019/008638 filed on Jul. 12, 2019, which claims priority to and the benefits of Korean Patent Application No. 10-2018-0081632, filed with the Korean Intellectual Property Office on Jul. 13, 2018, the entire contents of which are incorporated herein by reference.

TECHNICAL FIELD

The present specification relates to a heterocyclic compound, and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often famed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification is directed to providing a heterocyclic compound, and an organic light emitting device including the same.

Technical Solution

One embodiment of the present specification provides a heterocyclic compound of Chemical Formula 1:

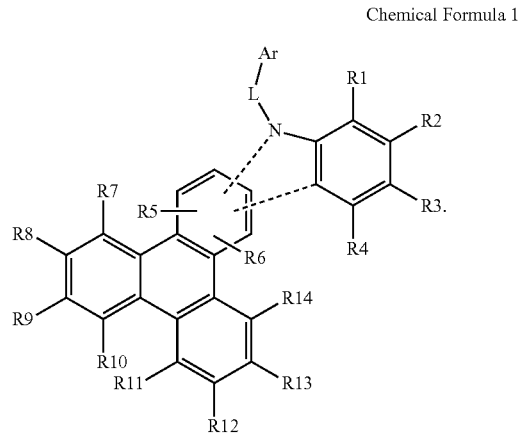

Chemical Formula 1

In Chemical Formula 1:

L is a substituted or unsubstituted tricyclic or higher divalent heterocyclic group including two or more heteroatoms selected from among N, O and S;

Ar is a substituted or unsubstituted alkyl group, a substituted or unsubstituted aryl group, or a substituted or unsubstituted heteroaryl group; and R1 to R14 are the same as or different from each other, and each independently is hydrogen, a nitrile group, a halogen group, a substituted or unsubstituted alkyl group, a substituted or unsubstituted aryl group, or a substituted or unsubstituted heteroaryl group, or bond to adjacent groups to form at least one substituted or unsubstituted aromatic ring.

Another embodiment of the present specification provides an organic light emitting device including a first electrode; a second electrode provided opposite to the first electrode; and one, two or more organic material layers provided between the first electrode and the second electrode, wherein one or more layers of the organic material layers include the heterocyclic compound.

Advantageous Effects

A heterocyclic compound according to one embodiment of the present specification can be used as a material of an organic material layer of an organic light emitting device, and by using the same, efficiency can be enhanced, a low driving voltage can be obtained, and/or lifetime properties can be enhanced in the organic light emitting device.

DESCRIPTION OF THE DRAWINGS

FIG. 1 illustrates an organic light emitting device according to one embodiment of the present specification.

FIG. 2 illustrates an organic light emitting device according to one embodiment of the present specification.

REFERENCE NUMERALS

1: Substrate
2: First Electrode
3: Organic Material Layer

4: Second Electrode
5: Hole Injection Layer
6: Hole Transfer Layer
7: Electron Blocking Layer
8: Light Emitting Layer
9: Hole Blocking Layer
10: Electron Injection and Transfer Layer

DETAILED DESCRIPTION

Hereinafter, the present specification will be described in more detail.

One embodiment of the present specification provides a heterocyclic compound of Chemical Formula 1.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium; a nitrile group; a substituted or unsubstituted alkyl group; a substituted or unsubstituted cycloalkyl group; a substituted or unsubstituted silyl group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" can include an aryl group substituted with an aryl group, an aryl group substituted with a heteroaryl group, a heterocyclic group substituted with an aryl group, an aryl group substituted with an alkyl group, and the like.

In the present specification, the alkyl group can be linear or branched, and although not particularly limited thereto, the number of carbon atoms is preferably from 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methyl-hexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methyl-hexyl and the like, but are not limited thereto.

In the present specification, specific examples of the silyl group can include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the aryl group is not particularly limited, but preferably has 6 to 30 carbon atoms, and the aryl group can be monocyclic or polycyclic.

When the aryl group is a monocyclic aryl group, the number of carbon atoms is not particularly limited, but is preferably from 6 to 30. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group can include a naphthyl group, an anthracenyl group, a phenanthryl group, a triphenylene group, a pyrenyl group, a phenalenyl group, a perylenyl group, a chrysenyl group, a fluorenyl group and the like, but are not limited thereto.

In the present specification, the heterocyclic group includes one or more atoms that are not carbon, that is, heteroatoms, and specifically, the heteroatom can include one or more atoms selected from the group consisting of O, N, Se, S and the like. The number of carbon atoms is not particularly limited, but is preferably from 2 to 30, and the heterocyclic group can be monocyclic or polycyclic. Examples of the heterocyclic group can include a thiophene group, a furanyl group, a pyrrole group, an imidazolyl group, a triazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, a dibenzofuranyl group and the like, but are not limited thereto.

According to one embodiment of the present specification, R1 to R4 are the same as or different from each other, and each independently is hydrogen, or bond to adjacent substituents to form an aromatic ring.

According to one embodiment of the present specification, R1 to R4 bond to adjacent groups to form at least one substituted or unsubstituted aromatic ring, and substituents that do not form the ring are hydrogen.

In the present specification, Chemical Formula 1 is any one of the following Chemical Formulae 1-1 to 1-3:

Chemical Formula 1-1

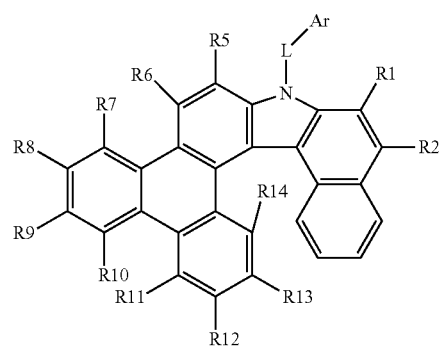

-continued

Chemical Formula 1-2

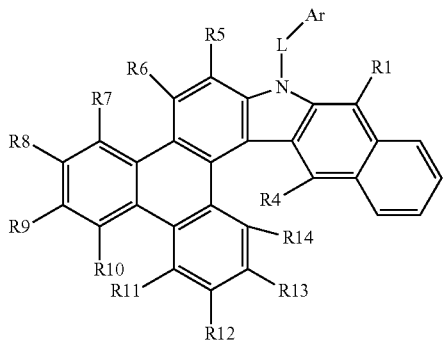

Chemical Formula 1-3

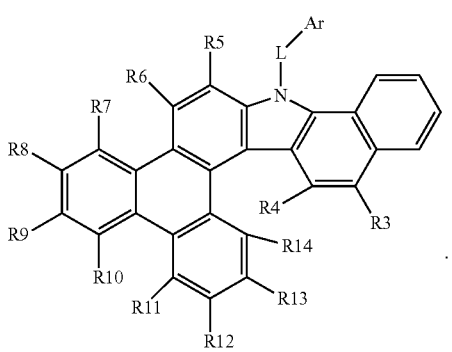

In Chemical Formulae 1-1 to 1-3, R1 to R14, L and Ar have the same definitions as in Chemical Formula 1.

According to one embodiment of the present specification, L is the following Chemical Formula 3 or Chemical Formula 4:

Chemical Formula 3

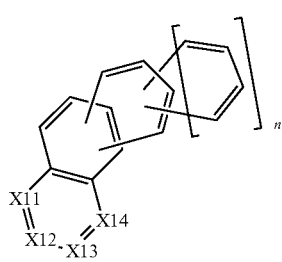

Chemical Formula 4

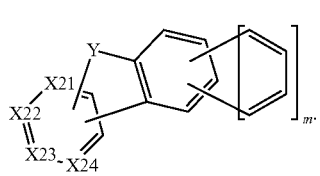

In Chemical Formula 3 and Chemical Formula 4:
X11 to X14 and X21 to X24 are the same as or different from each other, and are each N or C—Ar1;
one of X11 to X14 bonds to N of Chemical Formula 1;
one of X21 to X24 bonds to N of Chemical Formula 1;
two or more of X11 to X14 are N;
two or more of X21 to X24 are N;
Y is O, S or C(CH$_3$)$_2$;
Ar1 is a substituted or unsubstituted alkyl group, a substituted or unsubstituted aryl group, or a substituted or unsubstituted heteroaryl group; and
n and m are 0 or 1.

According to one embodiment of the present specification, Chemical Formula 3 can be any one of the following Chemical Formula 3-1 to Chemical Formula 3-4:

Chemical Formula 3-1

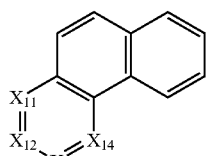

Chemical Formula 3-2

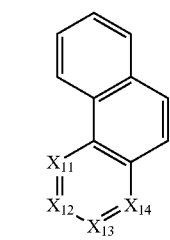

Chemical Formula 3-3

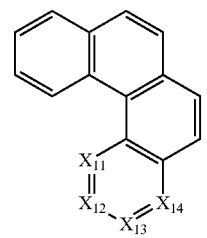

Chemical Formula 3-4

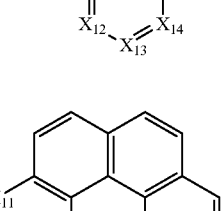

In Chemical Formulae 3-1 to 3-4, X11 to X14 have the same definitions as in Chemical Formula 3.

According to one embodiment of the present specification, Chemical Formula 4 can be any one of the following Chemical Formula 4-1 or Chemical Formula 4-2:

Chemical Formula 4-1

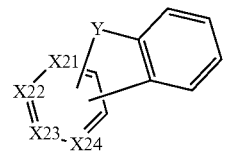

Chemical Formula 4-2

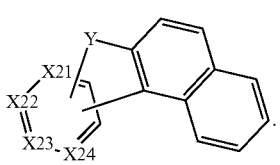

In Chemical Formulae 4-1 and 4-2, X21 to X24 and Y have the same definitions as in Chemical Formula 4.

According to one embodiment of the present specification, L is any one selected from among the following substituents:

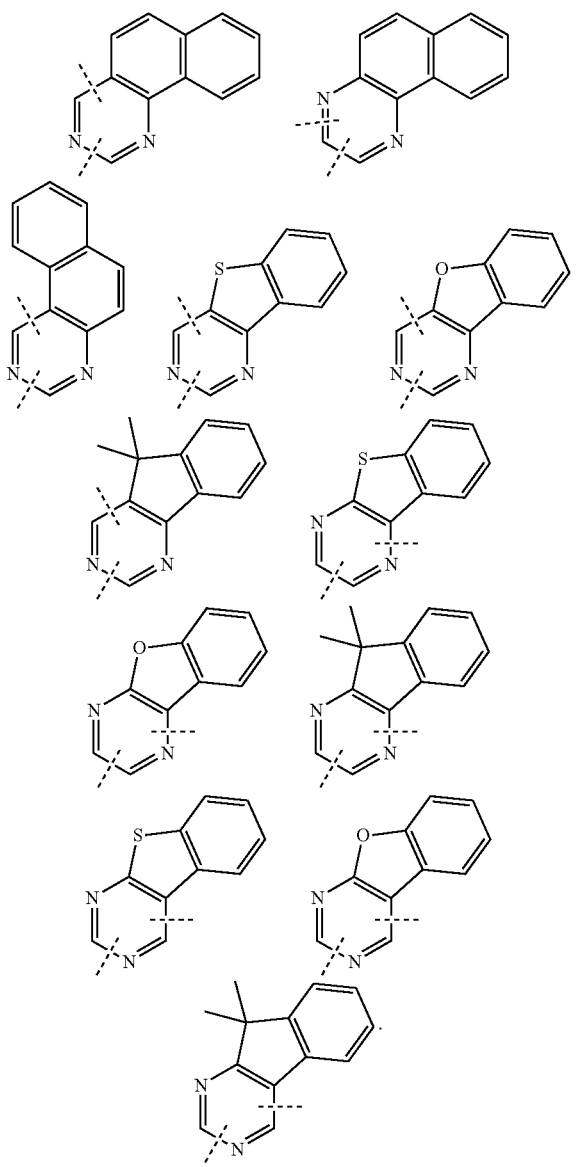

One of the dotted lines bonds to N of Chemical Formula 1, and the other one bonds to Ar.

According to one embodiment of the present specification, Ar is a substituted or unsubstituted alkyl group having 1 to 10 carbon atoms, a substituted or unsubstituted aryl group having 6 to 20 carbon atoms, or a substituted or unsubstituted heteroaryl group having 3 to 30 carbon atoms.

According to one embodiment of the present specification, Ar is a substituted or unsubstituted aryl group having 6 to 20 carbon atoms, or a substituted or unsubstituted heteroaryl group having 3 to 30 carbon atoms.

According to one embodiment of the present specification, Ar is a substituted or unsubstituted aryl group having 6 to 20 carbon atoms, or a heteroaryl group having 3 to 30 carbon atoms unsubstituted or substituted with an aryl group.

According to one embodiment of the present specification, Ar is a phenyl group, a biphenyl group, a naphthyl group, a phenanthrene group, a triphenylene group, a dibenzofuran group, a dibenzothiophene group, or a carbazole group, and the phenyl group, the biphenyl group, the naphthyl group, the phenanthrene group, the triphenylene group, the dibenzofuran group, the dibenzothiophene group, or the carbazole group is unsubstituted or substituted with an alkyl group having 1 to 10 carbon atoms, an aryl group having 6 to 20 carbon atoms, or a heteroaryl group having 3 to 30 carbon atoms.

According to one embodiment of the present specification, Ar is a phenyl group, a biphenyl group, a naphthyl group, a phenanthrene group, a triphenylene group, a dibenzofuran group, a dibenzothiophene group, or a carbazole group, and the phenyl group, the biphenyl group, the naphthyl group, the phenanthrene group, the triphenylene group, the dibenzofuran group, the dibenzothiophene group, or the carbazole group is unsubstituted or substituted with a phenyl group or a naphthyl group.

According to another embodiment of the present specification, the heterocyclic compound of Chemical Formula 1 can be any one of the following compounds:

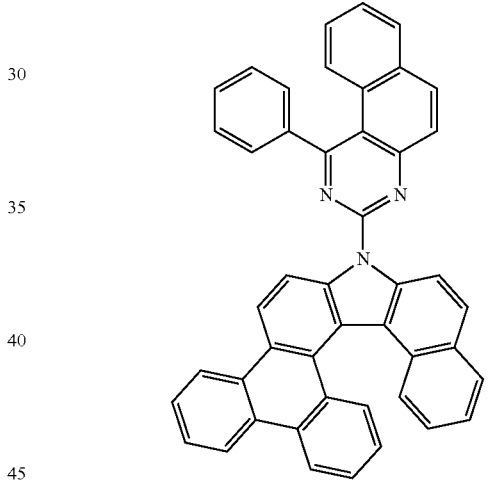

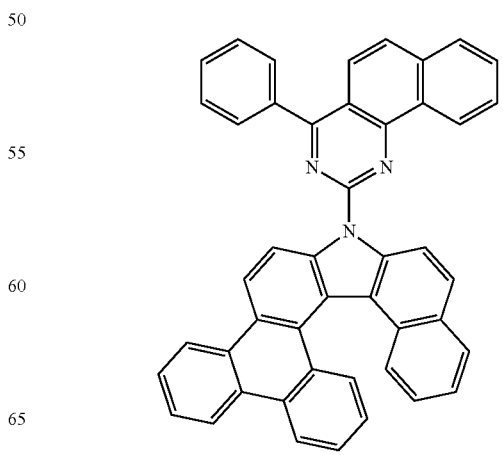

9
-continued
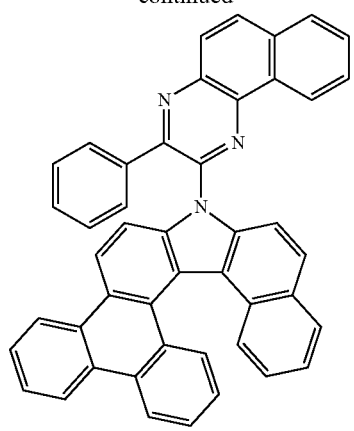
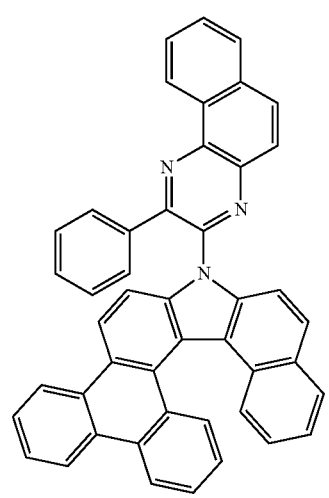
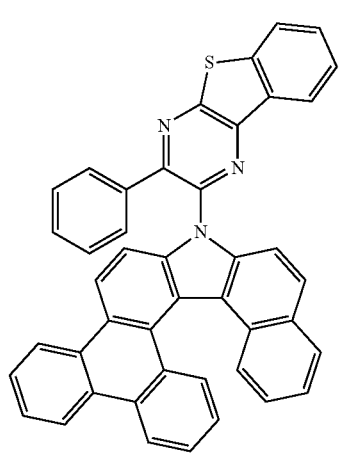
10
-continued
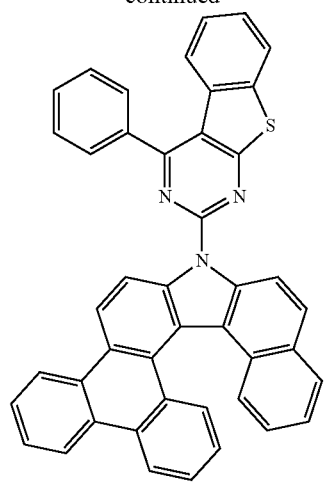
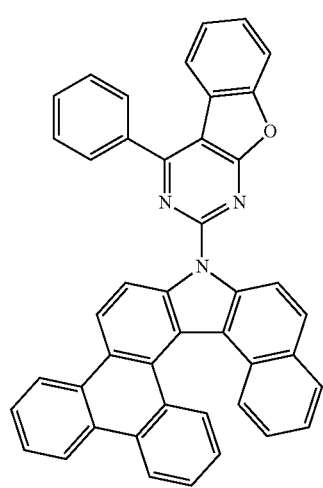
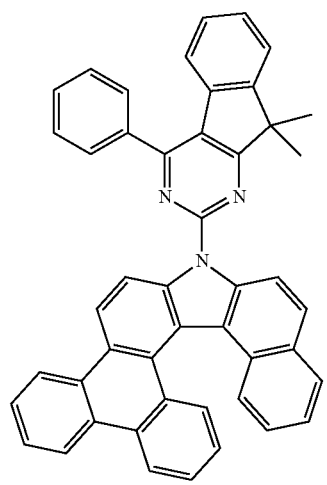

11
-continued
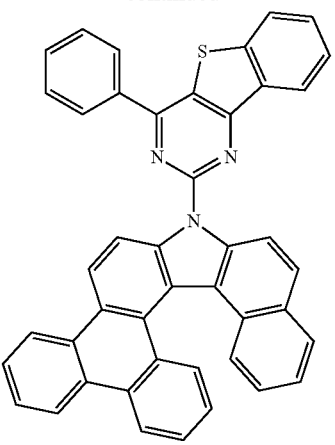
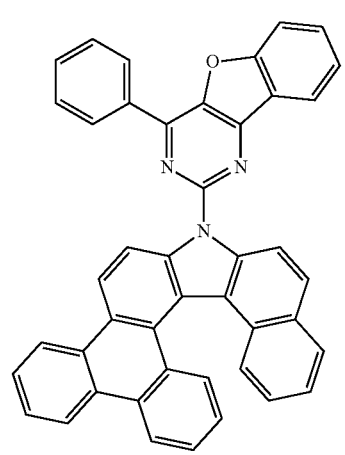
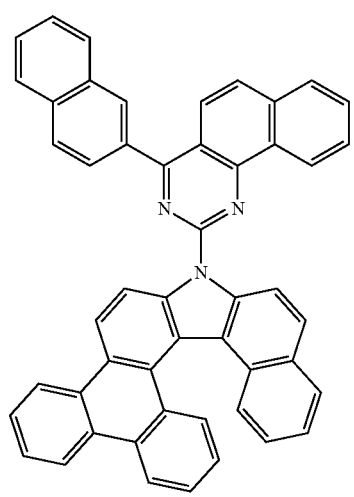
12
-continued
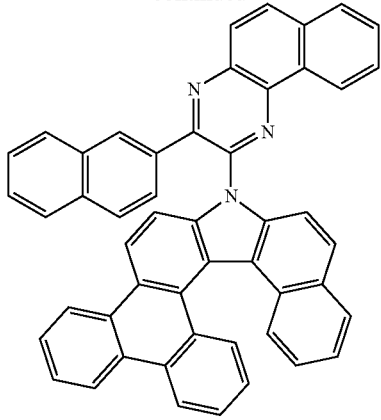
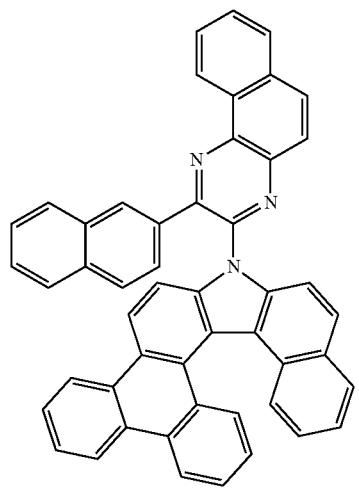
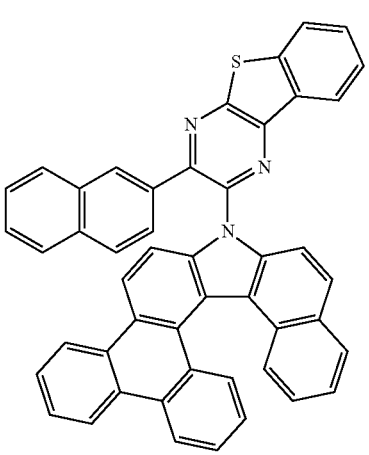

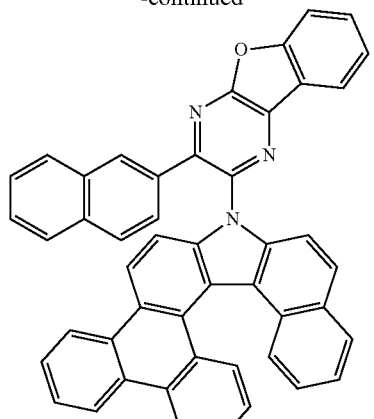
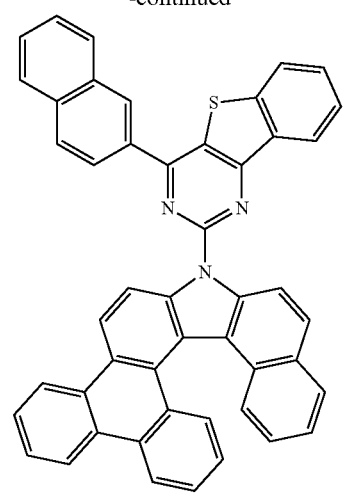
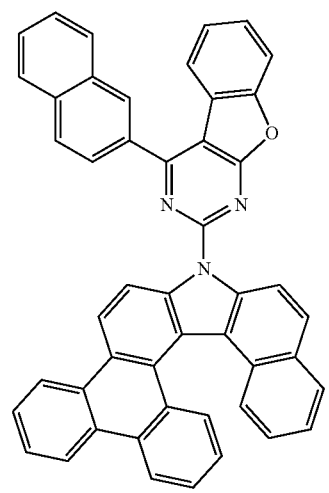
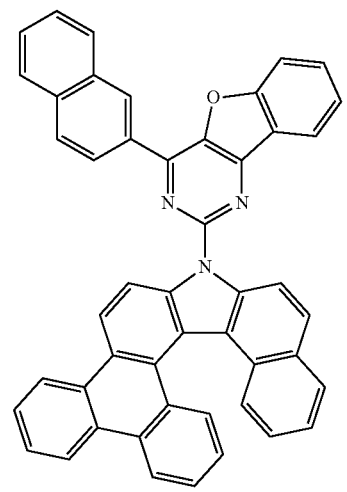
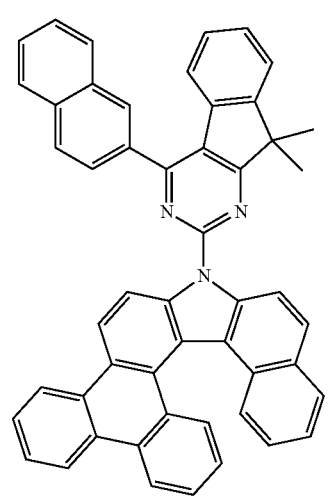
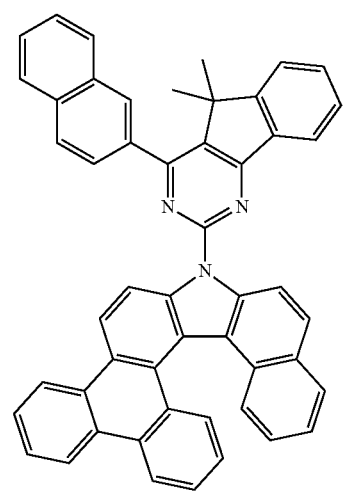

-continued
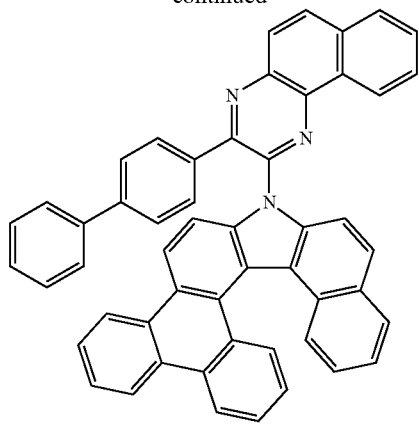
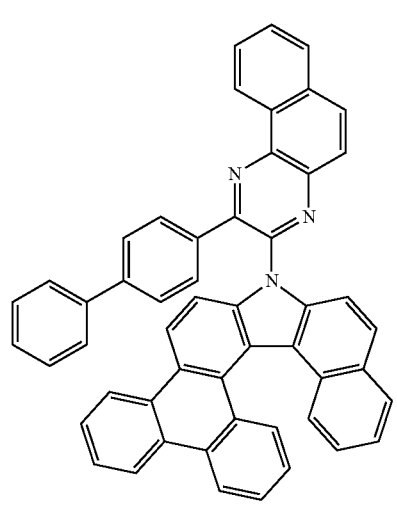
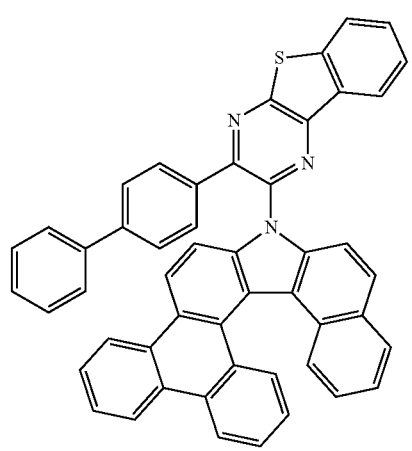
-continued
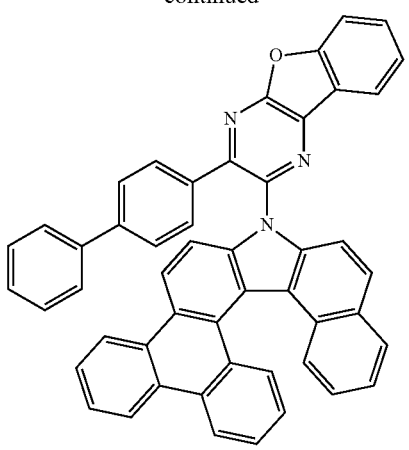
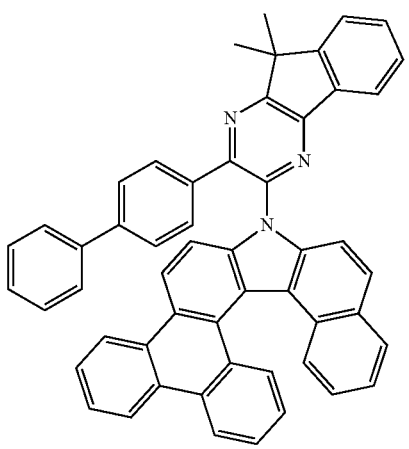
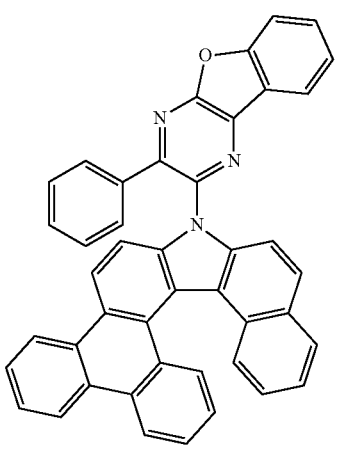

17
-continued
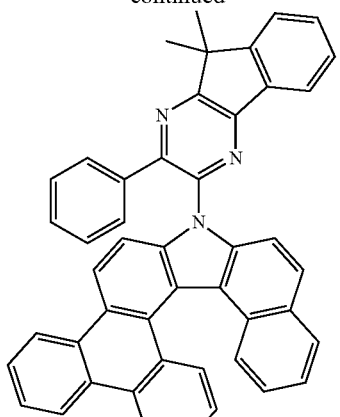
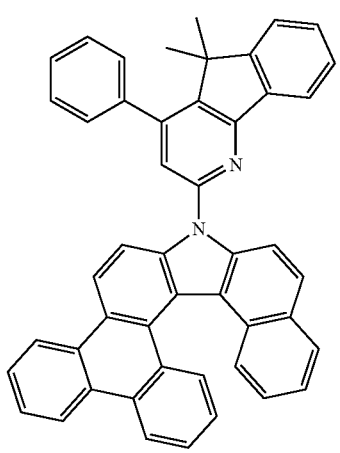
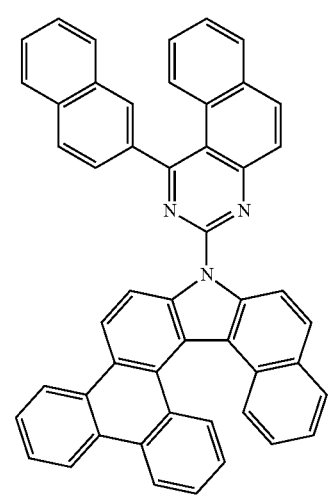
18
-continued
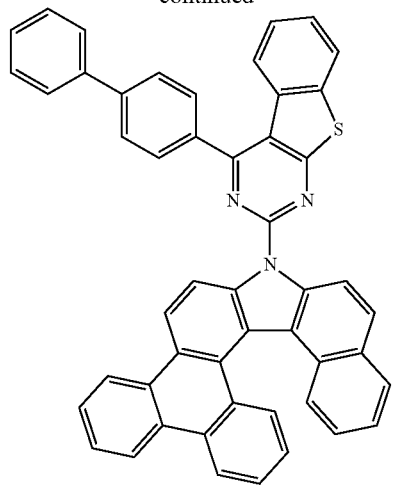
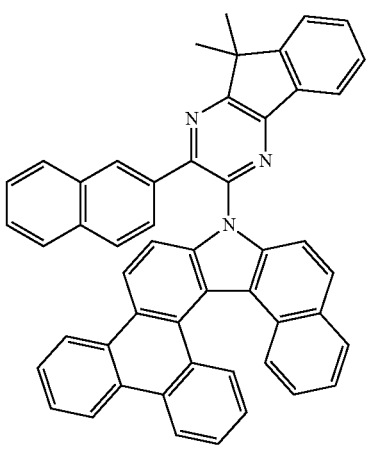
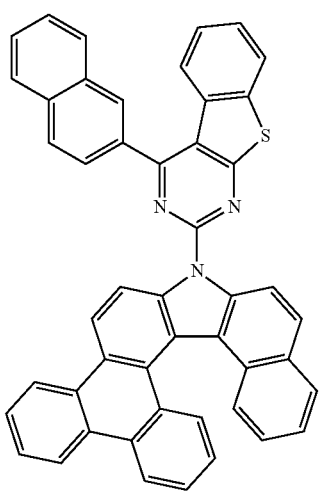

-continued
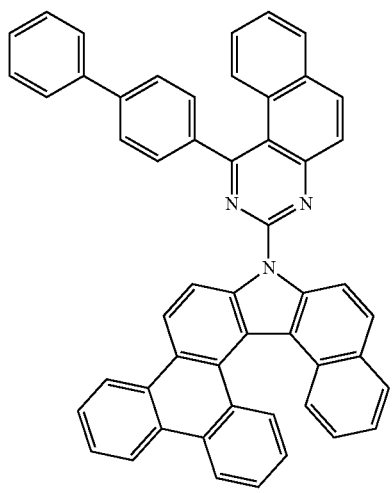
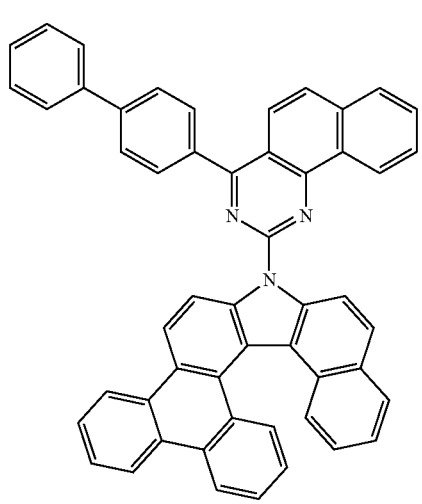
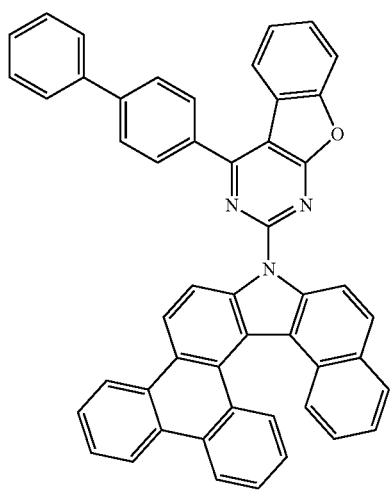
-continued
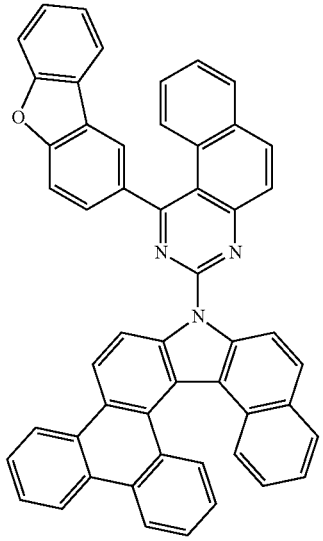
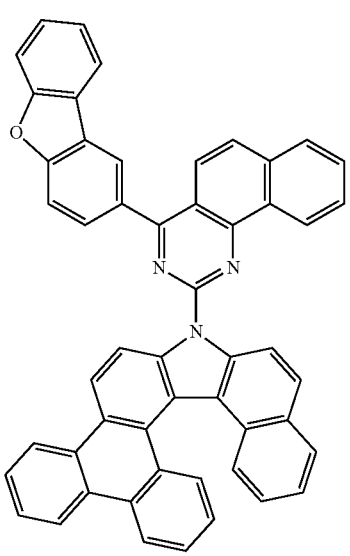
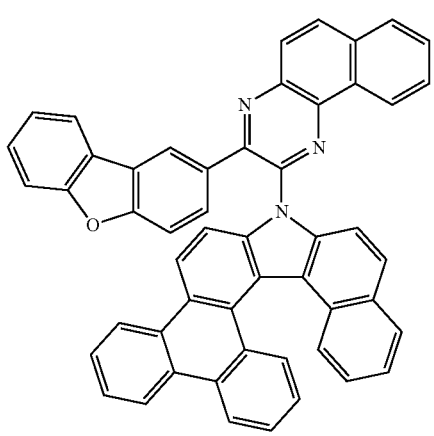

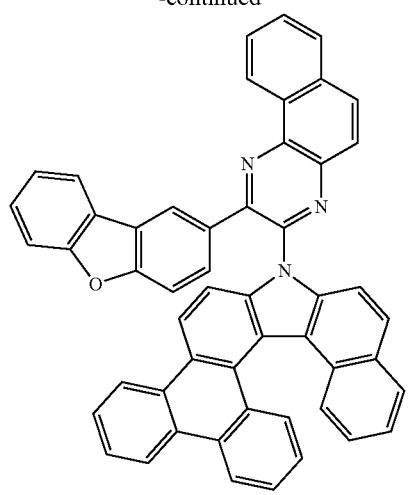
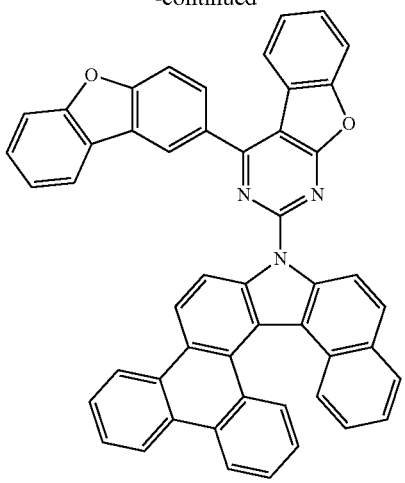
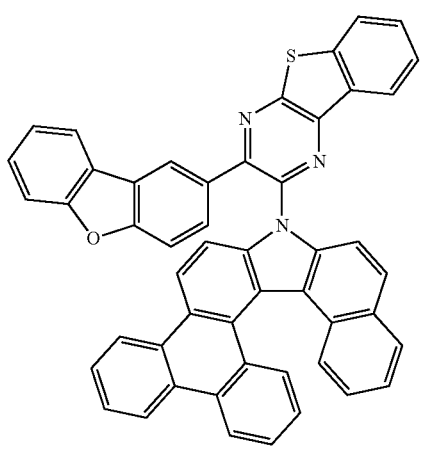
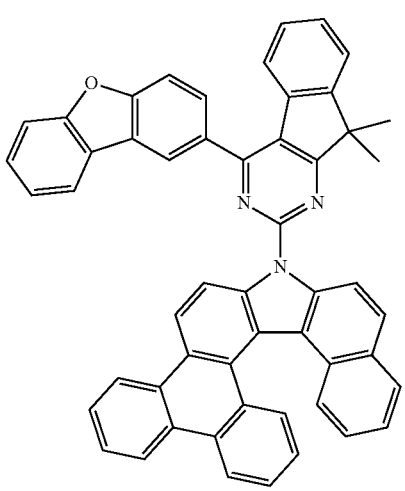
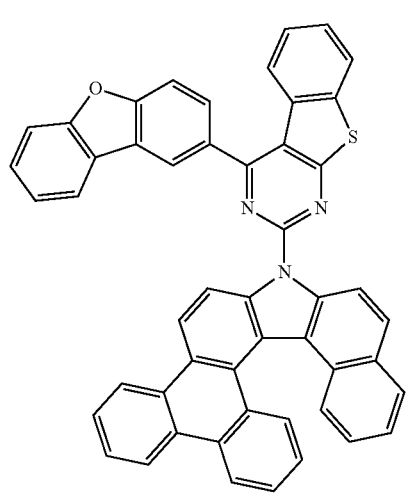
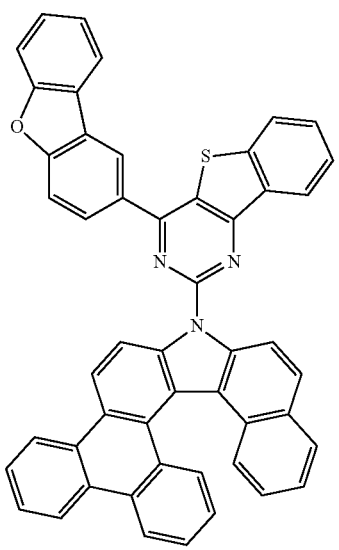

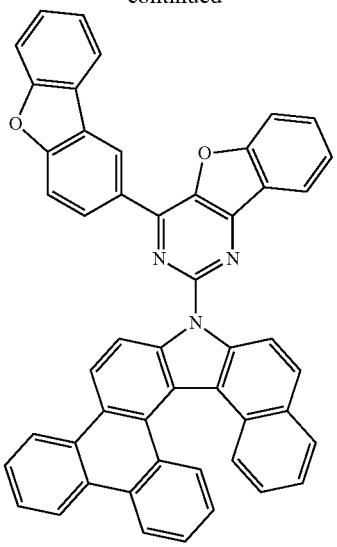
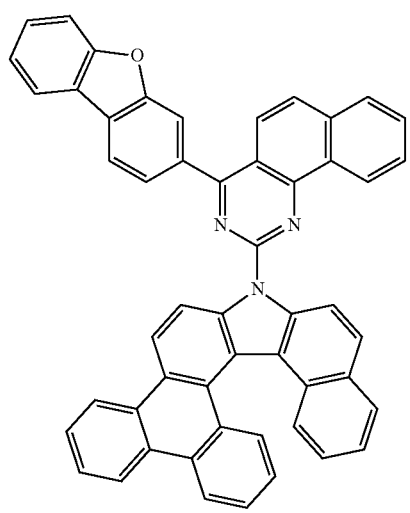
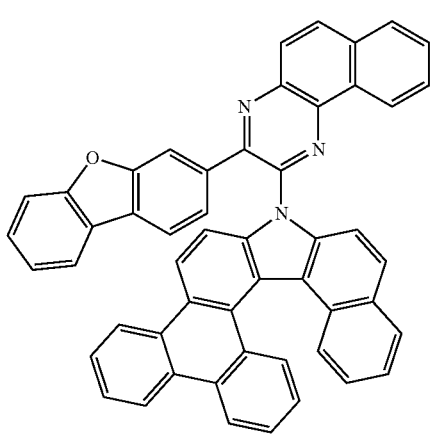
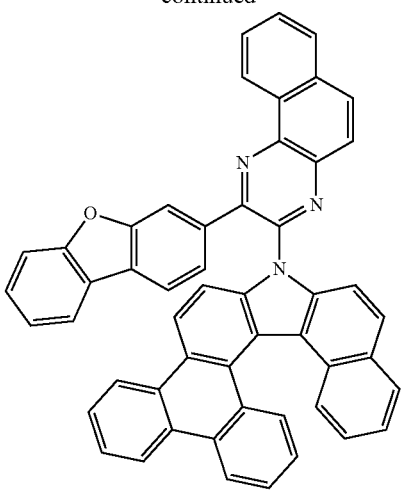
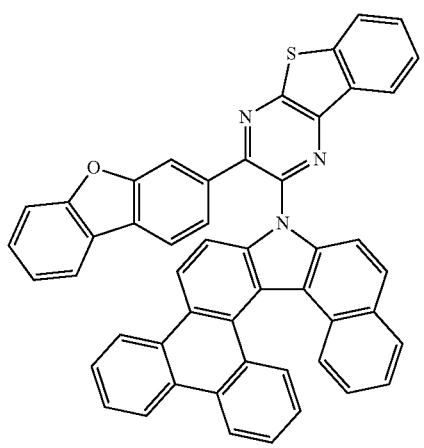
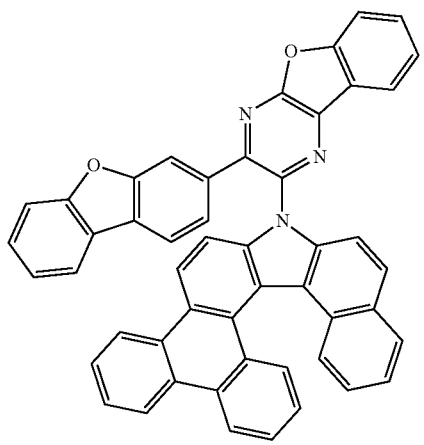

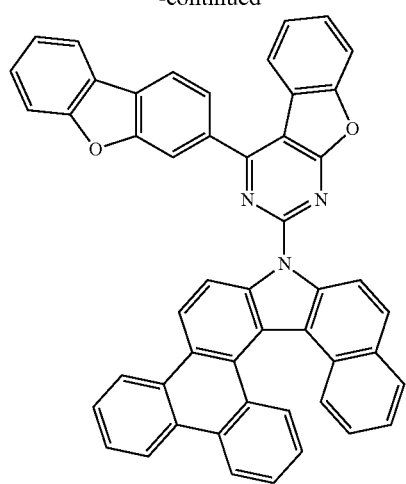
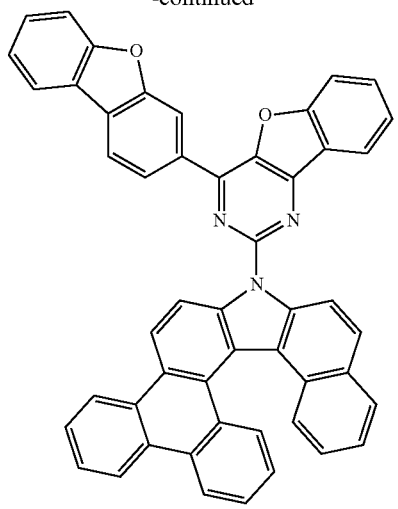
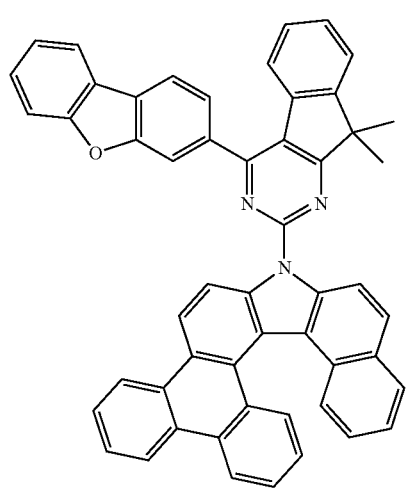
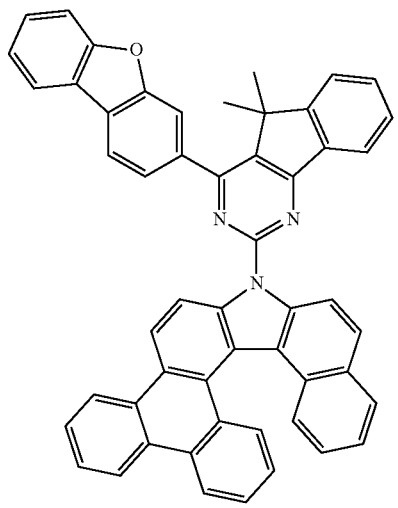
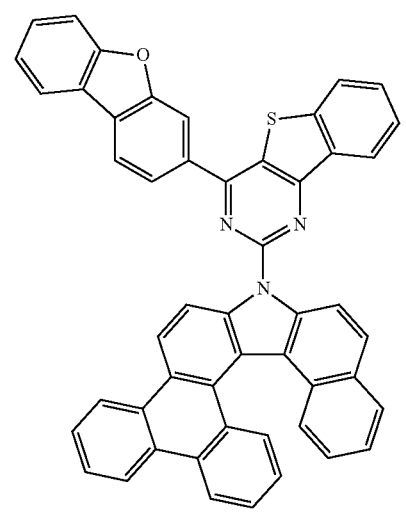
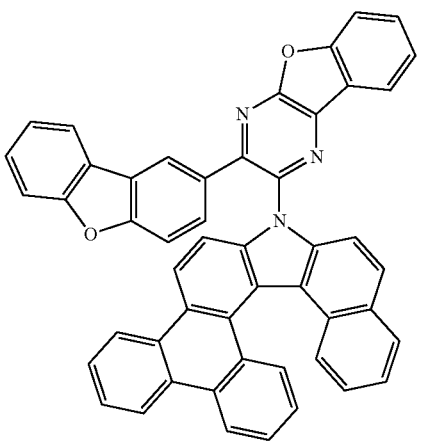

27
-continued
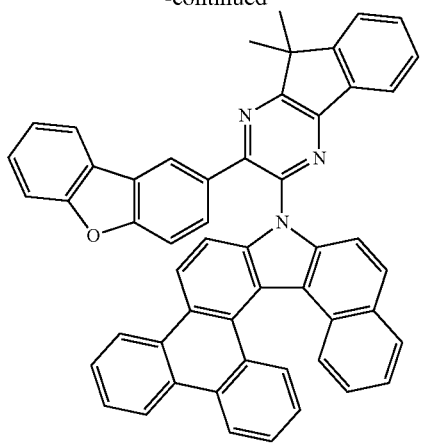
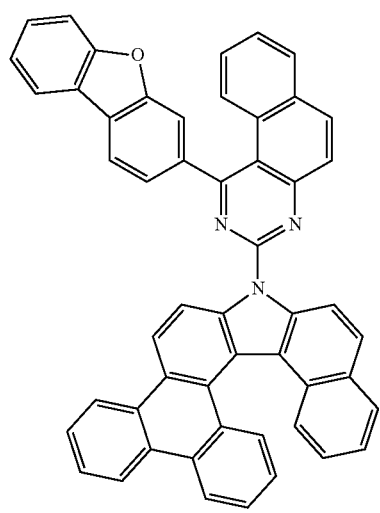
28
-continued
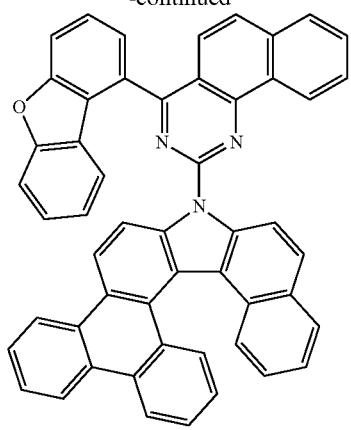
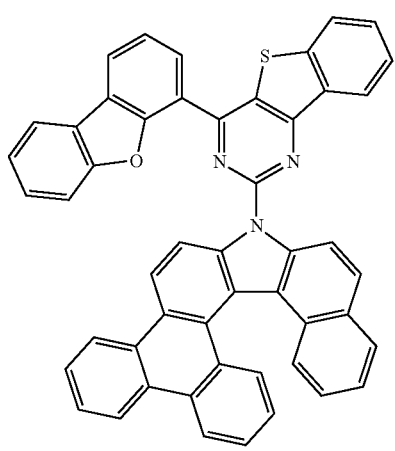

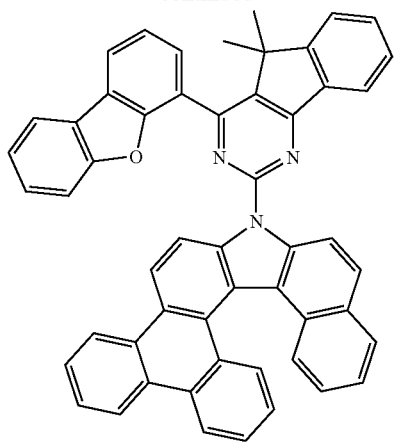
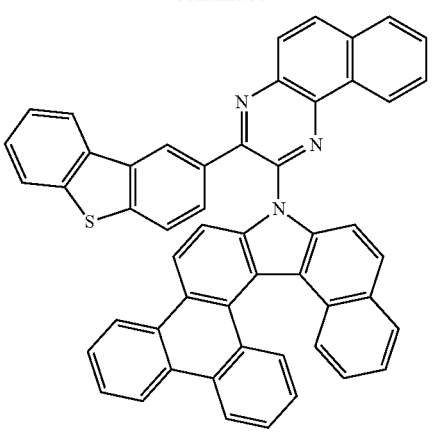
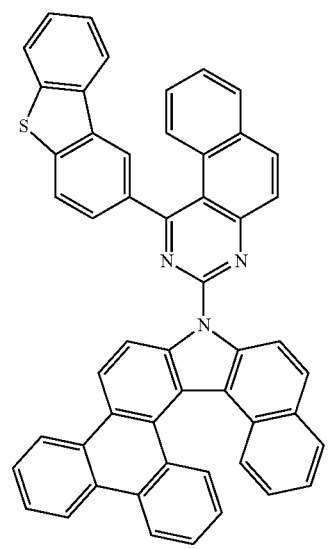
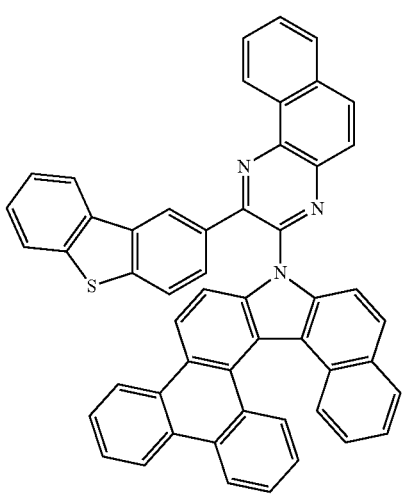
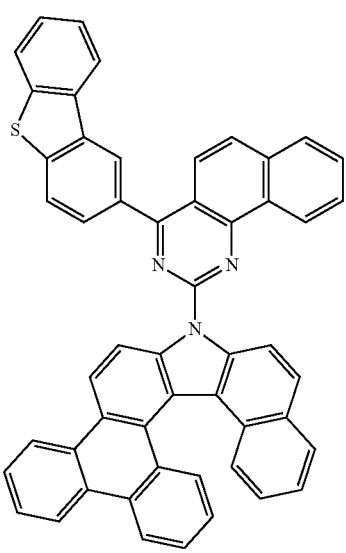
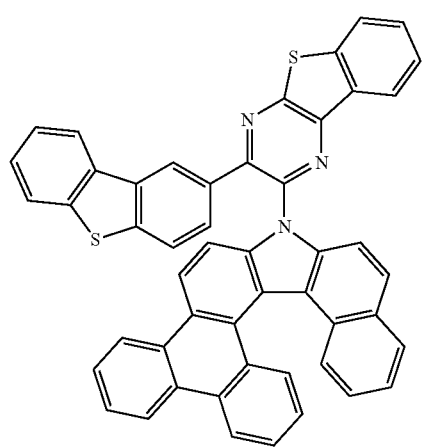

31
-continued
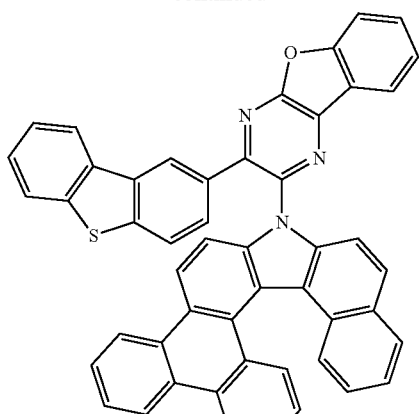
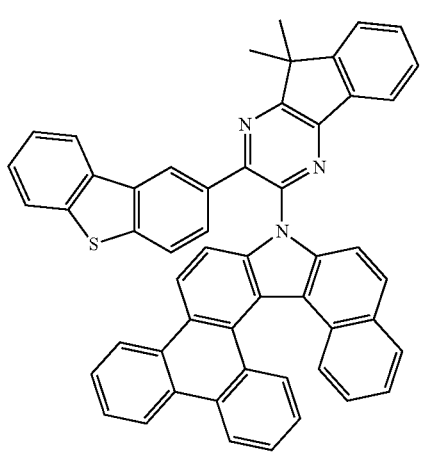
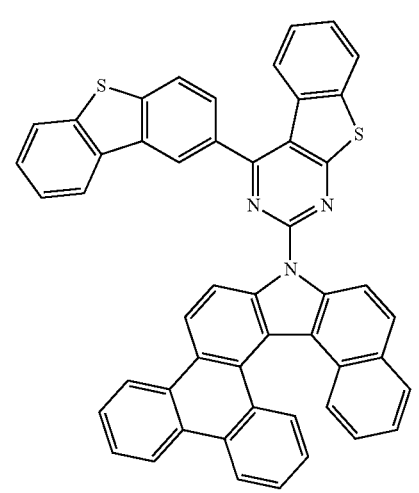
32
-continued
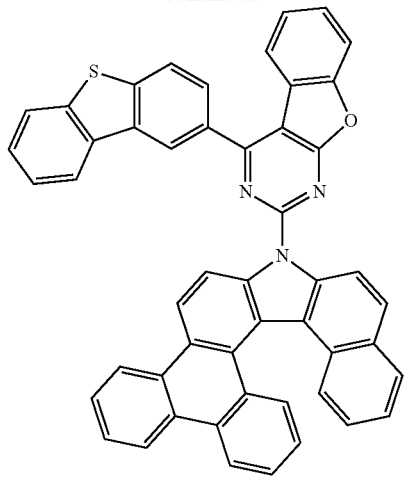
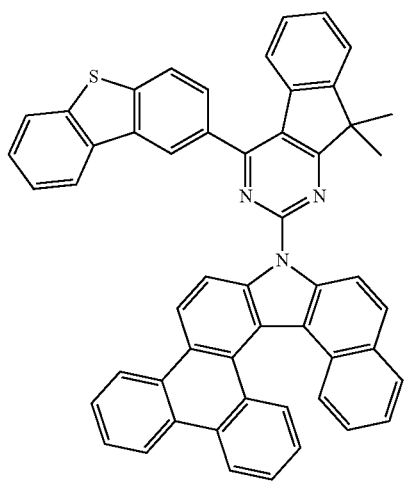
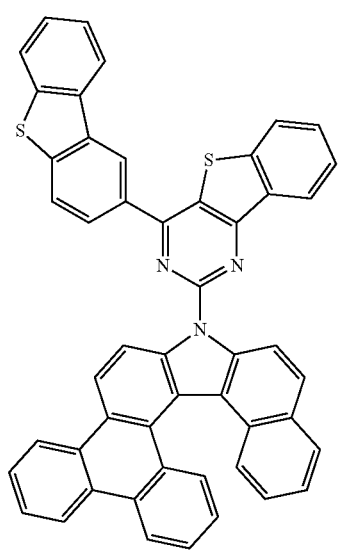

33
-continued
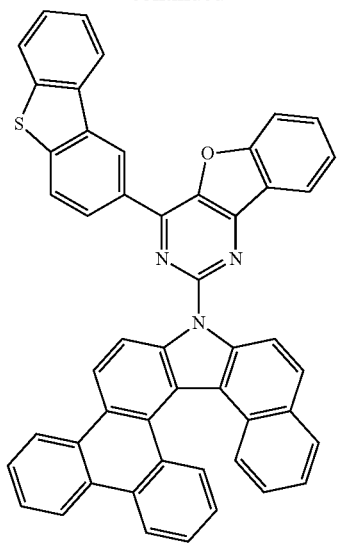
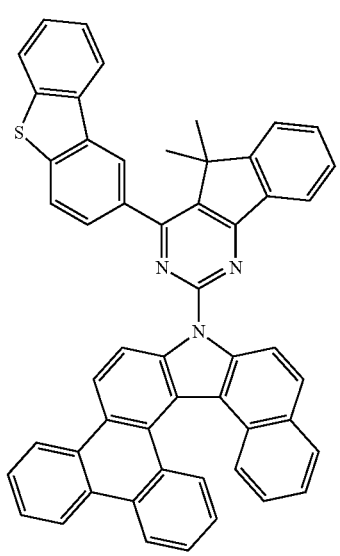
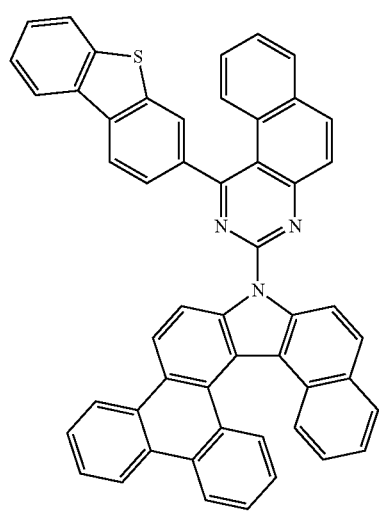
34
-continued
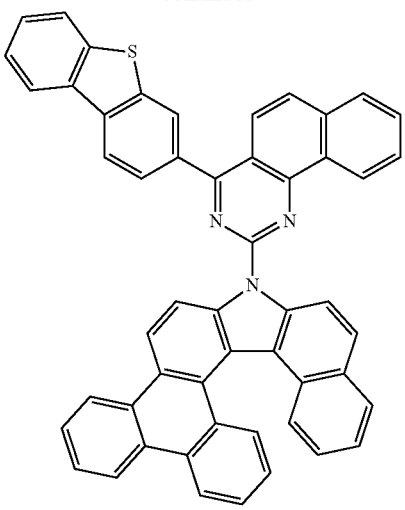
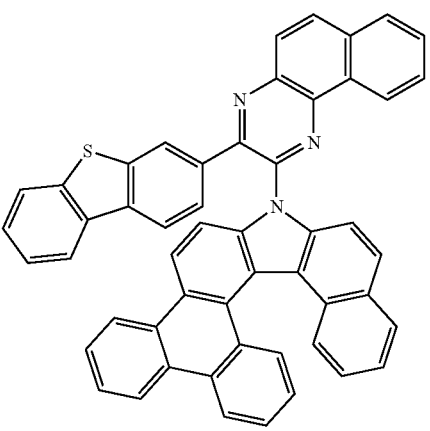
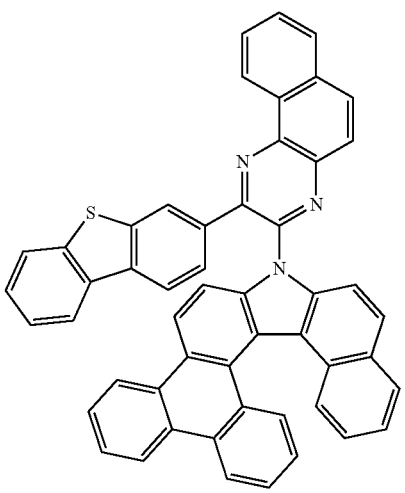

35
-continued
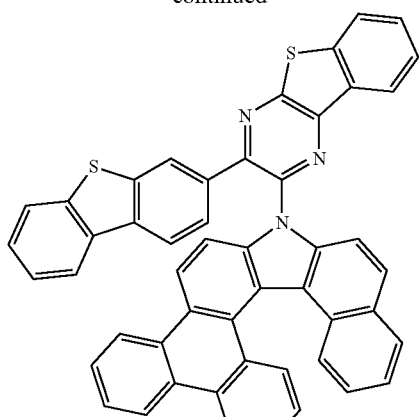
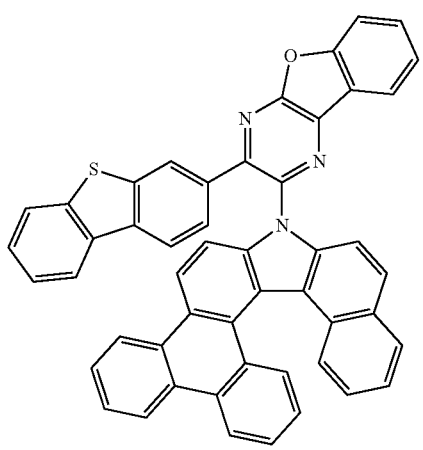
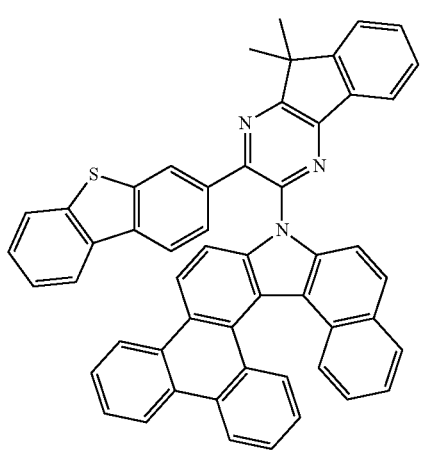
36
-continued
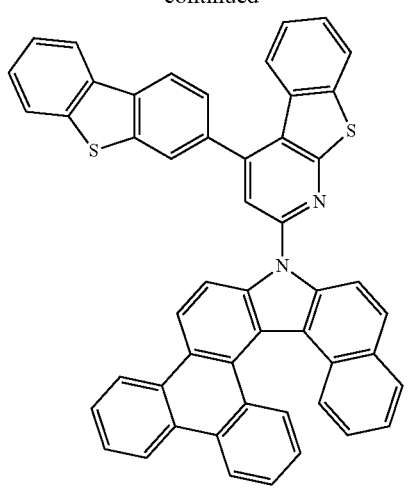
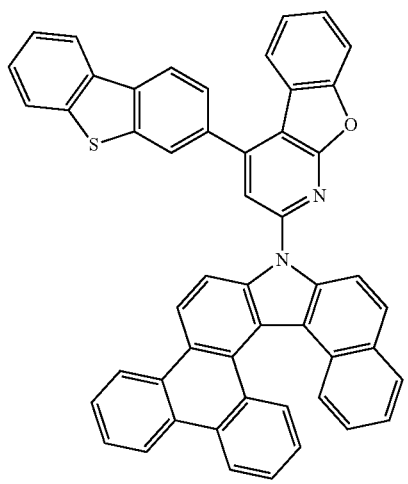
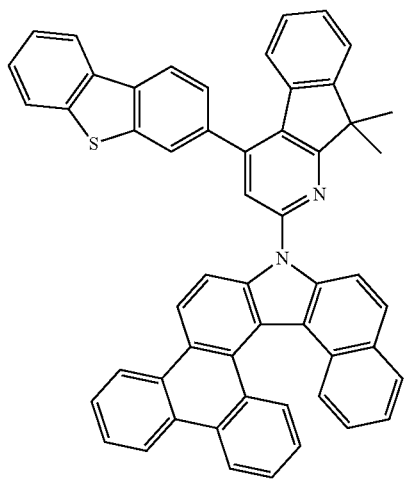

37
-continued
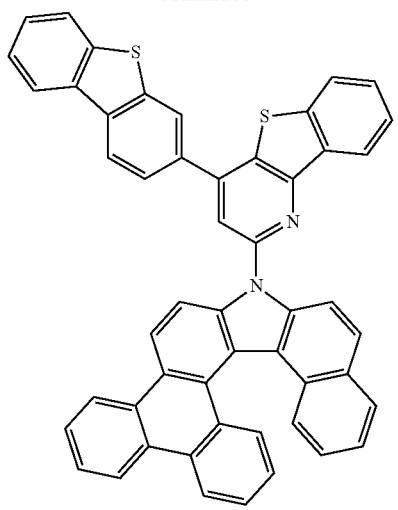
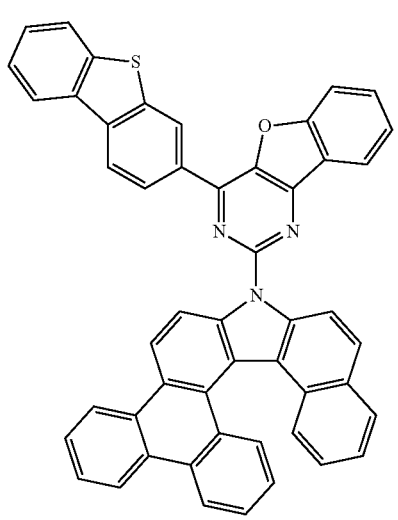
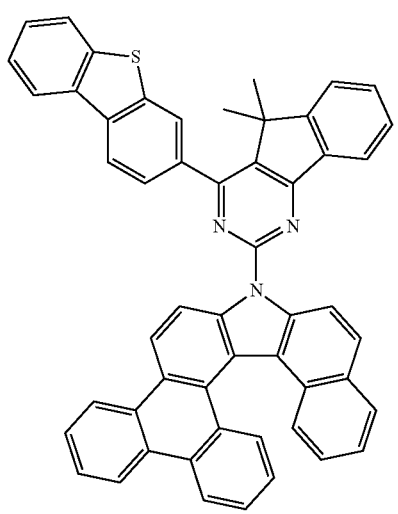
38
-continued
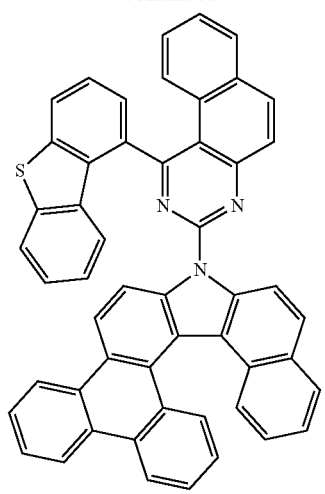
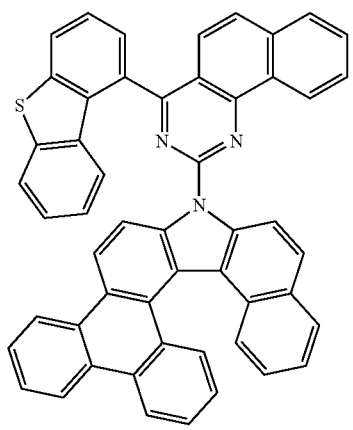
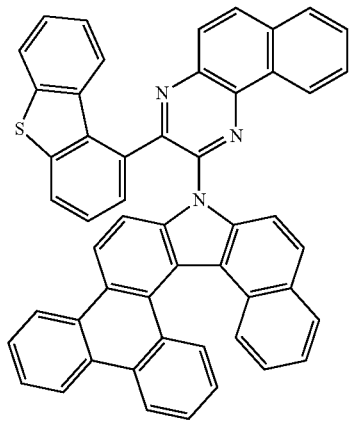

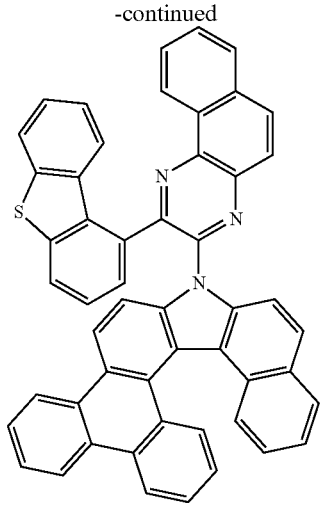
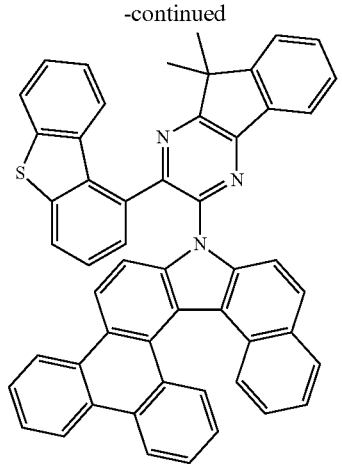
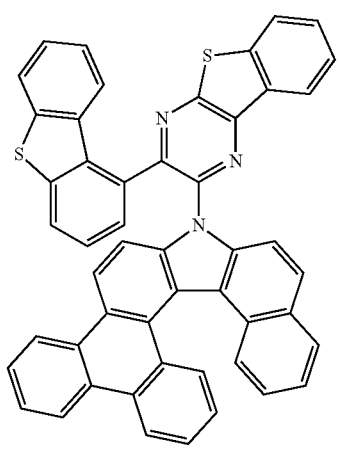
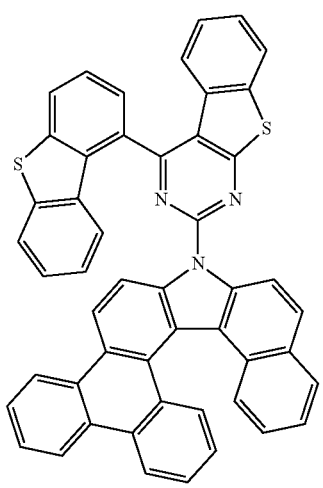
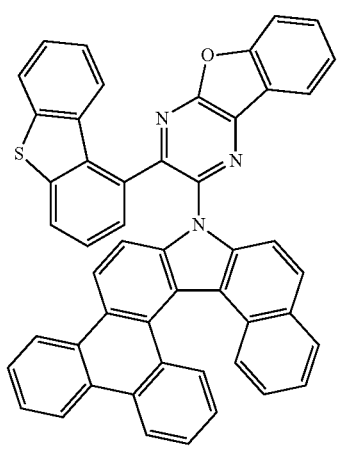
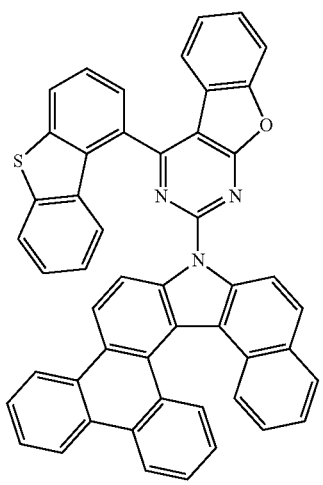

41
-continued
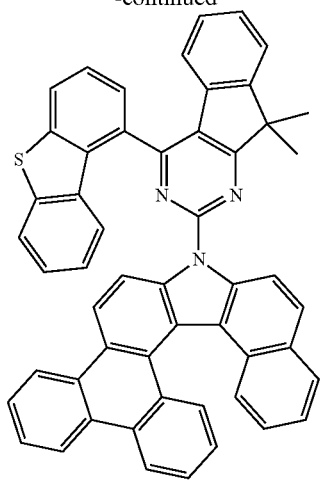
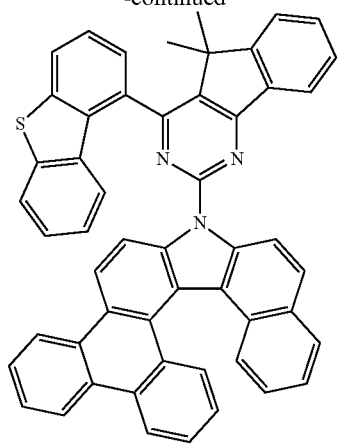
42
-continued
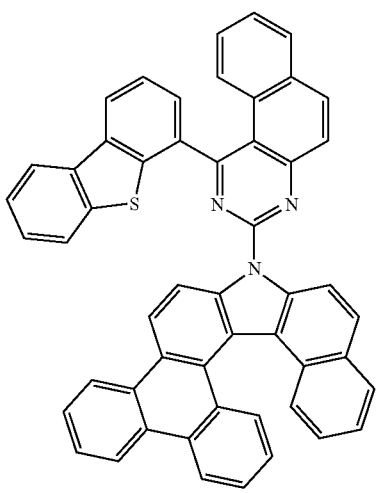
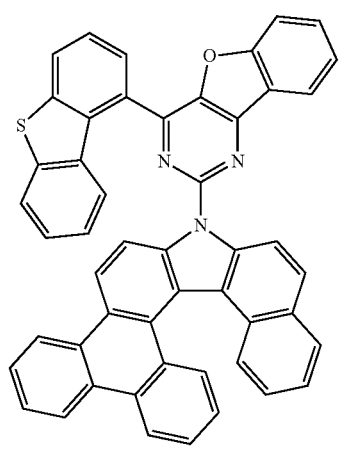
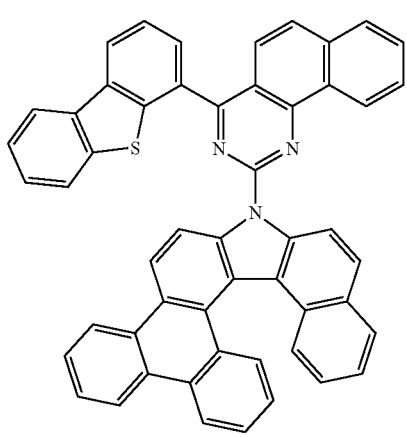

43
-continued
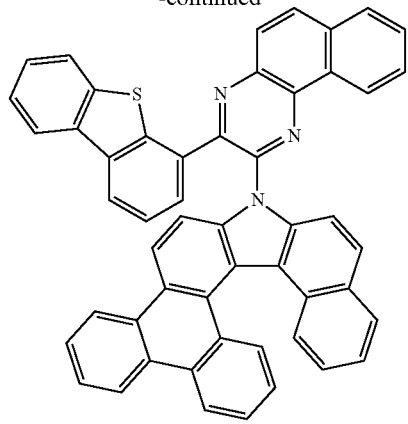
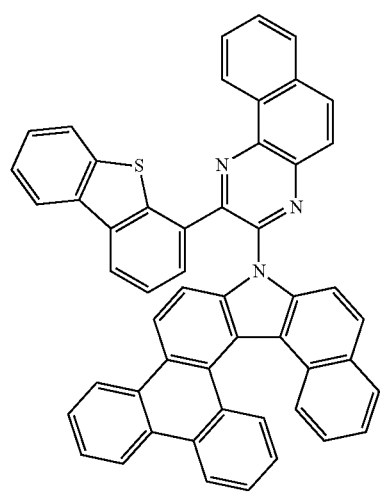
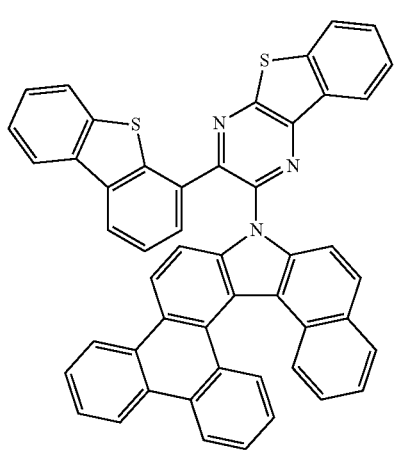
44
-continued
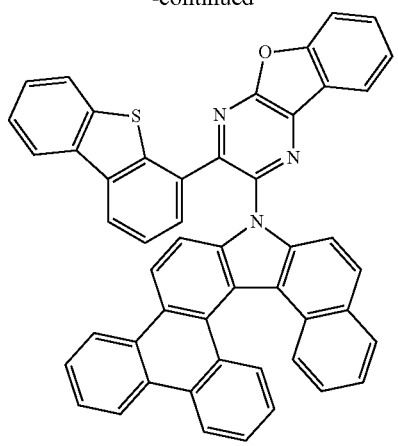
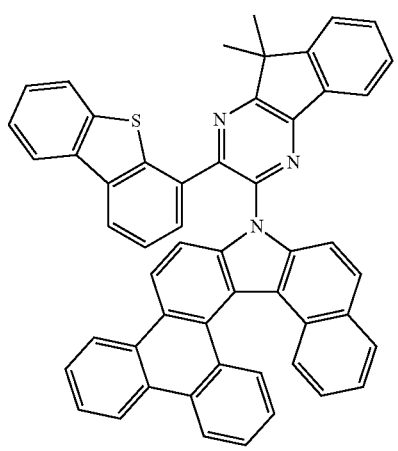
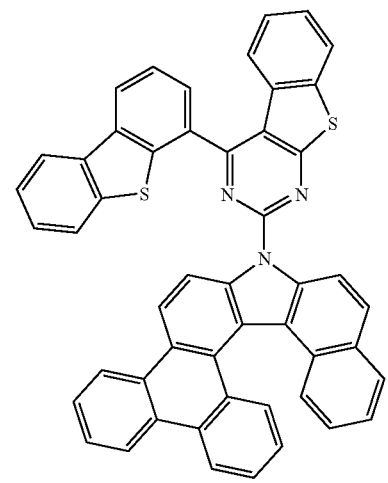

45
-continued
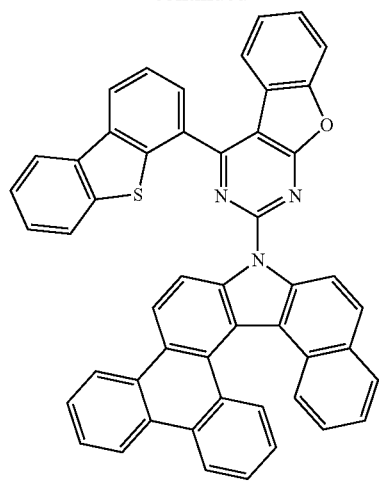
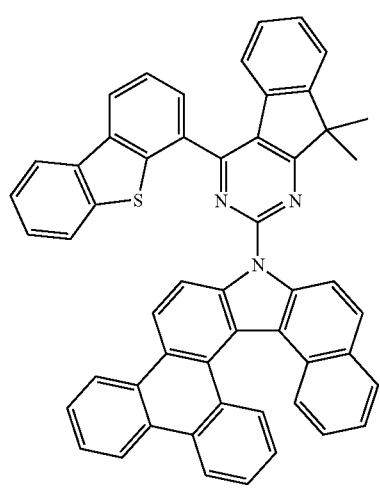
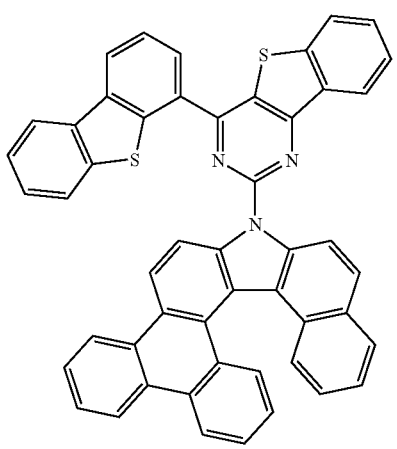
46
-continued
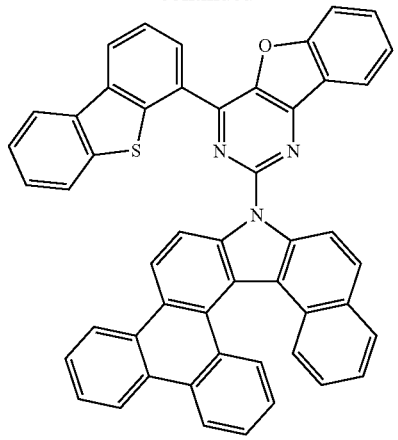
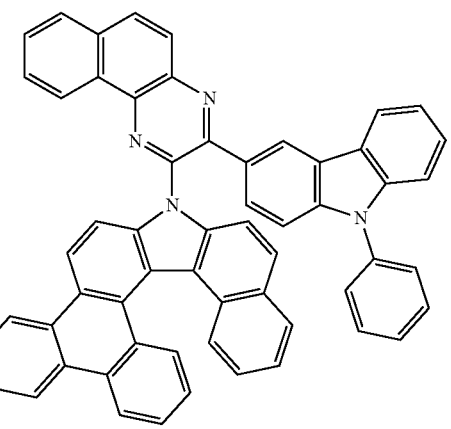
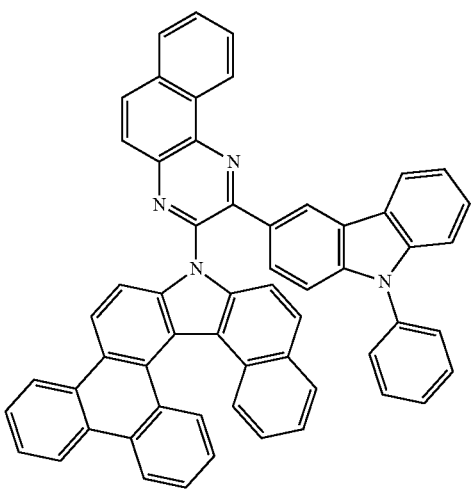

47
-continued
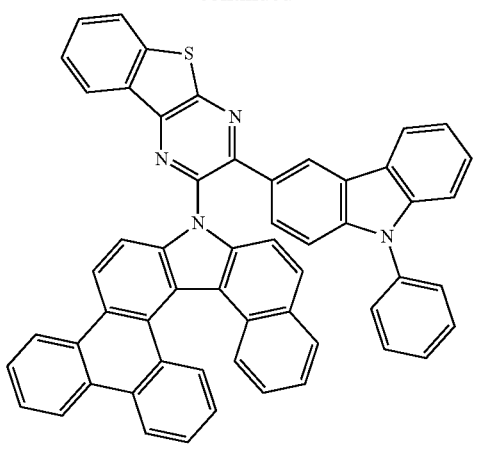
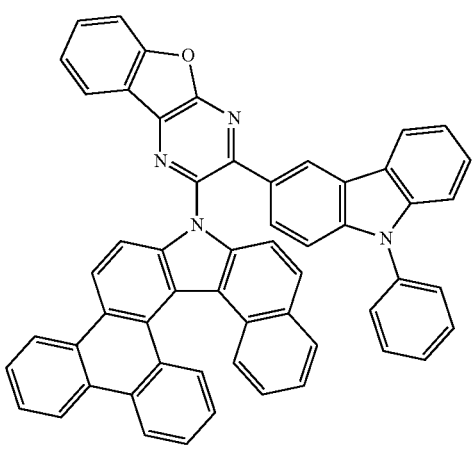
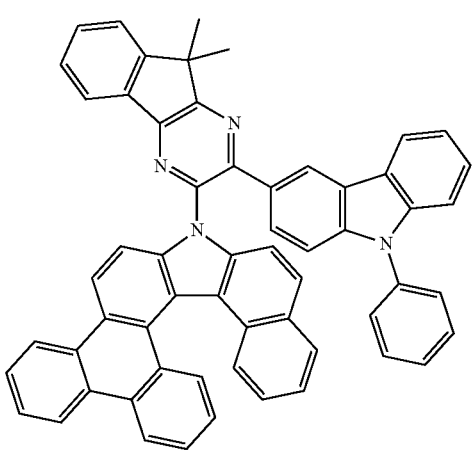
48
-continued
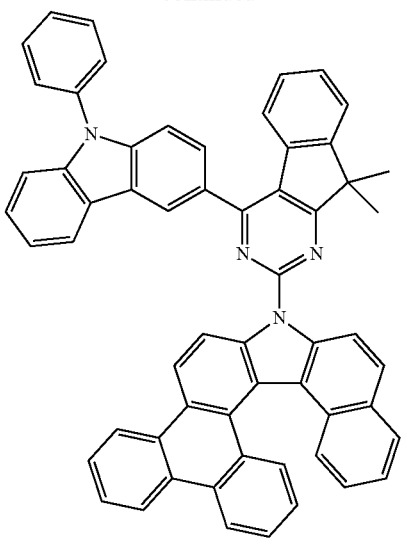
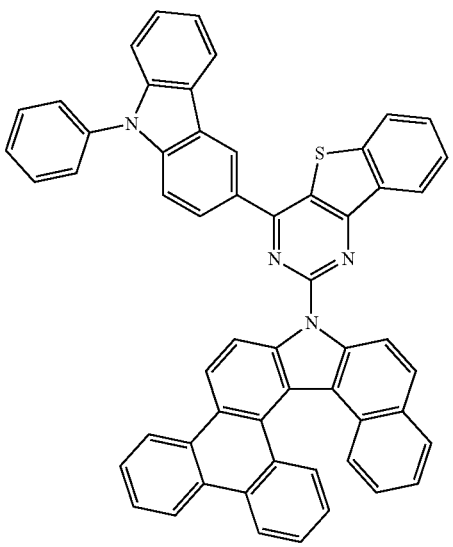
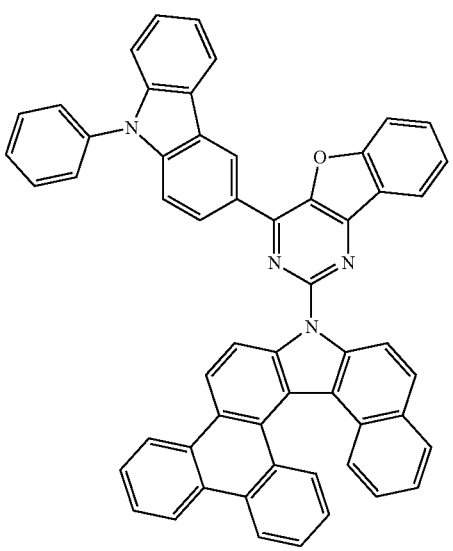

-continued
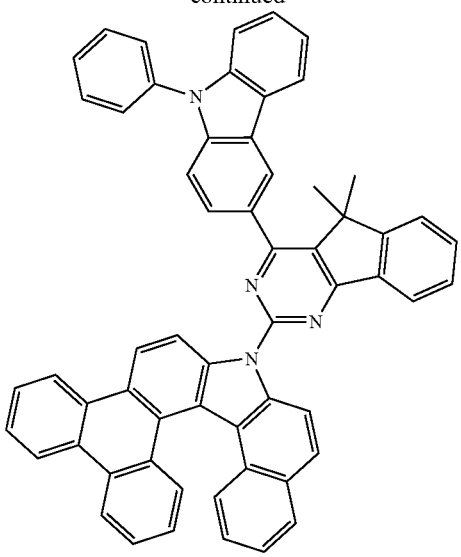
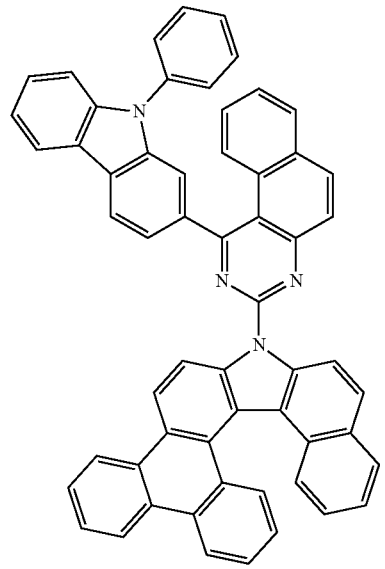
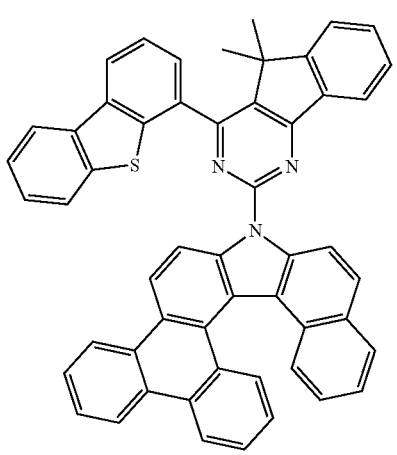
-continued
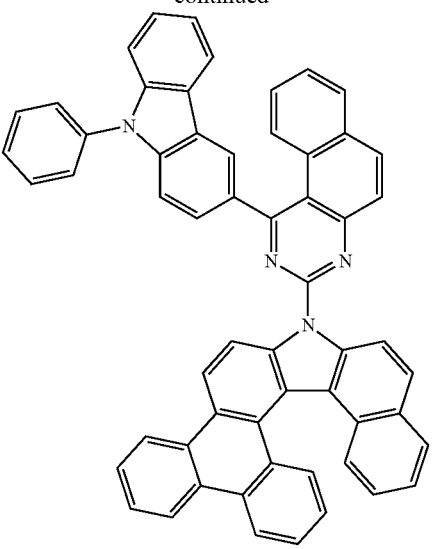
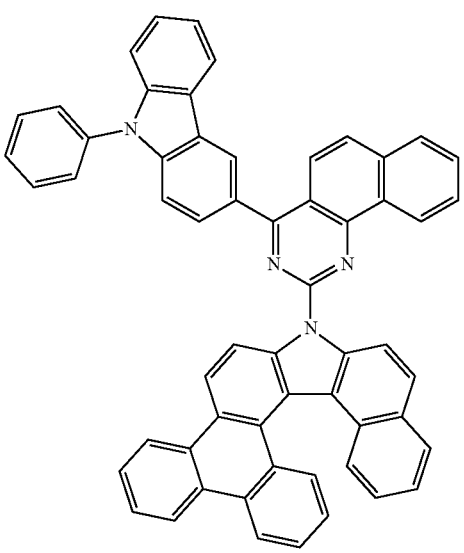
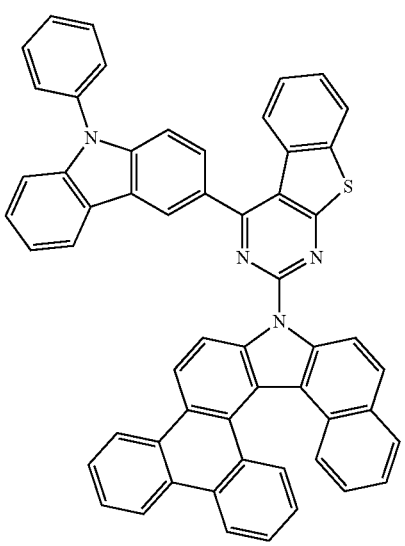

51
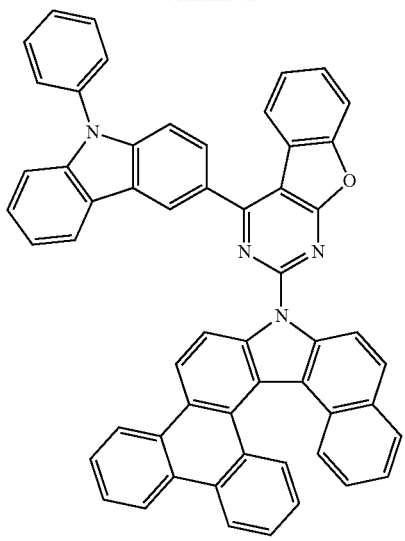
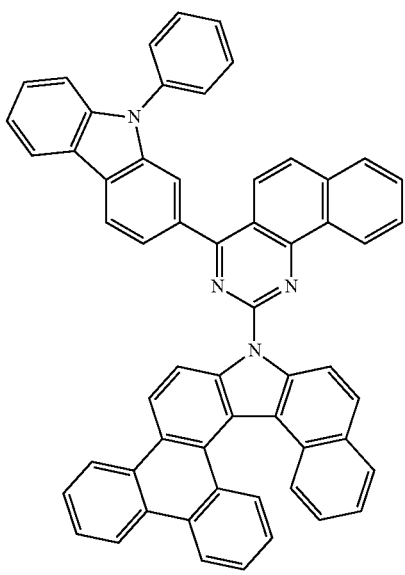
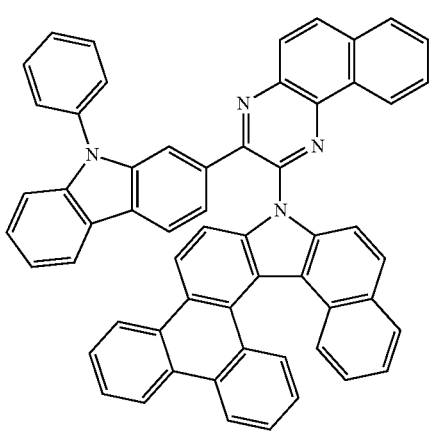
52
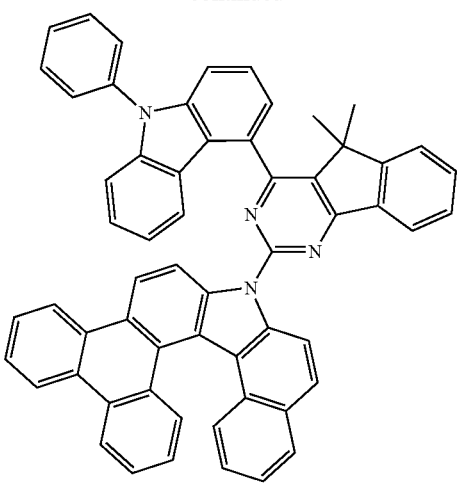
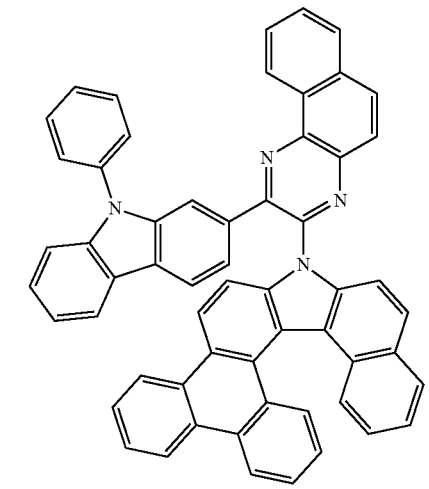
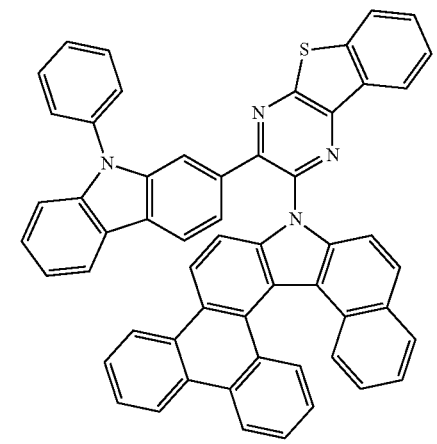

53
-continued
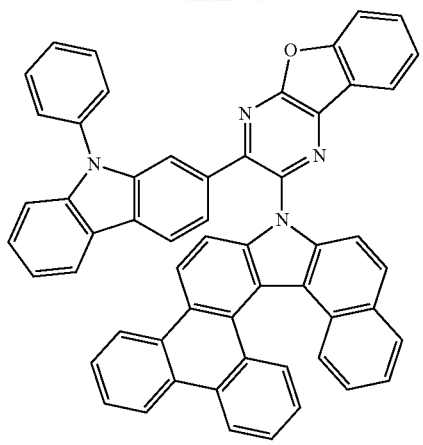
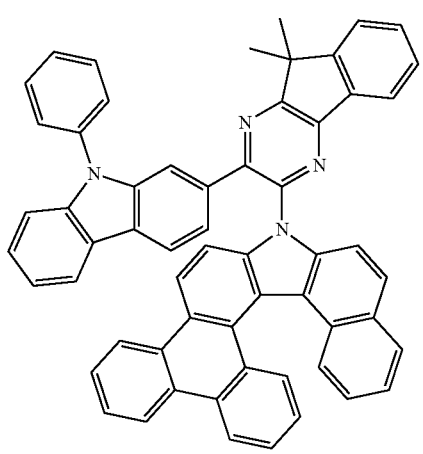
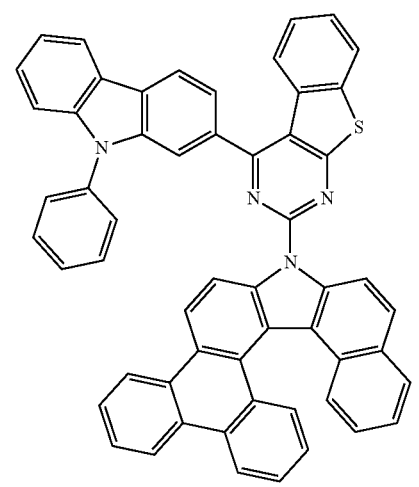
54
-continued
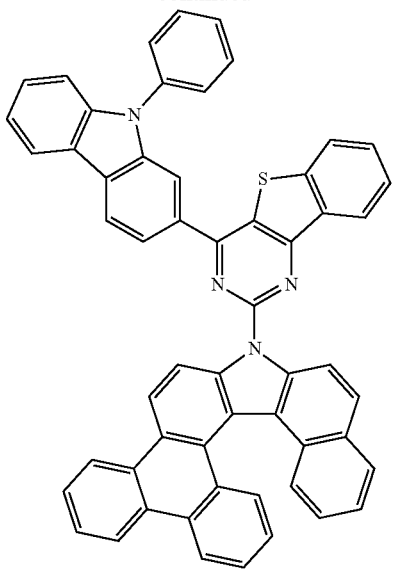
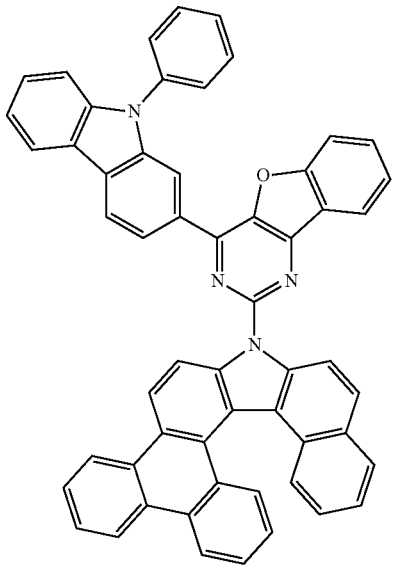
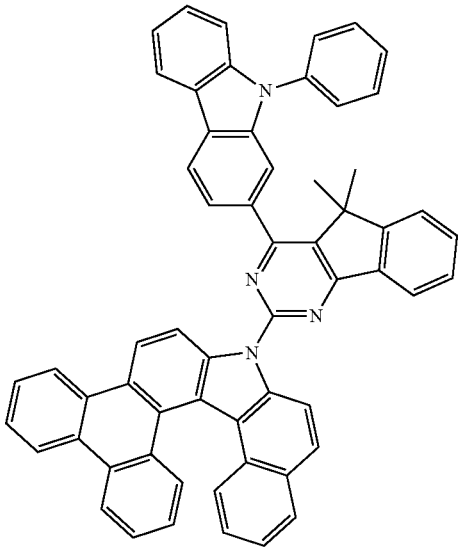

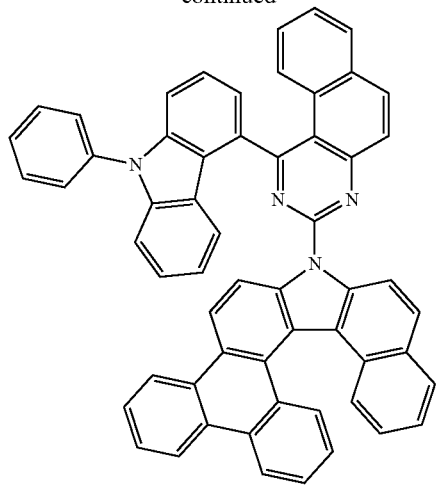
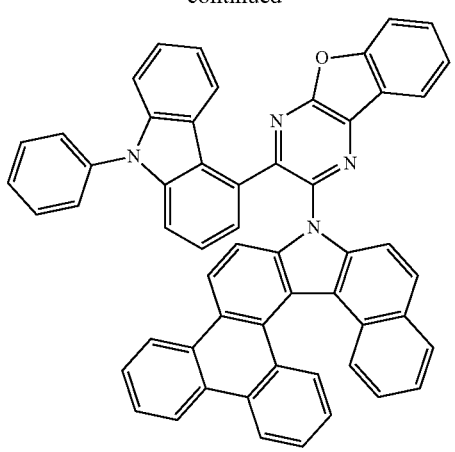
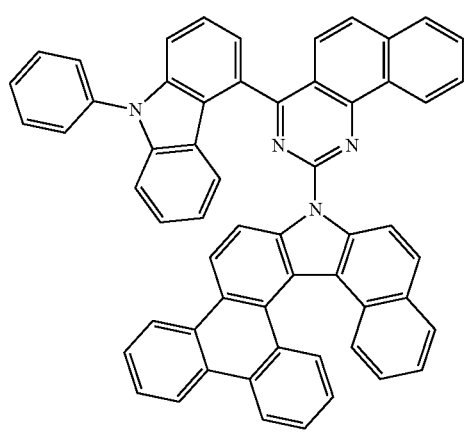
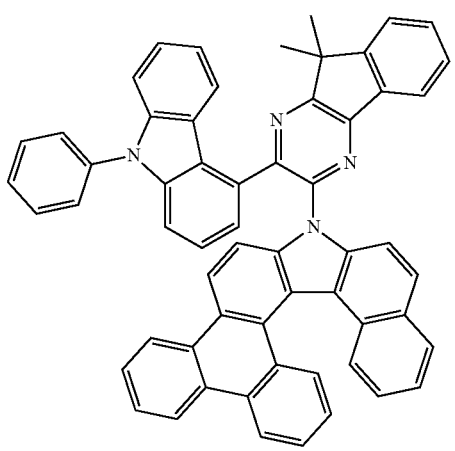
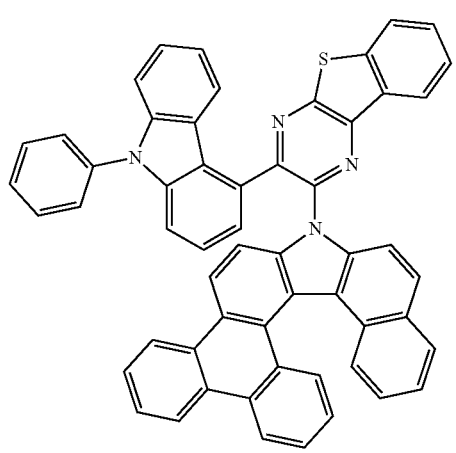
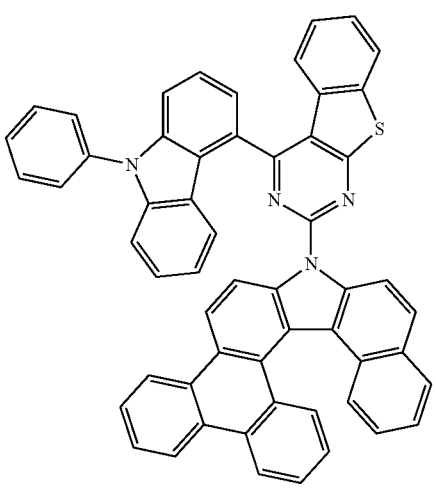

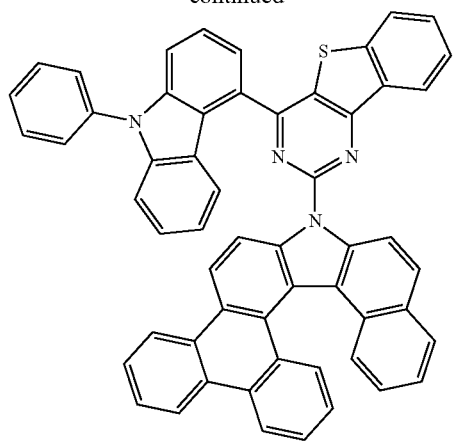
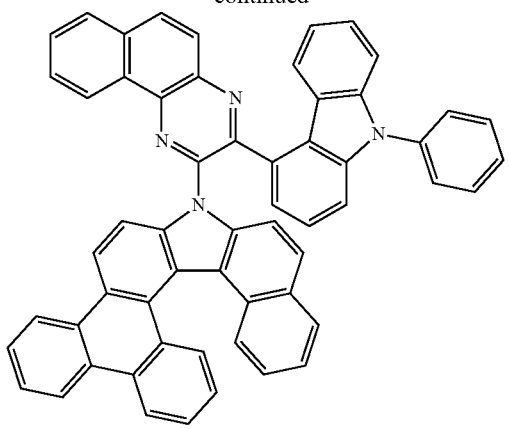
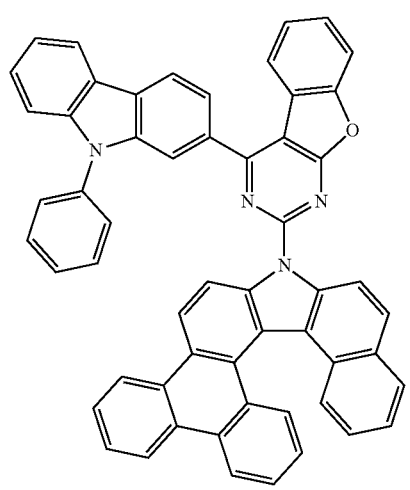
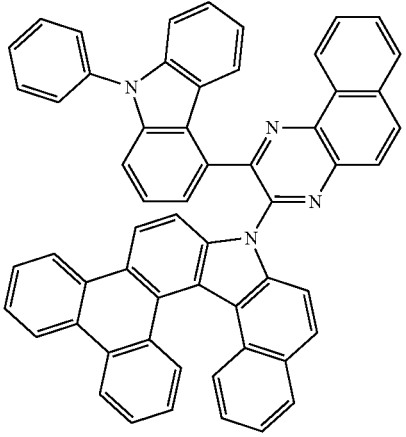
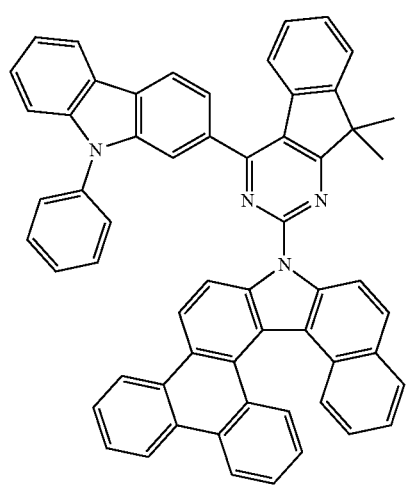
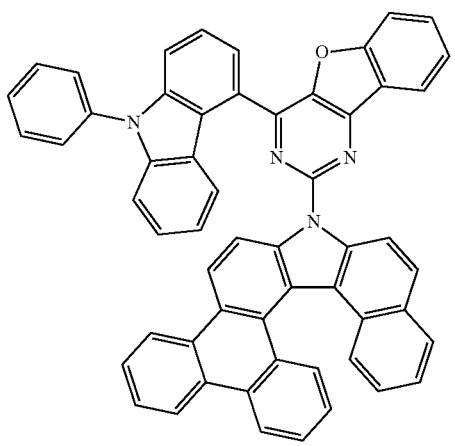

59
-continued

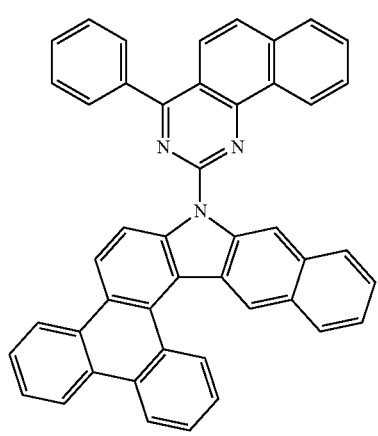
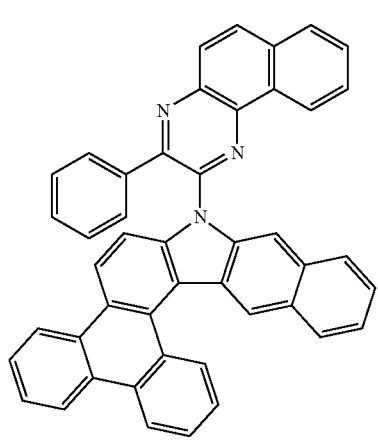
60
-continued
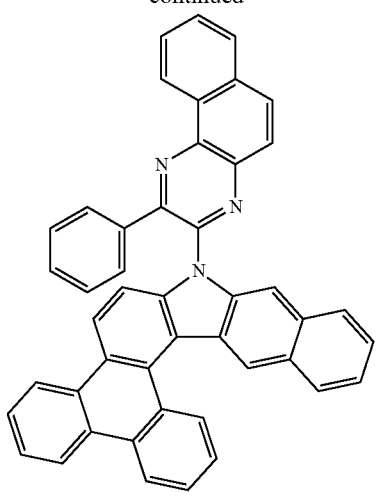
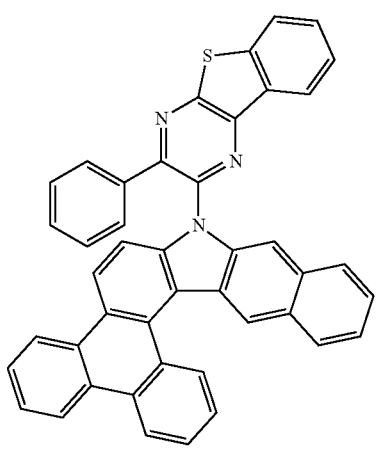
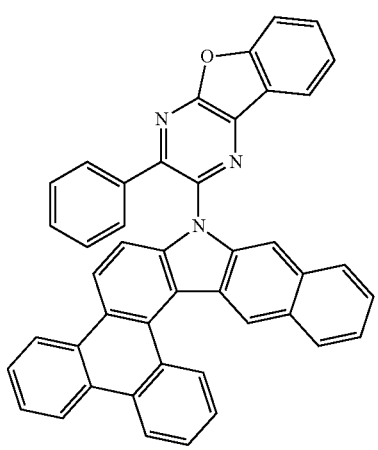

61
-continued
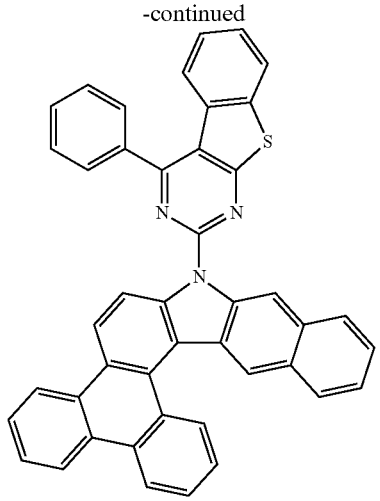
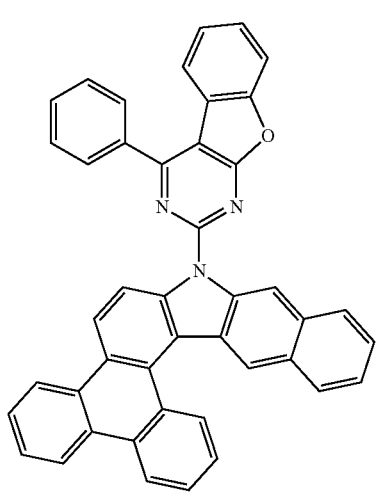
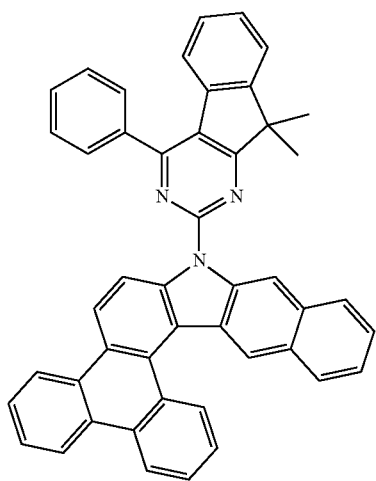
62
-continued
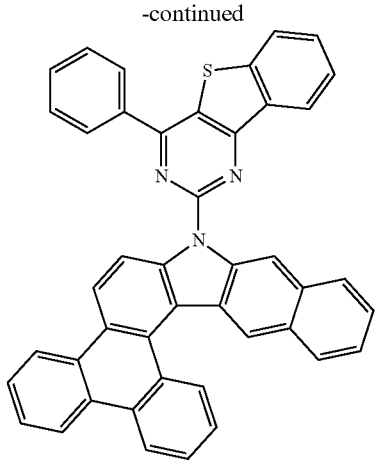
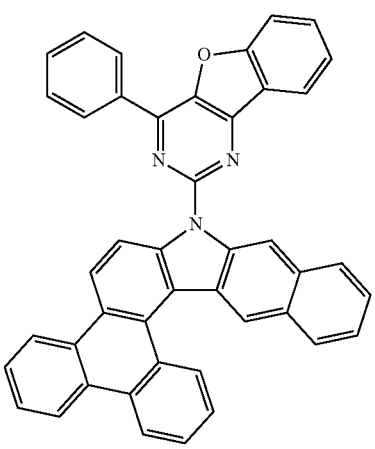
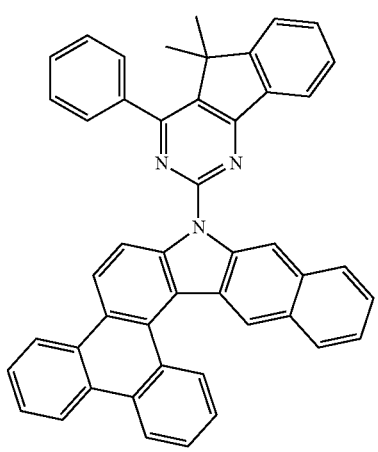

63
-continued
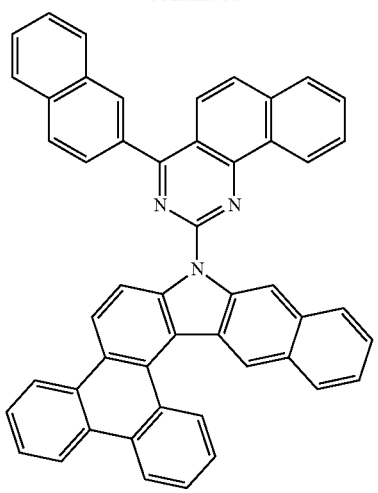
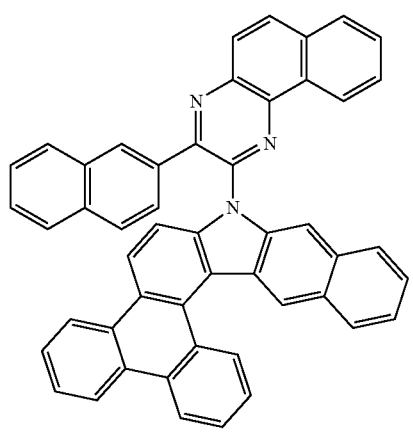
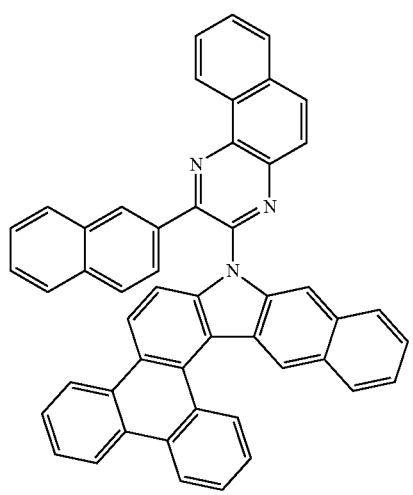
64
-continued
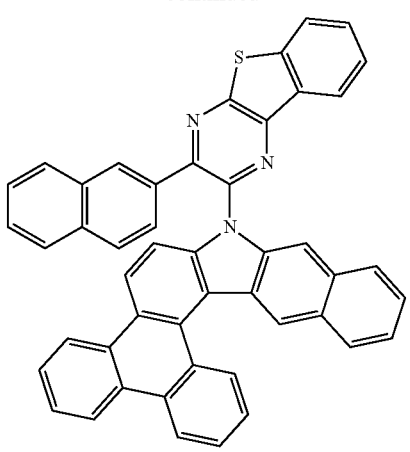
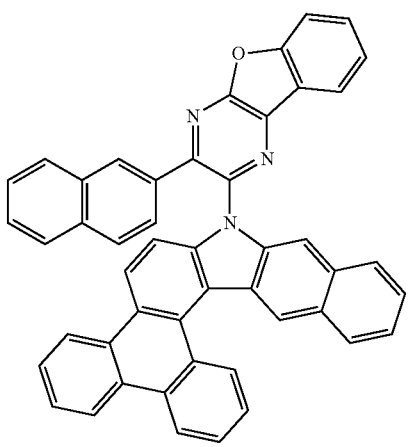
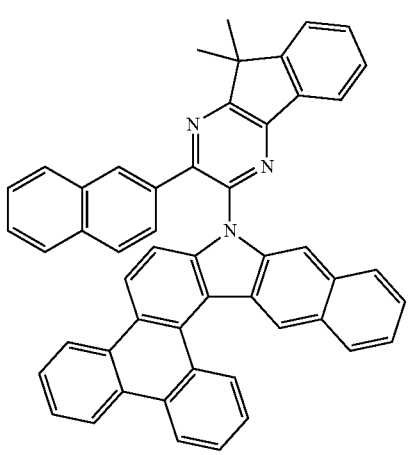

65
-continued
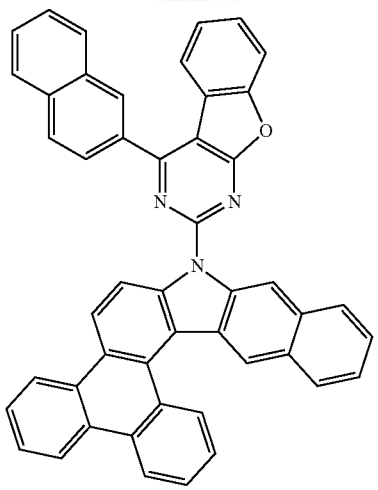
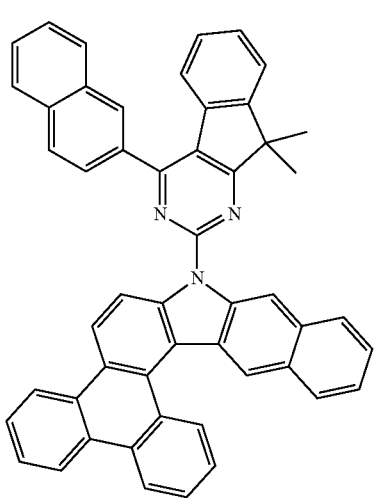
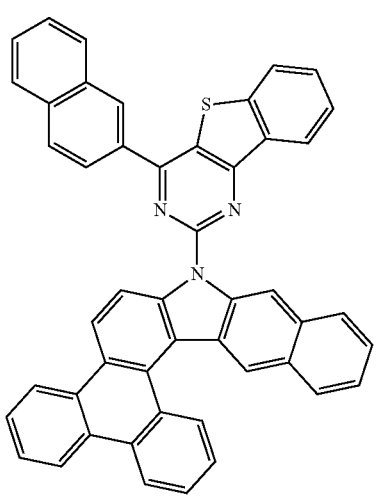
66
-continued
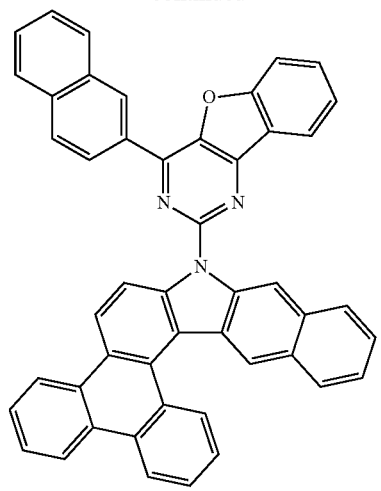
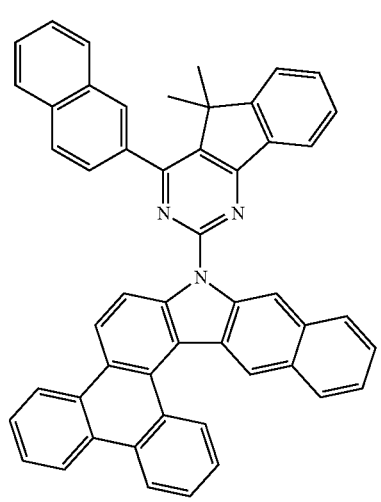
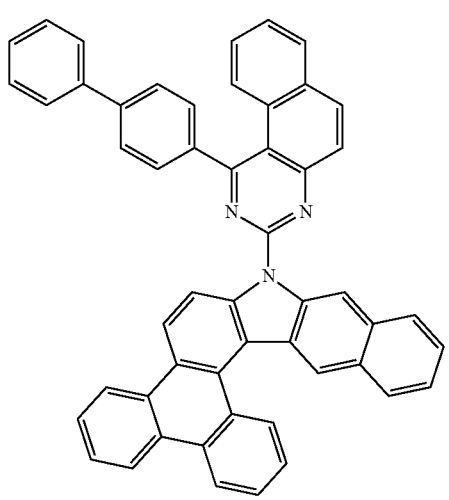

67
-continued
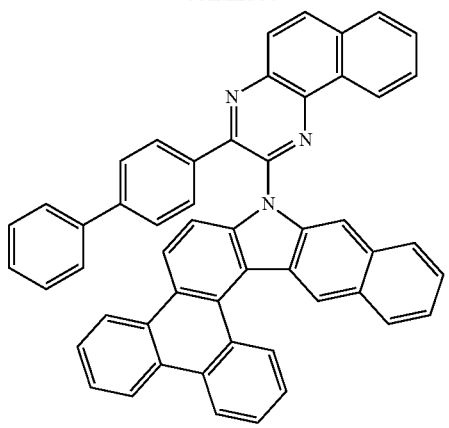
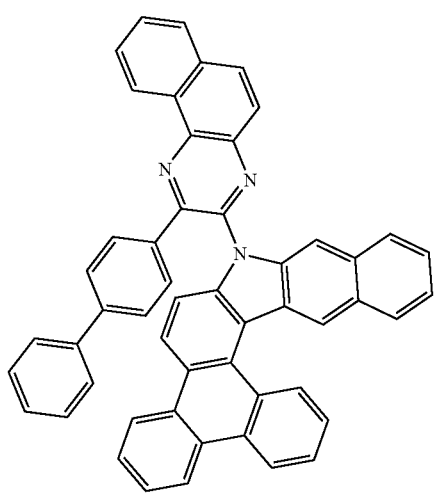
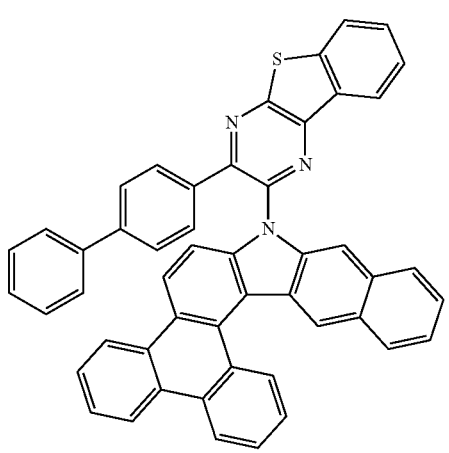
68
-continued
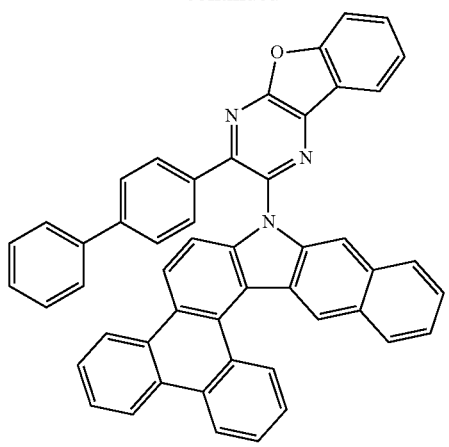
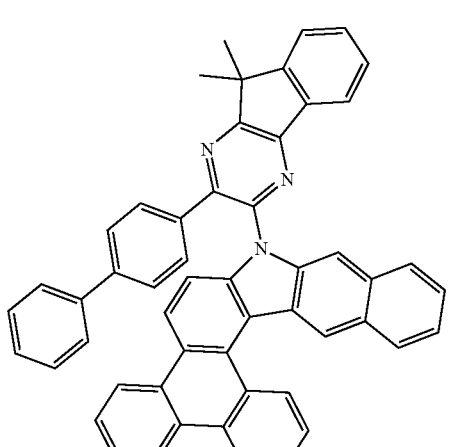
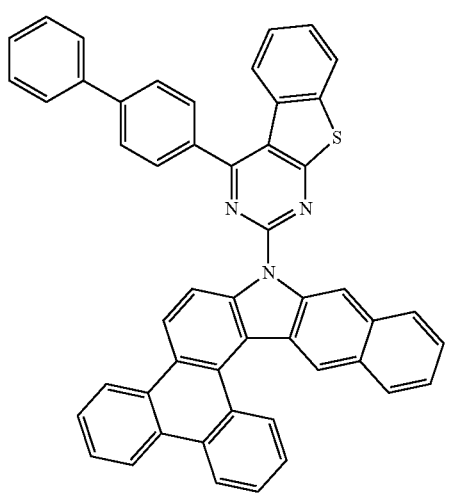

-continued
69
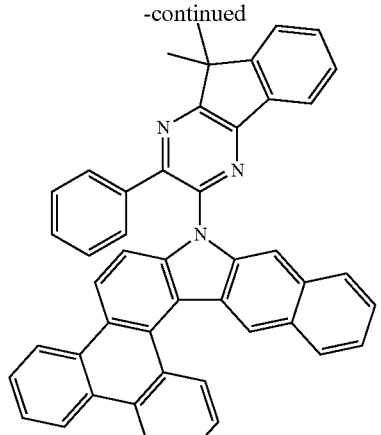
70
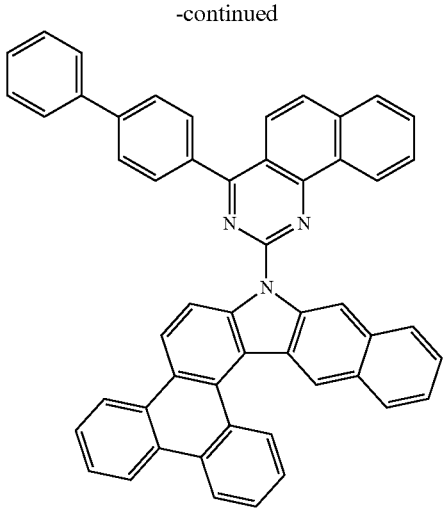
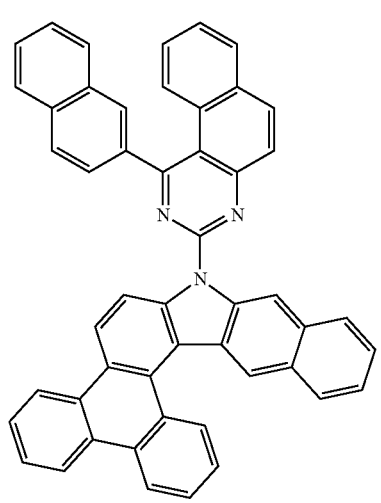
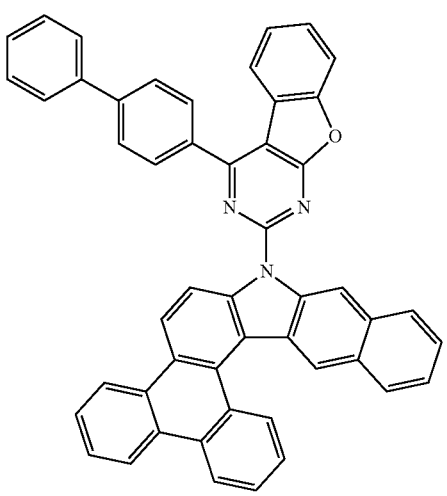
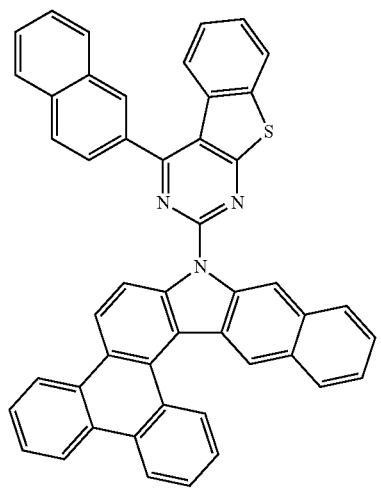
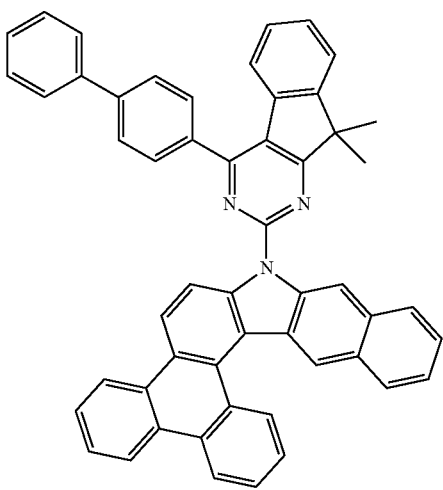

| 71 -continued | 72 -continued |
|---|---|
| 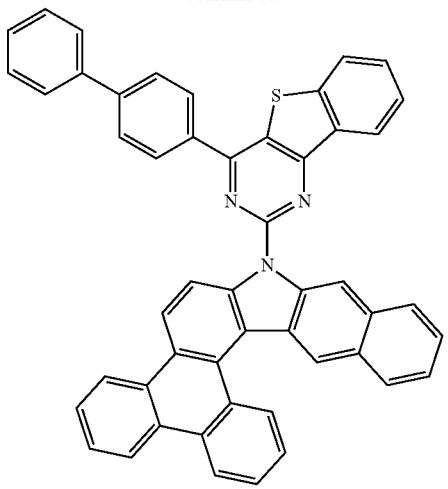 | 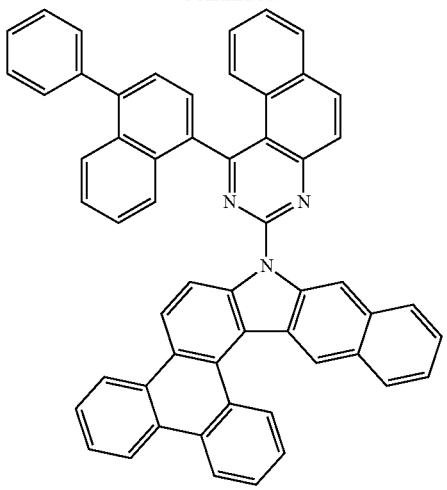 |
| 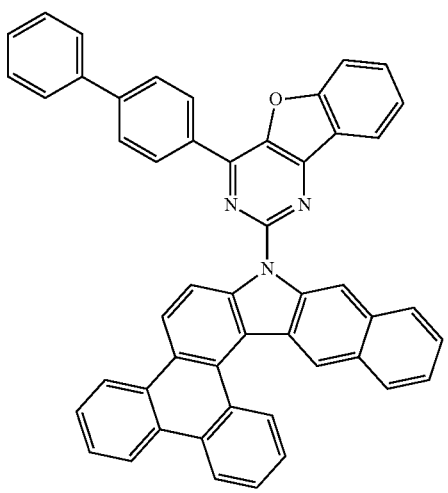 | 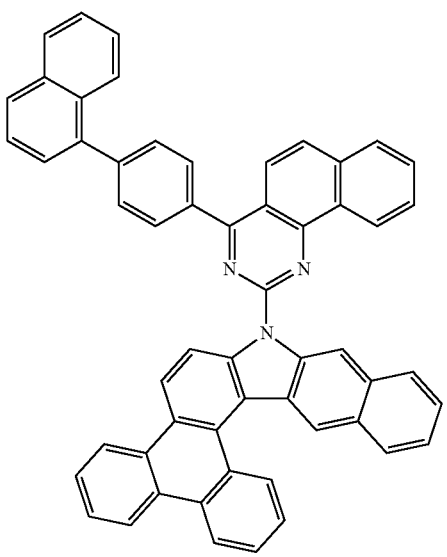 |
| 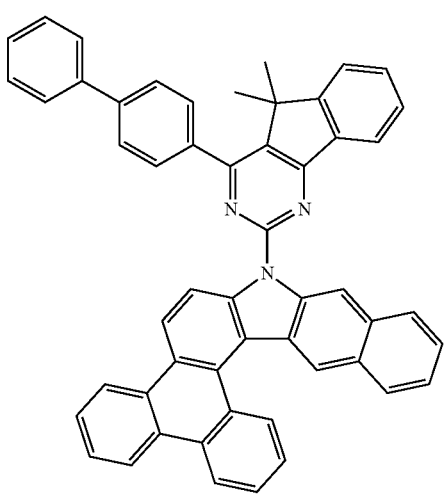 | 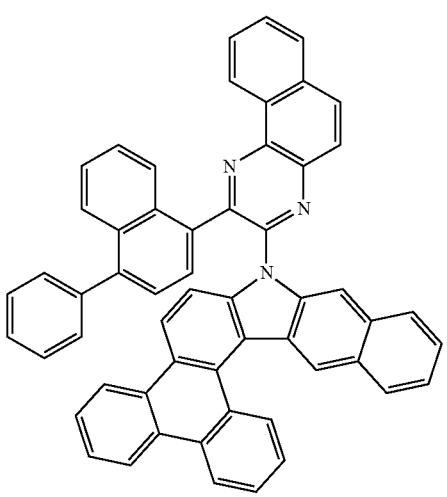 |

-continued
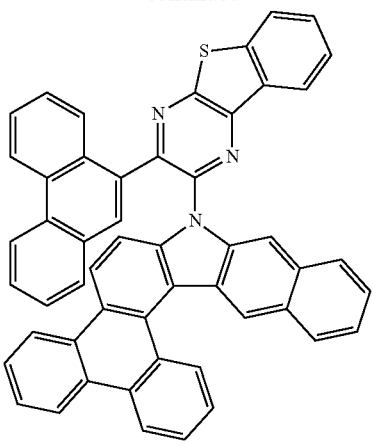
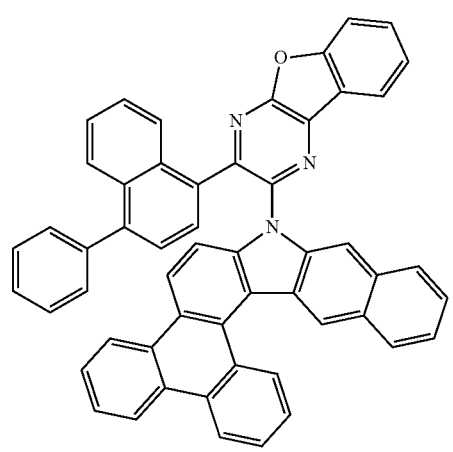
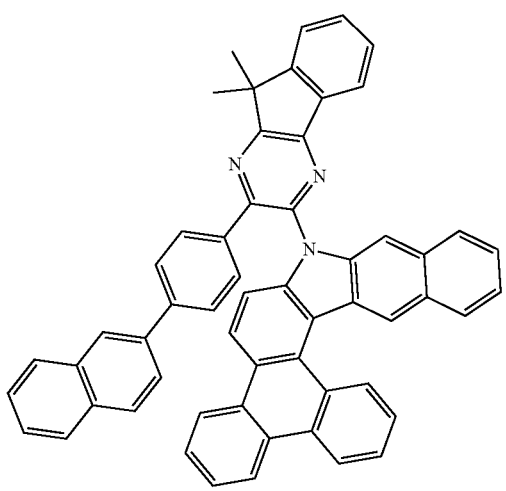
-continued
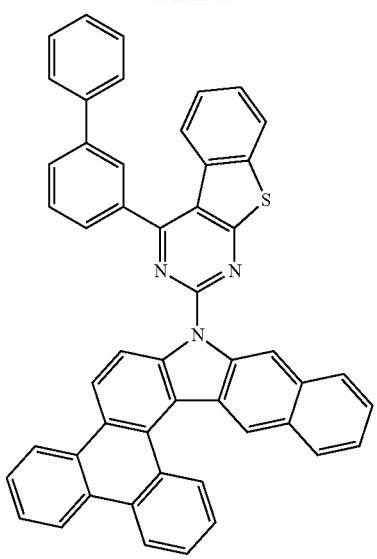
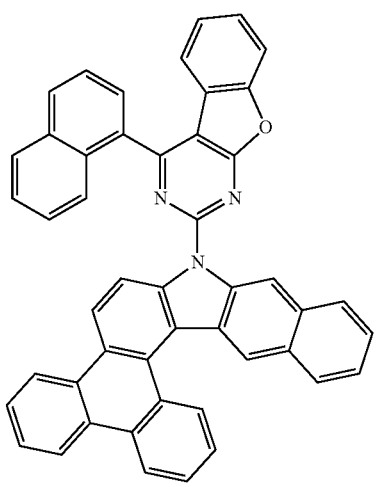
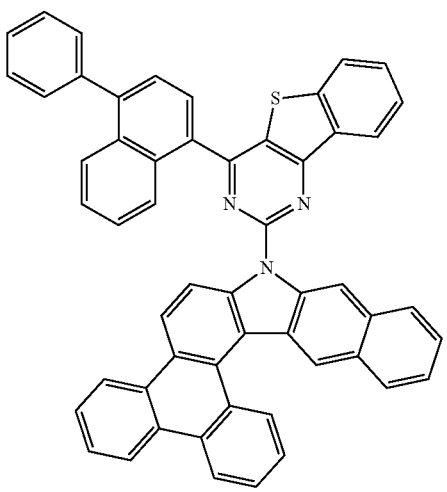

75
-continued
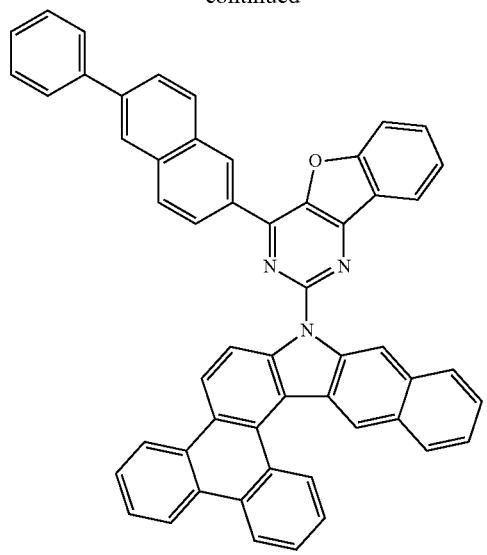
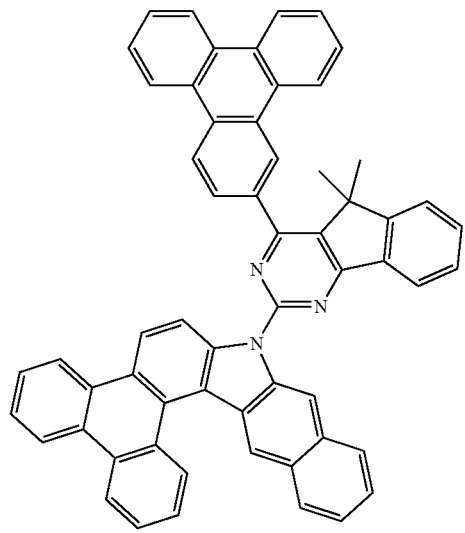
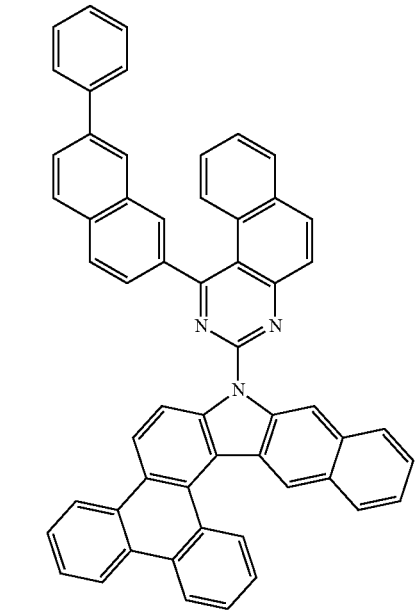
76
-continued
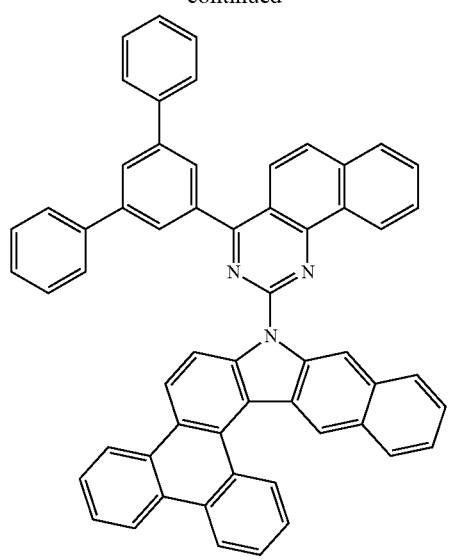
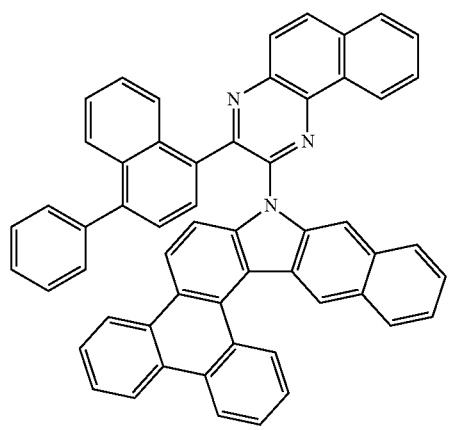
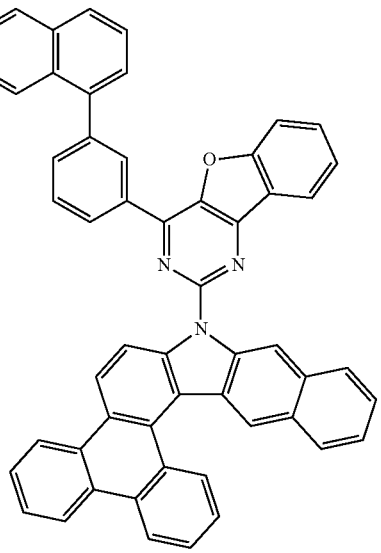

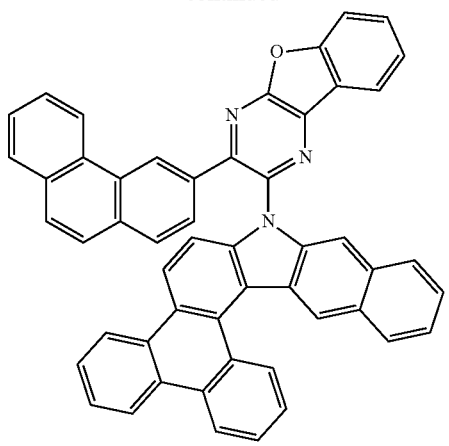
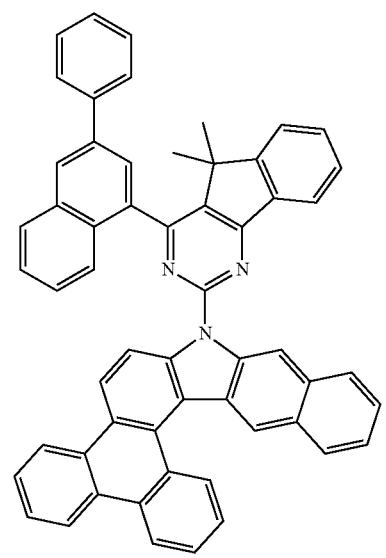
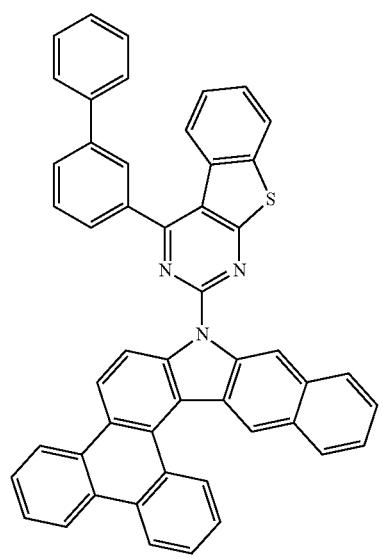
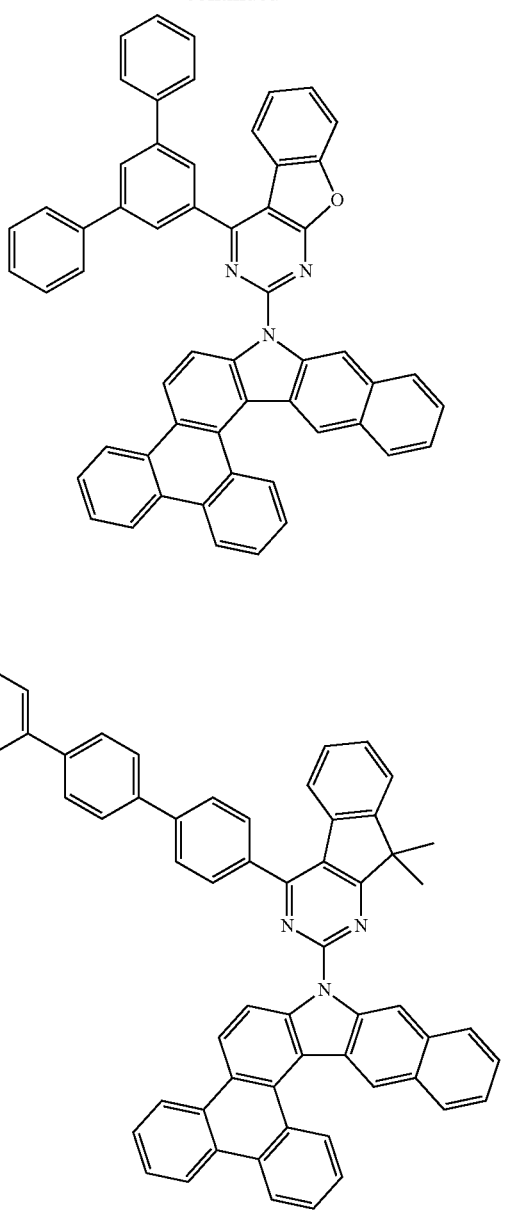
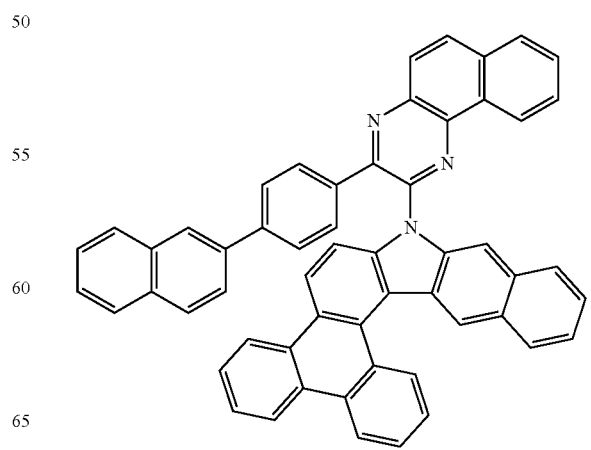

79
-continued
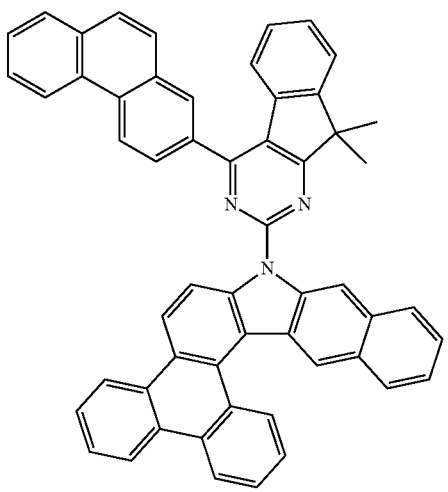
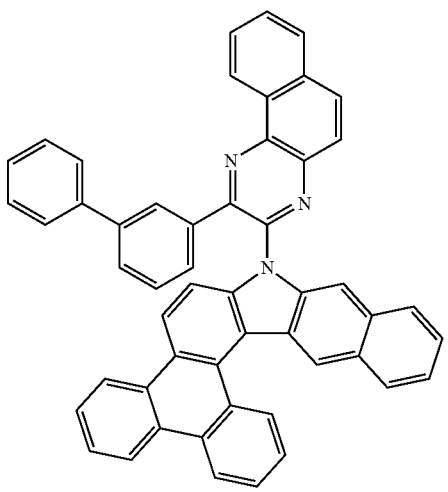
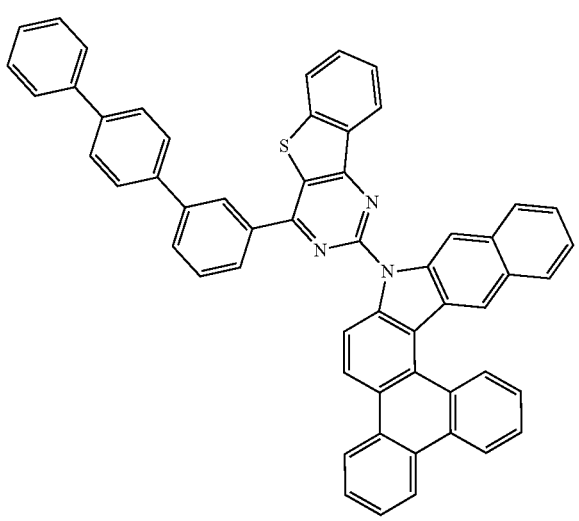
80
-continued
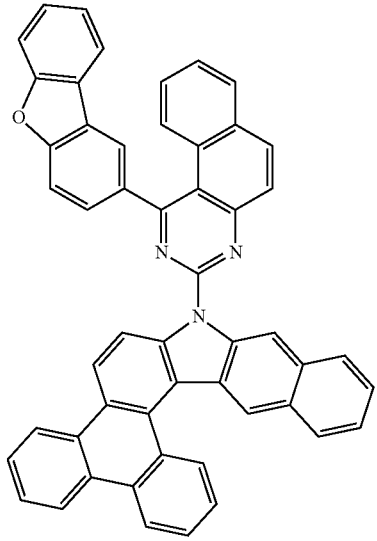
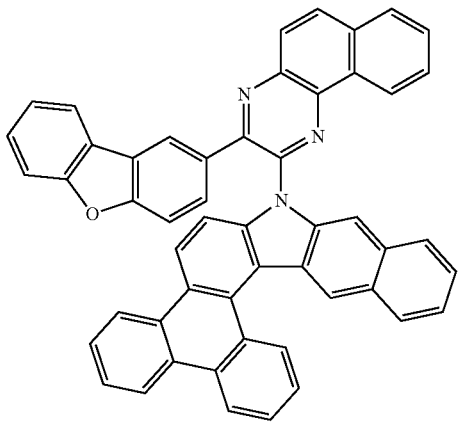

81
-continued
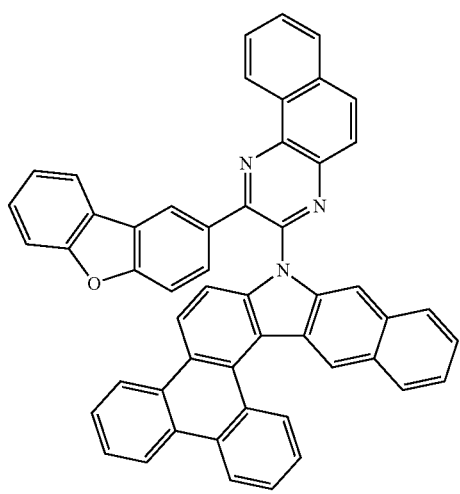
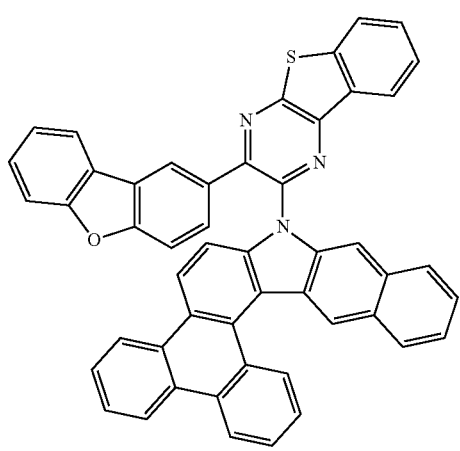
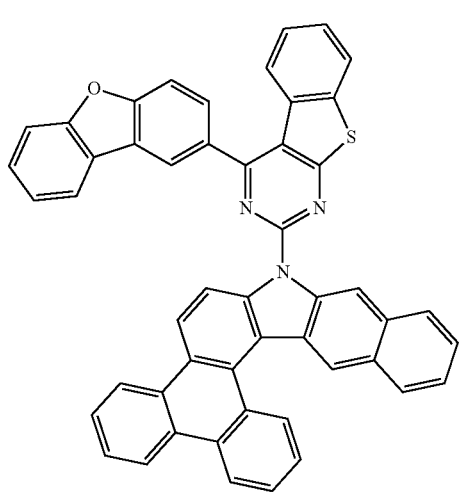
82
-continued
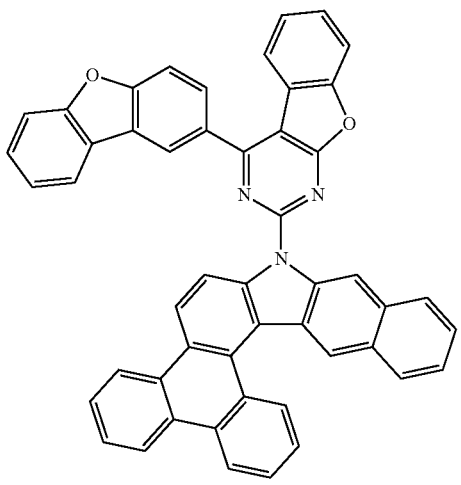
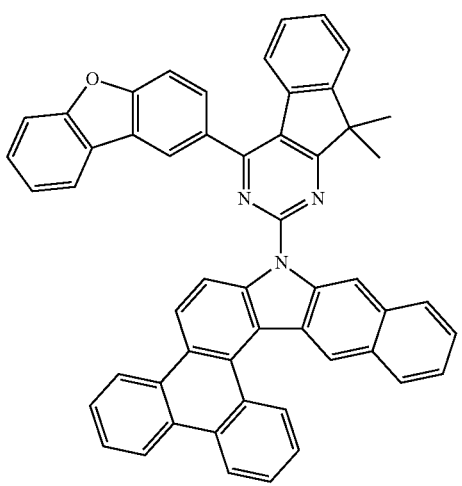
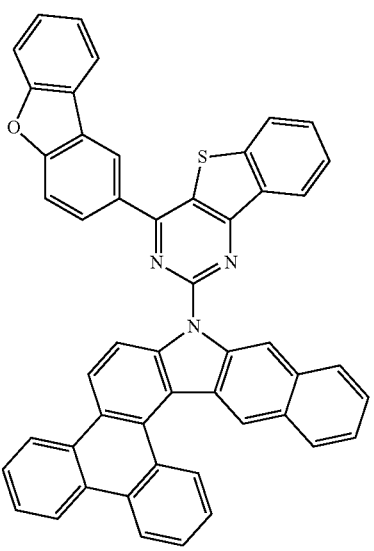

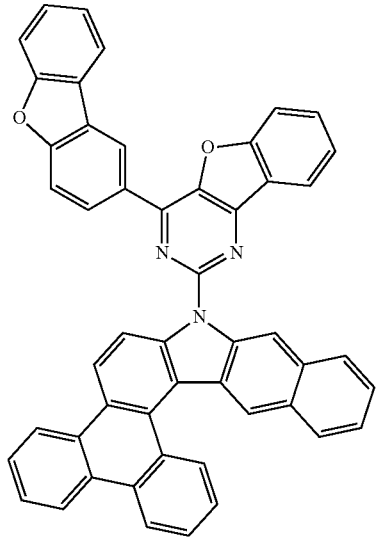
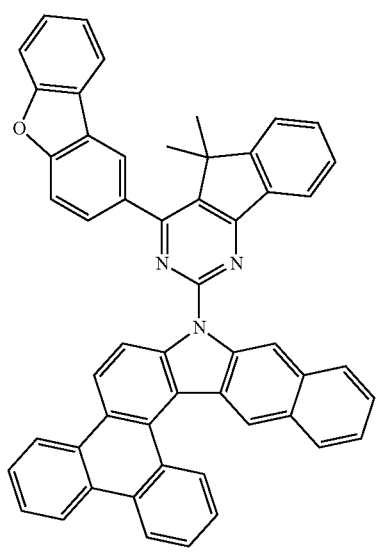
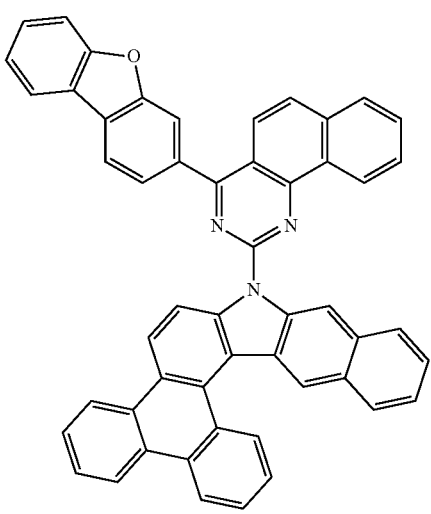
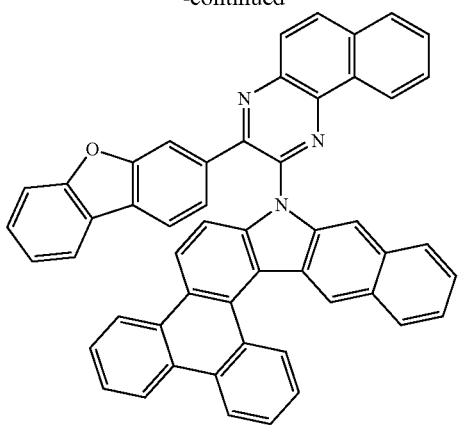
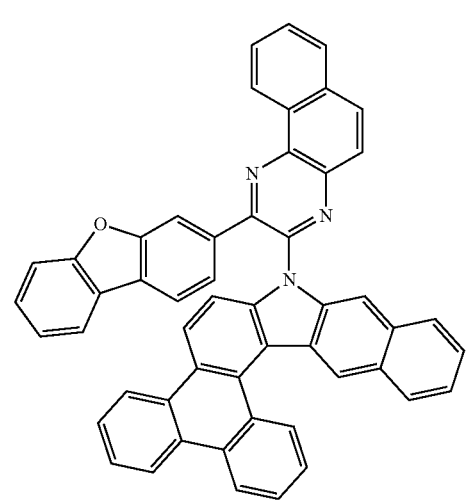
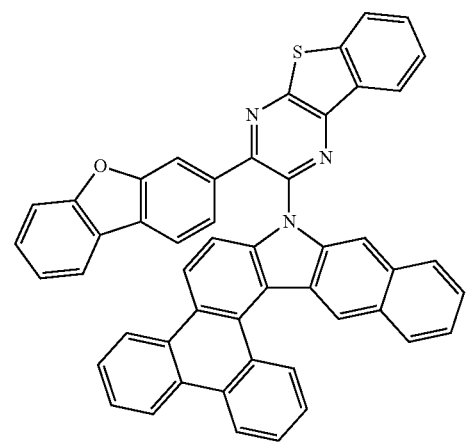

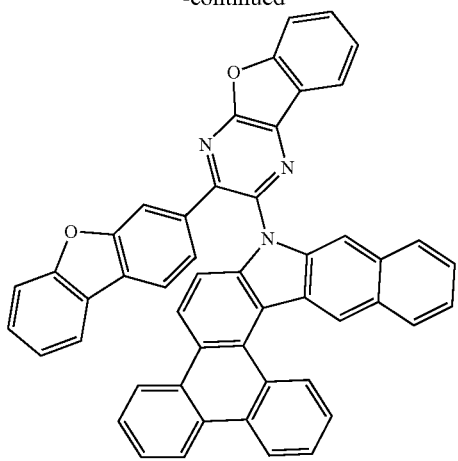
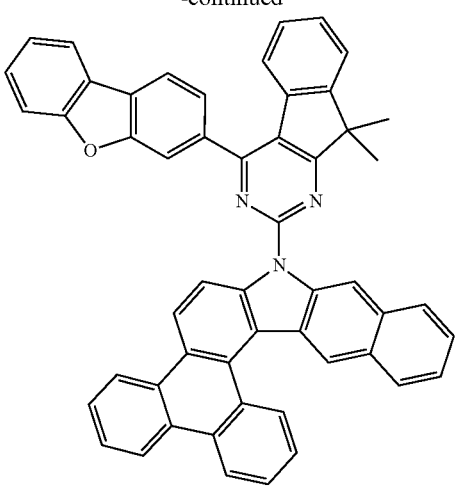
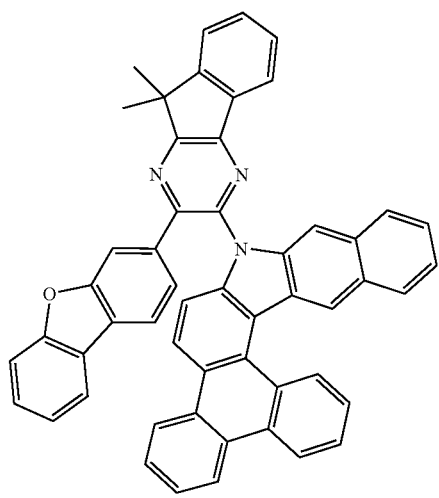
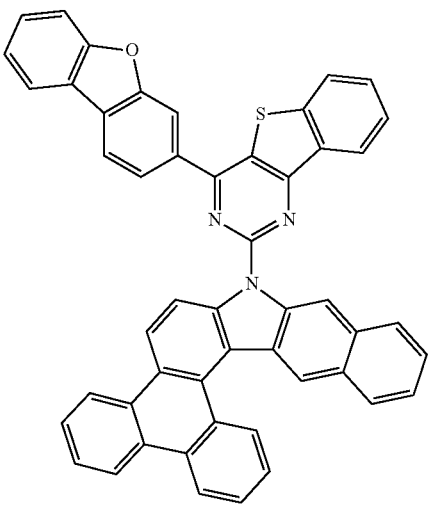
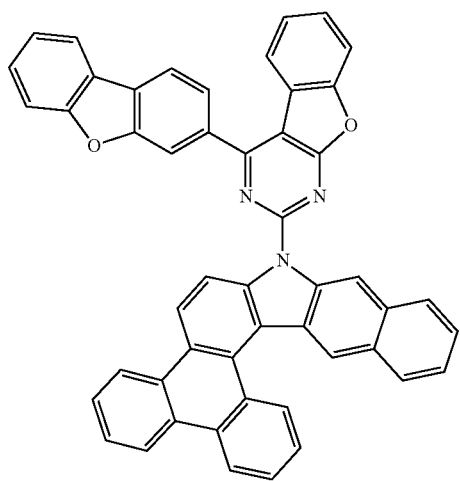
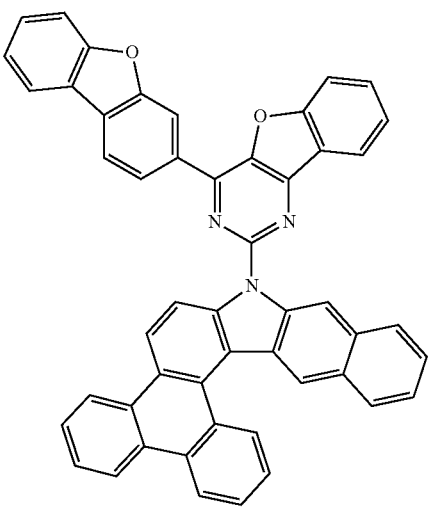

87
-continued
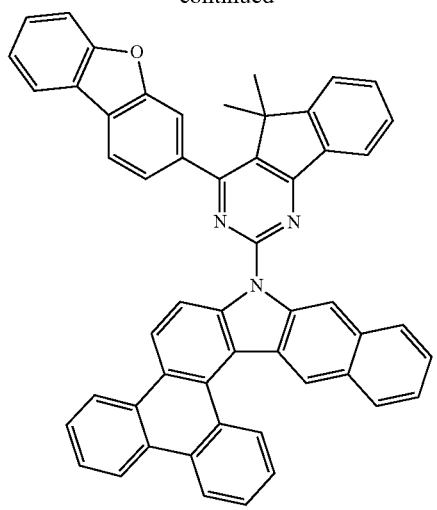
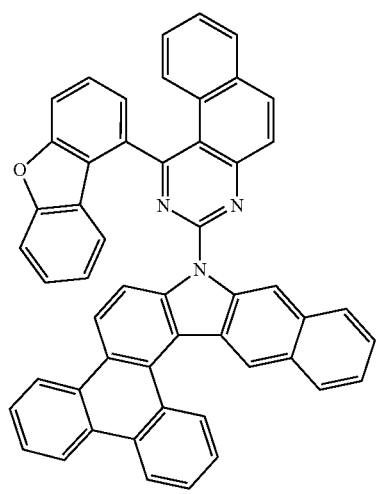
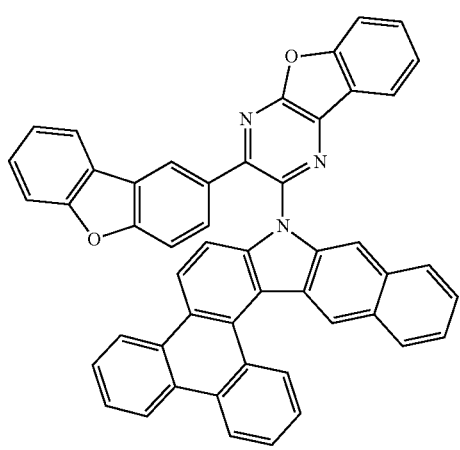
88
-continued
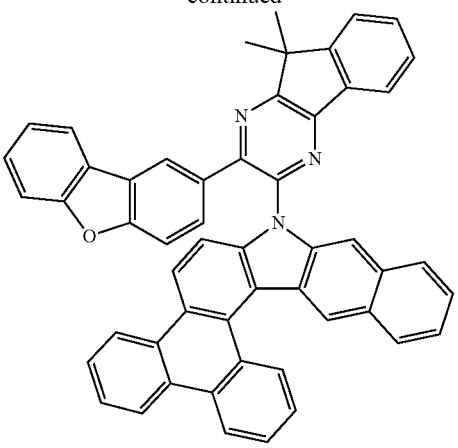
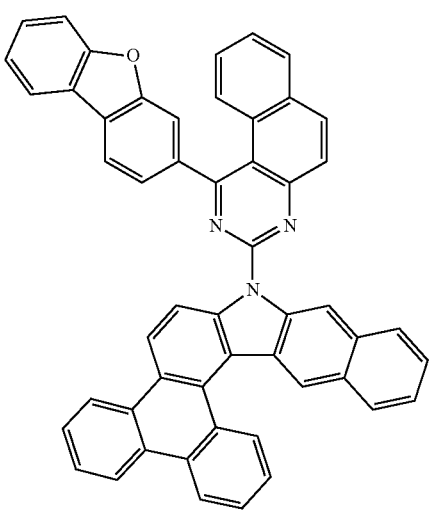
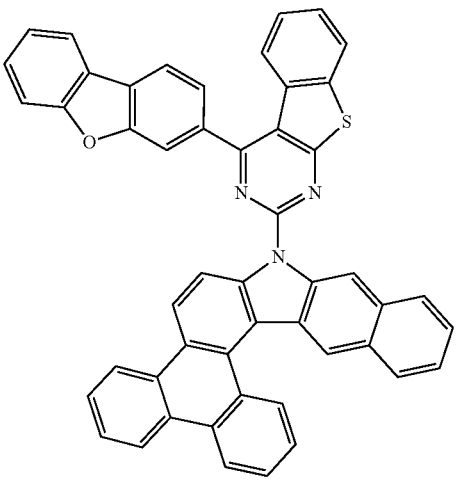

89
-continued
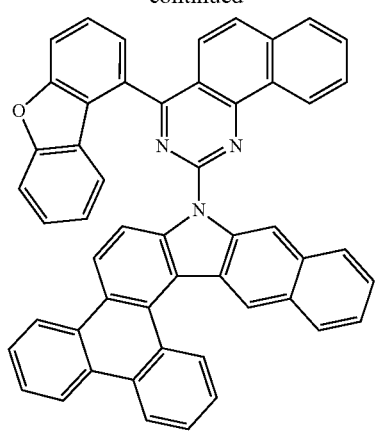
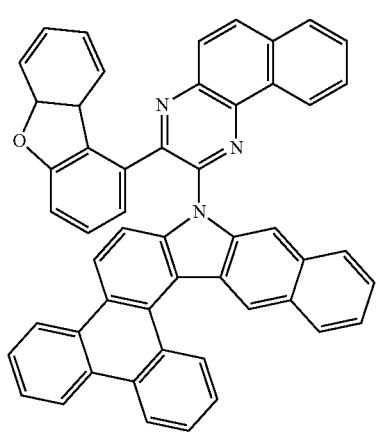
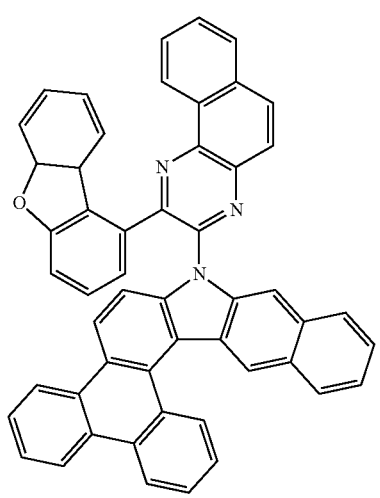
90
-continued
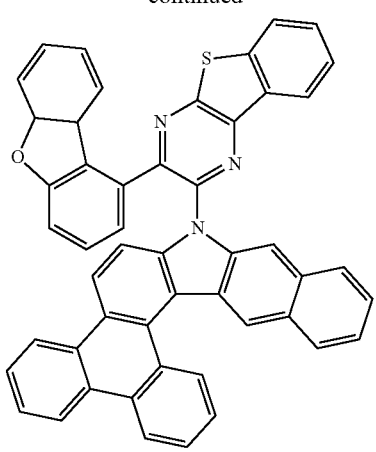
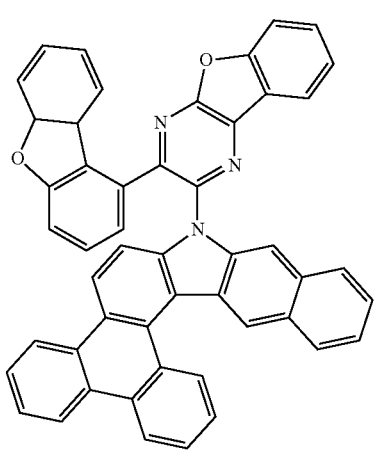
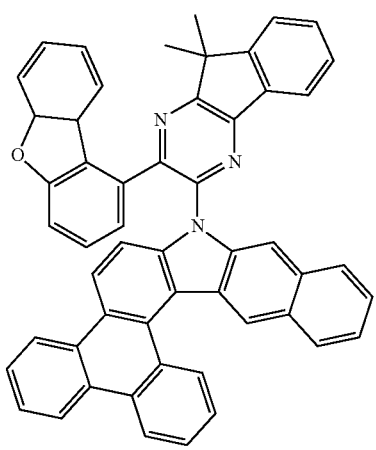

91
-continued
92
-continued
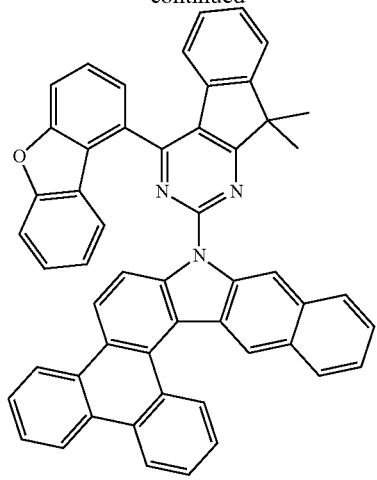
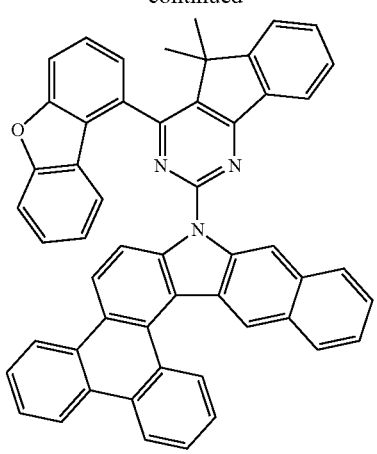
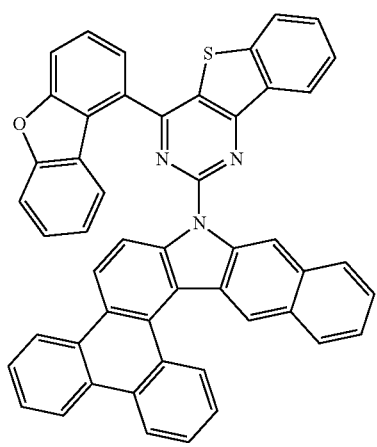
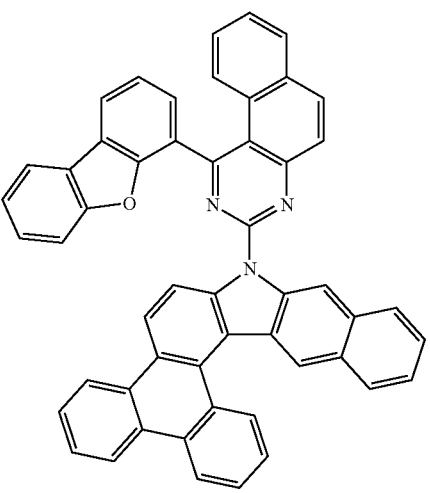
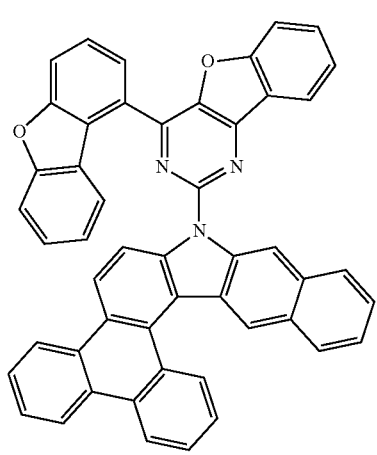
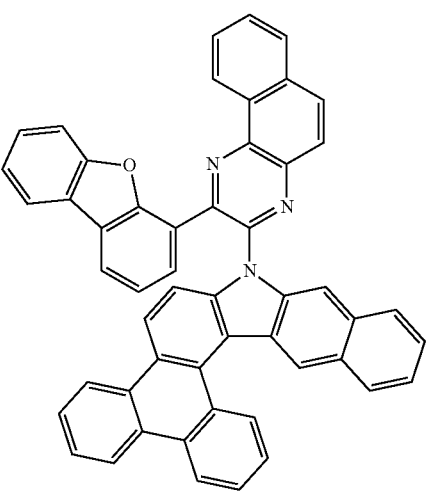

93
-continued
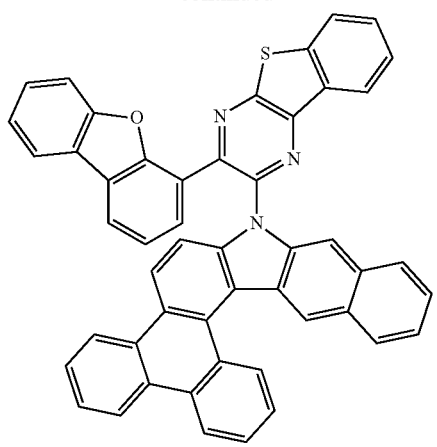
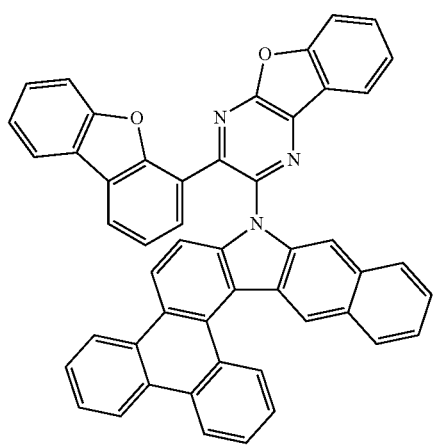
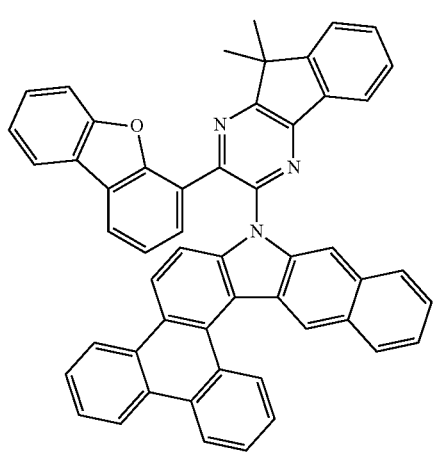
94
-continued
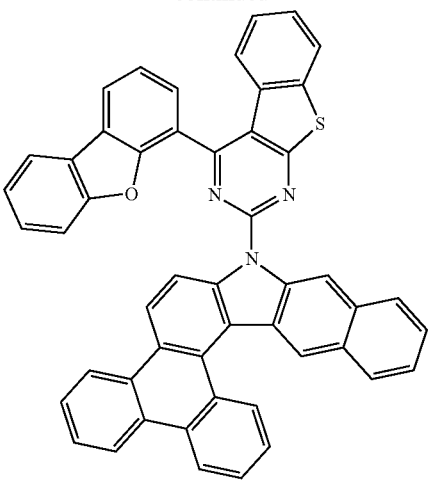
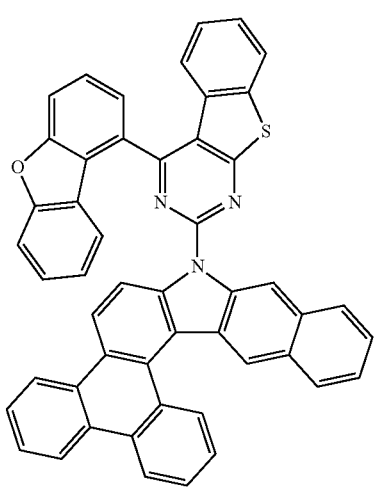
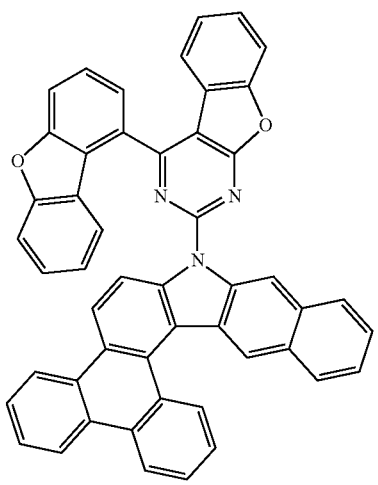

95
-continued
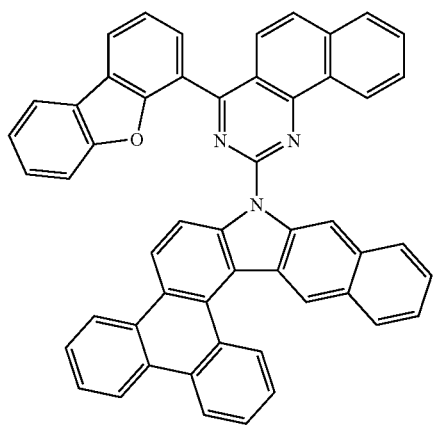
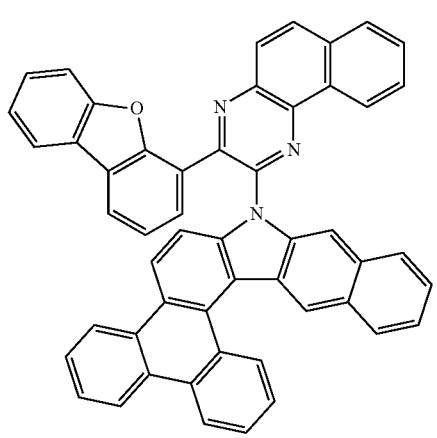
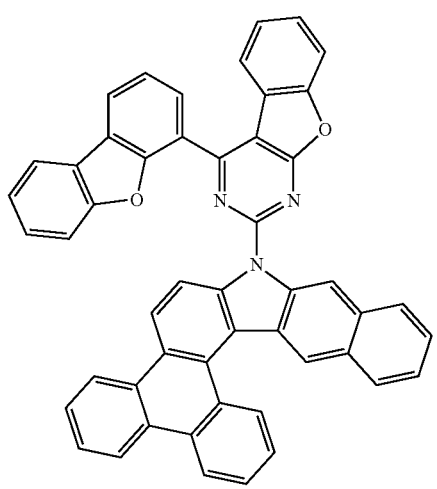
96
-continued
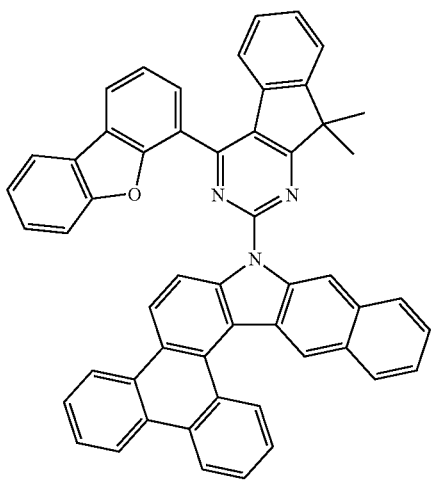
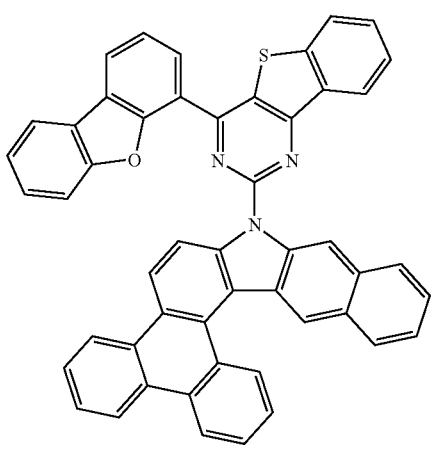
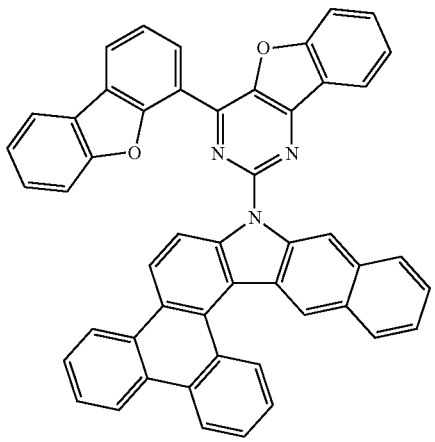

97
-continued
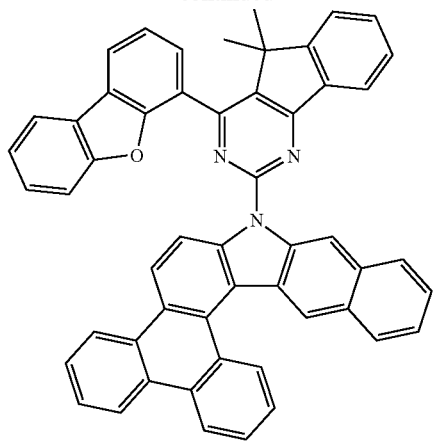
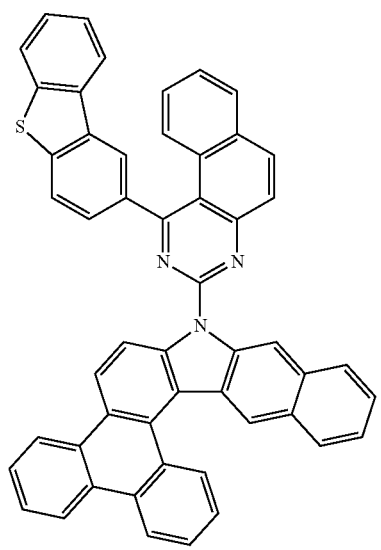
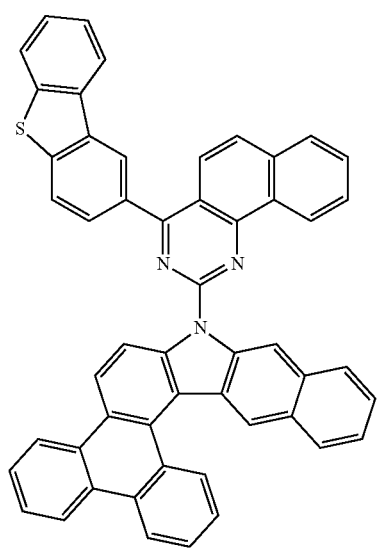
98
-continued
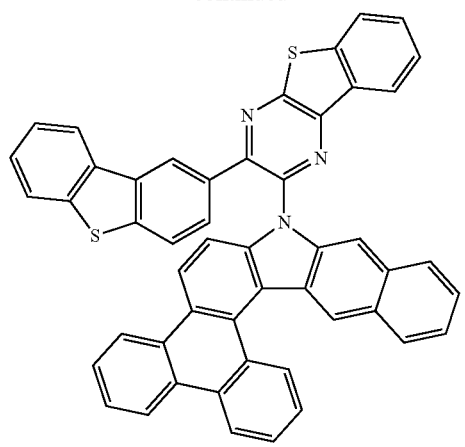
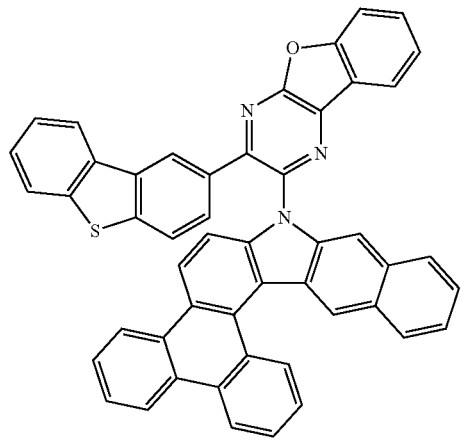
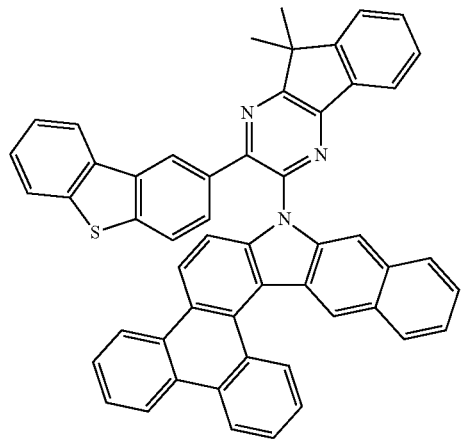

99
-continued
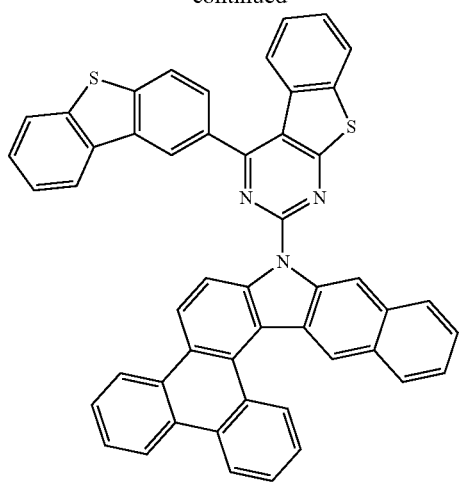
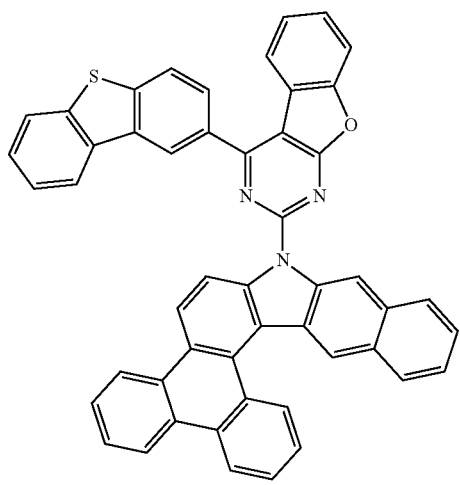
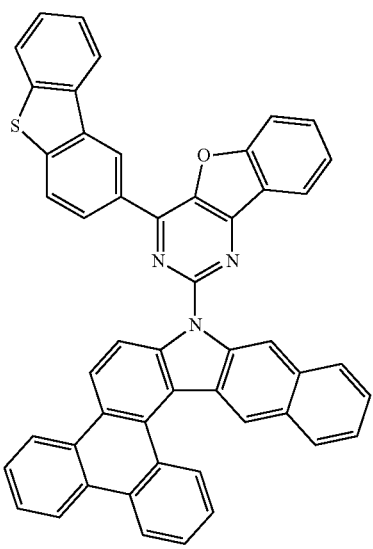
100
-continued
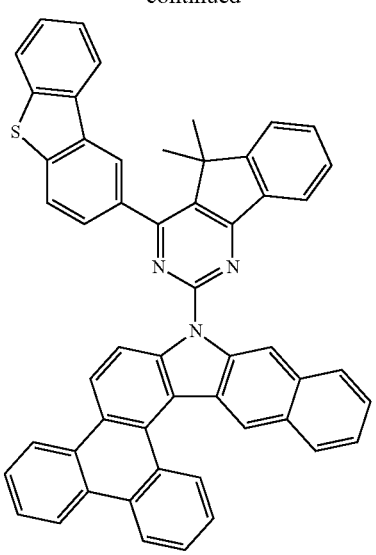
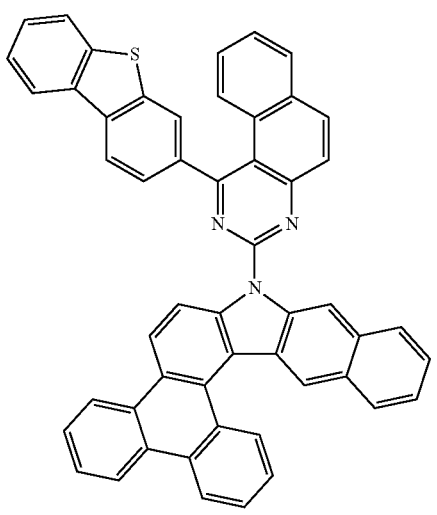
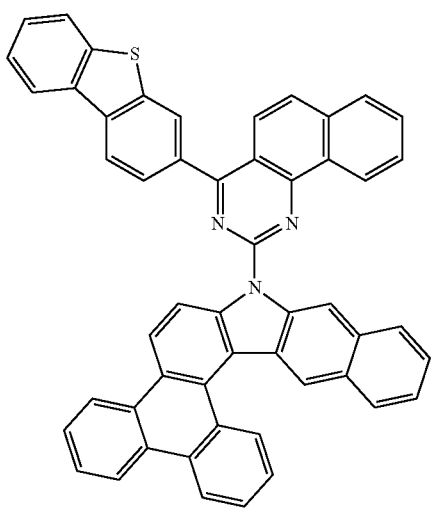

101
-continued
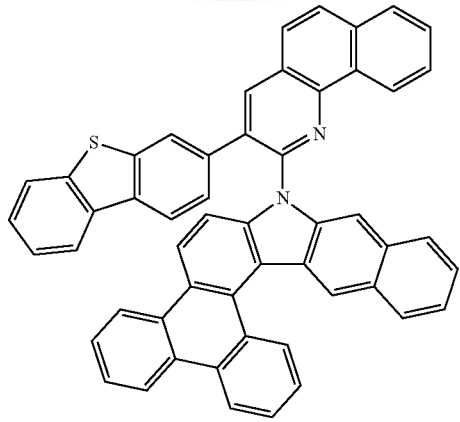
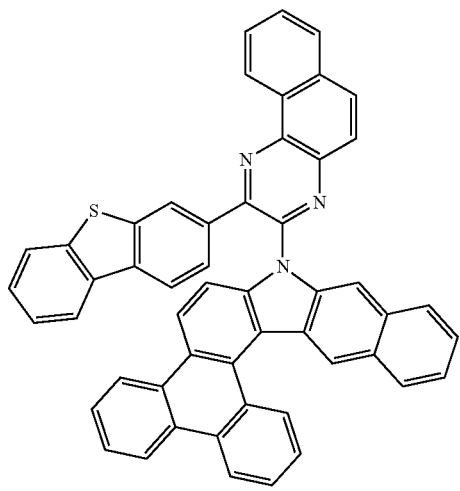
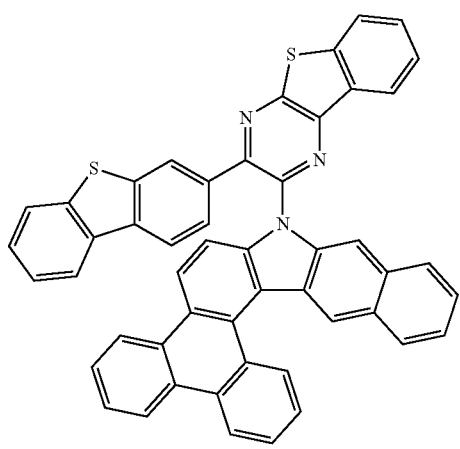
102
-continued
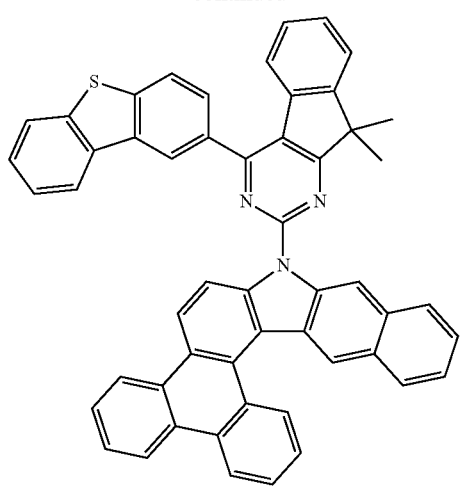
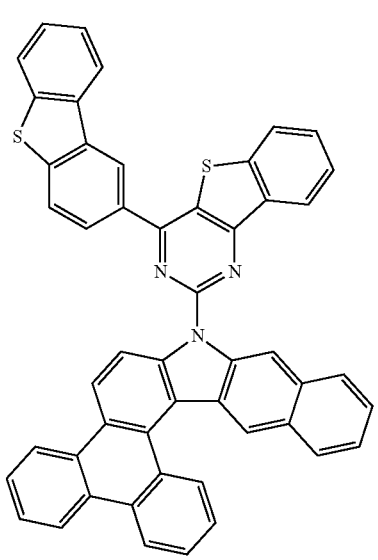
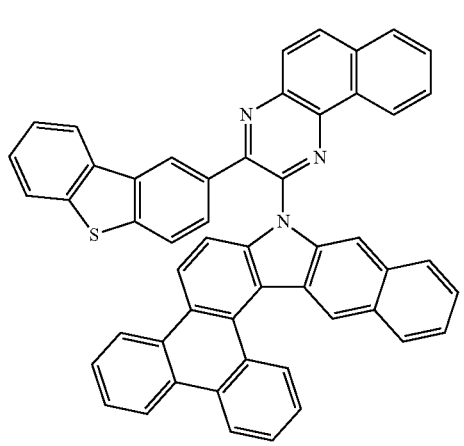

103
-continued
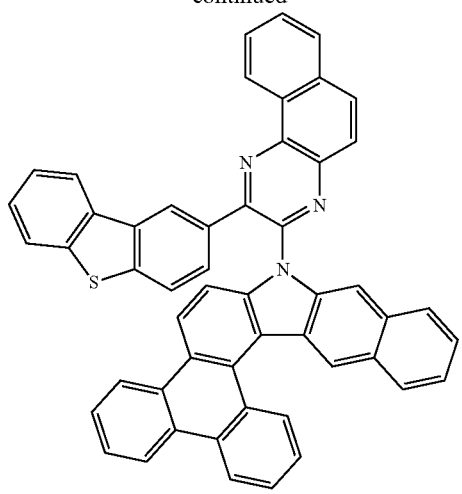
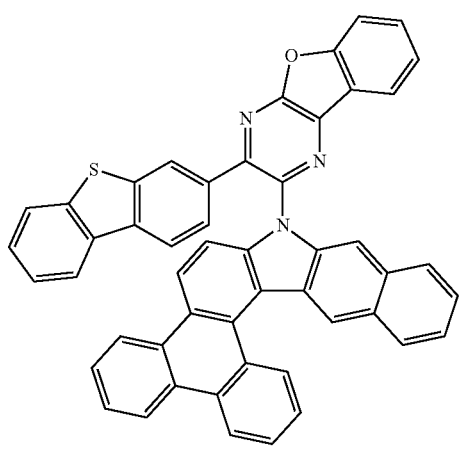
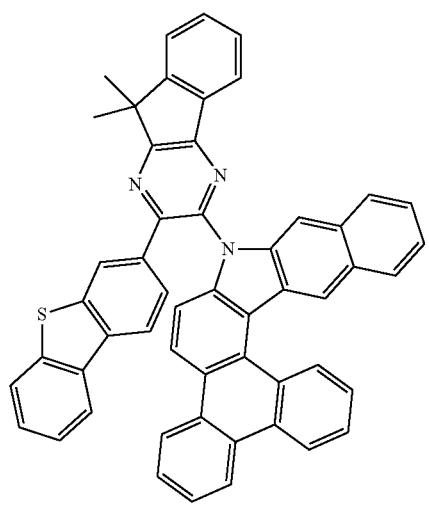
104
-continued
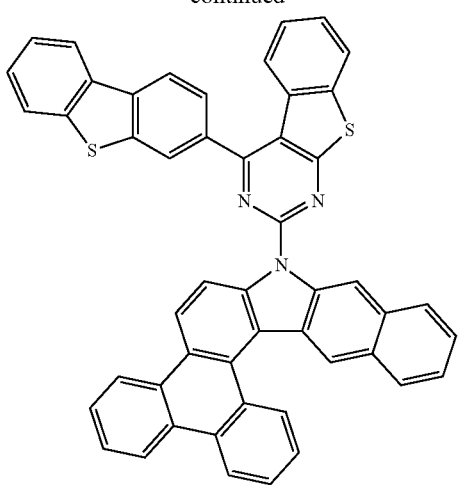
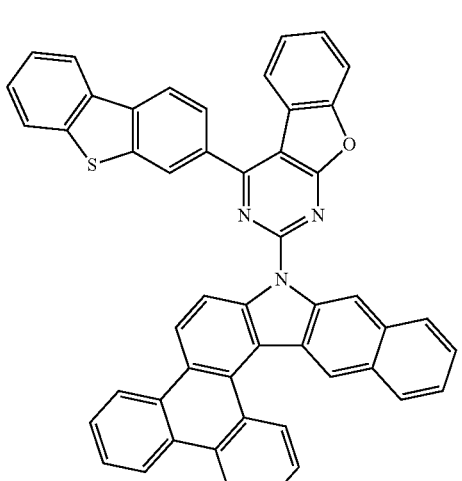
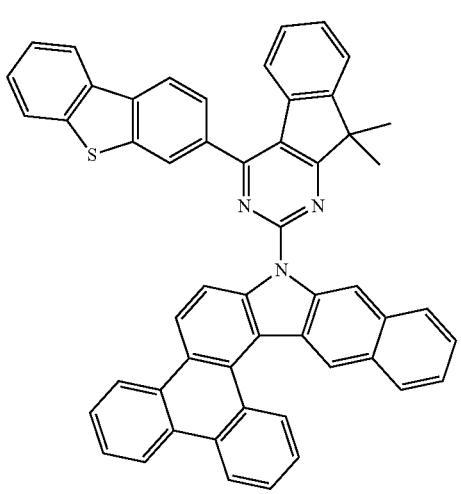

105
-continued
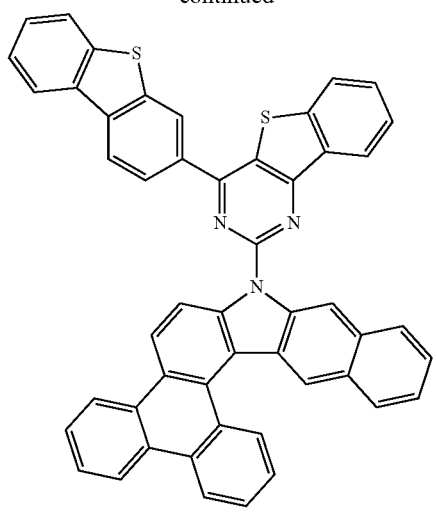
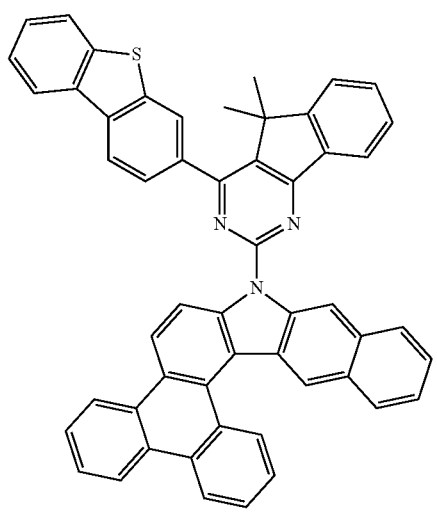
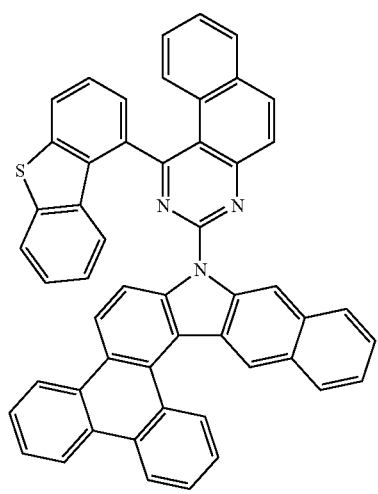
106
-continued
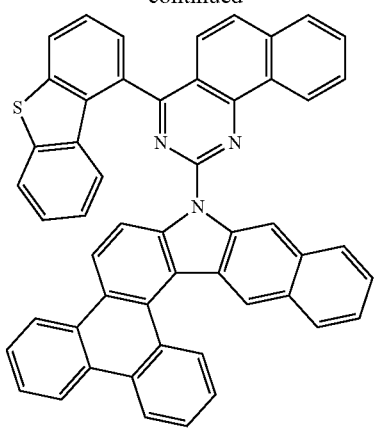
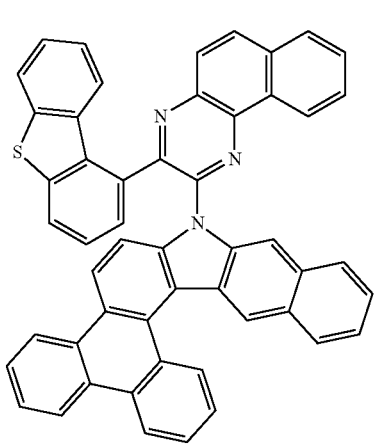
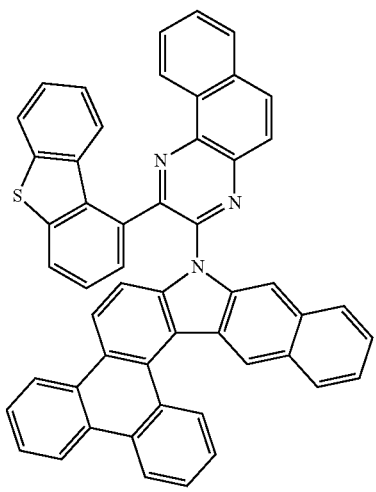

107
-continued
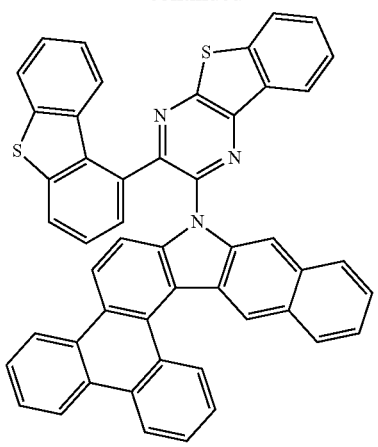
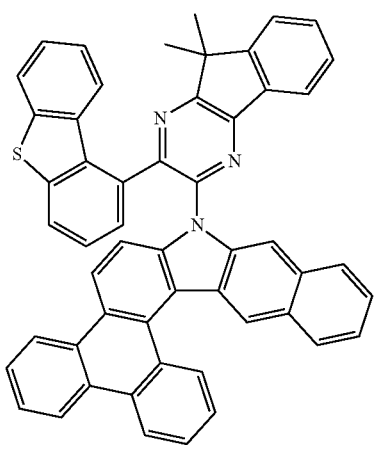
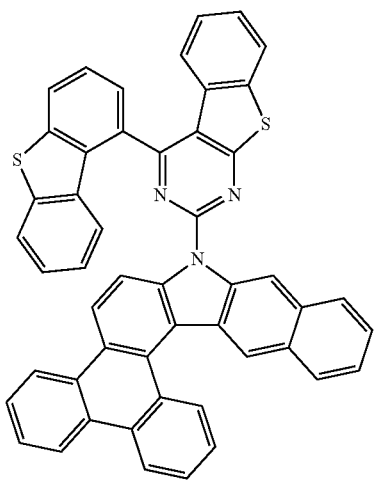
108
-continued
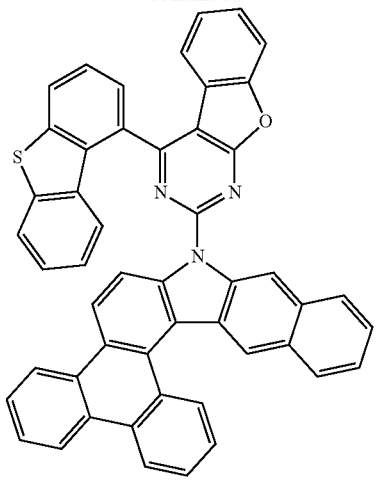
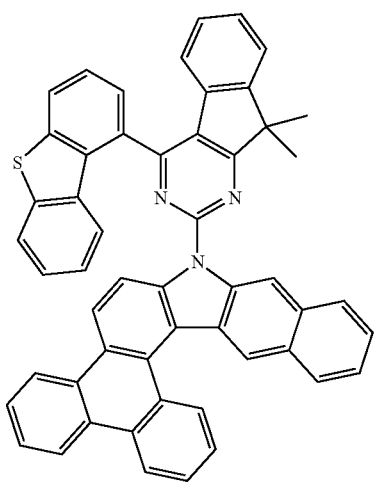
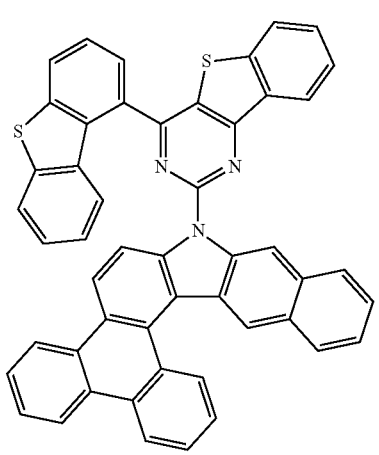

109
-continued
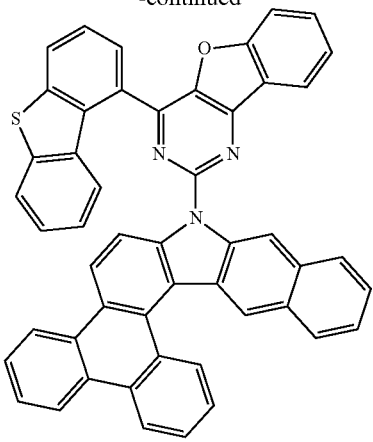
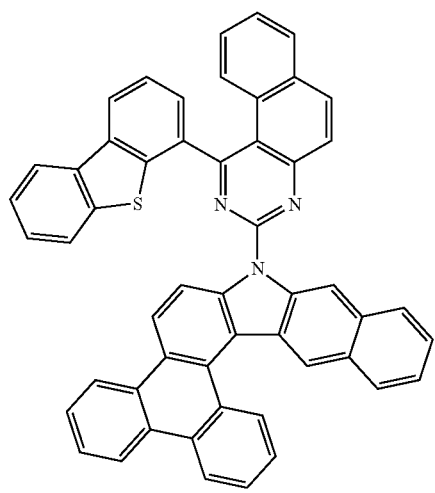
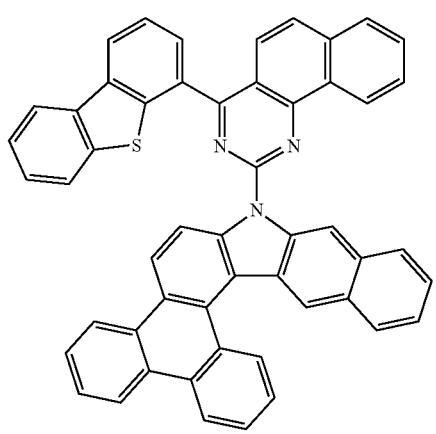
110
-continued
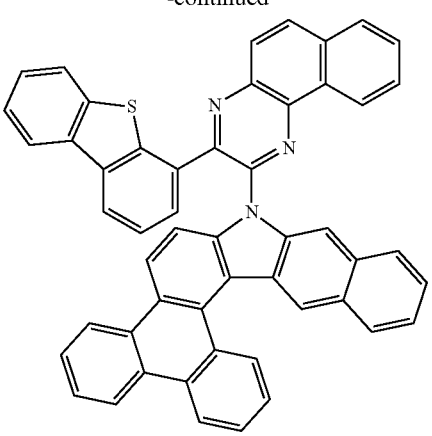
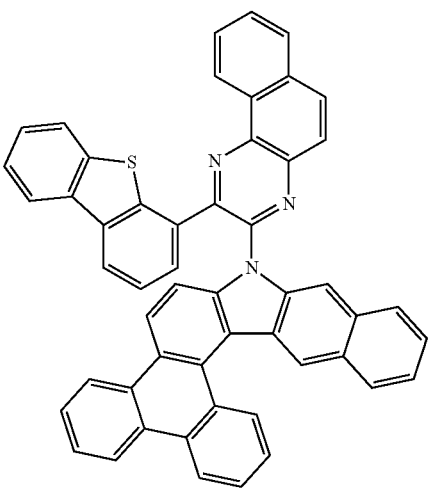
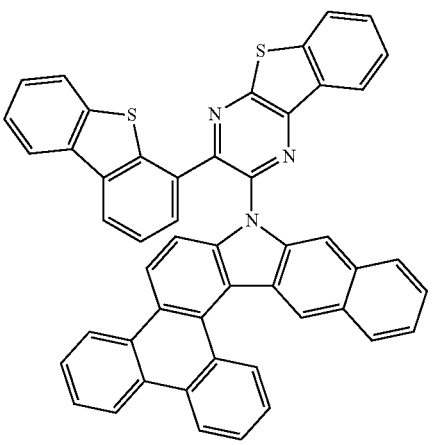

111
-continued
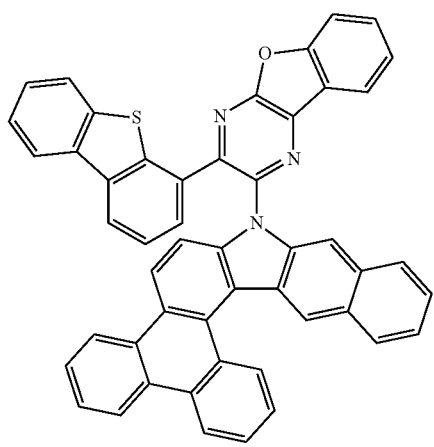
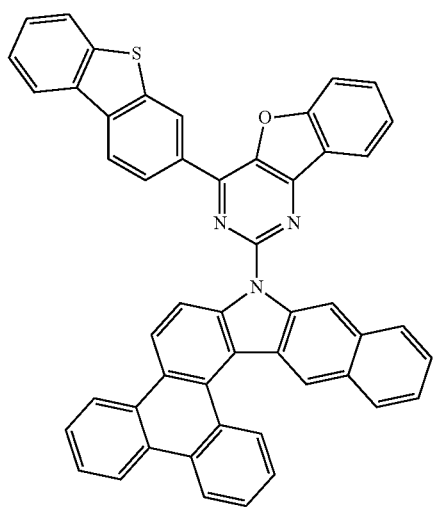
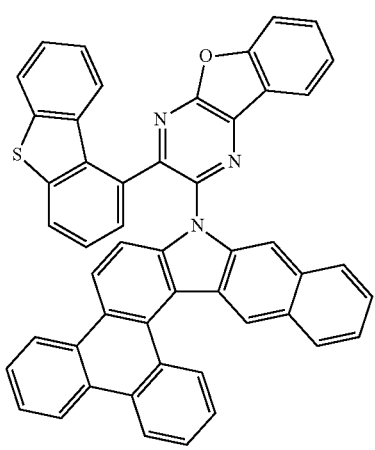
112
-continued

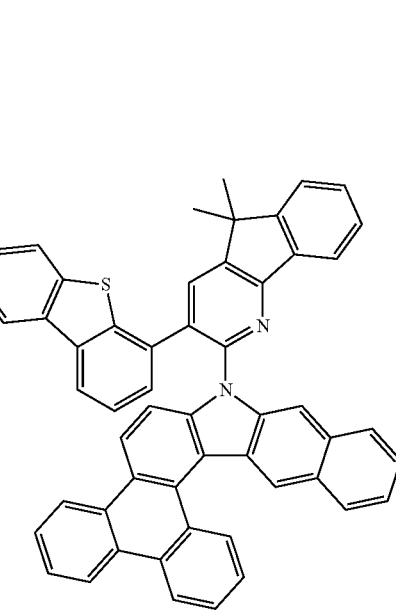
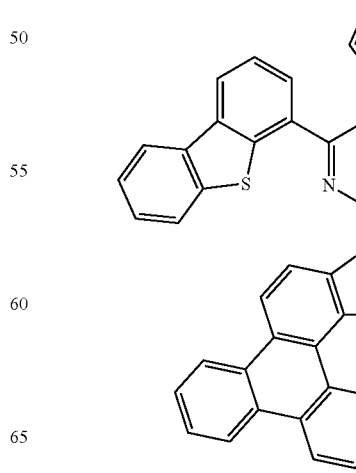

113
-continued
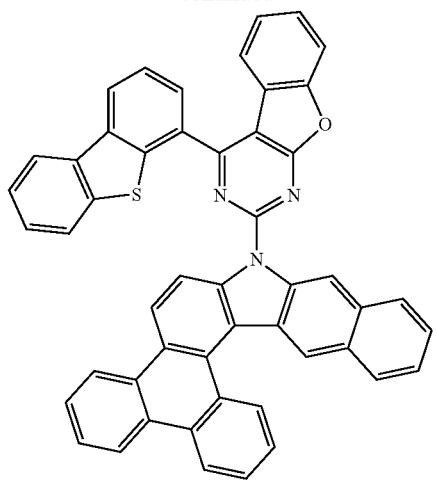
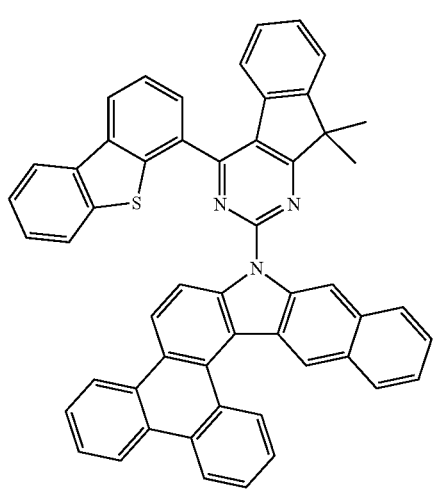
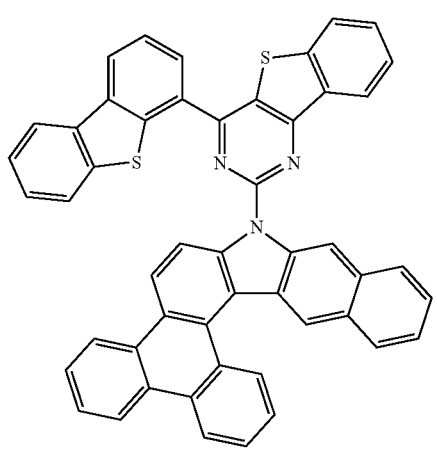
114
-continued
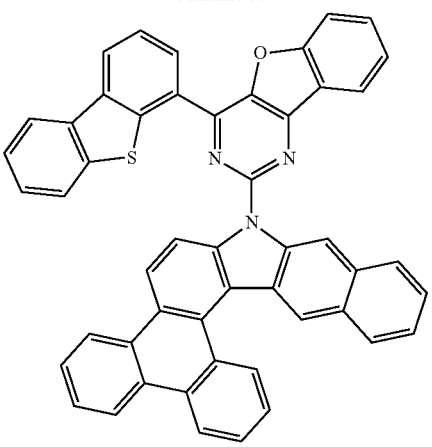
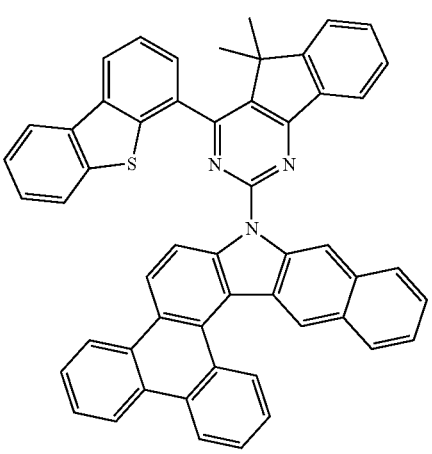
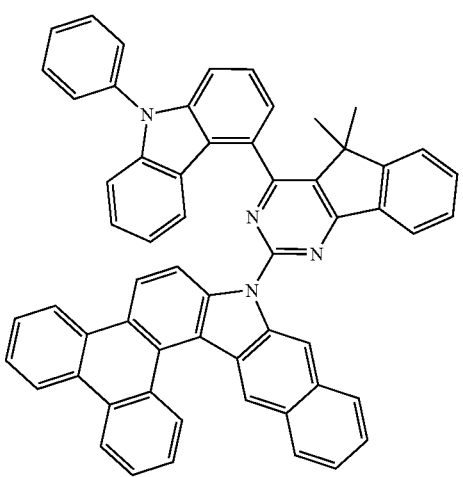

115
-continued
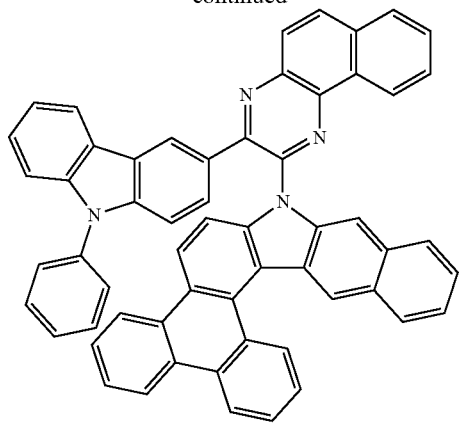
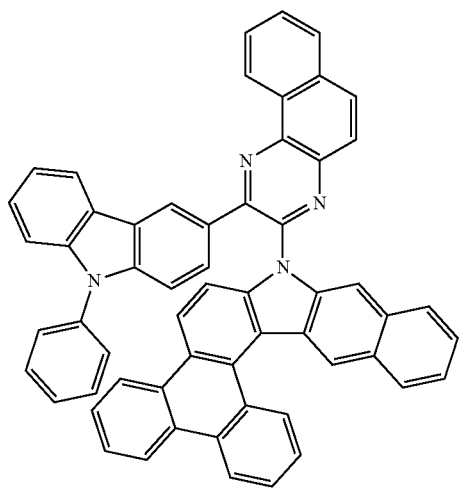
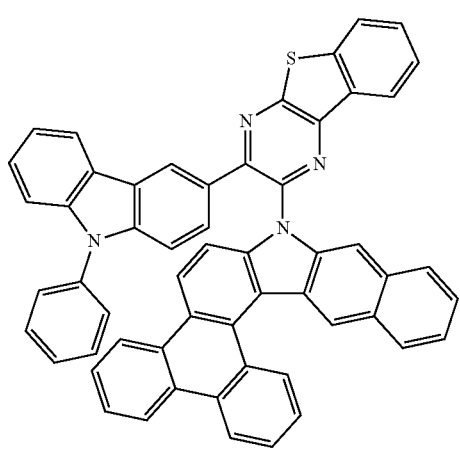
116
-continued
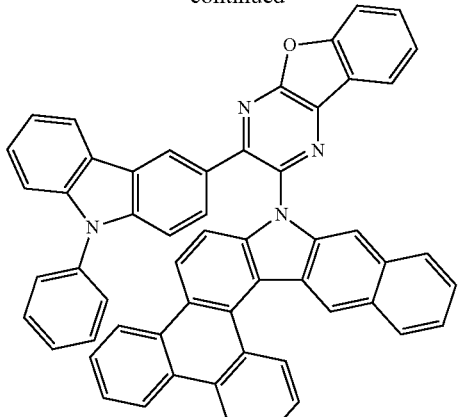
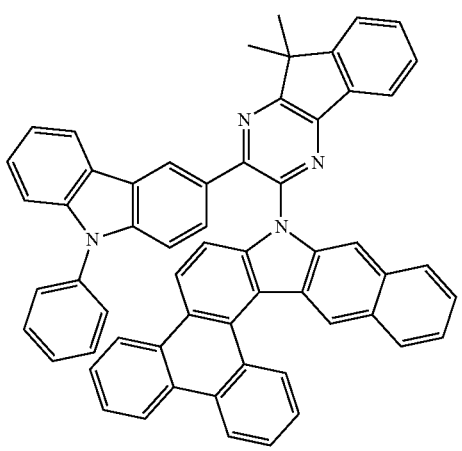
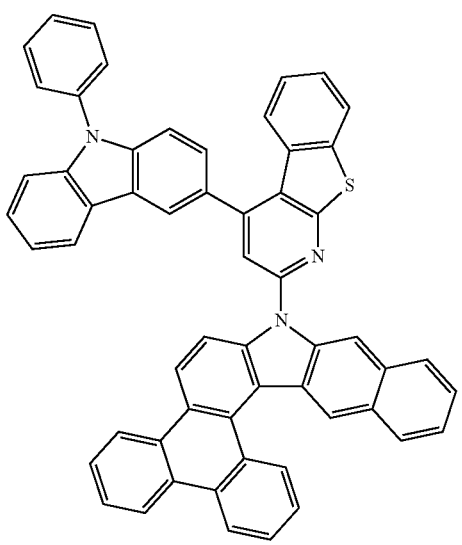

117
-continued
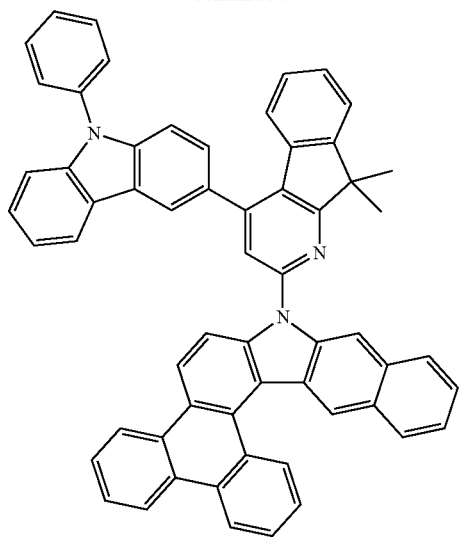
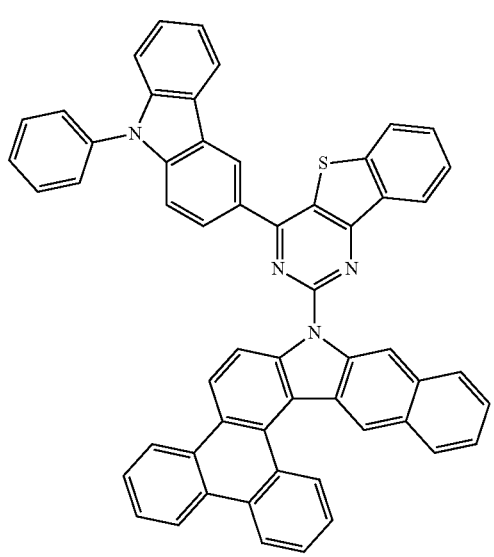
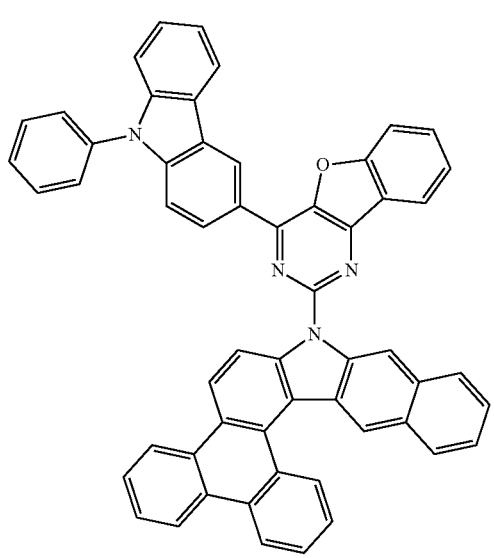
118
-continued
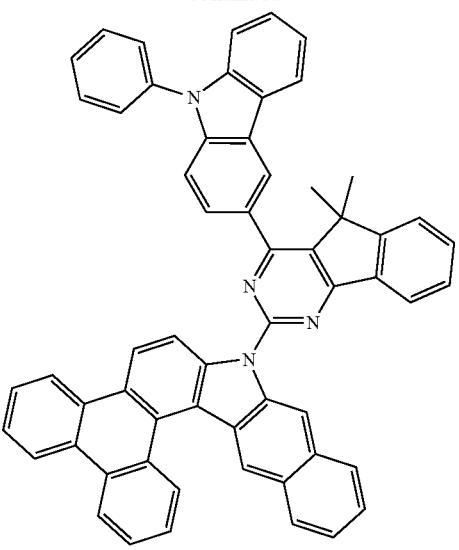
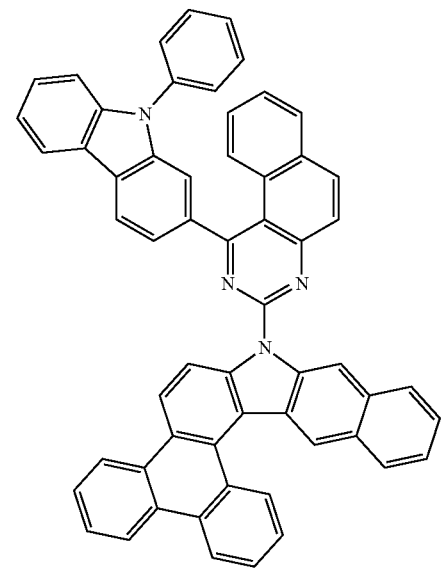
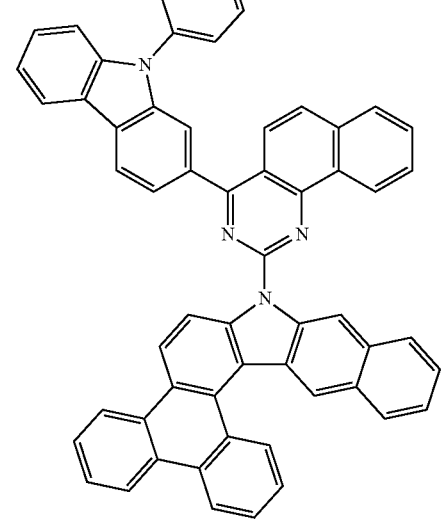

119
-continued
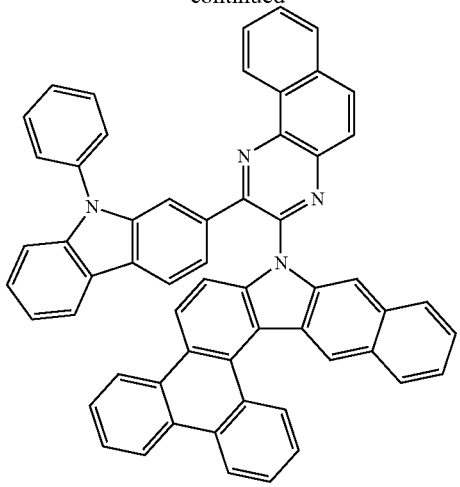
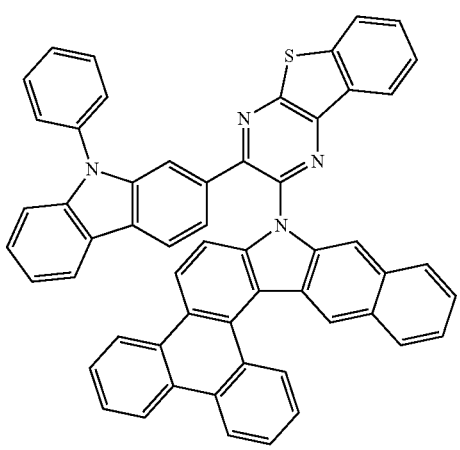
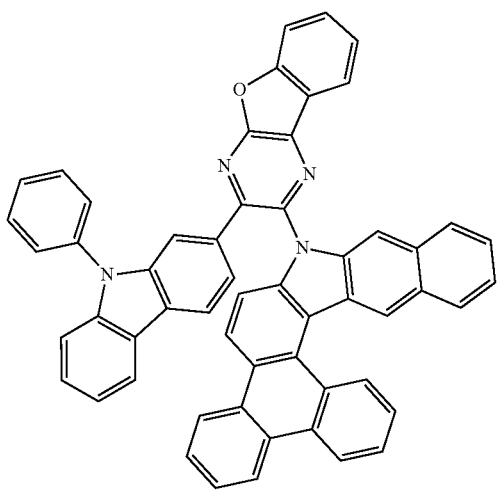
120
-continued
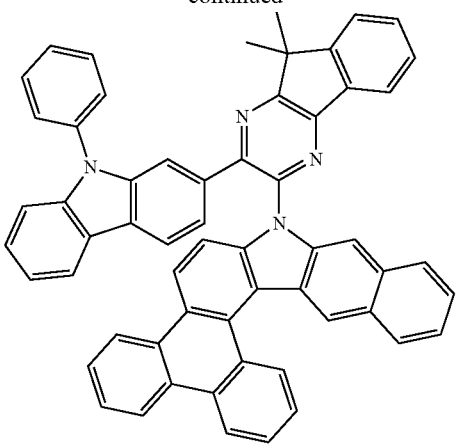
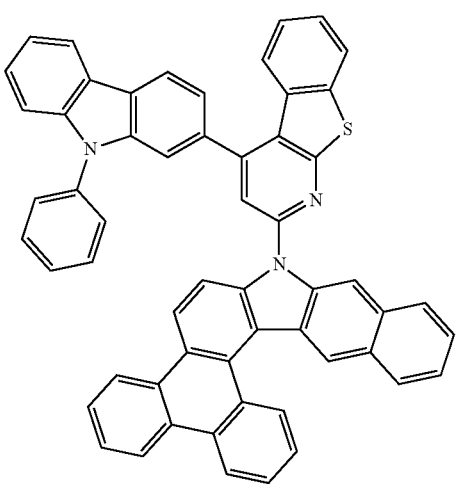
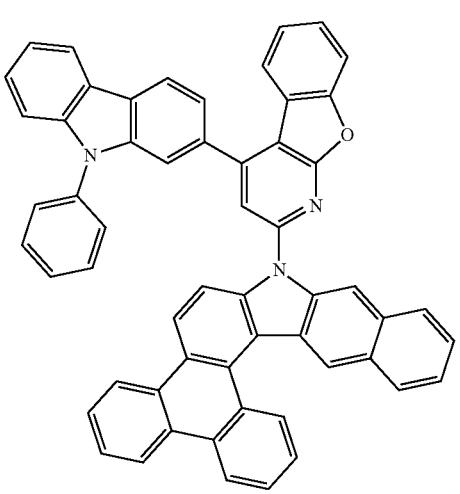

121
-continued
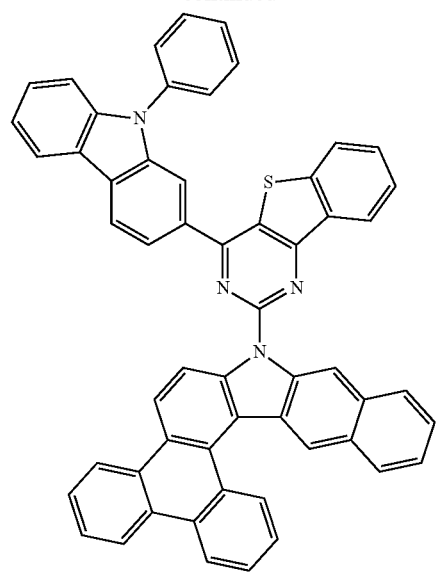
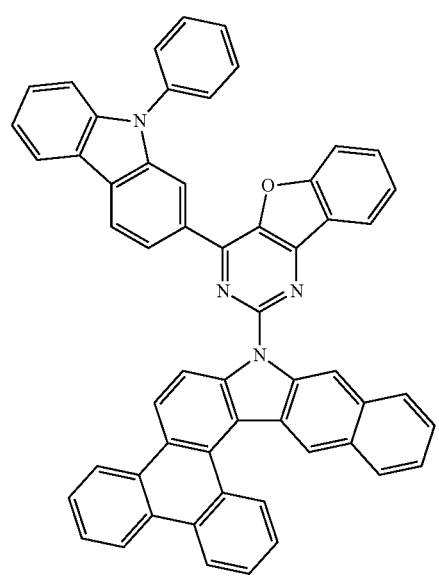
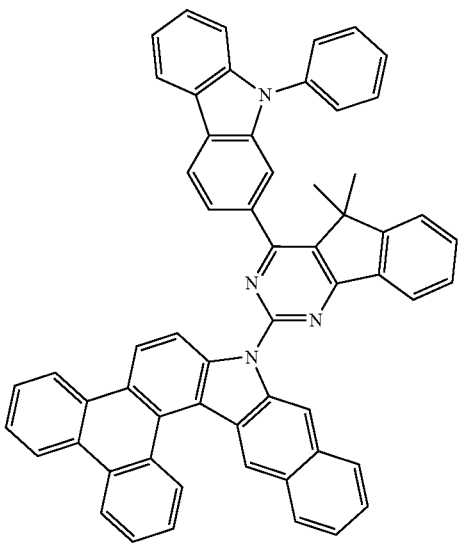
122
-continued
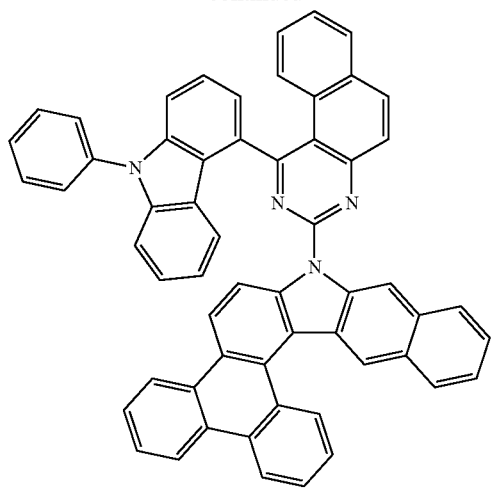
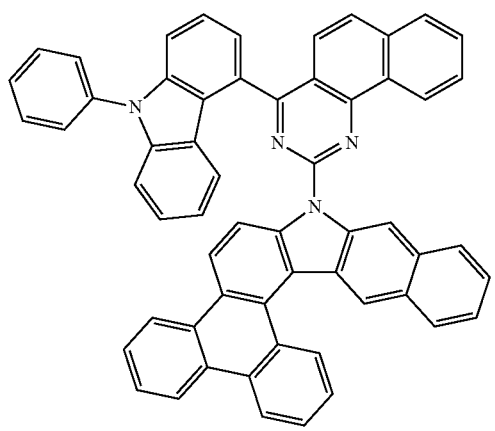
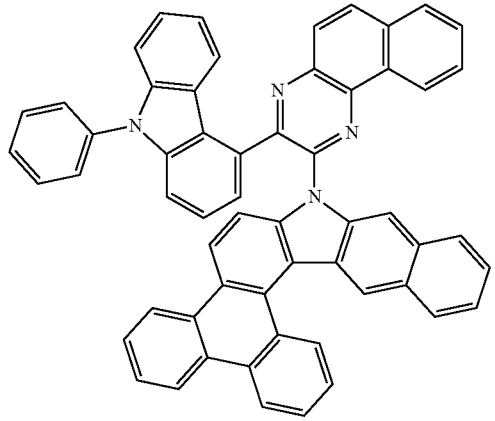

123
-continued
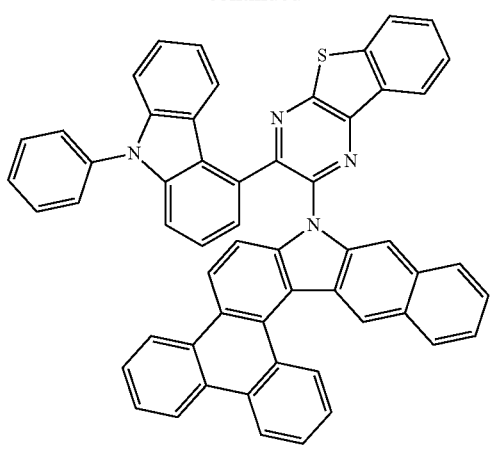
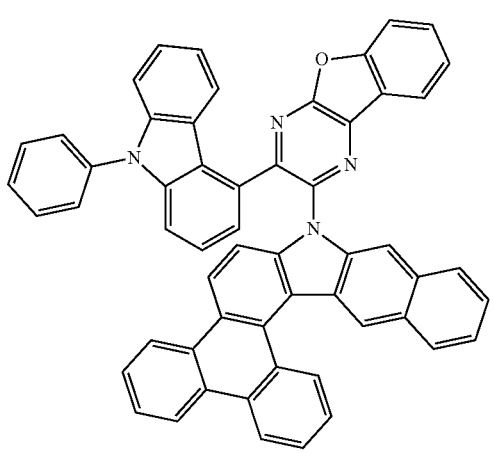
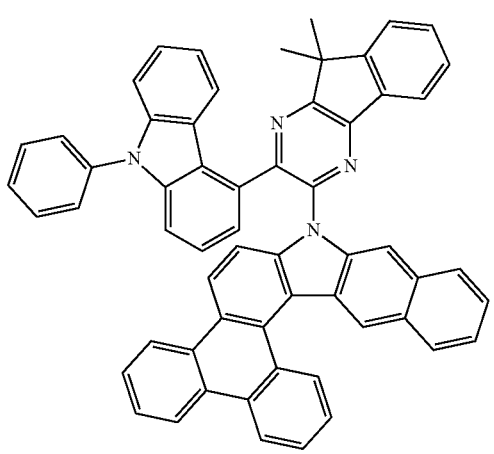
124
-continued
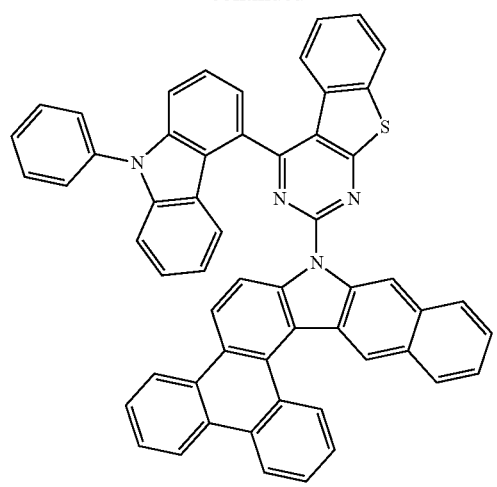
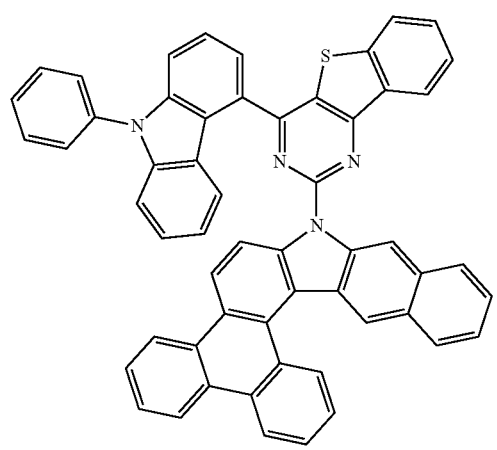
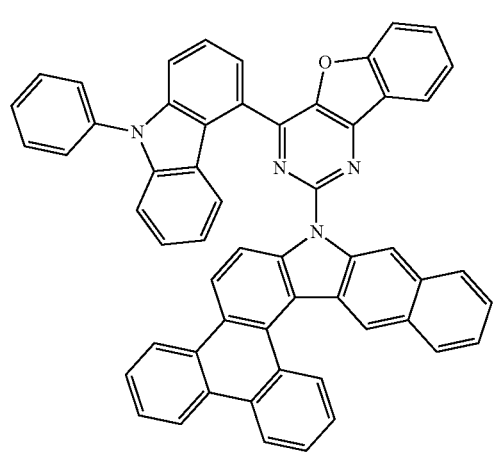

-continued

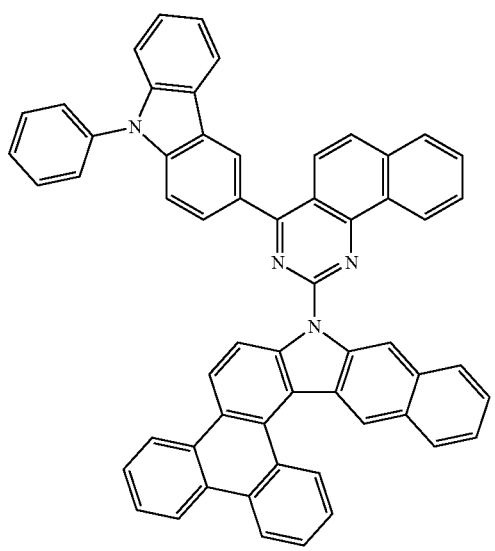
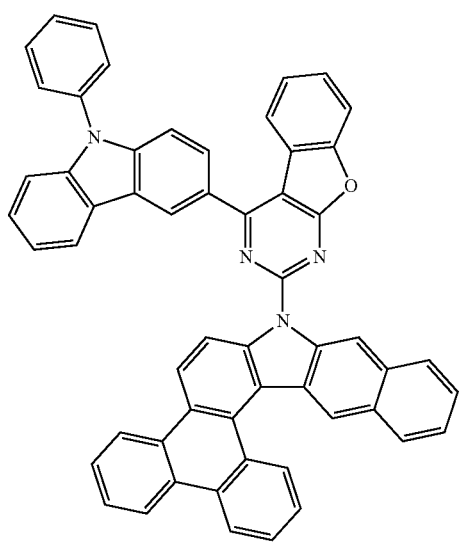
-continued
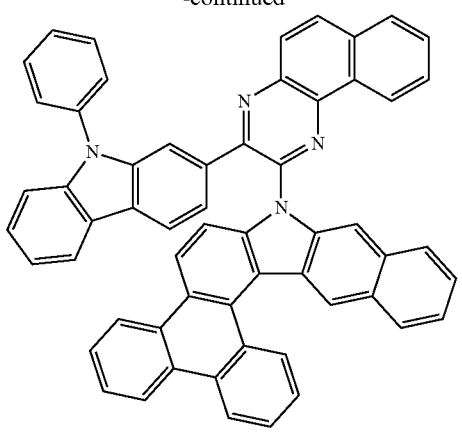
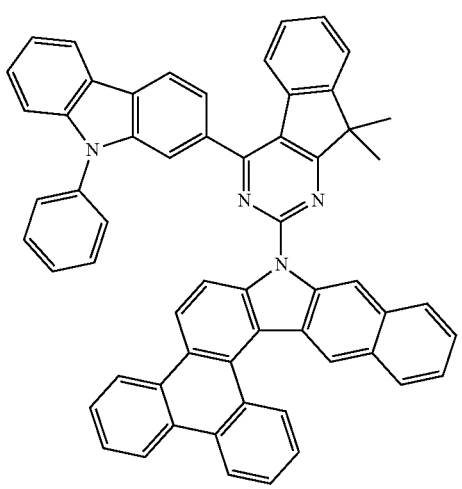
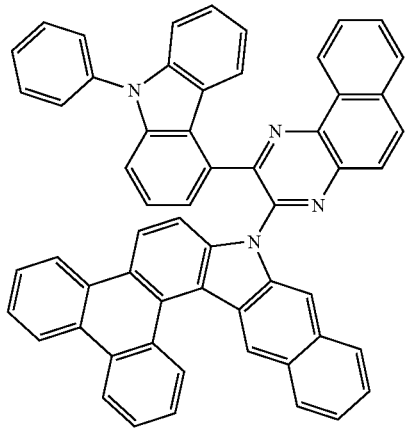

127
-continued
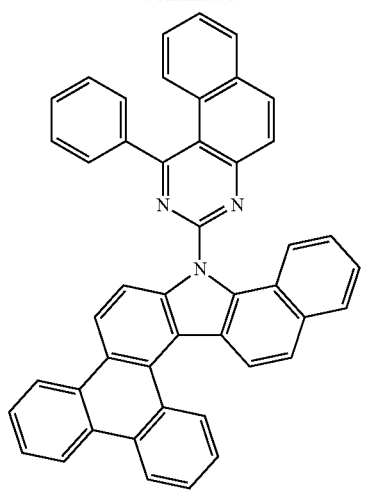
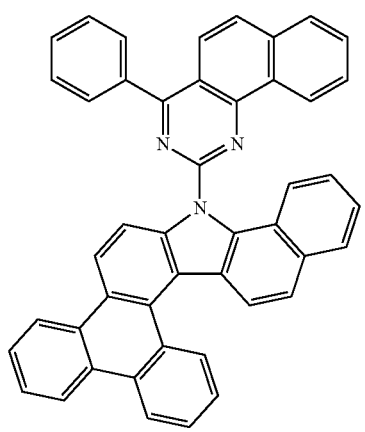
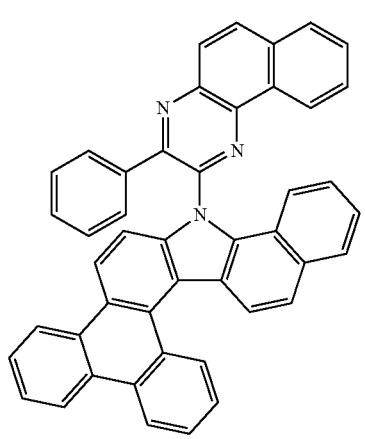
128
-continued
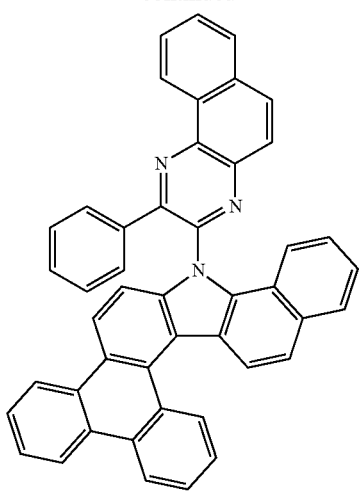
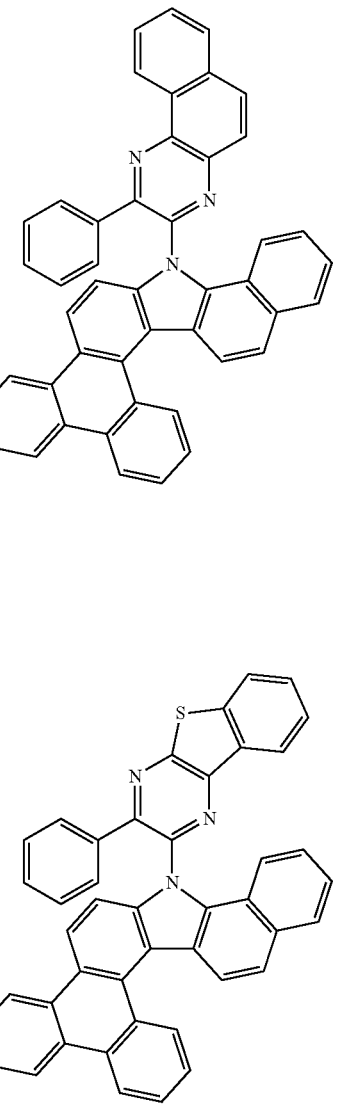
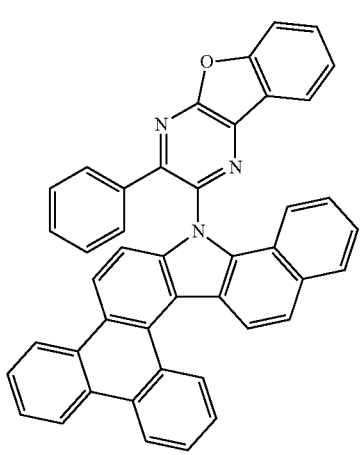

129
-continued
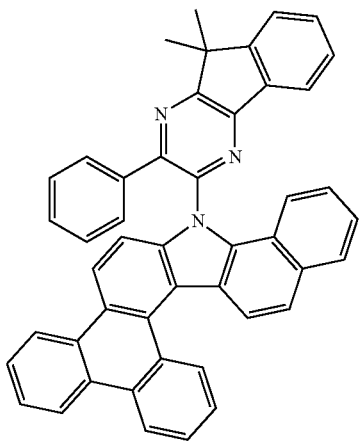
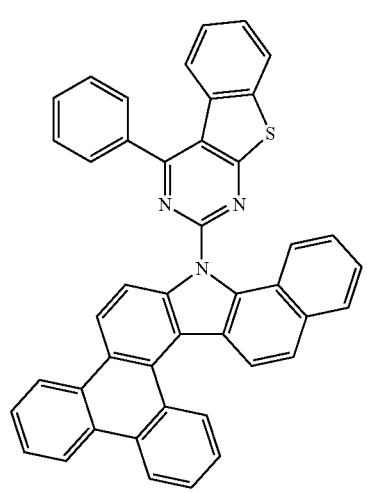
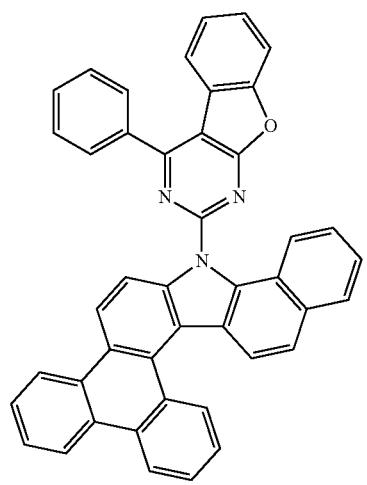
130
-continued
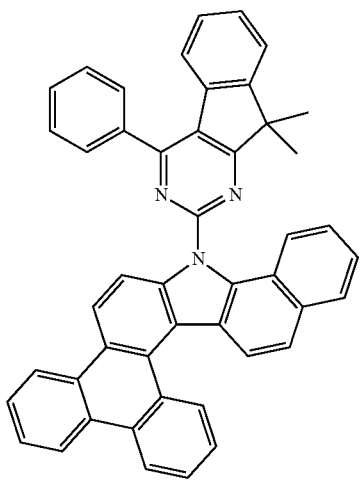
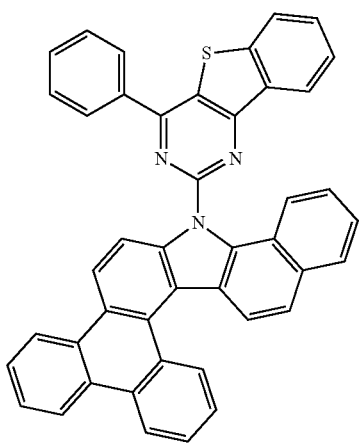
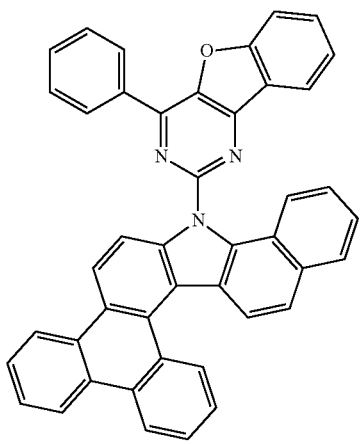

131
-continued
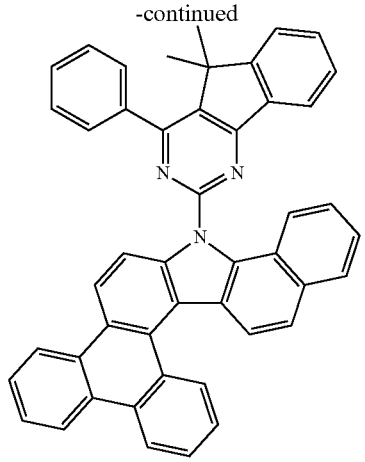
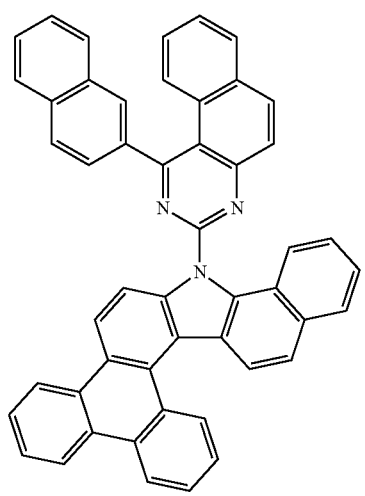
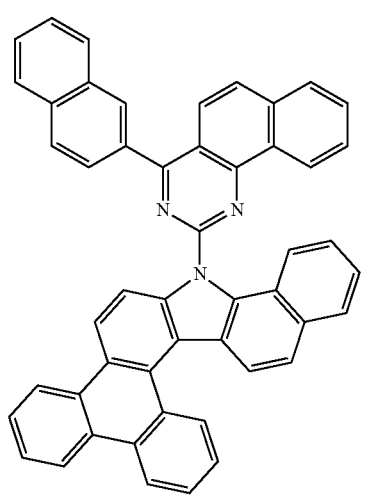
132
-continued
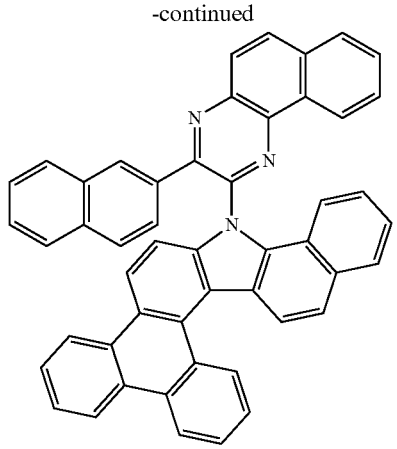
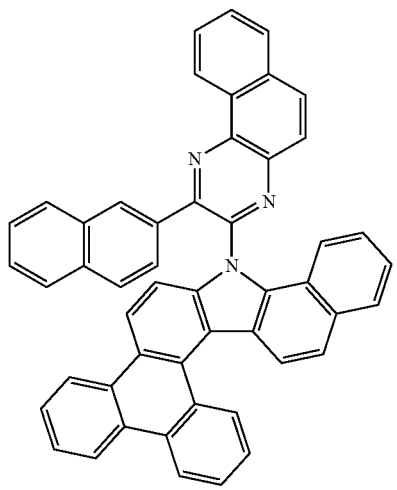
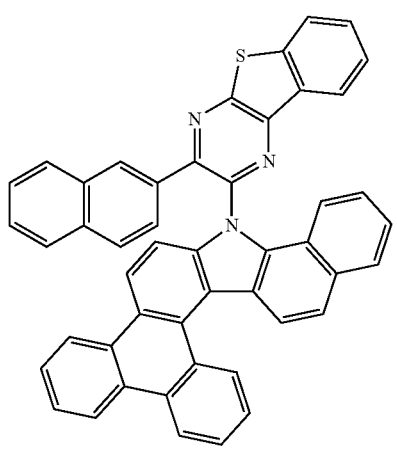

133
-continued
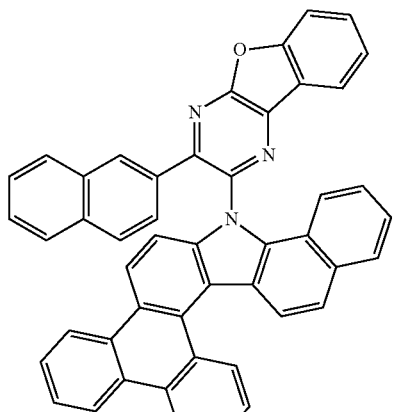
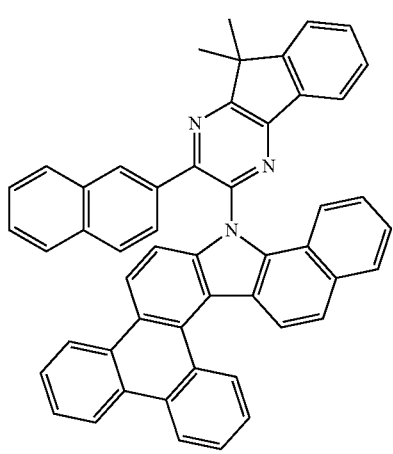
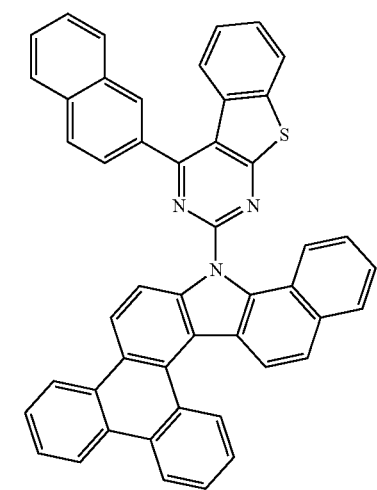
134
-continued
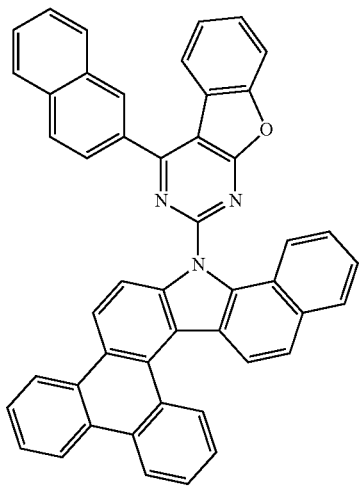
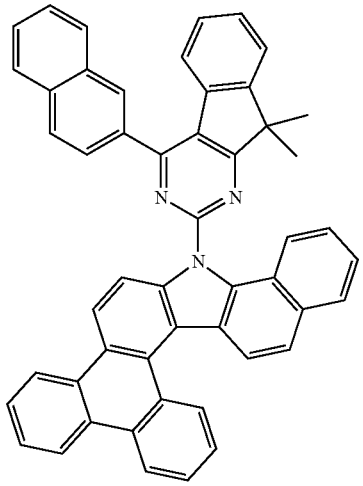
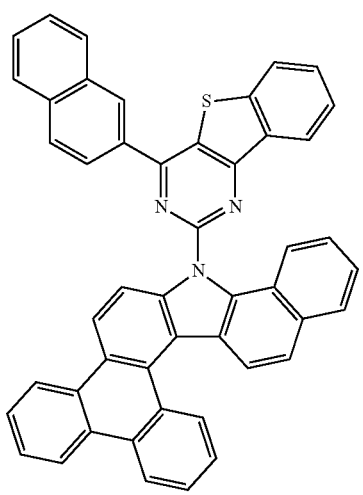

135
-continued
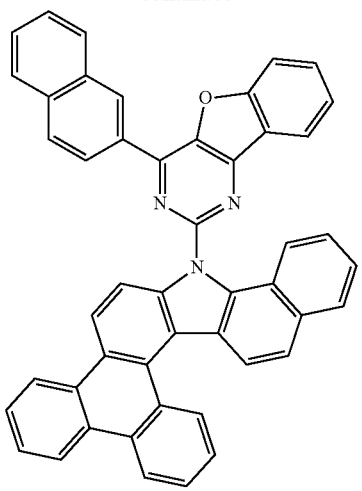
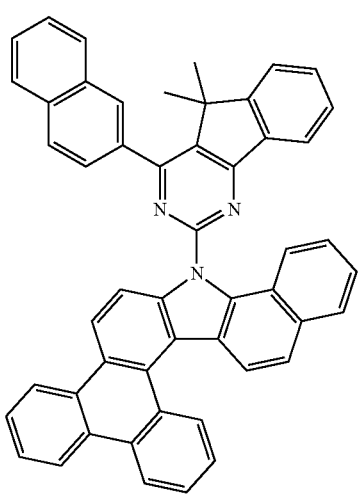
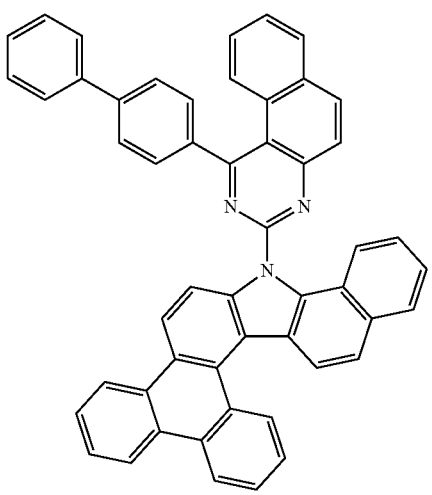
136
-continued
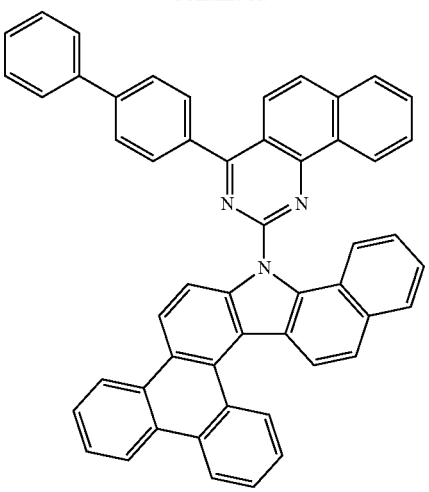
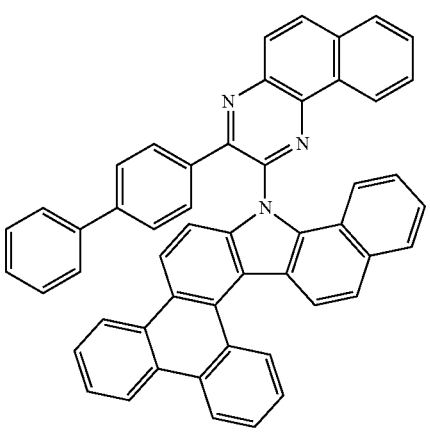
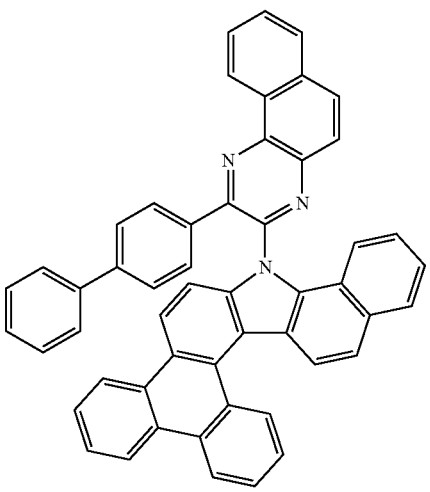

137
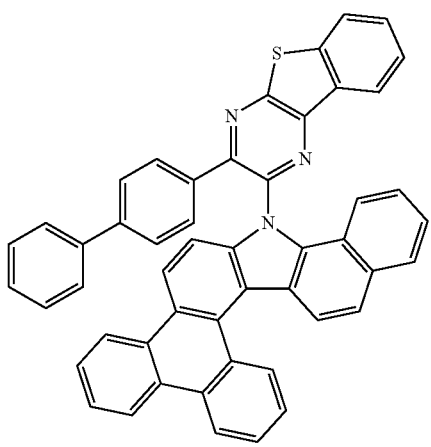
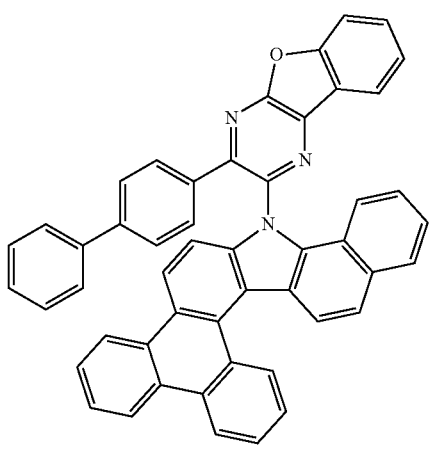
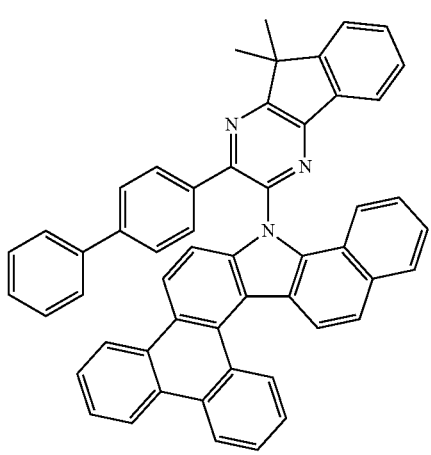
138
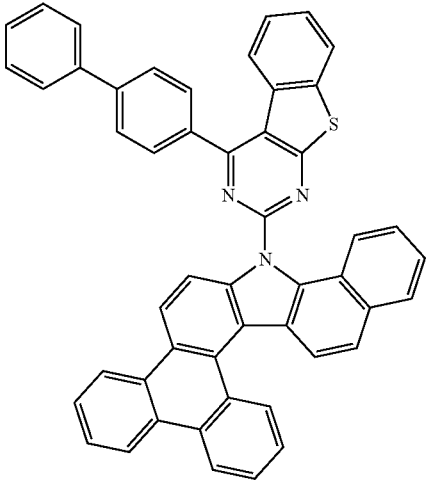
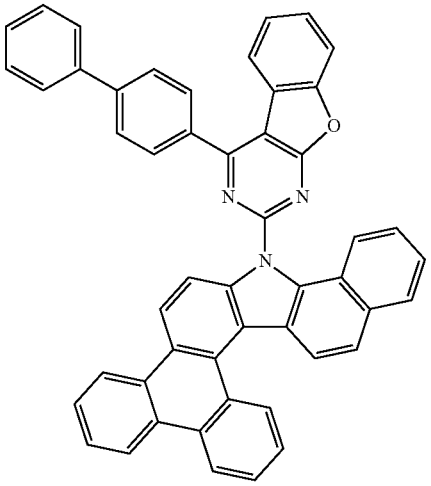
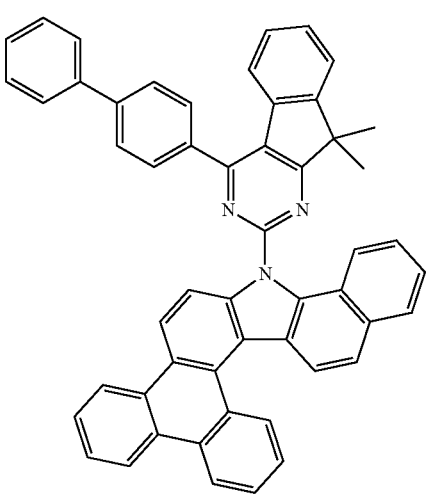

139
-continued
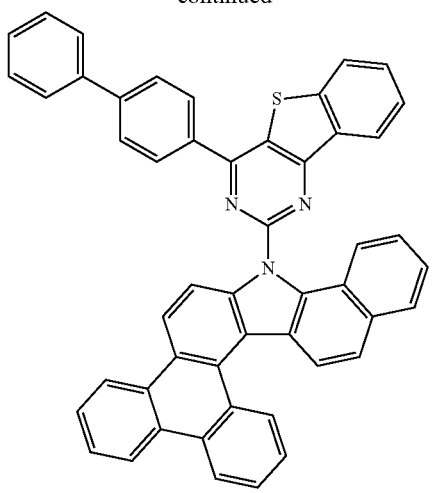
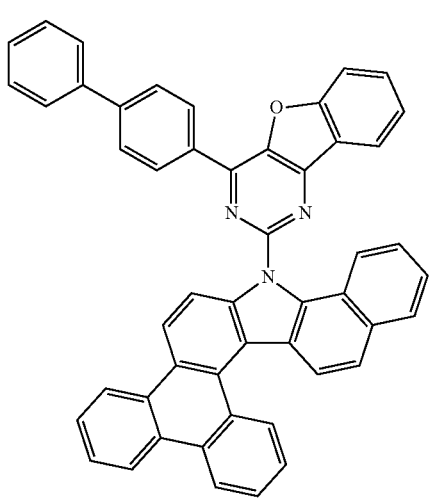
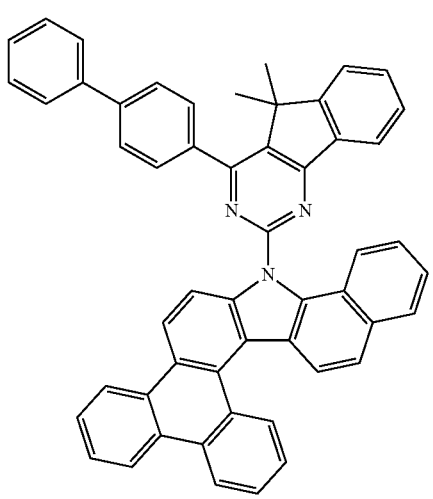
140
-continued
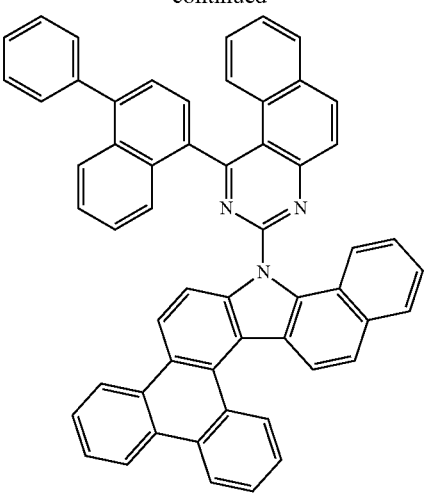
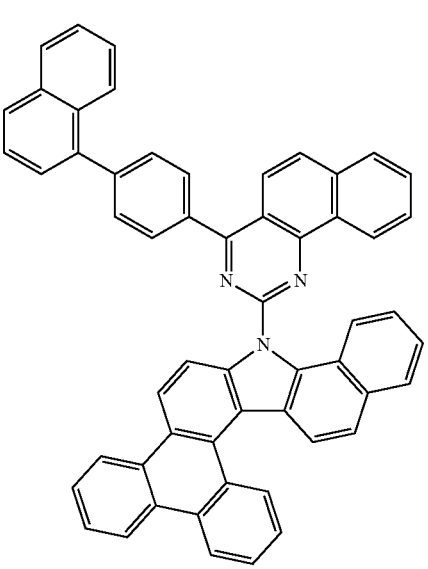
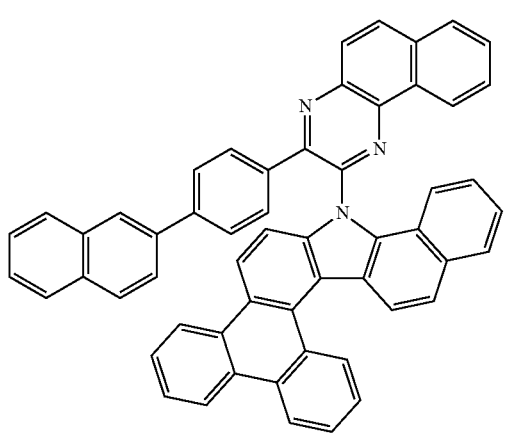

141
-continued
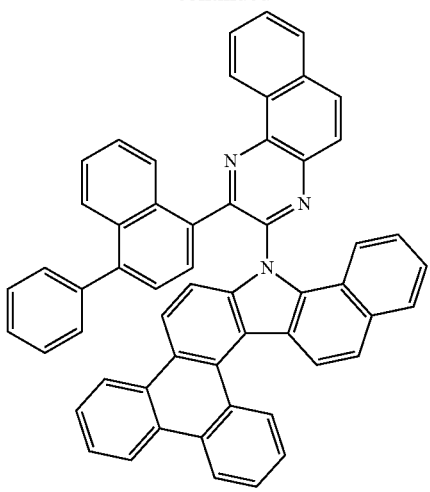
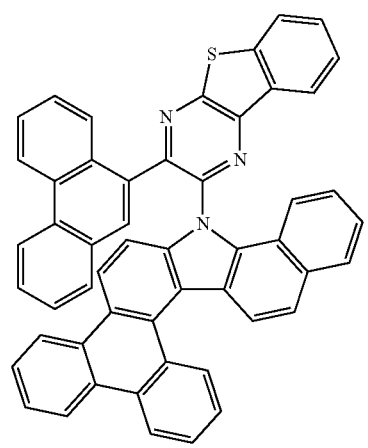
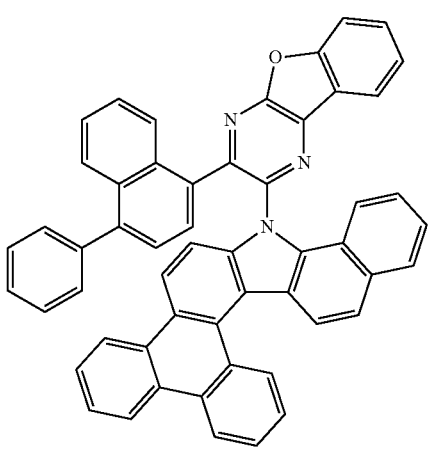
142
-continued
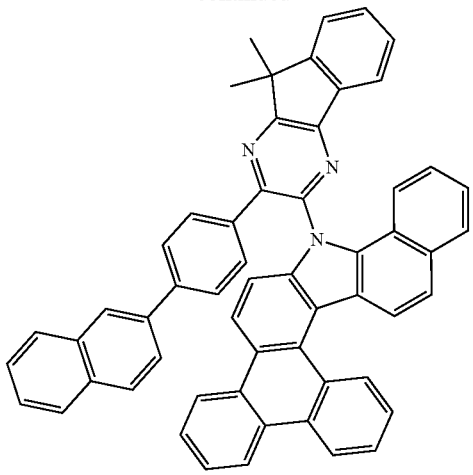
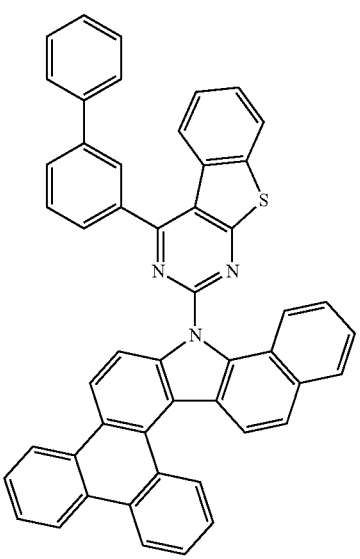
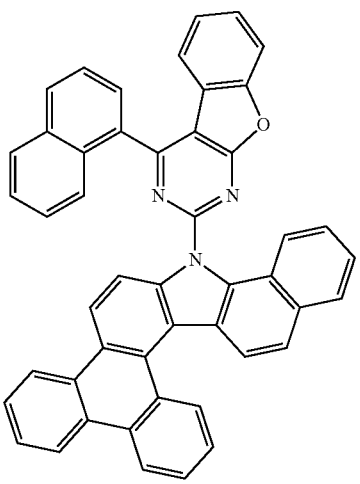

143
-continued
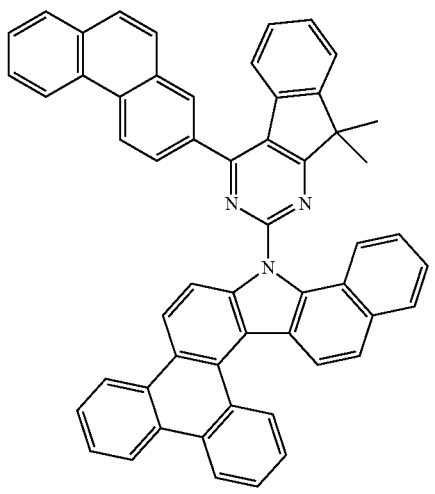
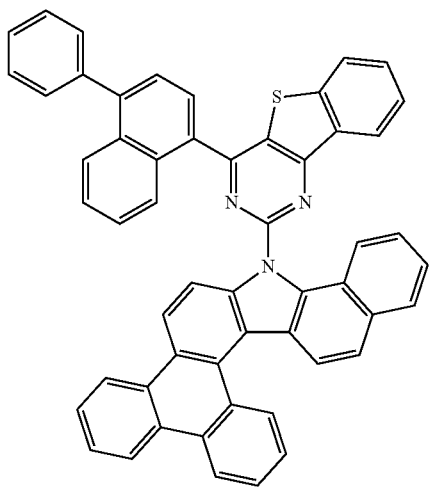
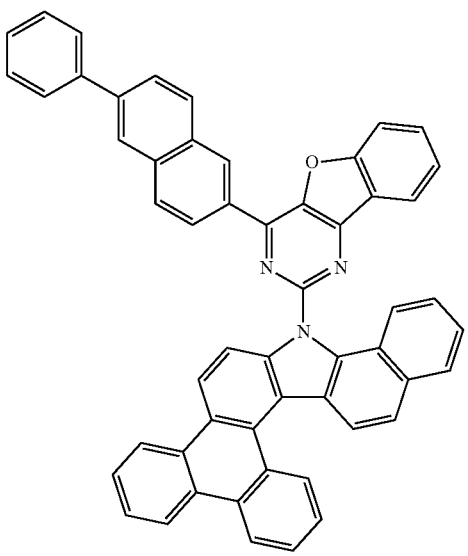
144
-continued
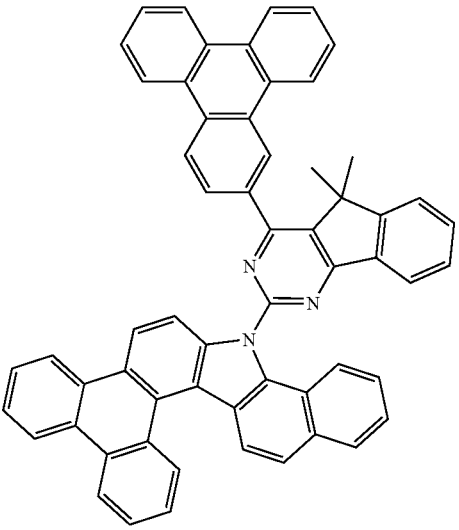
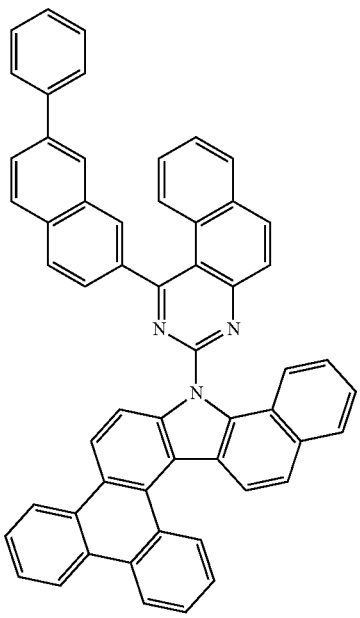
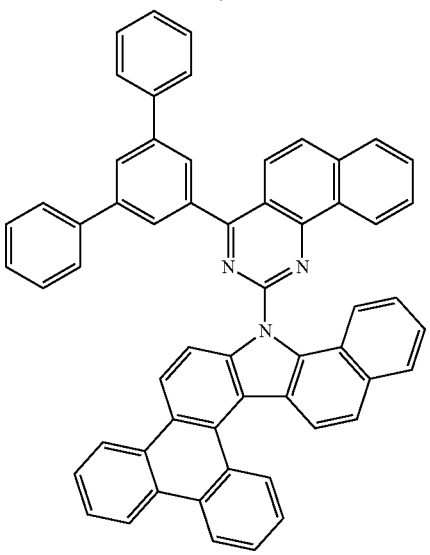

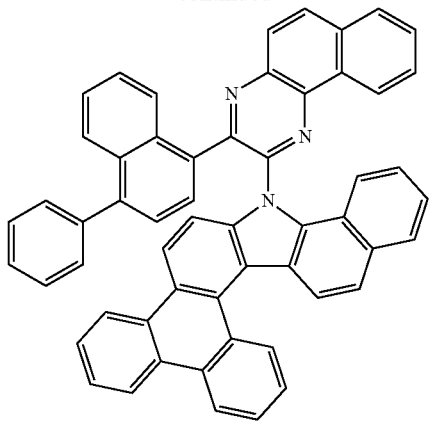
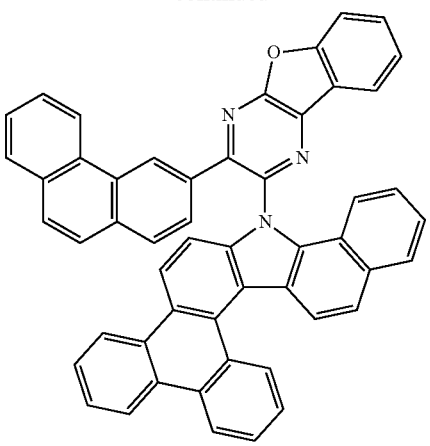
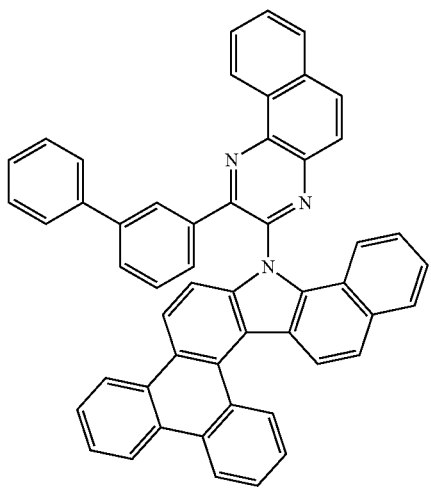
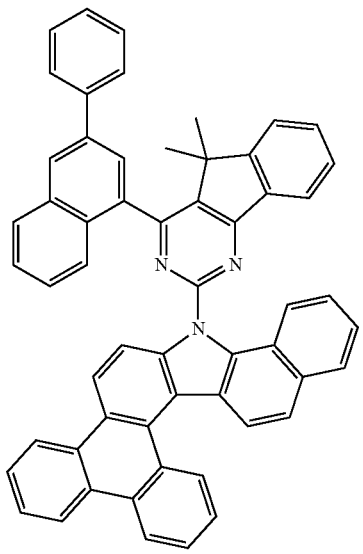
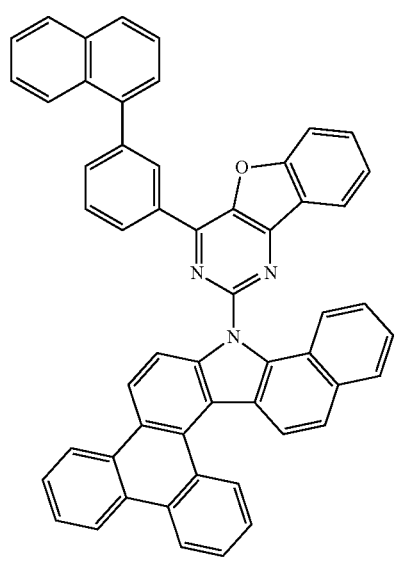
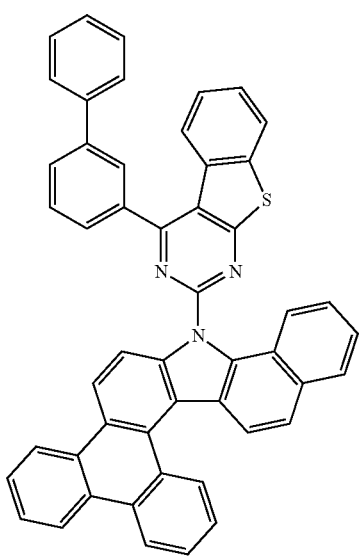

147
-continued
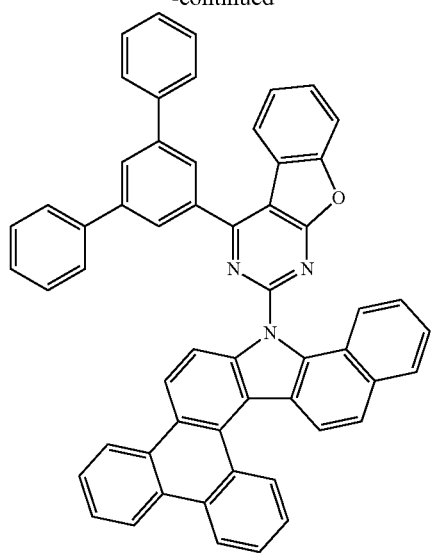
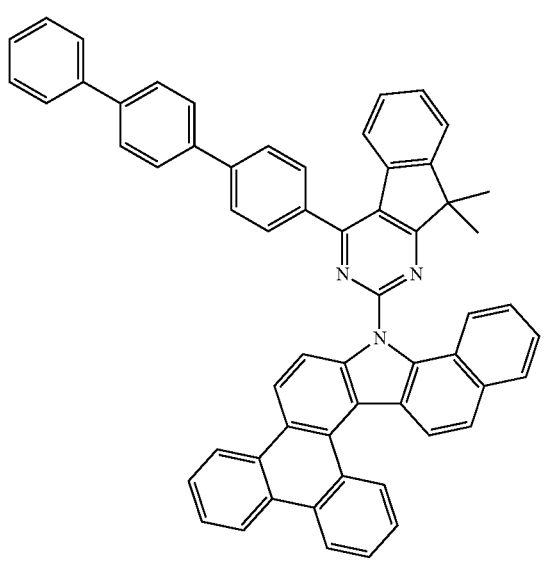
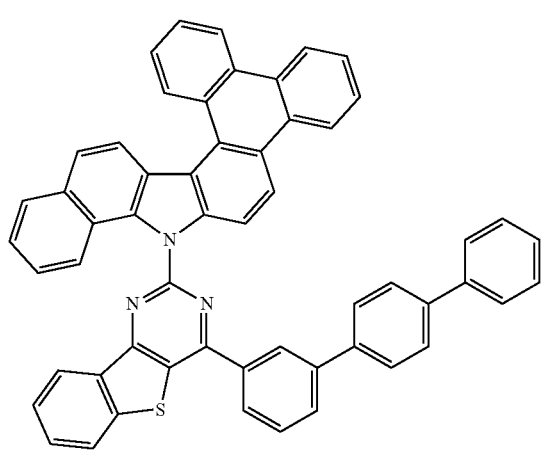
148
-continued
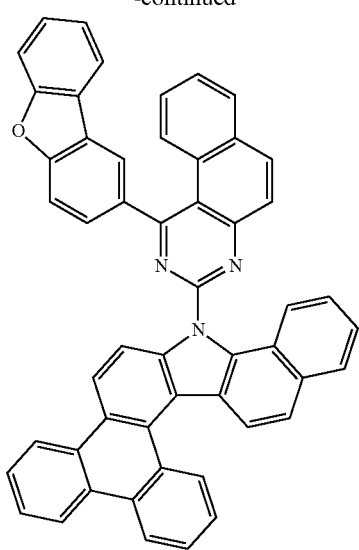
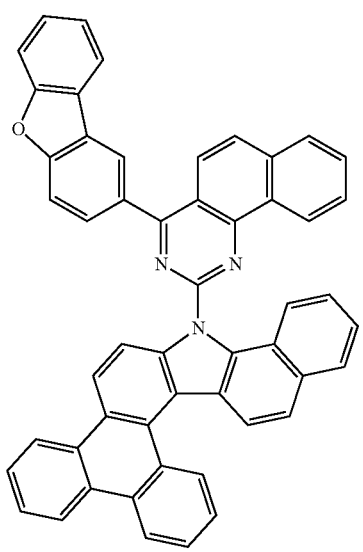
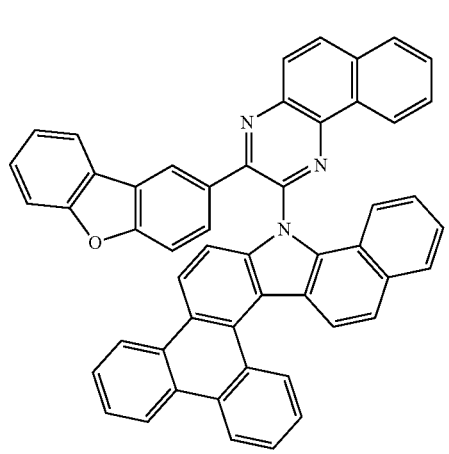

149
-continued
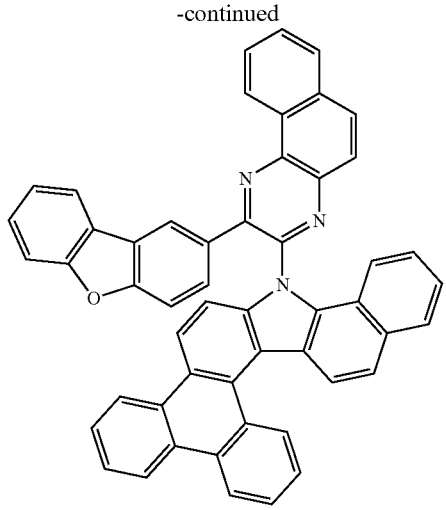
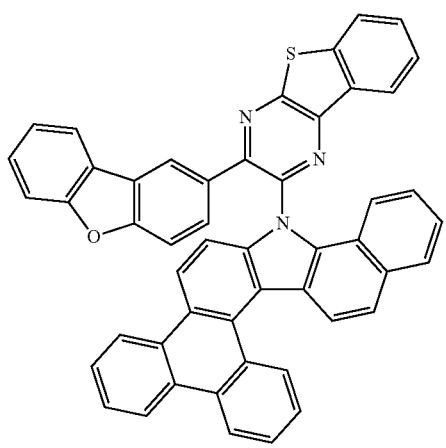
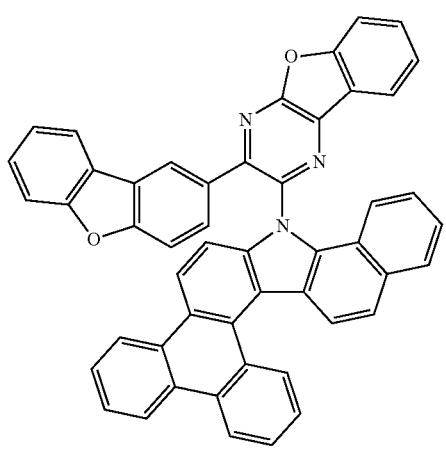
150
-continued
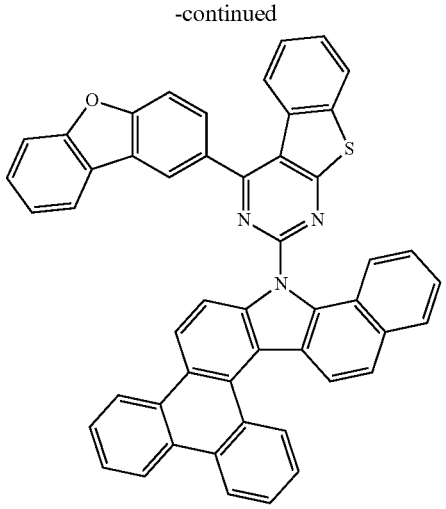
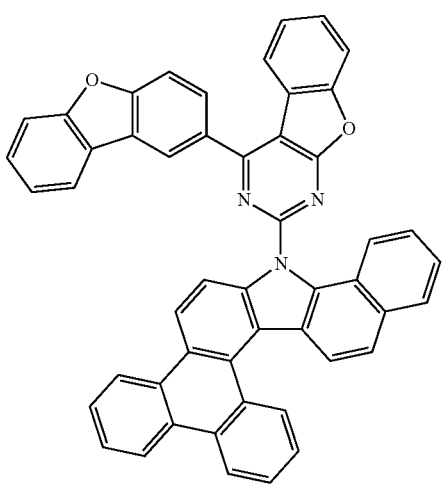
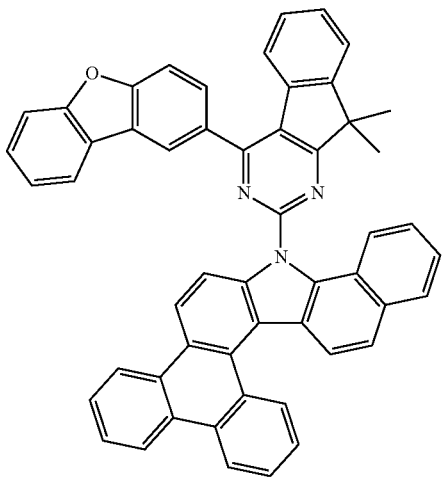

151
-continued
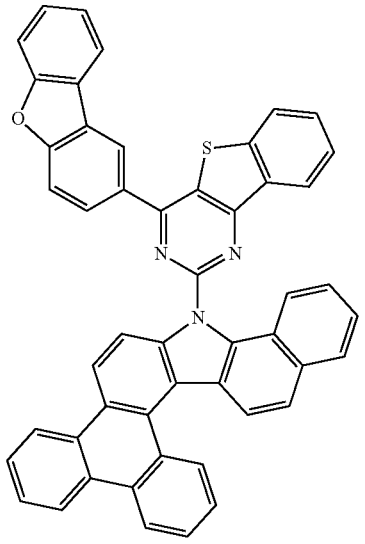
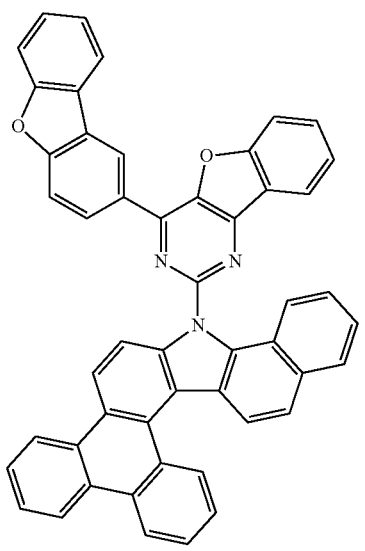
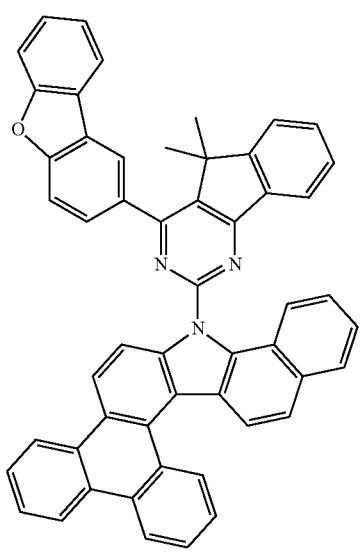
152
-continued
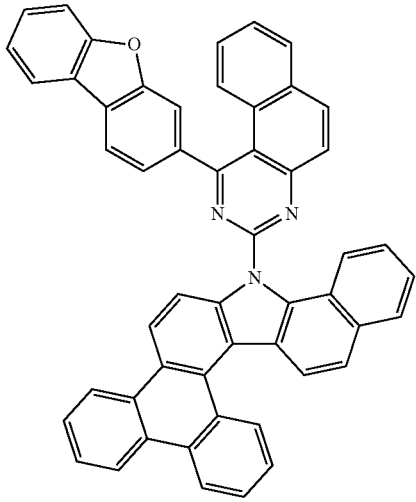
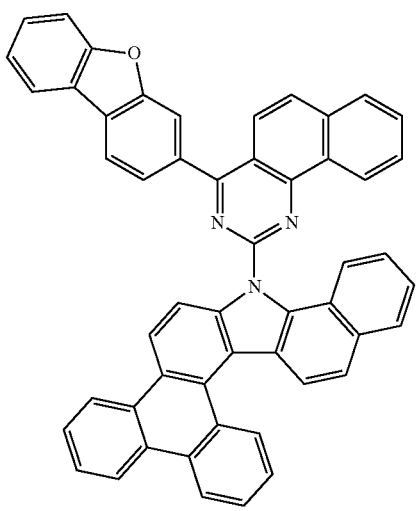
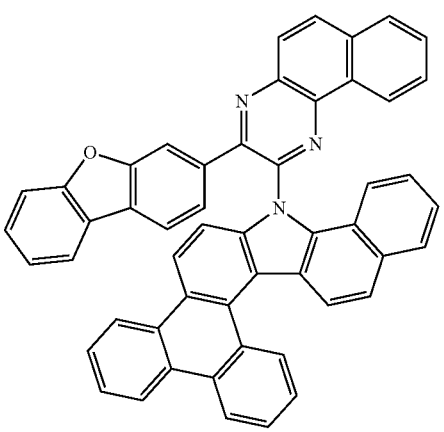

153
-continued
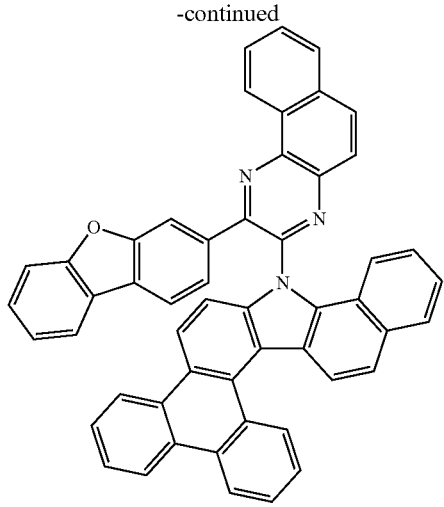
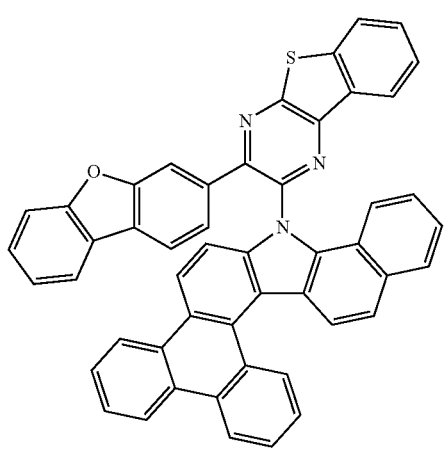
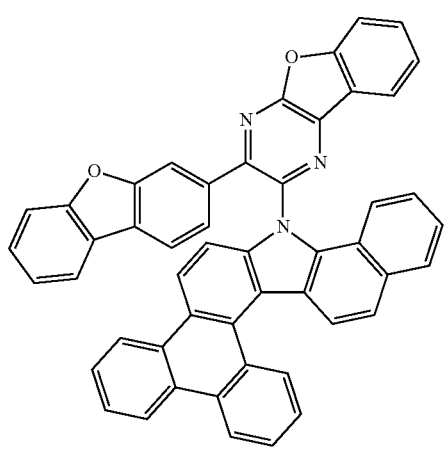
154
-continued
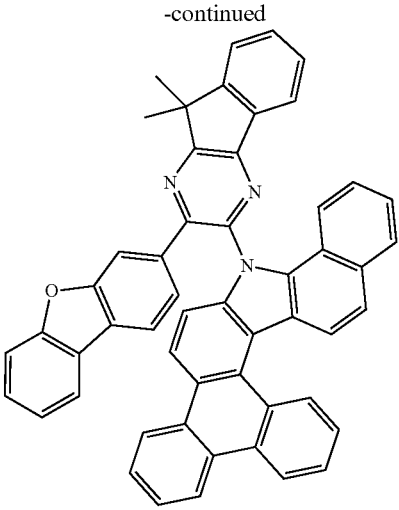
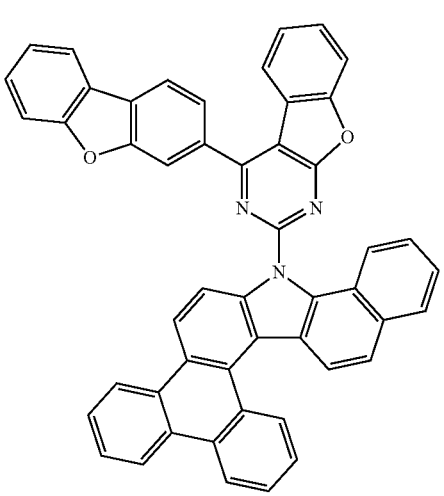
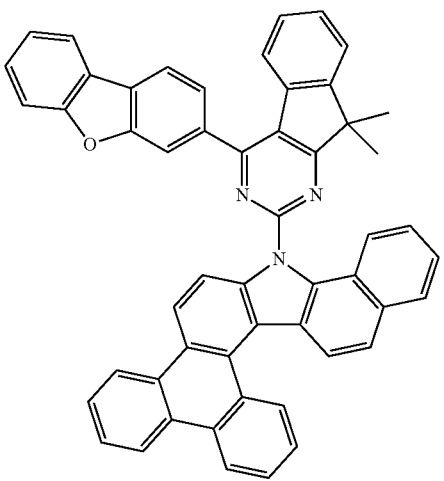

155
-continued
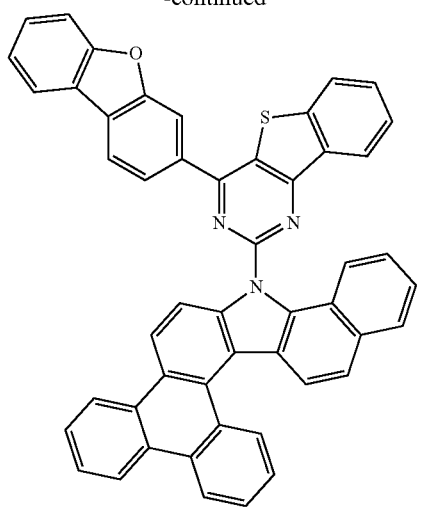
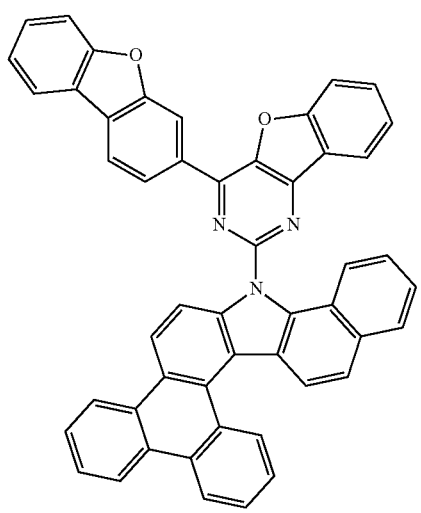
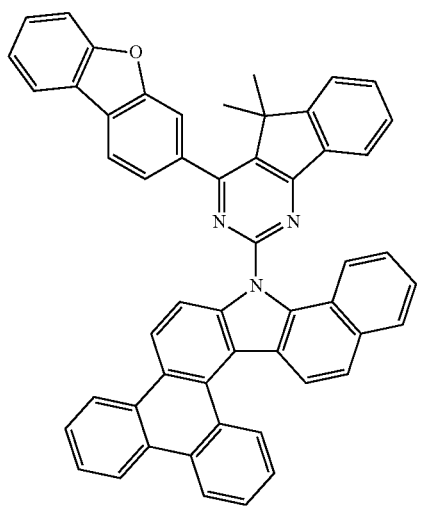
156
-continued
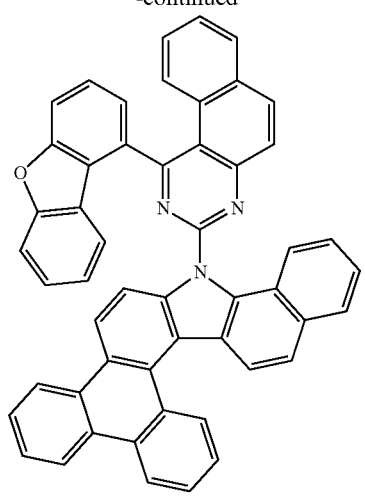
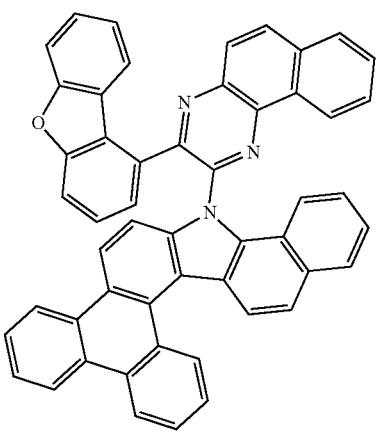
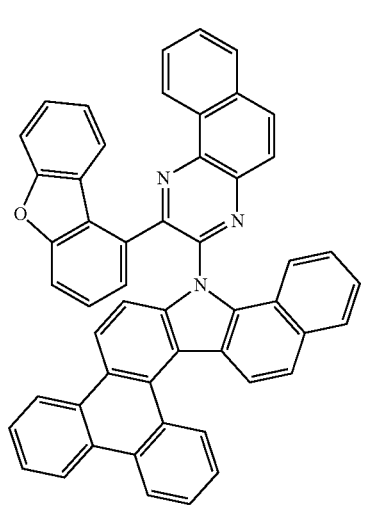

157
-continued
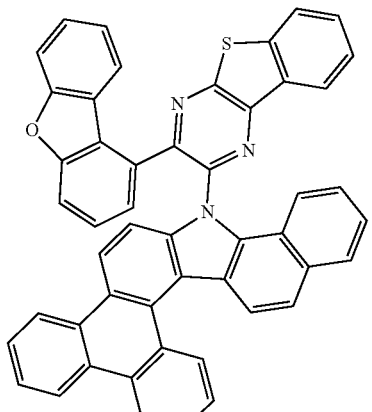
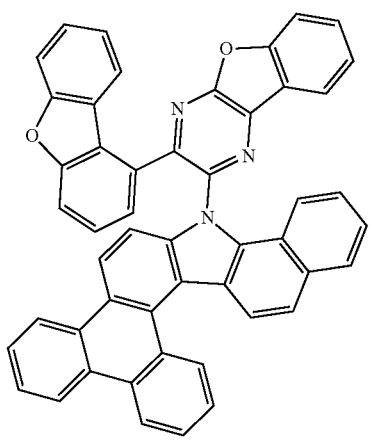
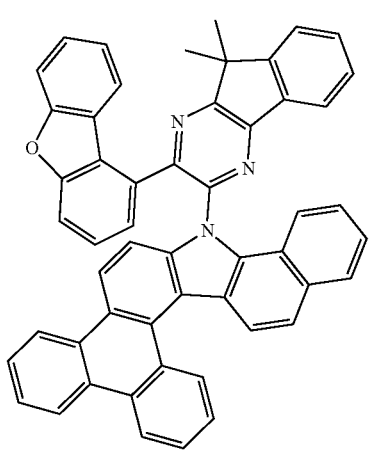
158
-continued
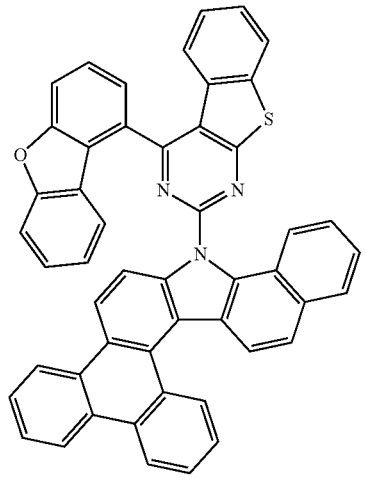
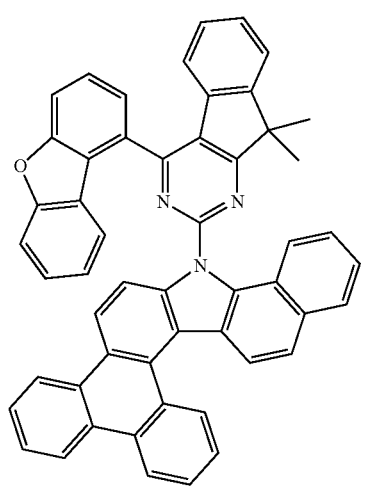
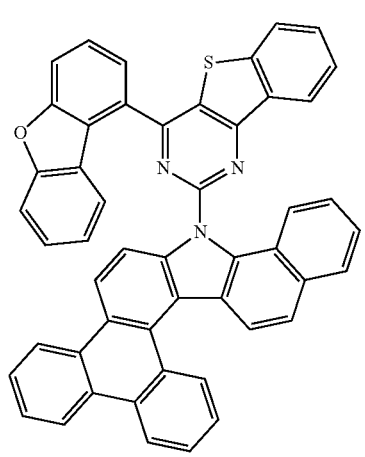

159
-continued
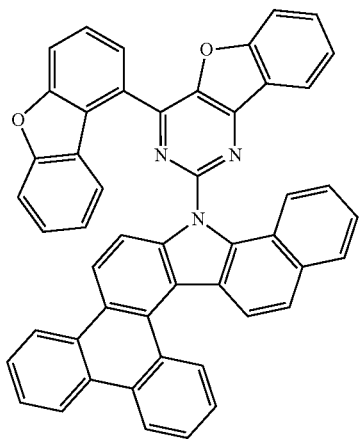
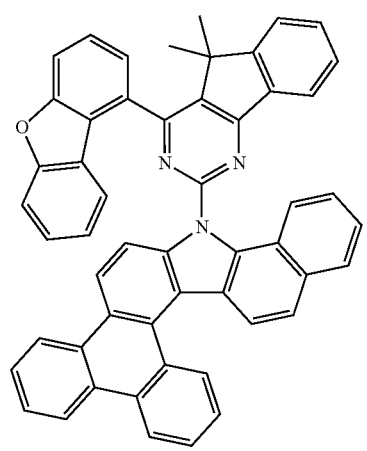
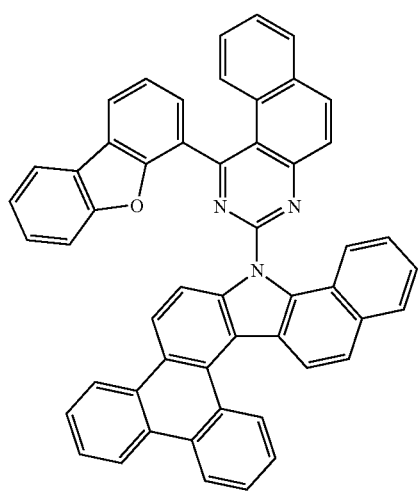
160
-continued
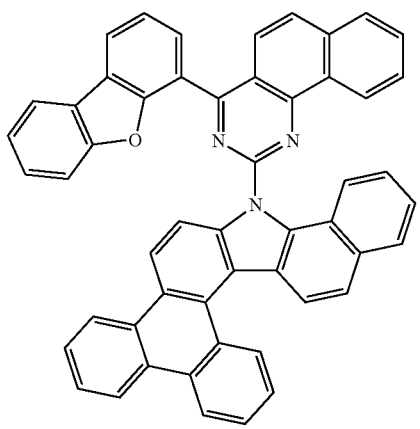
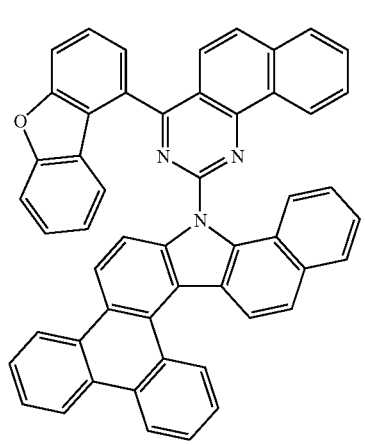
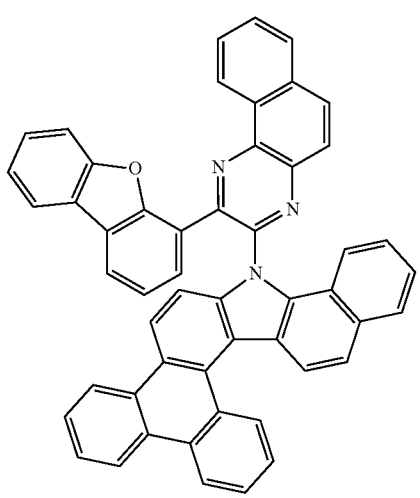

161
-continued
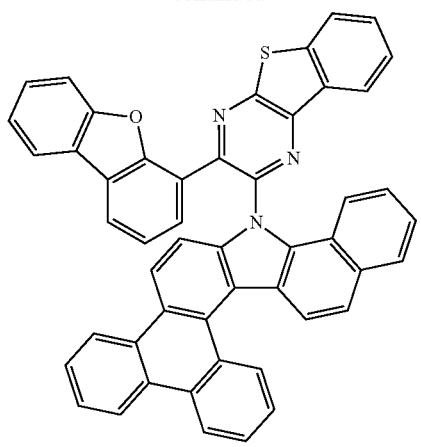
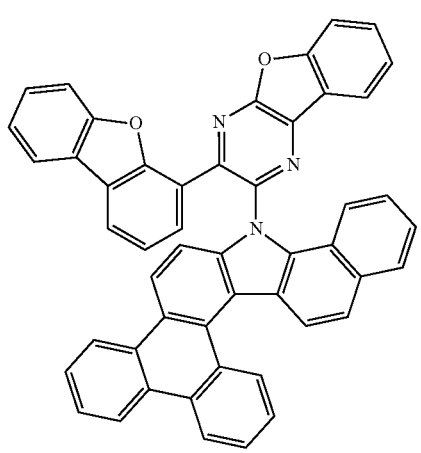
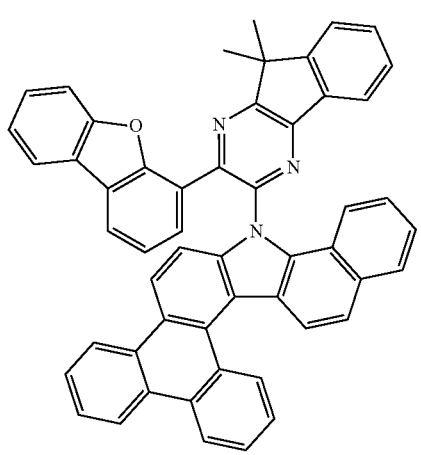
162
-continued
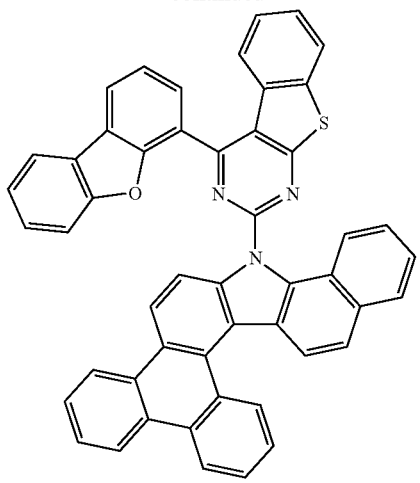
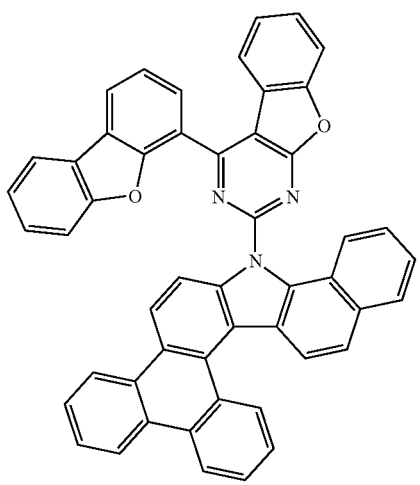
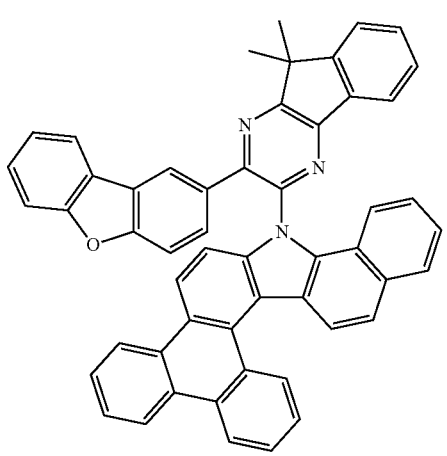

163
-continued
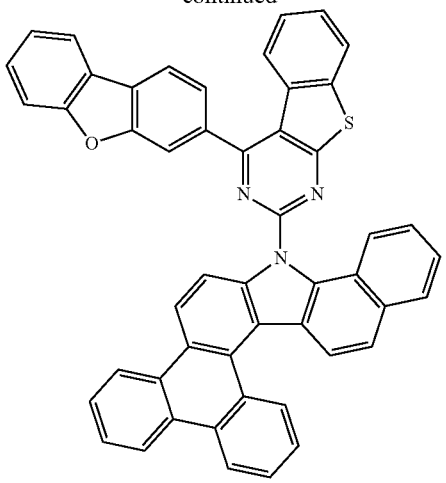
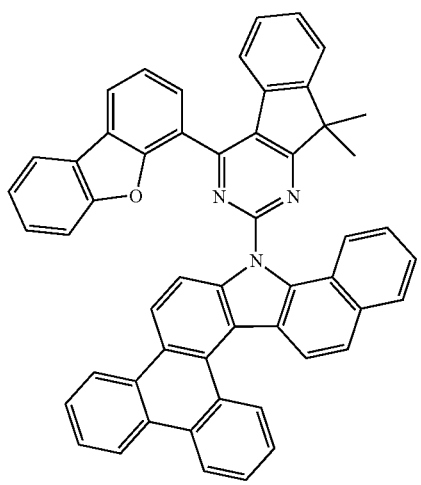
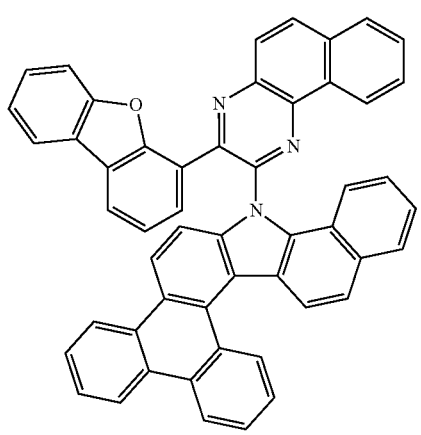
164
-continued
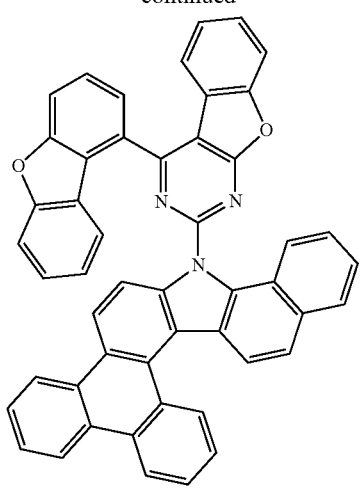
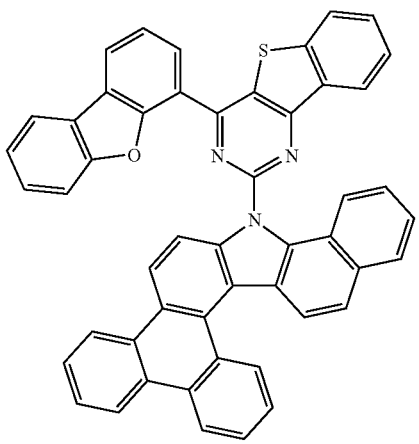
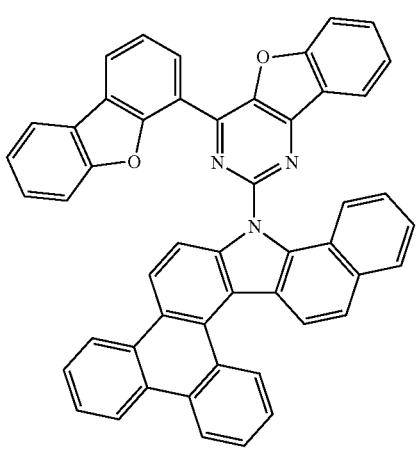

165
-continued
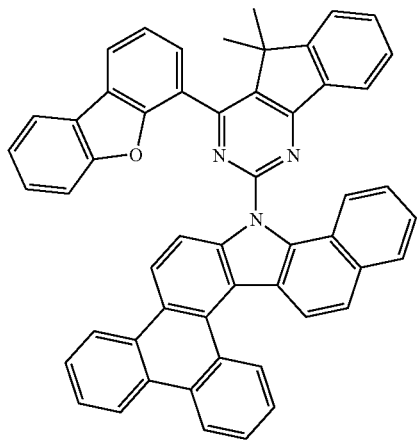
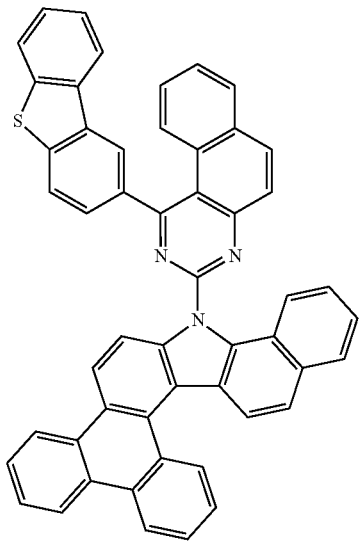
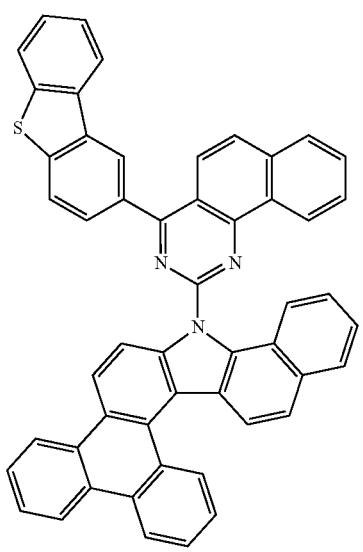
166
-continued
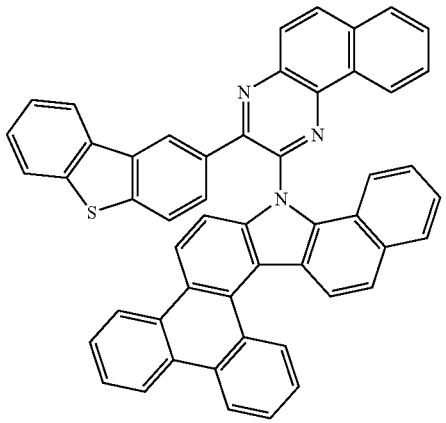
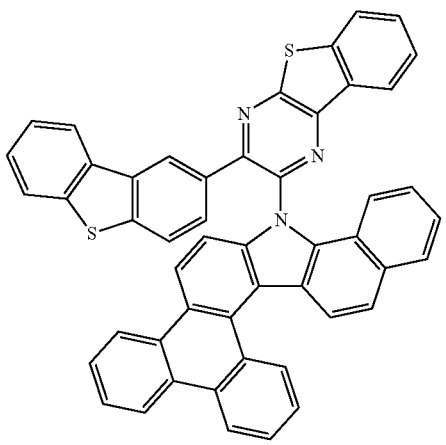
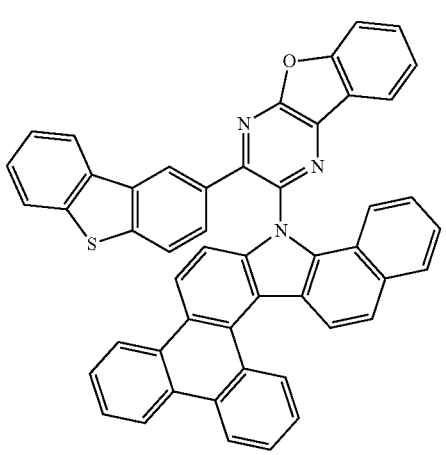

167
-continued
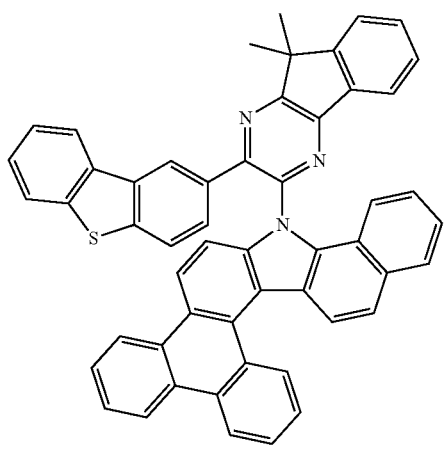
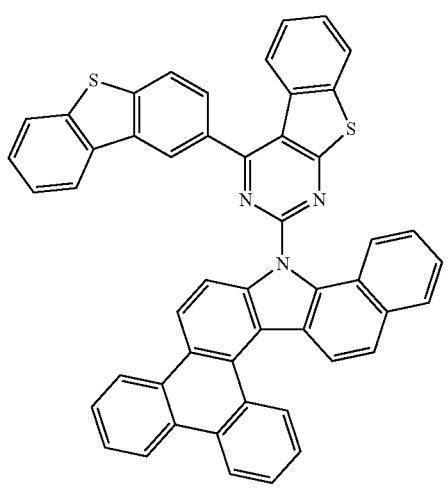
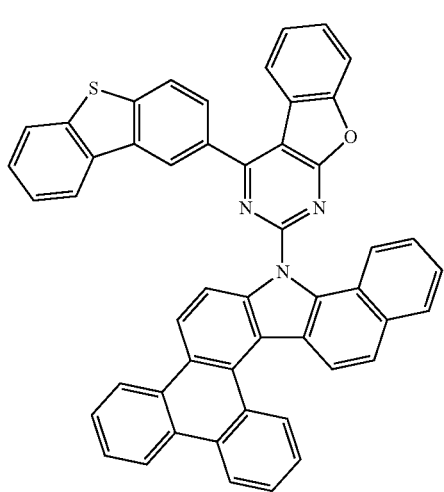
168
-continued
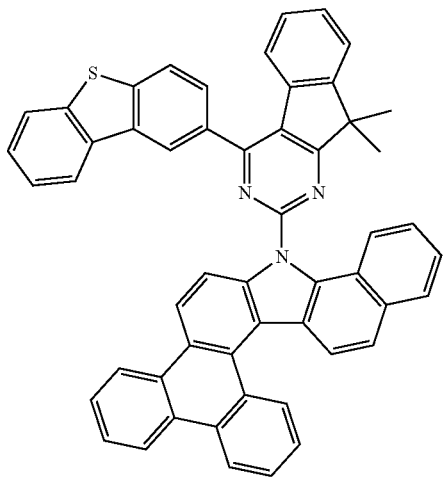
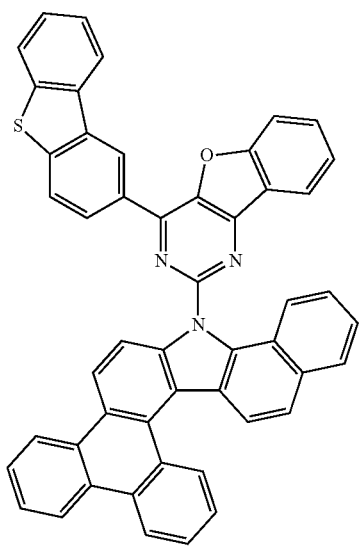
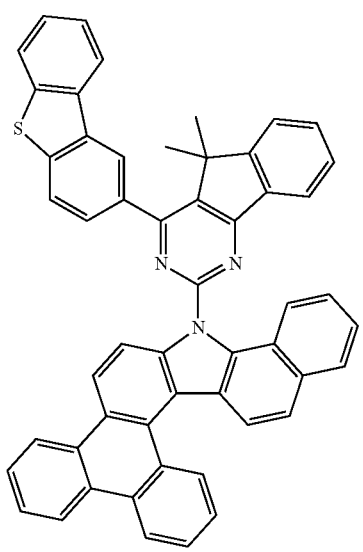

169
-continued
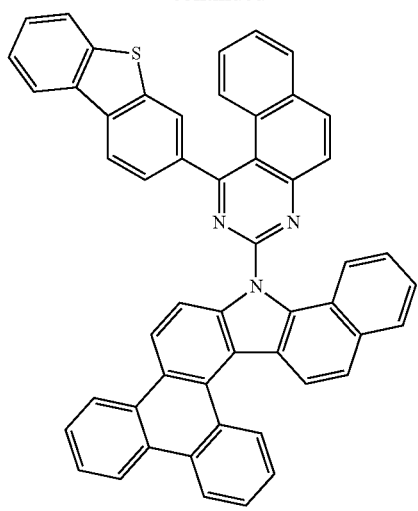
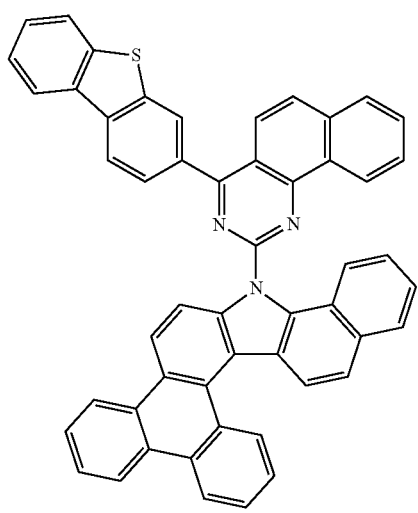
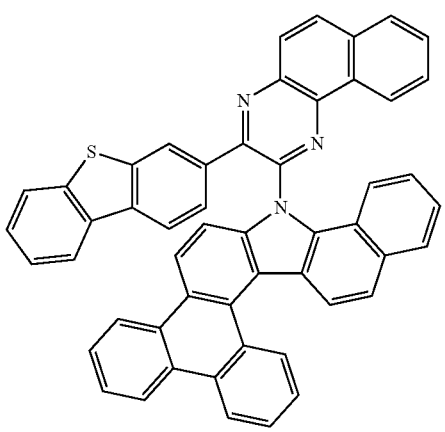
170
-continued
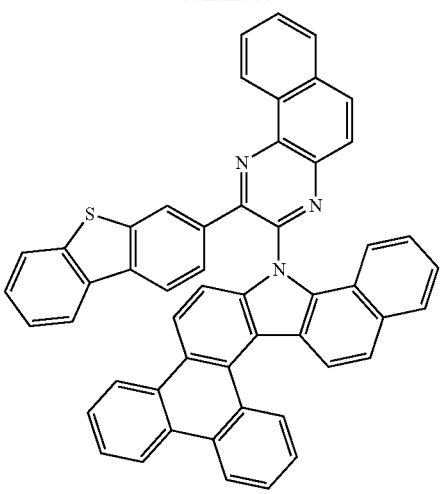
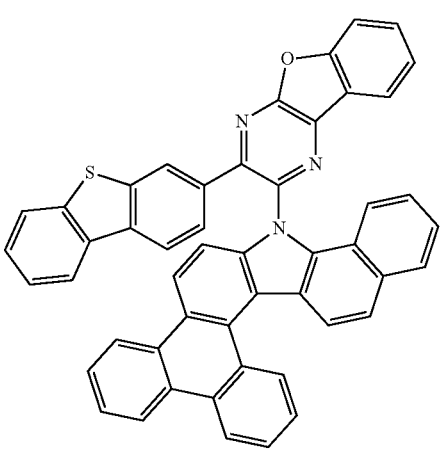
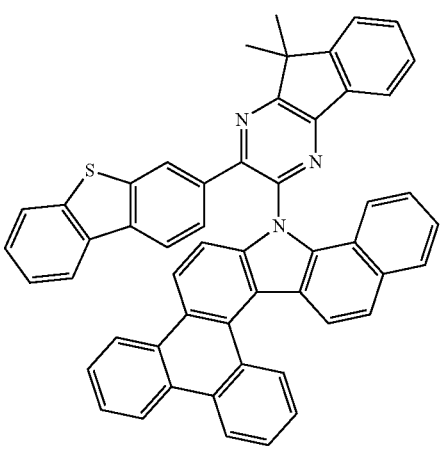

171
-continued
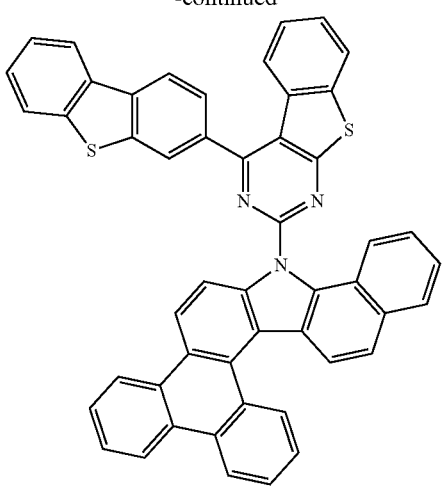
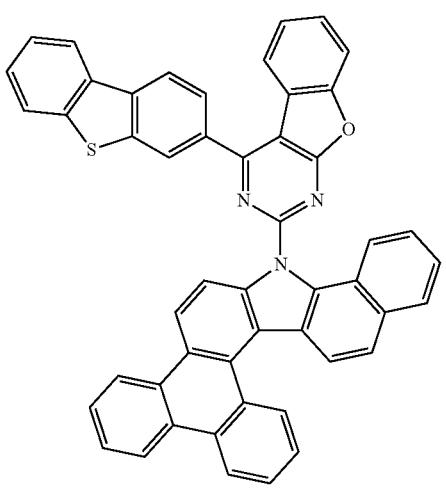
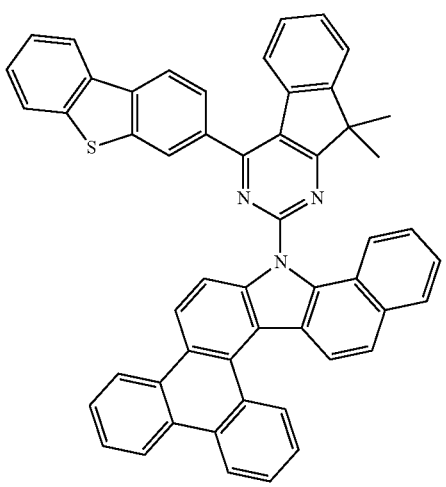
172
-continued
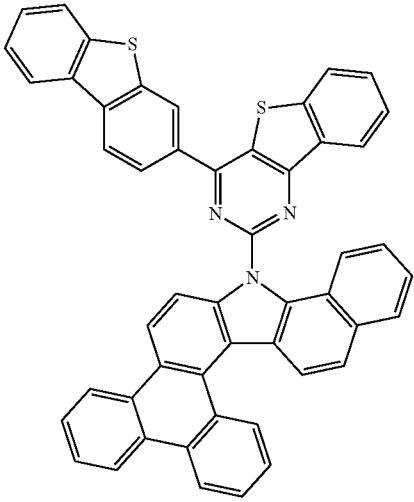
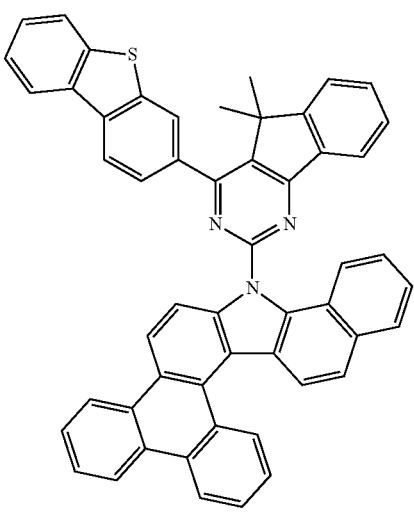
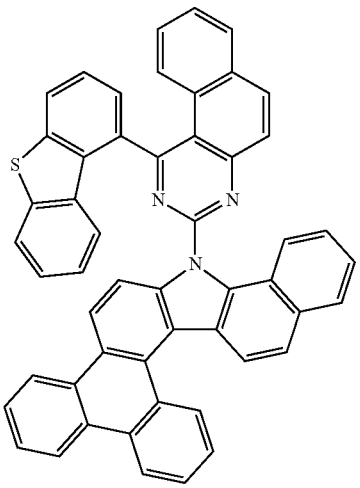

173
-continued
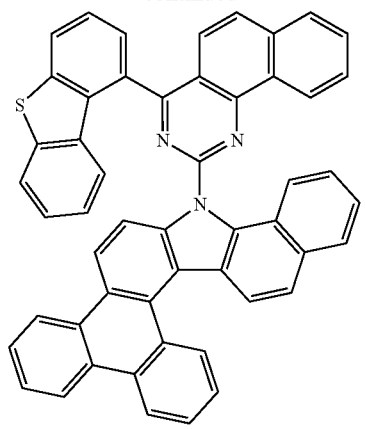
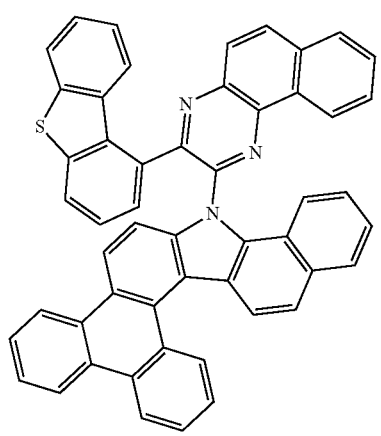
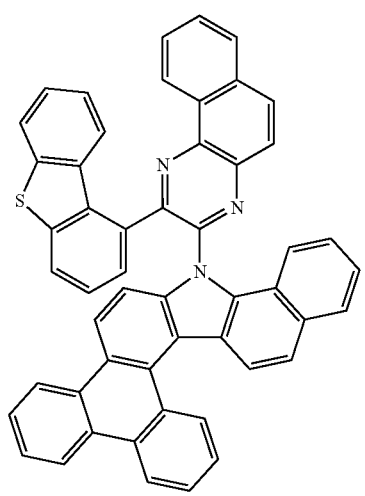
174
-continued
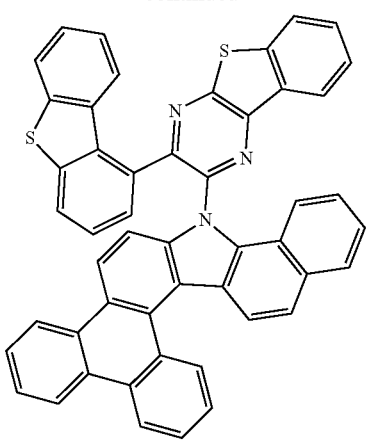
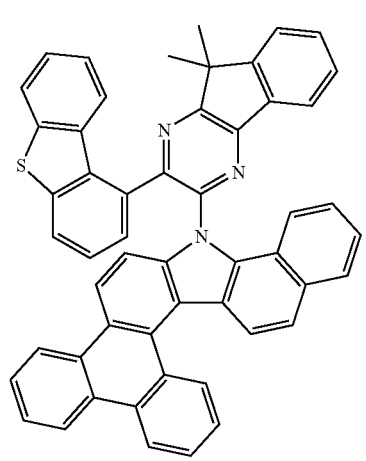
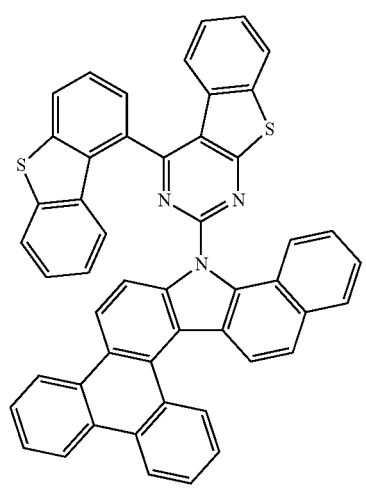

175
-continued
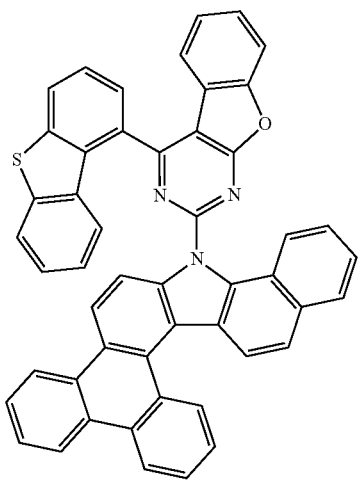
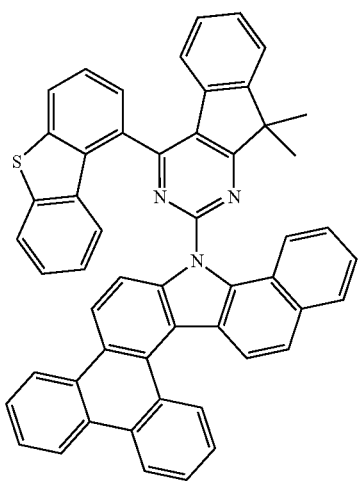
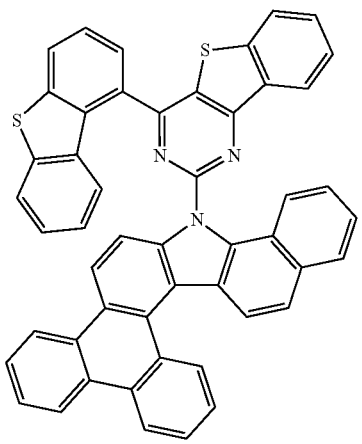
176
-continued
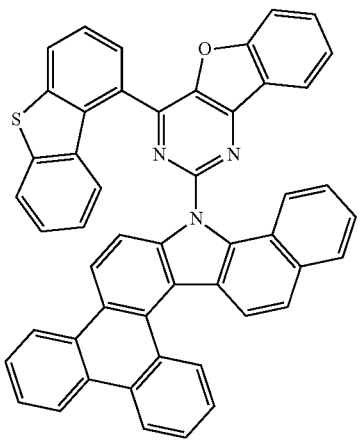
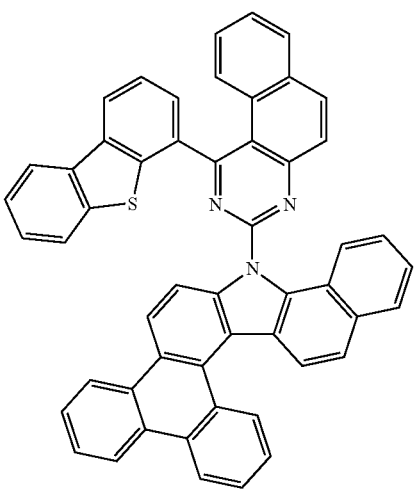
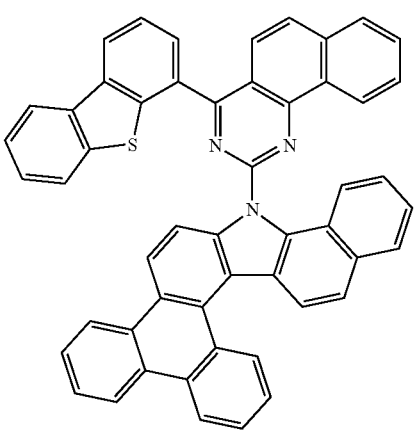

177
-continued
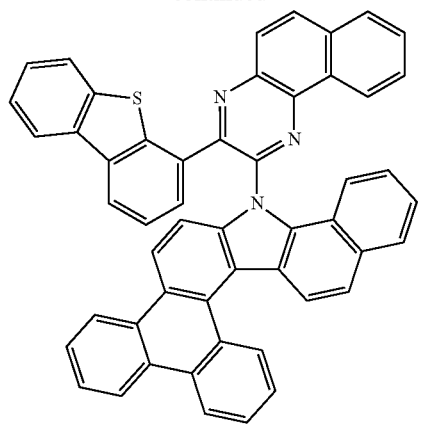
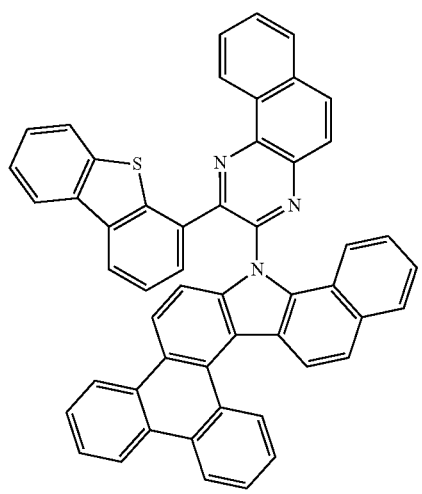
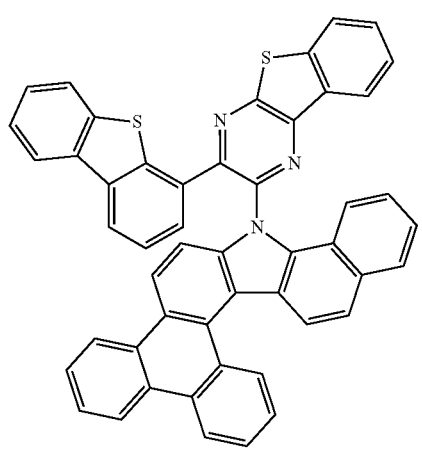
178
-continued
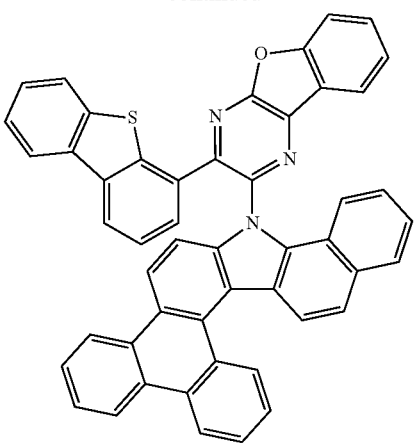
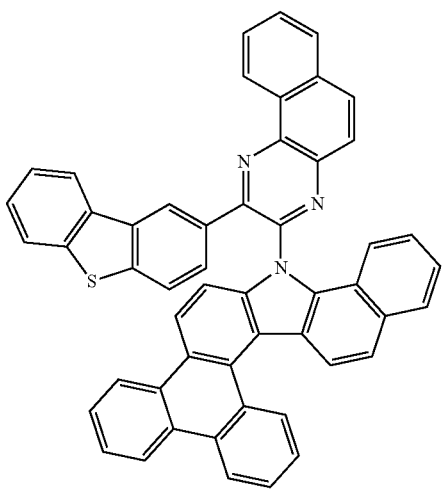
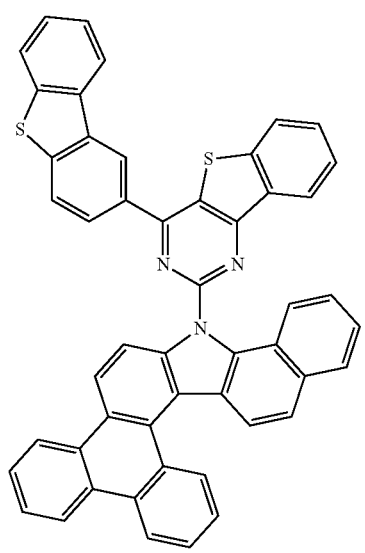

179
-continued
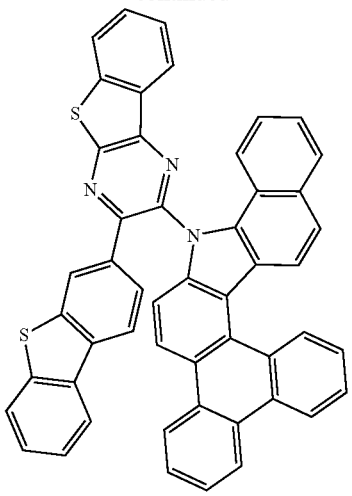
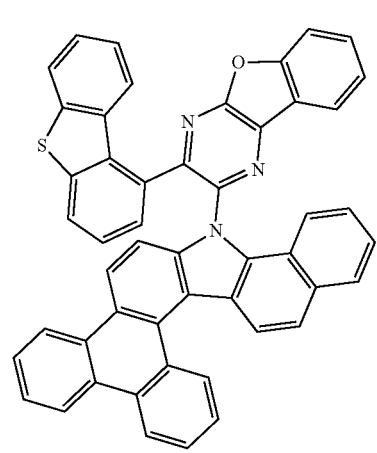
180
-continued
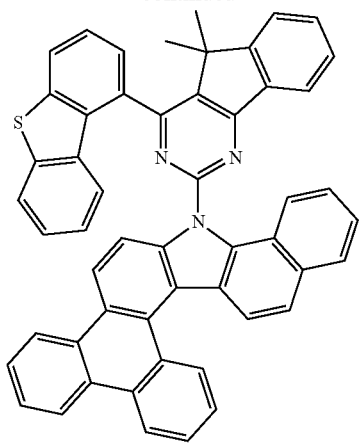
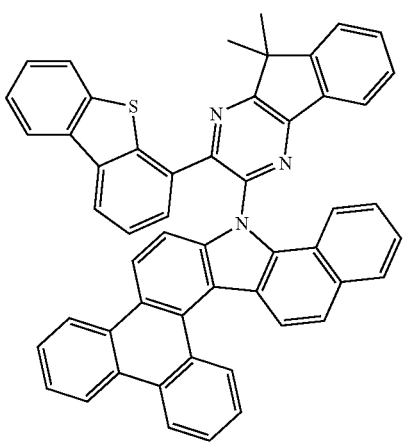
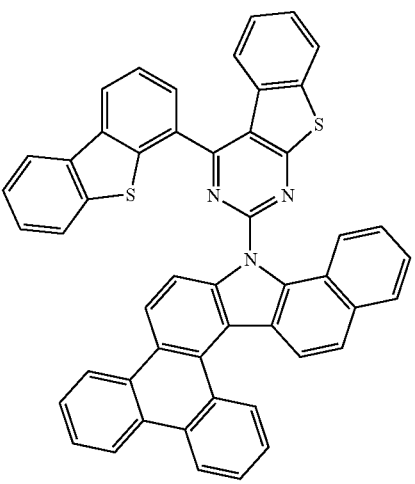

181
-continued
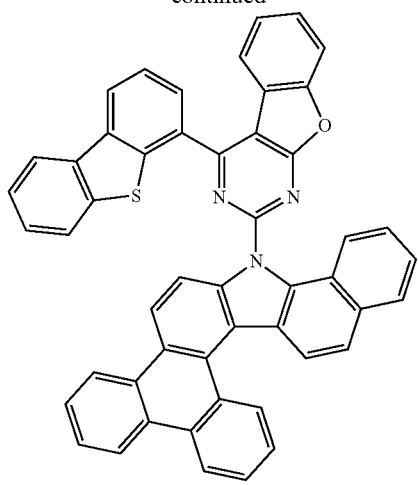
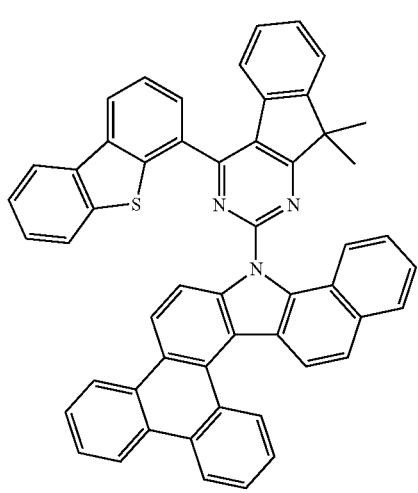
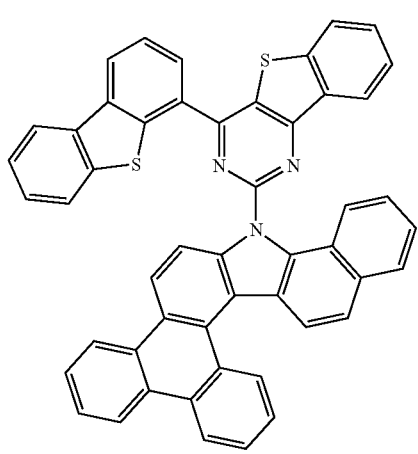
182
-continued
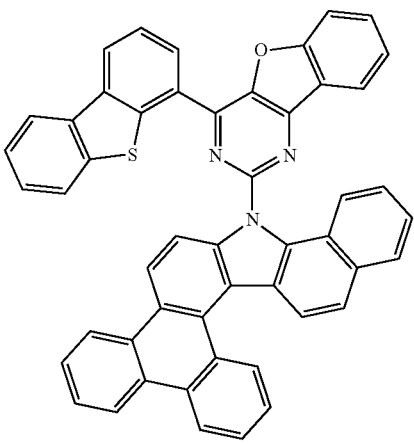
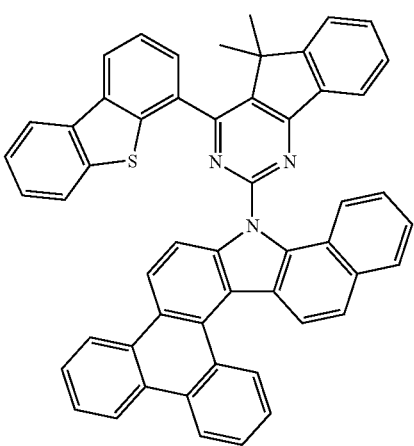
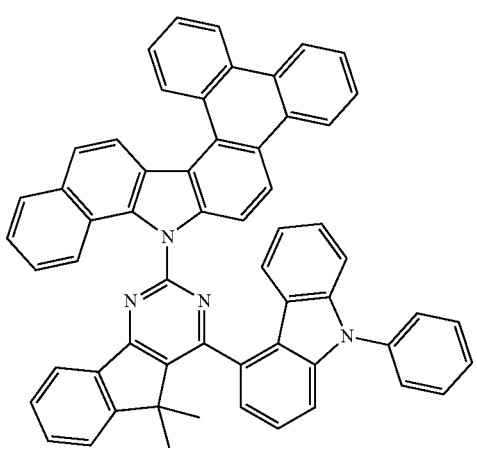

183
-continued
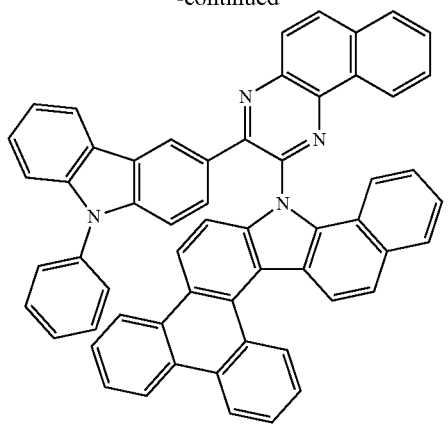
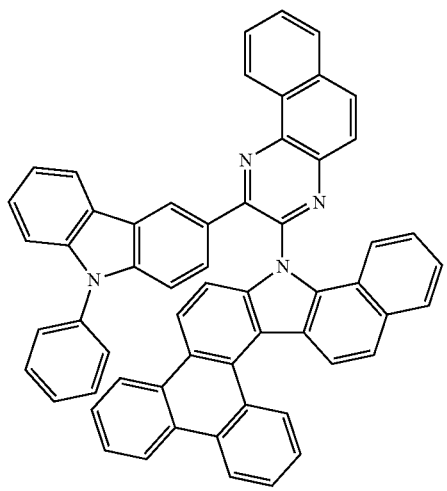
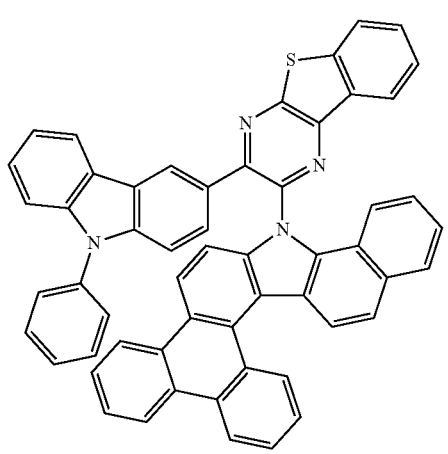
184
-continued
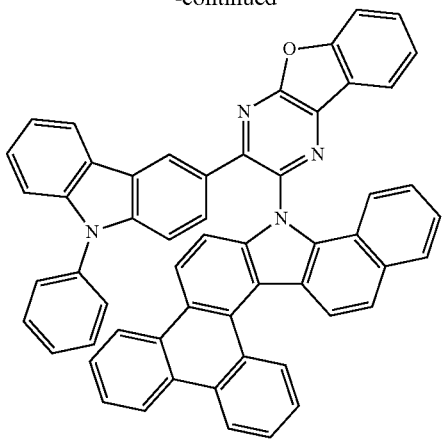
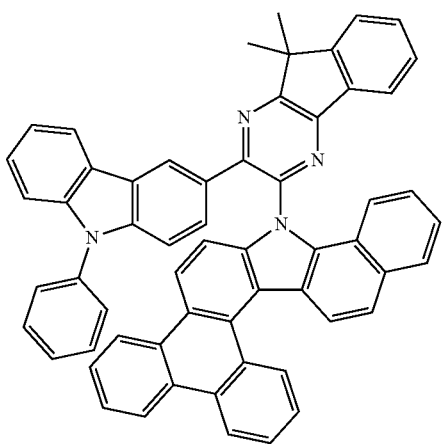
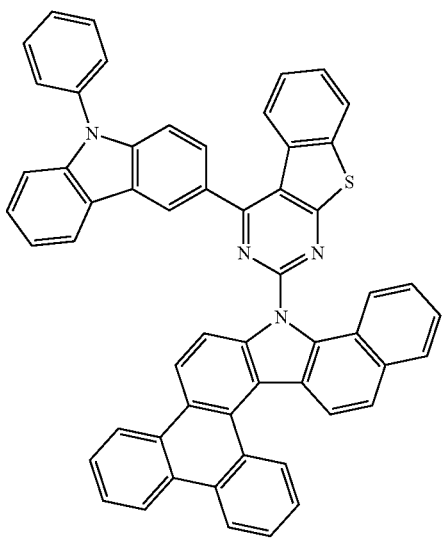

185
-continued
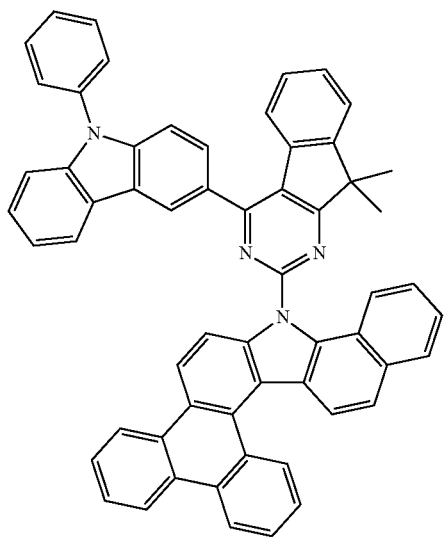
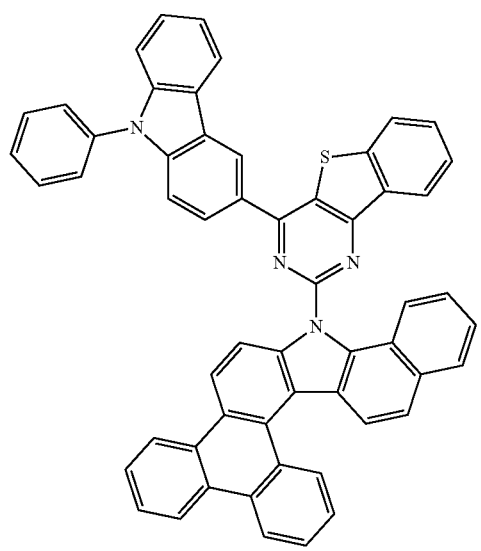
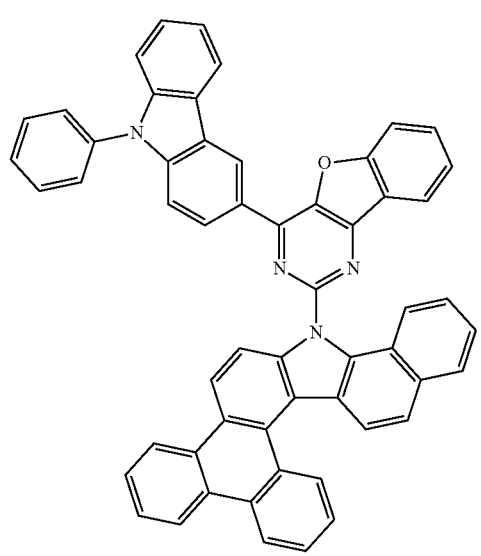
186
-continued
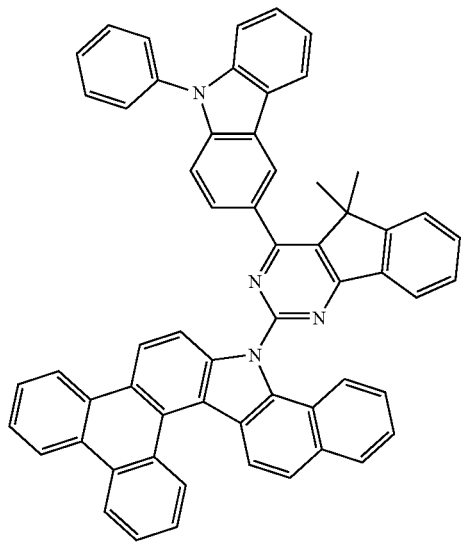
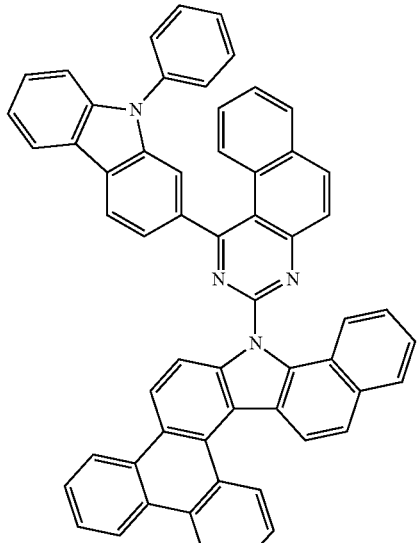
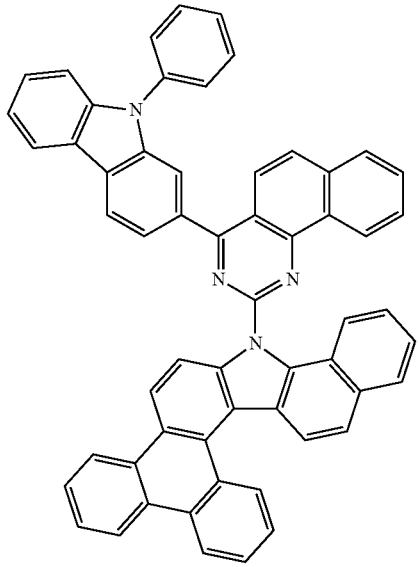

187
-continued
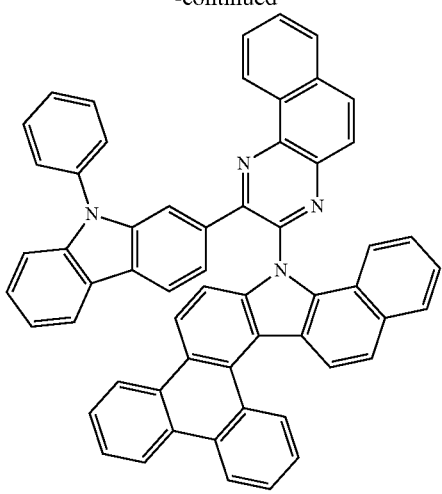
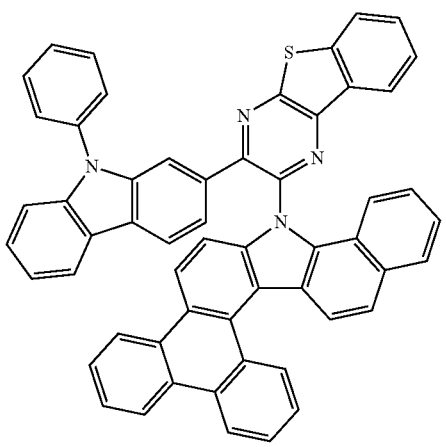
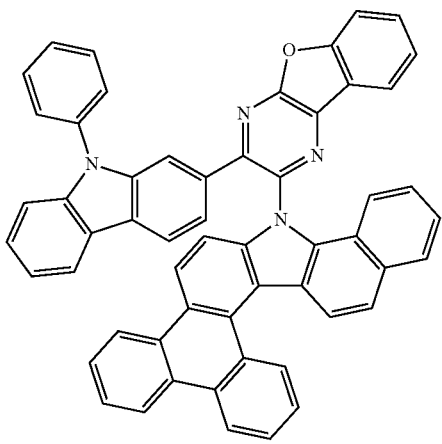
188
-continued
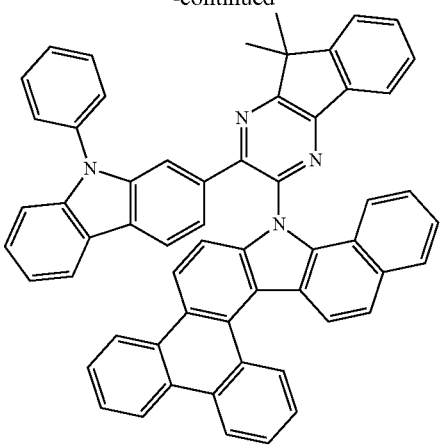
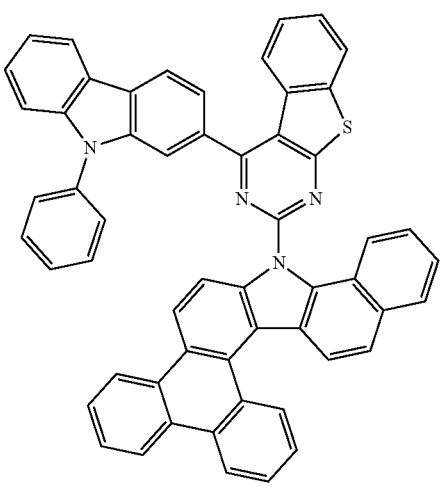
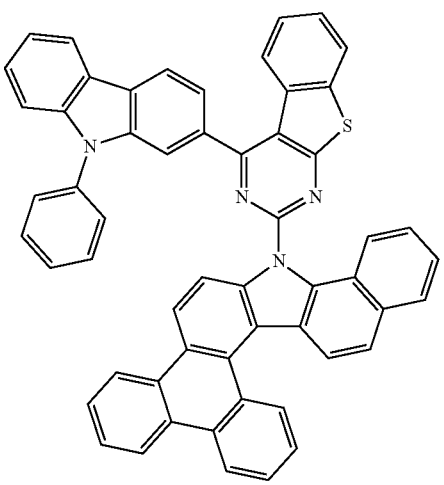

189
-continued
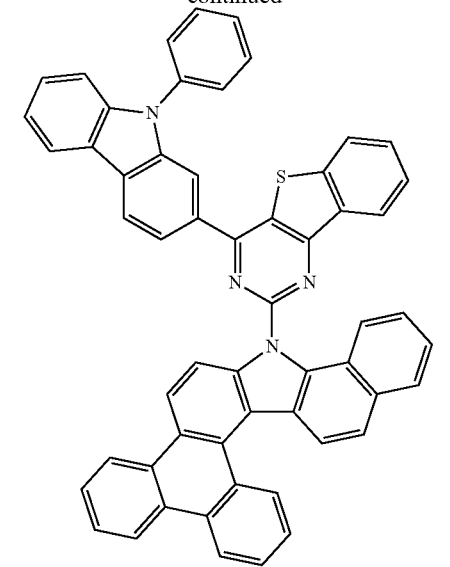
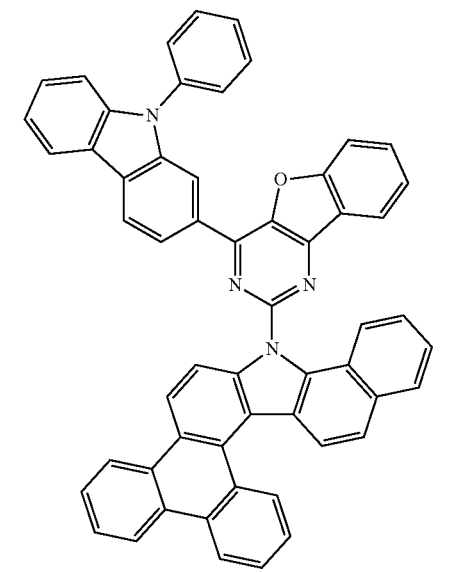
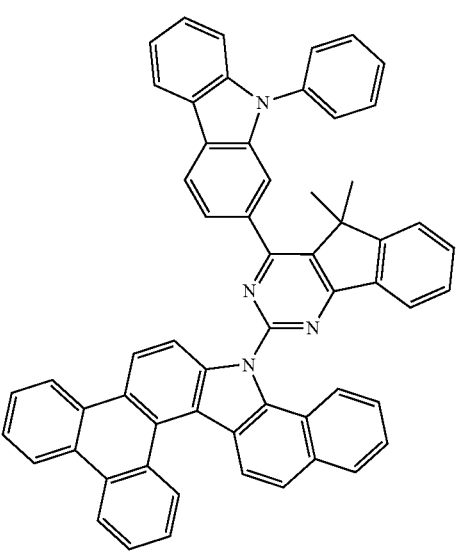
190
-continued
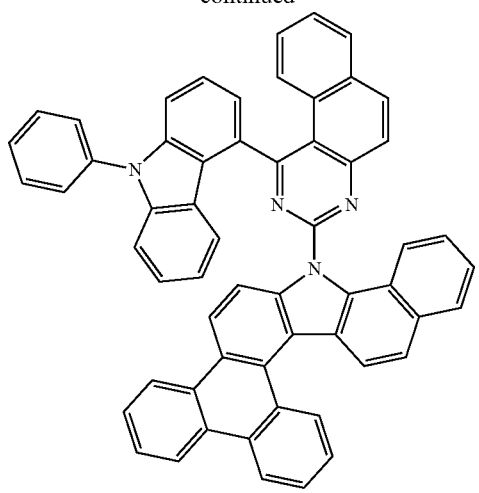
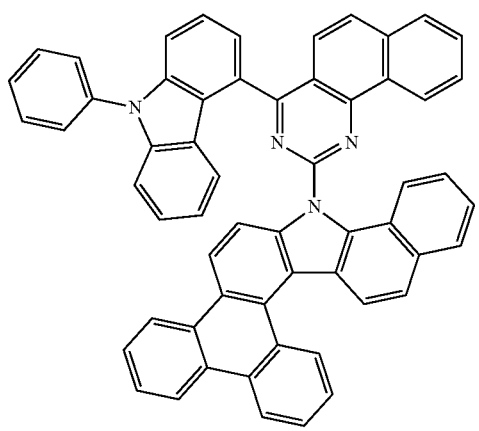
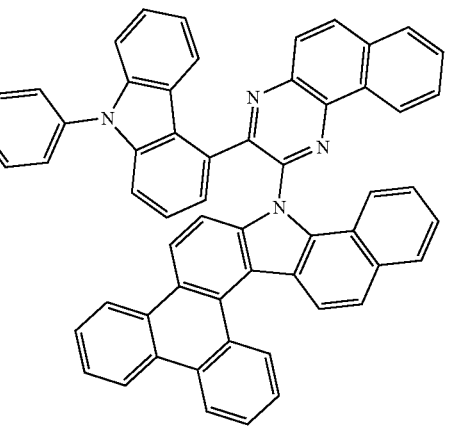

191
-continued
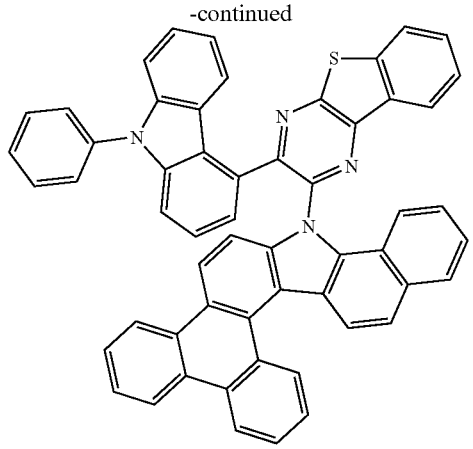
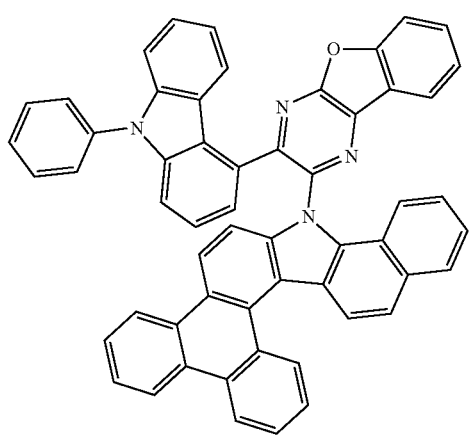
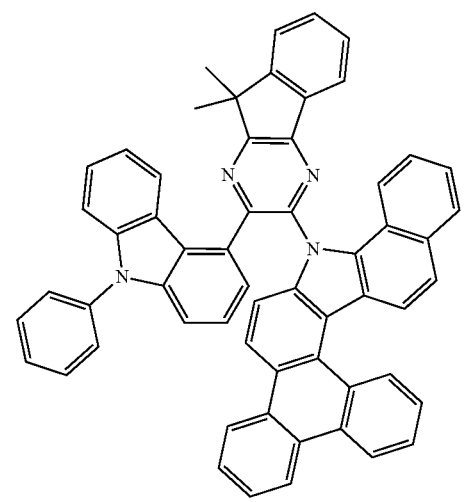
192
-continued
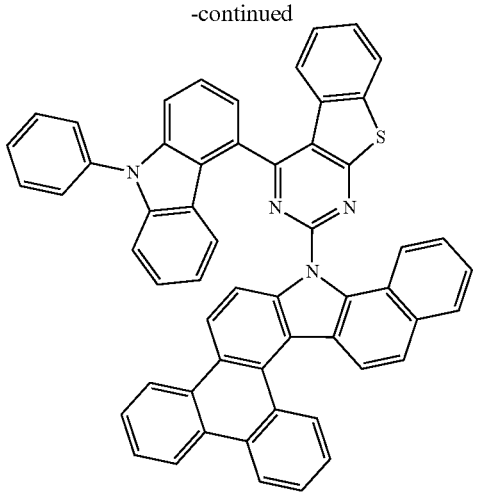
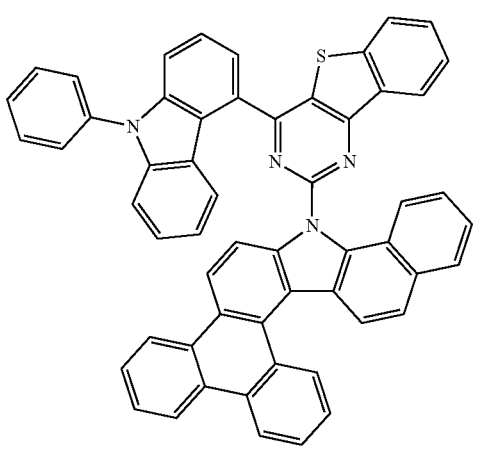
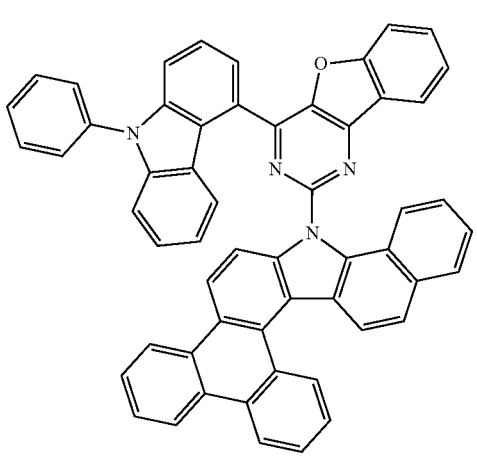

193
-continued

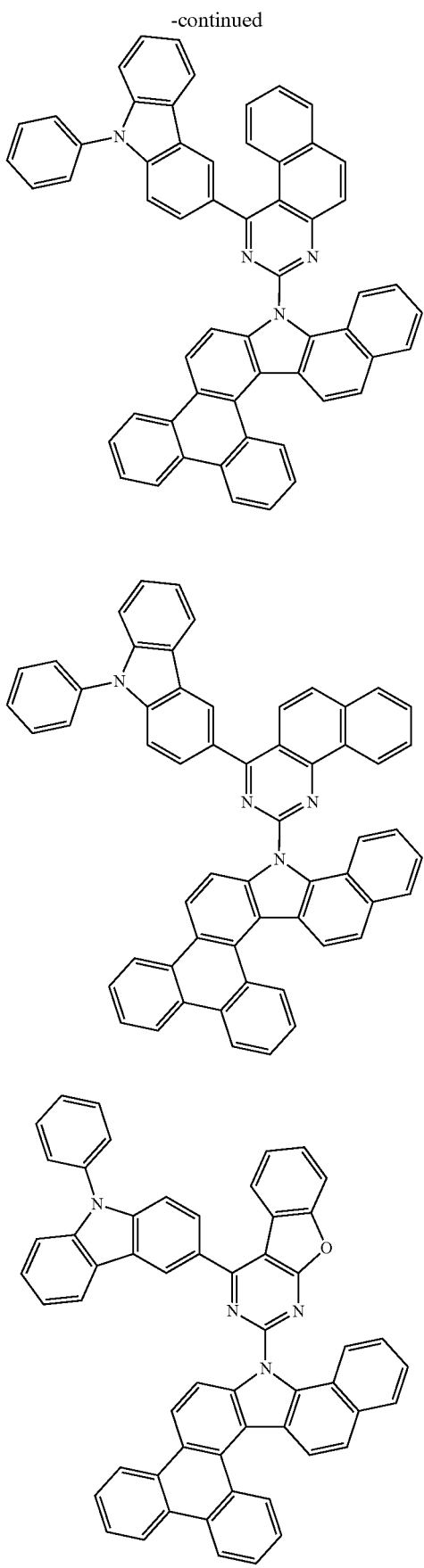

194
-continued

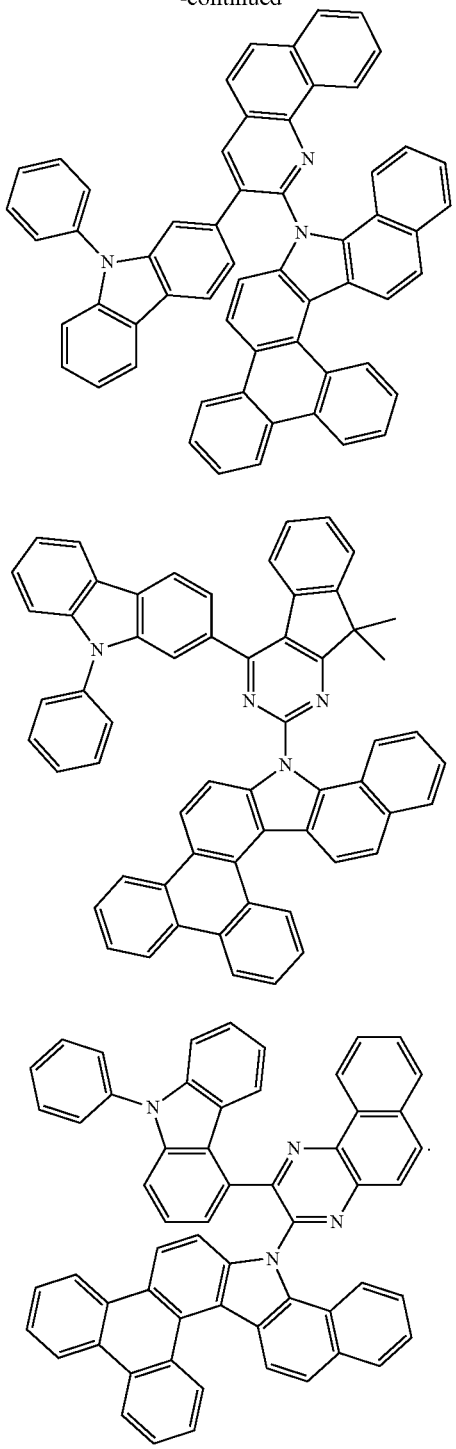

One embodiment of the present specification provides an organic light emitting device including a first electrode; a second electrode provided opposite to the first electrode; and one, two or more organic material layers provided between the first electrode and the second electrode, wherein one or more layers of the organic material layers include the heterocyclic compound.

According to one embodiment of the present disclosure, the organic material layer includes a light emitting layer, and the light emitting layer includes the heterocyclic compound.

According to one embodiment of the present disclosure, the organic material layer includes a light emitting layer, and the light emitting layer includes the heterocyclic compound as a host.

According to one embodiment of the present disclosure, the organic material layer includes a light emitting layer, and the light emitting layer includes the heterocyclic compound as a red host.

According to one embodiment of the present disclosure, the light emitting layer further includes a dopant.

According to one embodiment of the present disclosure, the light emitting layer includes a metal complex as the dopant.

According to one embodiment of the present disclosure, the light emitting layer includes an iridium-based complex as the dopant.

According to one embodiment of the present disclosure, the light emitting layer includes any one of the following compounds as the dopant:

Dp-1

Dp-2

Dp-3

Dp-4

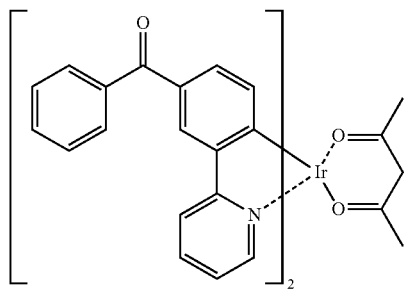

Dp-5

Dp-6

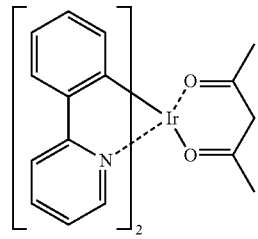

Dp-7

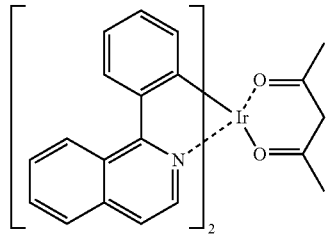

Dp-8

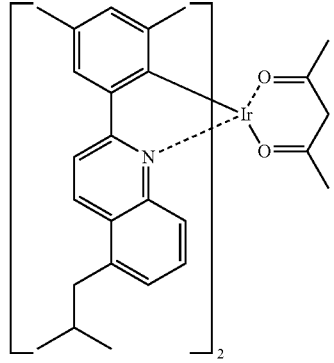

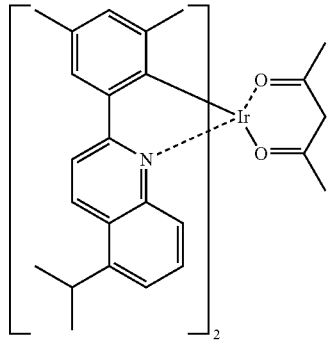

Dp-9
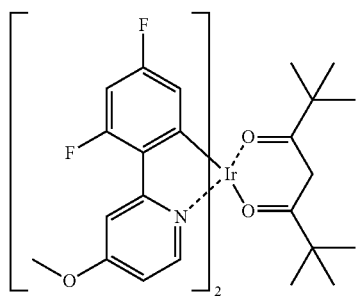
Dp-10
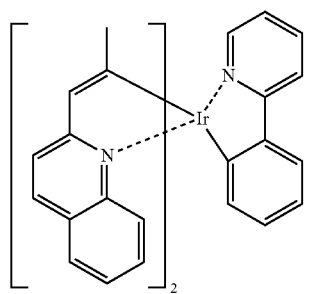
Dp-11
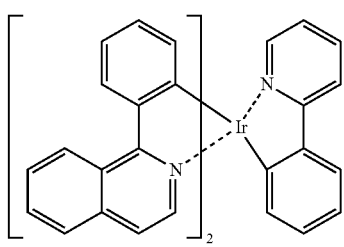
Dp-12
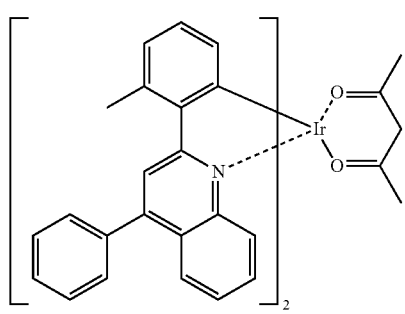
Dp-13
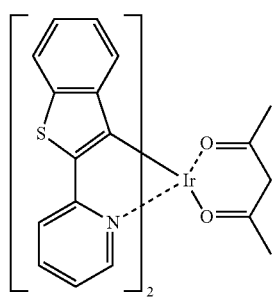
Dp-14
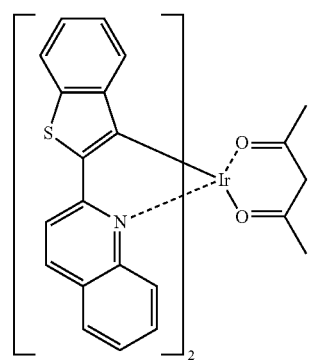
Dp-15
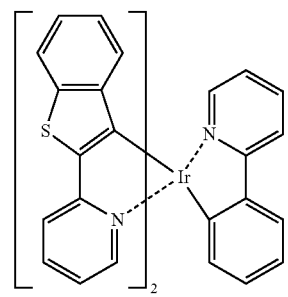
Dp-16
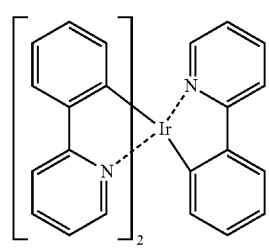
Dp-17
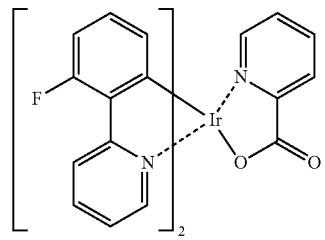
Dp-18
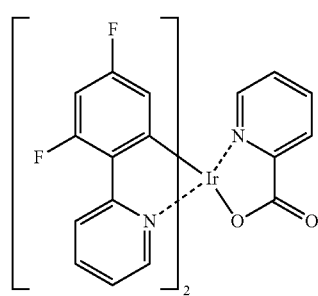

Dp-19
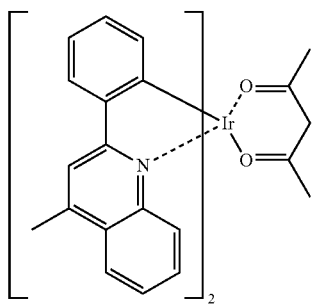
Dp-20
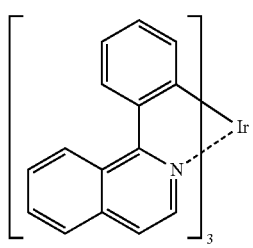
Dp-21
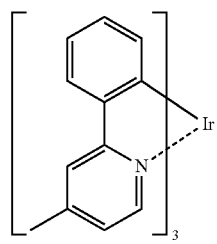
Dp-22
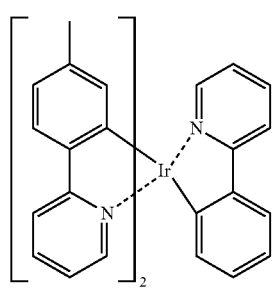
Dp-23
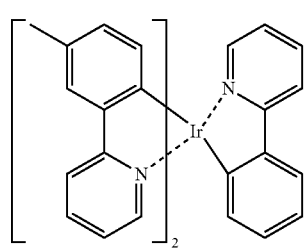
Dp-24
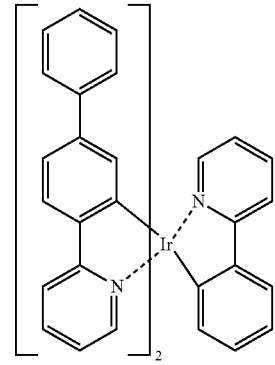
Dp-25
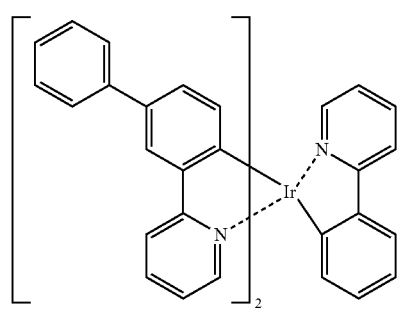
Dp-26
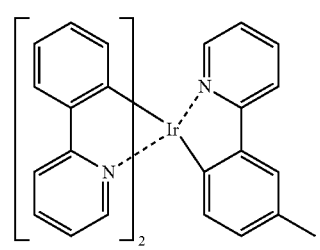
Dp-27
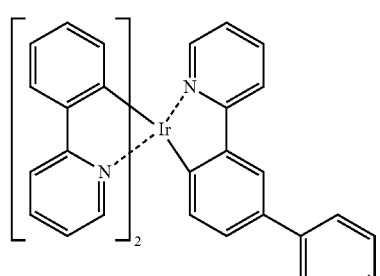
Dp-28
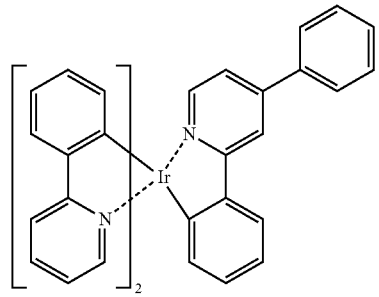

Dp-29
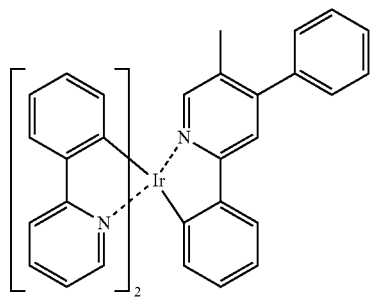
Dp-30
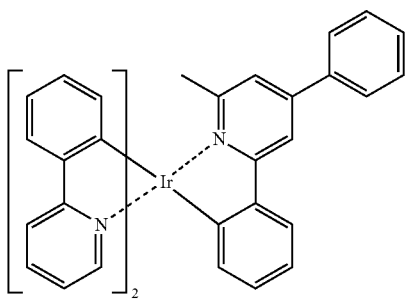
Dp-31
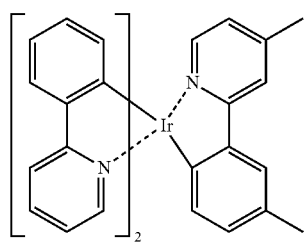
Dp-32
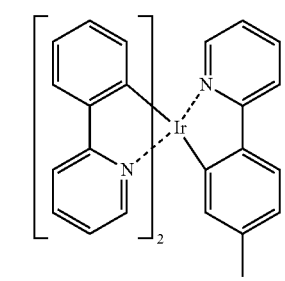
Dp-33
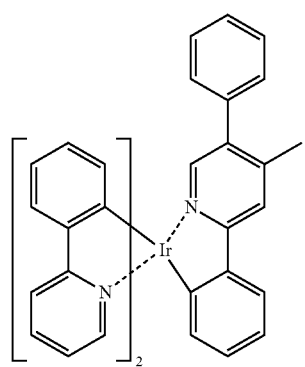
Dp-34
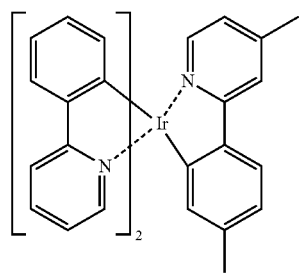
Dp-35
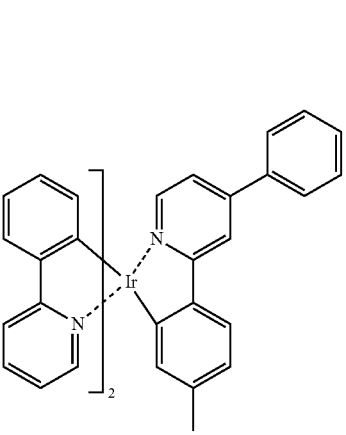
Dp-36
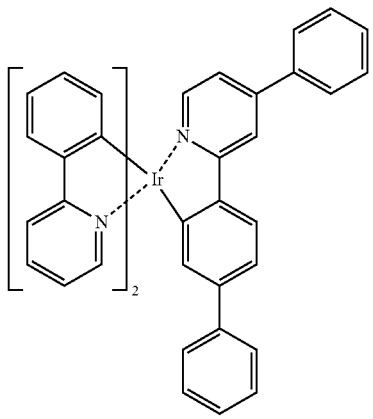
Dp-37
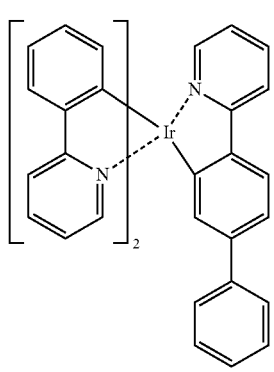

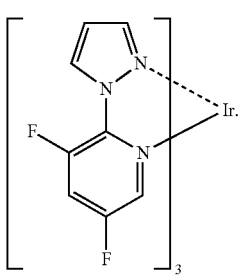

Dp-38

According to one embodiment of the present disclosure, the light emitting layer includes the host and the dopant in a weight ratio of 1:99 to 99:1.

According to one embodiment of the present disclosure, the light emitting layer includes the host and the dopant in a weight ratio of 50:50 to 99:1.

According to one embodiment of the present disclosure, the light emitting layer includes the host and the dopant in a weight ratio of 80:20 to 99:1.

According to one embodiment of the present disclosure, the light emitting layer includes the host and the dopant in a weight ratio of 90:10 to 99:1.

According to one embodiment of the present disclosure, the organic material layer includes an electron injection layer, an electron transfer layer, or an electron injection and transfer layer, and the electron injection layer, the electron transfer layer, or the electron injection and transfer layer includes the heterocyclic compound.

According to one embodiment of the present disclosure, the organic material layer includes a hole injection layer, a hole transfer layer, or a hole injection and transfer layer, and the hole injection layer, the hole transfer layer, or the hole injection and transfer layer includes the heterocyclic compound.

According to one embodiment of the present disclosure, the organic material layer includes an electron blocking layer or a hole blocking layer, and the electron blocking layer or the hole blocking layer includes the heterocyclic compound.

For example, the organic light emitting device of the present disclosure can have structures as illustrated in FIGS. 1 and 2, however, the structure is not limited thereto.

FIG. 1 illustrates a structure of the organic light emitting device in which a first electrode (2), an organic material layer (3) and a second electrode (4) are consecutively laminated on a substrate (1).

FIG. 2 illustrates a structure of the organic light emitting device in which a first electrode (2), a hole injection layer (5), a hole transfer layer (6), an electron blocking layer (7), a light emitting layer (8), a hole blocking layer (9), an electron injection and transfer layer (10) and a second electrode (4) are consecutively laminated on a substrate (1).

FIG. 2 illustrates the organic light emitting device, and the structure is not limited thereto, and additional organic material layers can be further included between each layer.

For example, the organic light emitting device according to the present disclosure can be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer or an electron transfer layer and an organic material layer including the heterocyclic compound of Chemical Formula 1 thereon, and then depositing a material usable as a cathode thereon. In addition to such a method, the organic light emitting device can also be manufactured by consecutively depositing a cathode material, an organic material layer and an anode material on a substrate.

As the anode material, materials having large work function are normally preferred so that hole injection to an organic material layer is smooth. Specific examples of the anode material usable in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is a material favorably receiving holes from an anode at a low voltage, and the highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, polyaniline, and polycompound-based conductive polymers, and the like, but are not limited thereto.

The hole transfer material is a material capable of receiving holes from an anode or a hole injection layer, moving the holes to a light emitting layer, and materials having high mobility for the holes are suited. Specific examples thereof include arylamine-based organic materials, conductive polymers, block copolymers having conjugated parts and non-conjugated parts together, and the like, but are not limited thereto.

The light emitting material is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

When the organic light emitting device includes a plurality of organic material layers, the organic material layers can be formed with materials the same as or different from each other.

The organic light emitting device of the present specification can be manufactured using materials and methods known in the art, except that one of more layers of the organic material layers are formed using the heterocyclic compound.

The dopant material can include aromatic heterocyclic compounds, styrylamine compounds, boron complexes, fluoranthene compounds, metal complexes and the like. Specifically, the aromatic heterocyclic compound is a fused aromatic ring derivative having a substituted or unsubstituted arylamino group, and arylamino group-including pyrene, anthracene, chrysene, periflanthene and the like can be included. The styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group can be substituted or unsubstituted. Specifically, styrylamine, styryldiamine, styryltriamine, styryltetramine and the like can be included, however, the styrylamine compound is not limited thereto. As the metal complex, iridium complexes, platinum complexes and the like can be included, however, the metal complex is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including $Alq_3$; organic radical compounds; hydroxyflavon-metal complexes, and the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and as the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxy-quinolinato lithium, bis(8-hydroxyquinolinato)zinc, bis(8-hydroxyquinolinato) copper, bis(8-hydroxyquinolinato)-manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)-beryllium, bis(10-hydroxybenzo[h]quinolinato)zinc, bis(2-methyl-8-quinolinato)chlorogallium, bis(2-methyl-8-quinolinato) (o-cresolato) gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and can be generally formed under the same condition as the hole injection layer. Specific examples thereof can include oxadiazole derivatives, triazole derivatives, phenanthroline derivatives, BCP, aluminum complexes and the like, but are not limited thereto.

The organic light emitting device according to the present specification can be a top-emission type, a bottom-emission type or a dual-emission type depending on the materials used.

EXAMPLES

The compounds of the present disclosure were prepared using, as a representative reaction, a Buchwald-Hartwig coupling reaction, a Suzuki coupling reaction or the like.

The following is a preparation example for a representative structure in the disclosure of the present specification, and by varying substituents, all the compounds of the present specification can be prepared.

Preparation Example 1

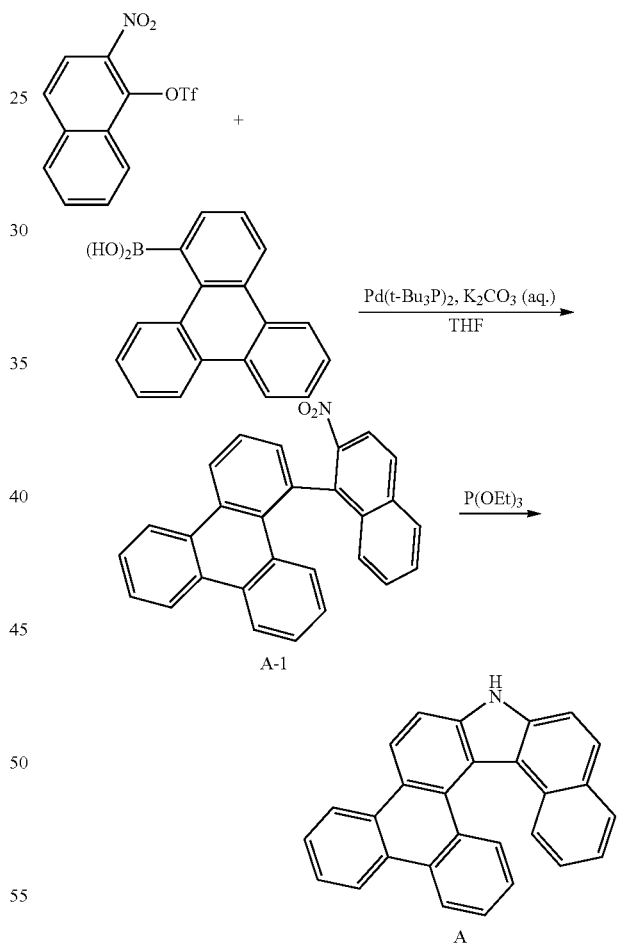

After dissolving 2-nitronaphthalen-1-yl trifluoromethane sulfonate (100.0 g, 1.0 eq.) and triphenylen-1-ylboronic acid (93.17 g, 1.1 eq.) in tetrahydrofuran (THF) (1000 ml), $K_2CO_3$ (86.05 g, 2.0 eq.) dissolved in water (300 ml) was introduced thereto. $Pd(t-Bu_3P)_2$ (1.59 g, 0.005 eq.) was introduced thereto, and the result was stirred under reflux. When the reaction was finished, the result was vacuumed to remove the solvent. After that, the result was completely dissolved in $CHCl_3$, washed with water, and treated with anhydrous magnesium sulfate. The result was vacuumed again to remove the solvent, and the result was column chromatographed to obtain Compound A-1 (88.28 g, yield 71%). [M+H]=400

Compound A-1 (88.28 g, 1.0 eq.) was introduced to triethylphosphite (200 mL), and the result was stirred under reflux. The reaction was terminated after 2 hours, and the reaction material was poured into ethanol (2 L) to precipitate solids. These solids were completely dissolved in CHCl₃, washed with water, and treated with anhydrous magnesium sulfate. The solution was vacuum concentrated and purified using column chromatography to obtain Compound A (49.37 g, yield 61%). [M+H]=218

Preparation Example 2

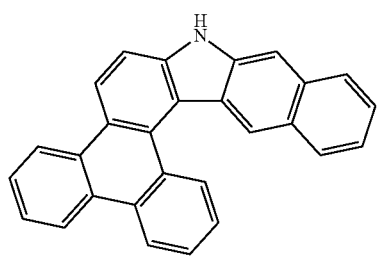

B

Compound B was synthesized in the same manner as in the method for preparing Compound A except that 3-nitronaphthalen-2-yl trifluoromethane sulfonate was used instead of 2-nitronaphthalen-1-yl trifluoromethane sulfonate in Preparation Example 1.

Preparation Example 3

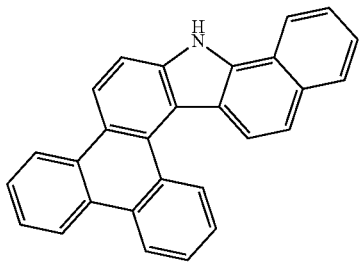

C

Compound C was synthesized in the same manner as in the method for preparing Compound A except that 3-1-nitronaphthalen-2-yl trifluoromethane sulfonate was used instead of 2-nitronaphthalen-1-yl trifluoromethane sulfonate in Preparation Example 1.

Synthesis Example

Synthesis Example 1

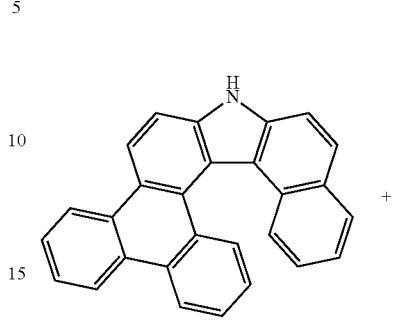

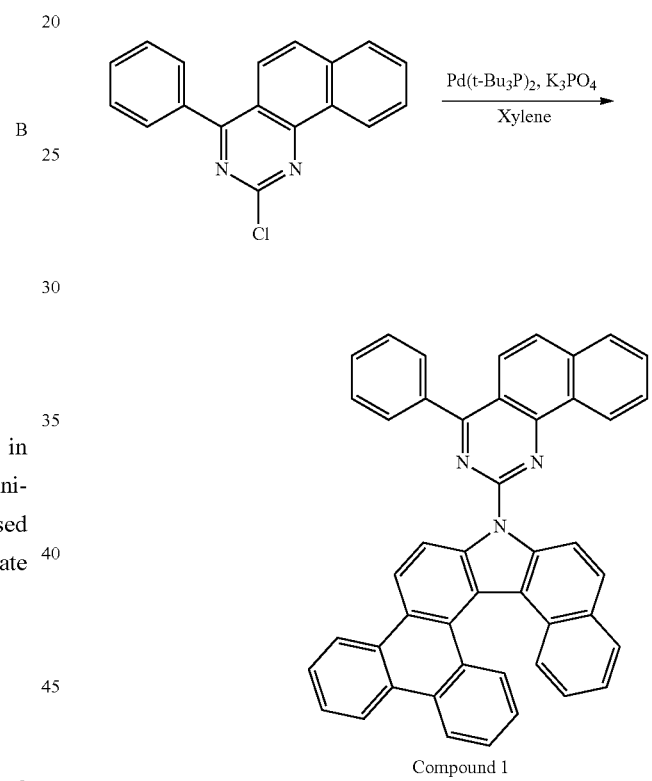

Compound 1

Compound A (10.0 g, 1.0 eq.), 2-chloro-4-phenylbenzo[h]quinazoline (8.73 g, 1.1 eq.), Pd(t-Bu₃P)₂(0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 1 (12.35 g, yield 73%). [M+H]=622

Synthesis Example 2

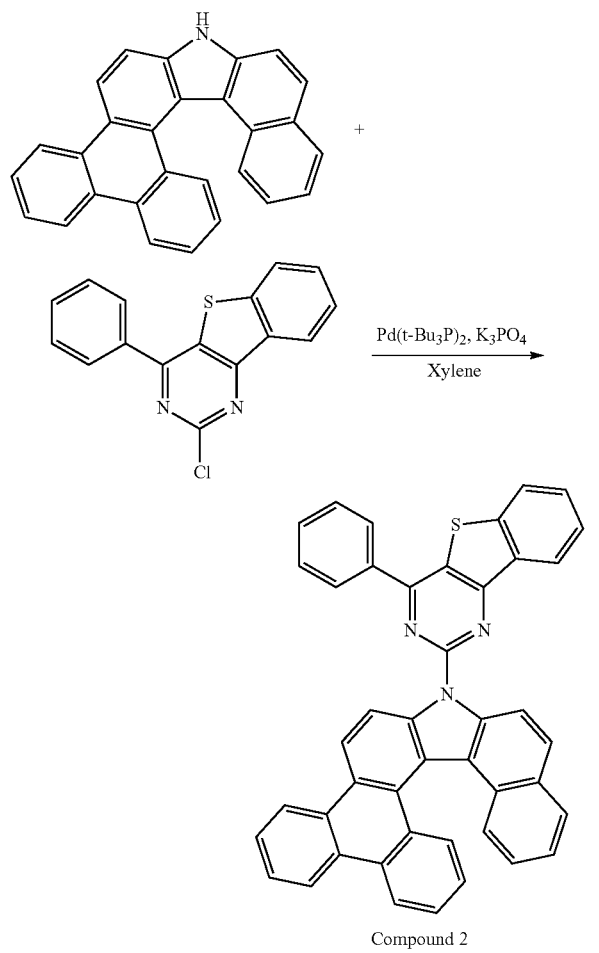

Compound 2

Compound A (10.0 g, 1.0 eq.), 2-chloro-4-phenylbenzo[4,5]thieno[3,2-d]pyrimidine (8.88 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 2 (10.42 g, yield 61%). [M+H]=628

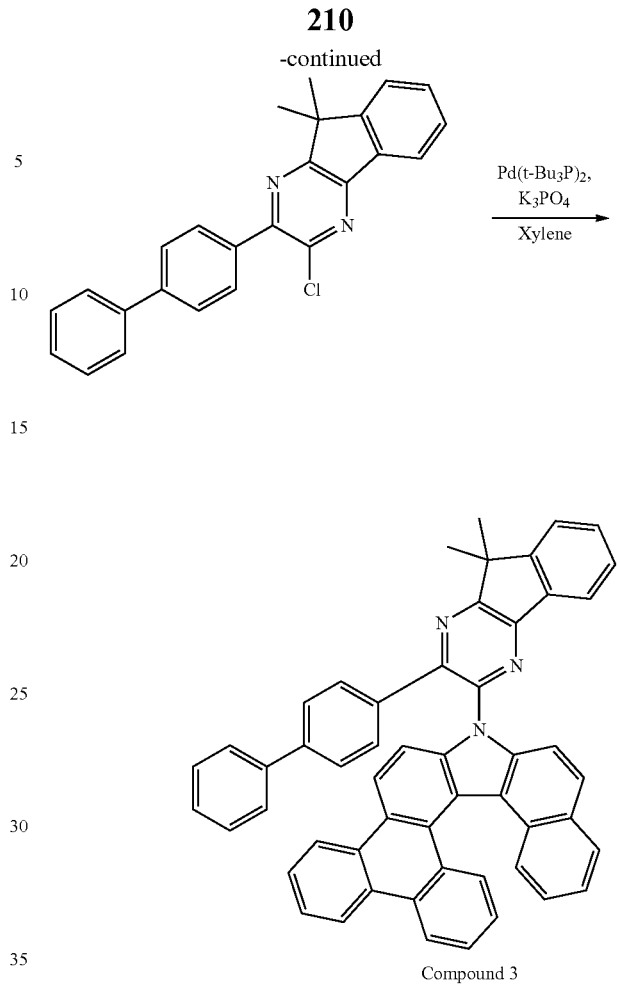

Compound 3

Compound A (10.0 g, 1.0 eq.), 2-([1,1'-biphenyl]-4-yl)-3-chloro-9,9-dimethyl-9H-indeno[1,2-b]pyrazine (11.46 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 3 (13.98 g, yield 72%). [M+H]=714

Synthesis Example 3

Synthesis Example 4

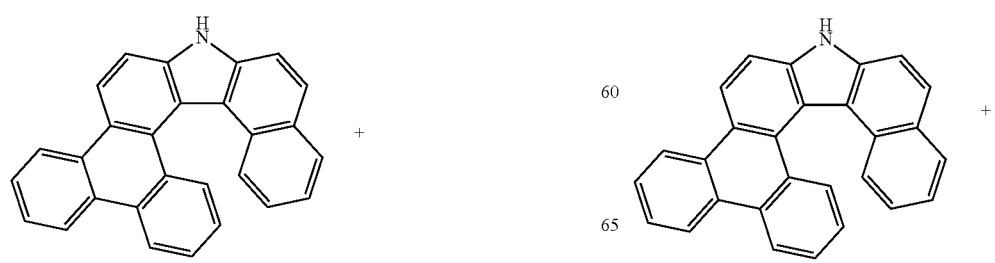

211

-continued

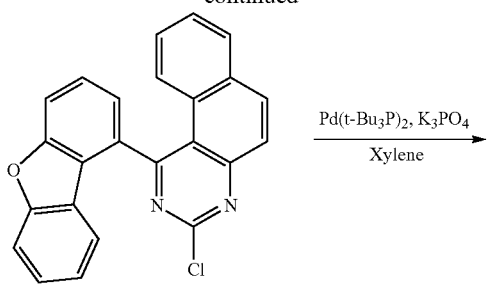

212

-continued

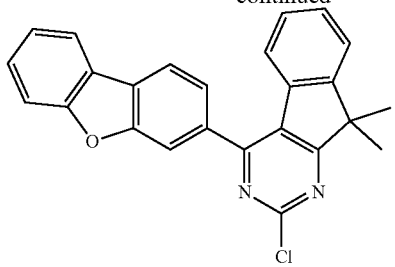

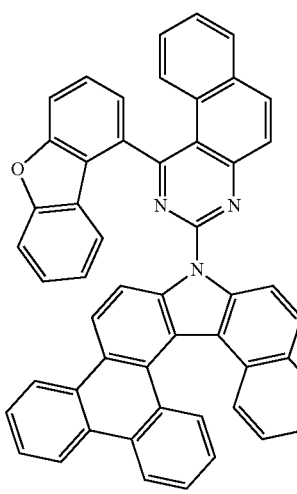

Compound 4

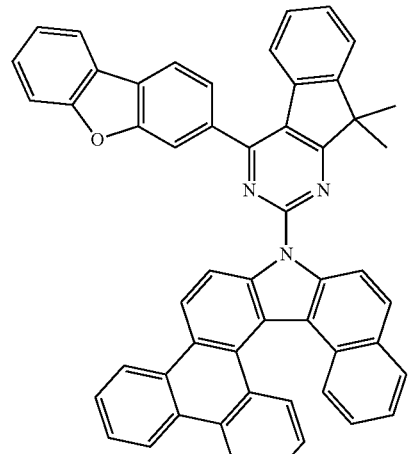

Compound 5

Compound A (10.0 g, 1.0 eq.), 3-chloro-1-(dibenzo[b,d]furan-1-yl)benzo[f]quinazoline (11.40 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 4 (13.17 g, yield 68%). [M+H]=712

Synthesis Example 5

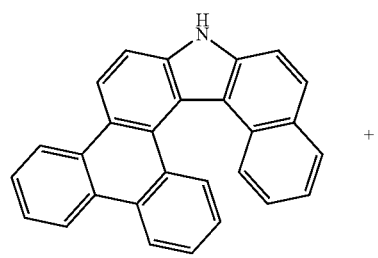 +

Compound A (10.0 g, 1.0 eq.), 2-chloro-4-(dibenzo[b,d]furan-3-yl)-9,9-dimethyl-9H-indeno[2,1-d]pyrimidine (11.88 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 5 (12.87 g, yield 65%). [M+H]=728

Synthesis Example 6

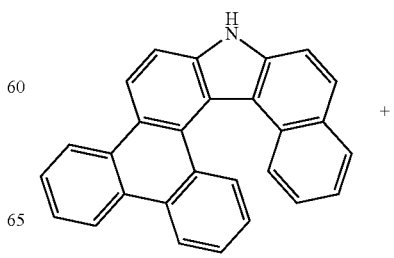 +

213
-continued

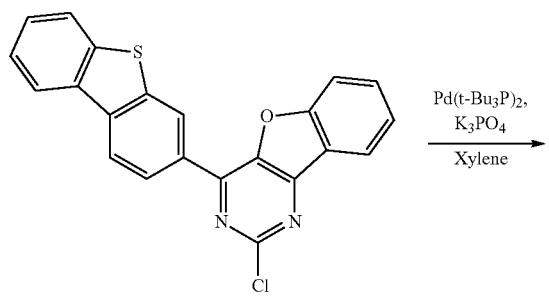

214
-continued

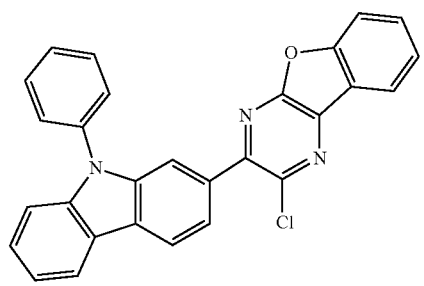

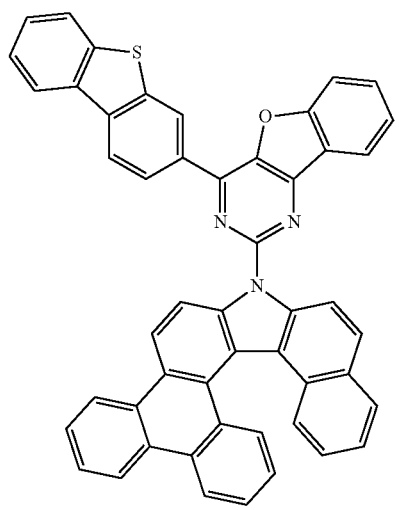

Compound 6

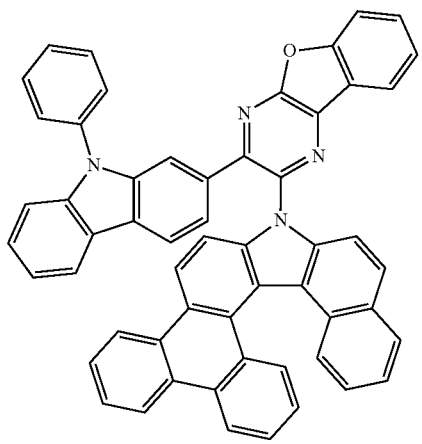

Compound 7

Compound A (10.0 g, 1.0 eq.), 2-chloro-4-(dibenzo[b,d]thiophen-3-yl)benzofuro[3,2-d]pyrimidine (11.58 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 6 (13.08 g, yield 67%). [M+H]=718

Synthesis Example 7

Compound A (10.0 g, 1.0 eq.), 2-chloro-3-(9-phenyl-9H-carbazol-2-yl)benzofuro[2,3-b]pyrazine (13.34 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 7 (14.58 g, yield 69%). [M+H]=777

Synthesis Example 8

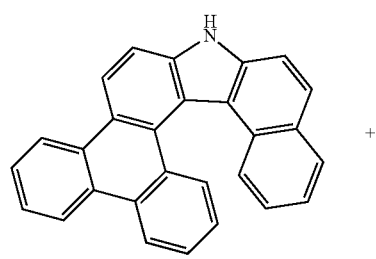

+

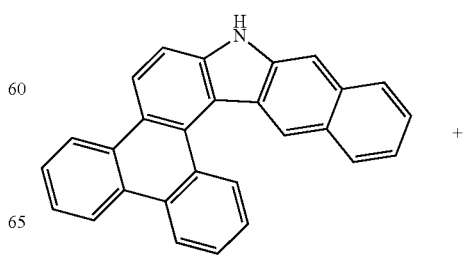

+

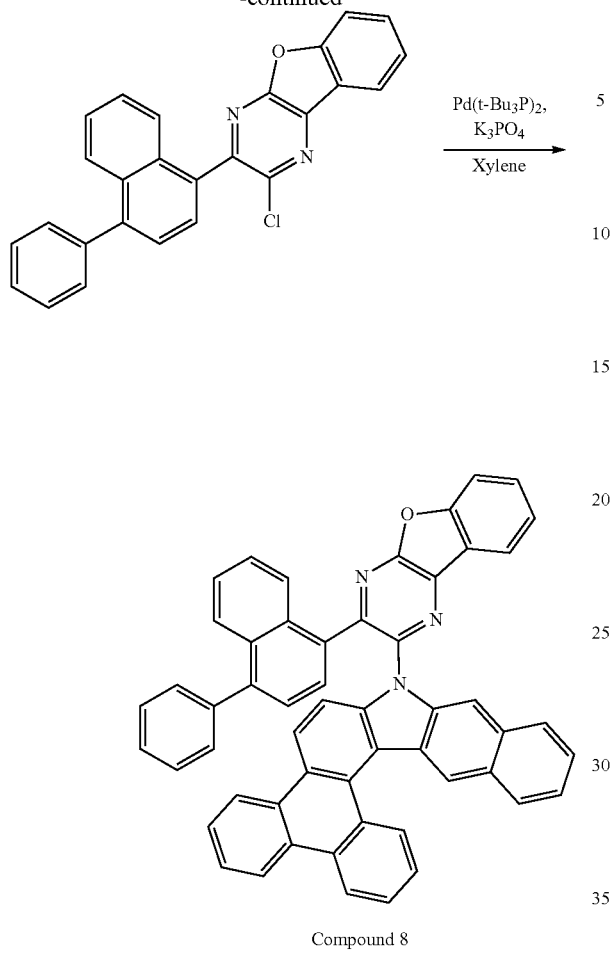

Compound 8

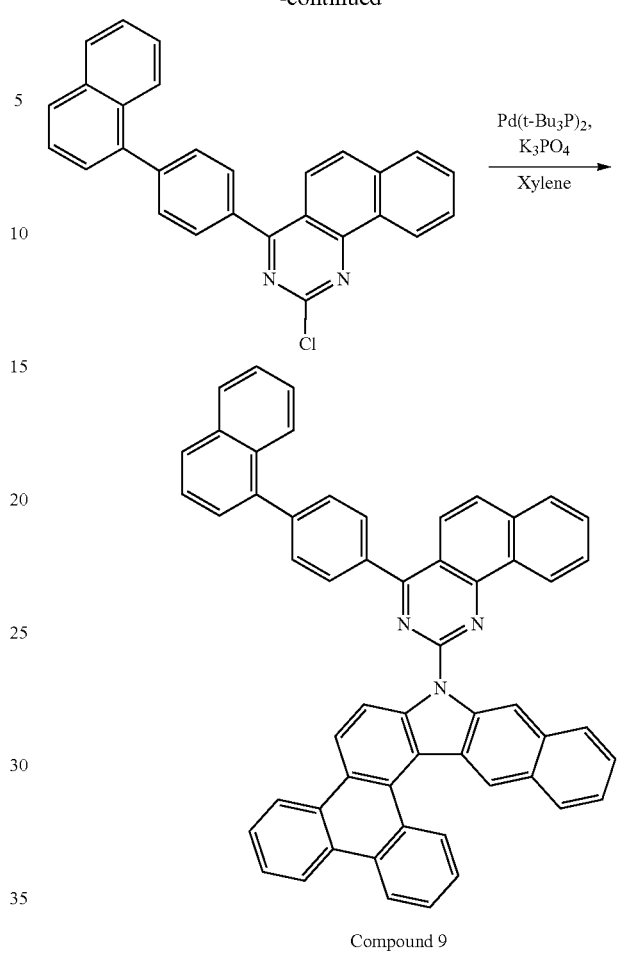

Compound 9

Compound B (10.0 g, 1.0 eq.), 2-chloro-3-(4-phenylnaphthalen-1-yl)benzofuro[2,3-b]pyrazine (12.18 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 8 (13.45 g, yield 67%). [M+H]=738

Compound B (10.0 g, 1.0 eq.), 2-chloro-4-(4-(naphthalen-1-yl)phenyl)benzo[h]quinazoline (12.48 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 9 (13.63 g, yield 61%). [M+H]=748

Synthesis Example 9

Synthesis Example 10

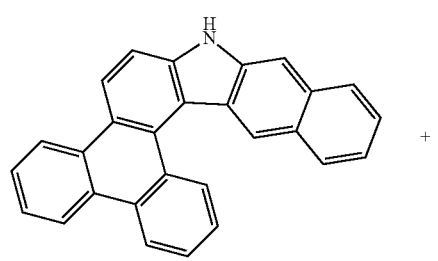

+

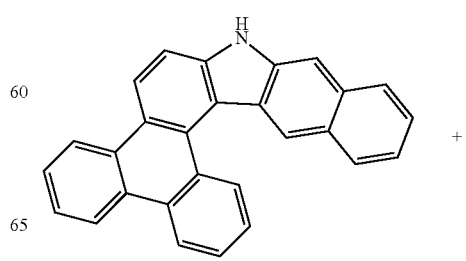

+

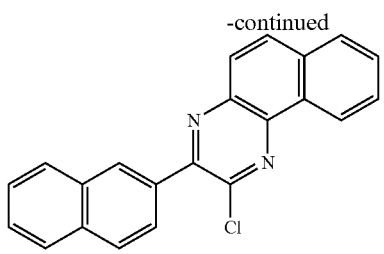

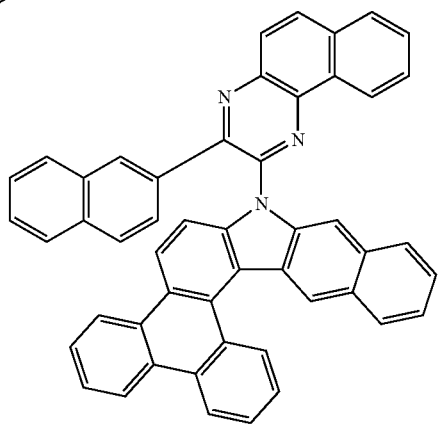

Compound 10

Compound B (10.0 g, 1.0 eq.), 2-chloro-3-(naphthalen-2-yl)benzo[f]quinoxaline (26.49 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 10 (13.34 g, yield 74%). [M+H]=672

Synthesis Example 11

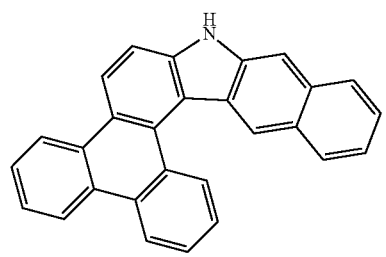

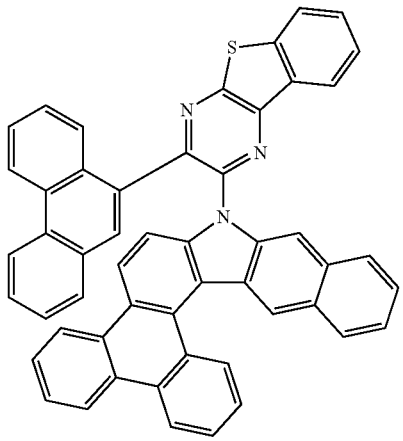

Compound 11

Compound B (10.0 g, 1.0 eq.), 2-chloro-3-(phenanthren-9-yl)benzo[4,5]thieno[2,3-b]pyrazine (11.88 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 11 (14.46 g, yield 71%). [M+H]=728

Synthesis Example 12

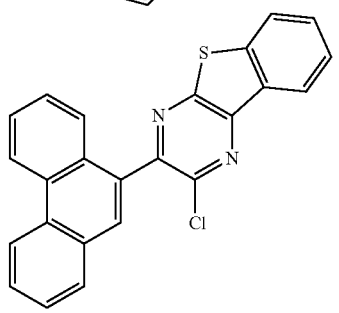

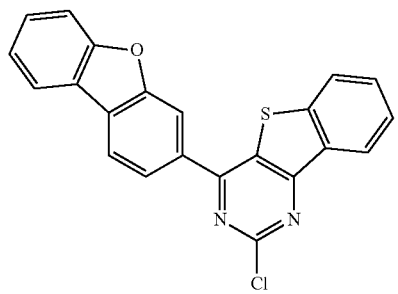

-continued

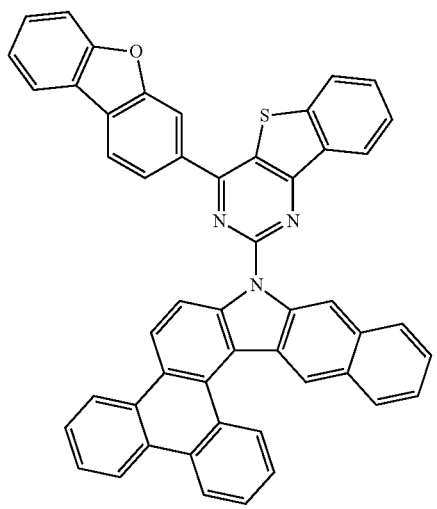

Compound 12

-continued

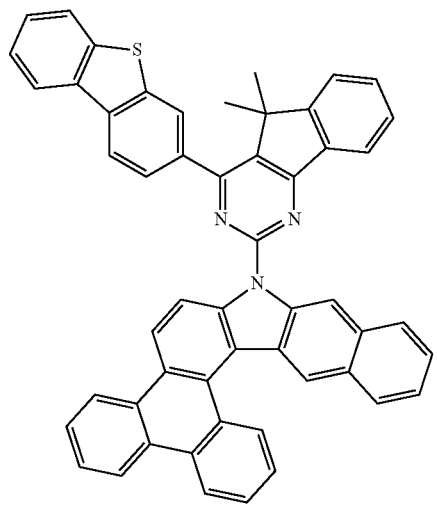

Compound 13

Compound B (10.0 g, 1.0 eq.), 2-chloro-4-(dibenzo[b,d]-furan-3-yl)benzo[4,5]thieno[3,2-d]pyrimidine (11.58 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 12 (14.45 g, yield 74%). [M+H]=718

Synthesis Example 13

Compound B (10.0 g, 1.0 eq.), 2-chloro-4-(dibenzo[b,d]-thiophen-3-yl)-5,5-dimethyl-5H-indeno[1,2-d]pyrimidine (12.36 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 13 (14.77 g, yield 73%). [M+H]=744

Synthesis Example 14

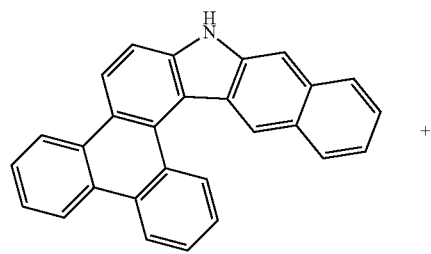

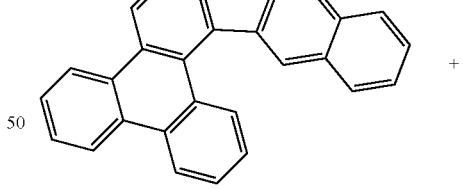

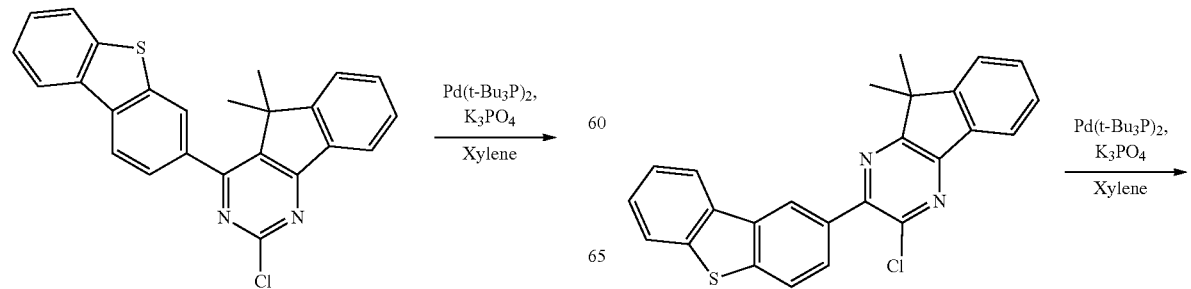

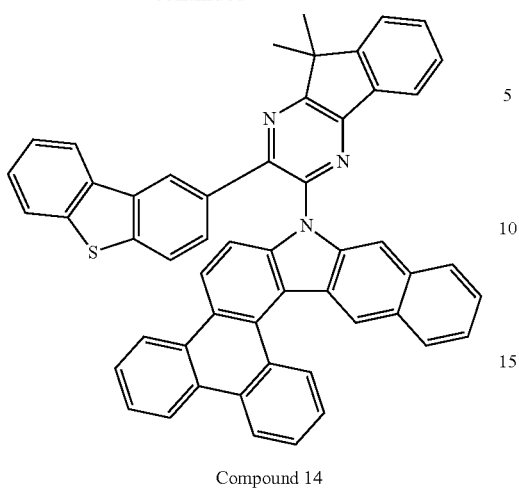

Compound 14

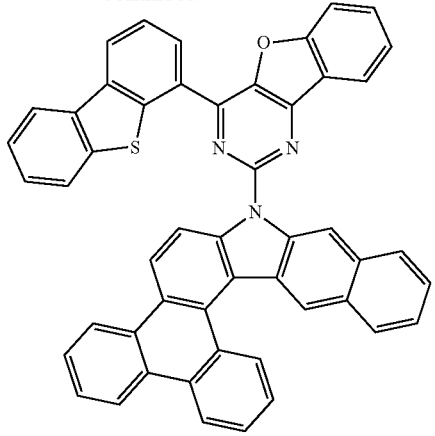

Compound 15

Compound B (10.0 g, 1.0 eq.), 3-chloro-2-(dibenzo[b,d]-thiophen-2-yl)-9,9-dimethyl-9H-indeno[1,2-b]pyrazine (12.36 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 14 (14.17 g, yield 70%). [M+H]=744

Synthesis Example 15

Compound B (10.0 g, 1.0 eq.), 2-chloro-4-(dibenzo[b,d]-thiophen-4-yl)benzofuro[3,2-d]pyrimidine (11.58 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 15 (14.26 g, yield 73%). [M+H]=718

Synthesis Example 16

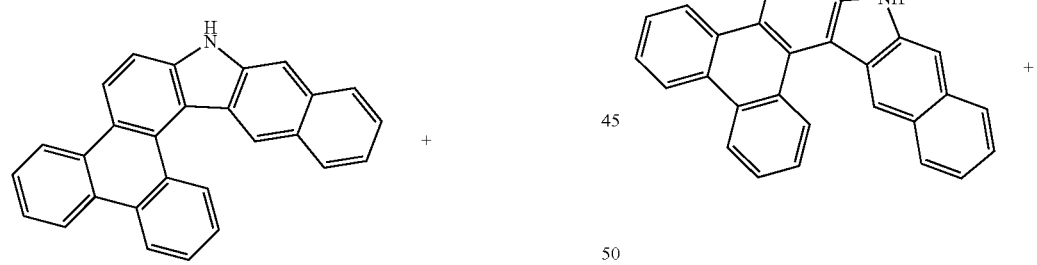

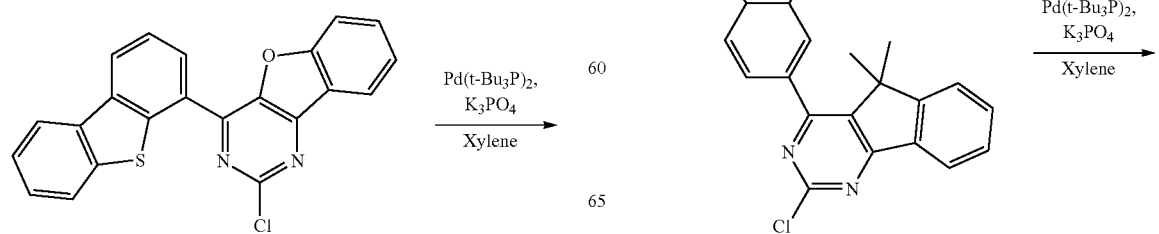

223
-continued

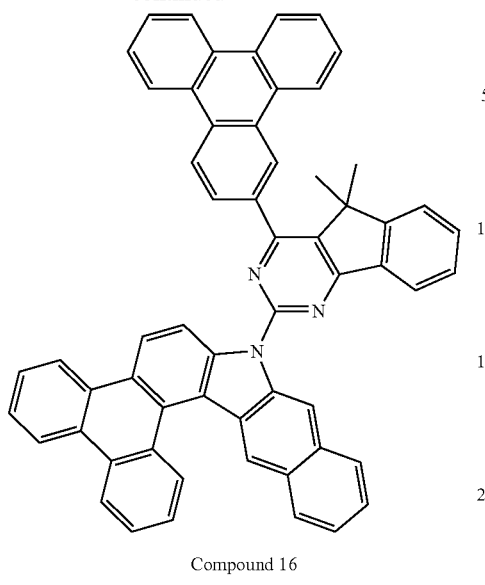

Compound 16

224
-continued

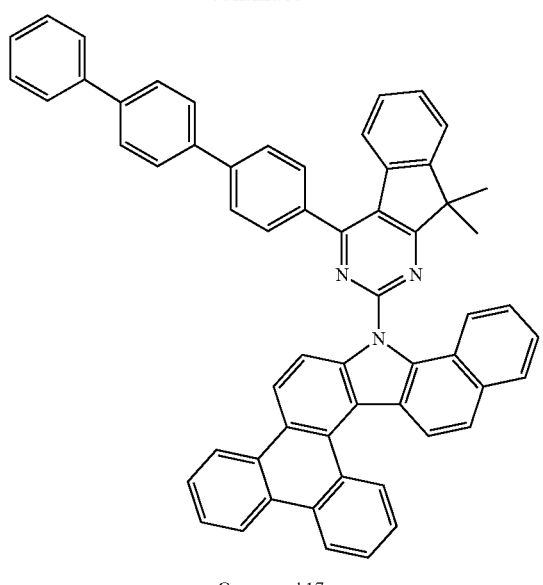

Compound 17

Compound B (10.0 g, 1.0 eq.), 2-chloro-5,5-dimethyl-4-(triphenylen-2-yl)-5H-indeno[1,2-d]pyrimidine (13.67 g, 1.1 eq.), Pd(t-Bu$_3$P)$_2$ (0.13 g, 0.01 eq.) and K$_3$PO$_4$ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl$_3$, washed with water, and vacuumed again to remove approximately 50% of the solvent. Under reflux again, crystals were precipitated while adding ethyl acetate thereto, and cooled and then filtered. The result was column chromatographed to obtain Compound 16 (15.65 g, yield 73%). [M+H]=788

Synthesis Example 17

Compound C (10.0 g, 1.0 eq.), 4-([1,1':4',1''-terphenyl]-4-yl)-2-chloro-9,9-dimethyl-9H-indeno[2,1-d]pyrimidine (13.74 g, 1.1 eq.), Pd(t-Bu$_3$P)$_2$ (0.13 g, 0.01 eq.) and K$_3$PO$_4$ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl$_3$, washed with water, and vacuumed again to remove approximately 50% of the solvent. Under reflux again, crystals were precipitated while adding ethyl acetate thereto, and cooled and then filtered. The result was column chromatographed to obtain Compound 17 (15.26 g, yield 71%). [M+H]=790

Synthesis Example 18

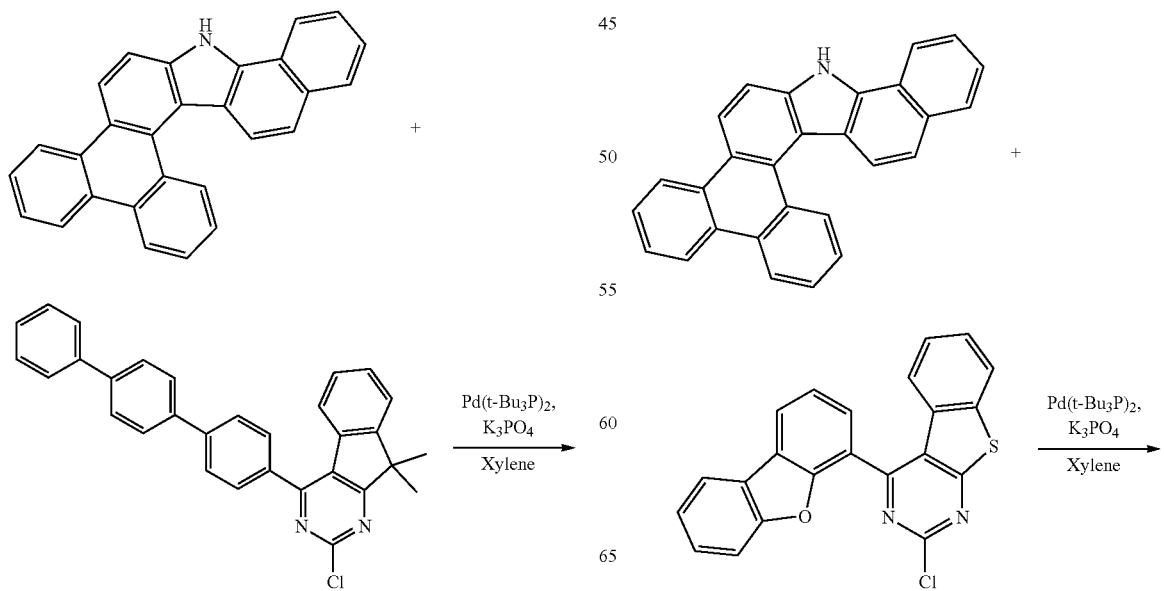

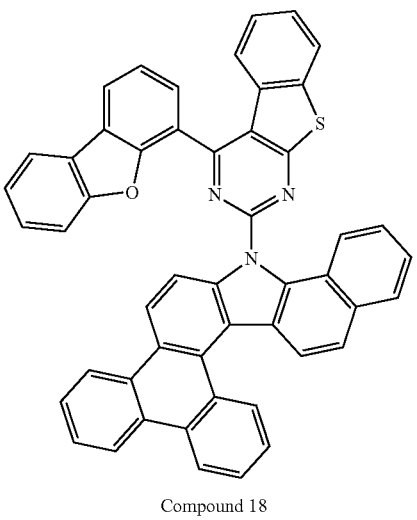

Compound 18

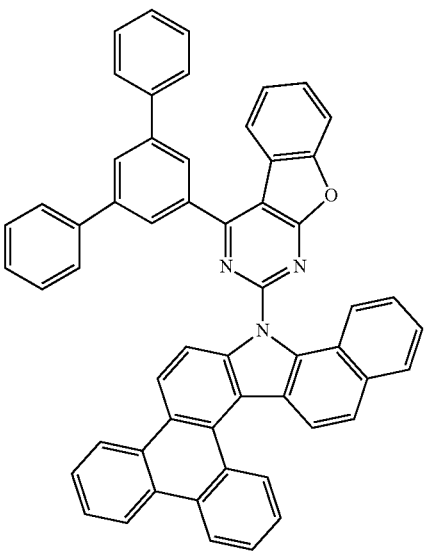

Compound 19

Compound C (10.0 g, 1.0 eq.), 2-chloro-4-(dibenzo[b,d]-furan-4-yl)benzo[4,5]thieno[2,3-d]pyrimidine (11.58 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 18 (12.11 g, yield 62%). [M+H]=718

Synthesis Example 19

Compound C (10.0 g, 1.0 eq.), 4-([1,1':3',1''-terphenyl]-5'-yl)-2-chlorobenzofuro[2,3-d]pyrimidine (12.95 g, 1.1 eq.), Pd(t-Bu₃P)₂ (0.13 g, 0.01 eq.) and K₃PO₄ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl₃, washed with water, and vacuumed again to remove approximately 50% of the solvent. Under reflux again, crystals were precipitated while adding ethyl acetate thereto, and cooled and then filtered. The result was column chromatographed to obtain Compound 19 (15.17 g, yield 73%). [M+H]=764

Synthesis Example 20

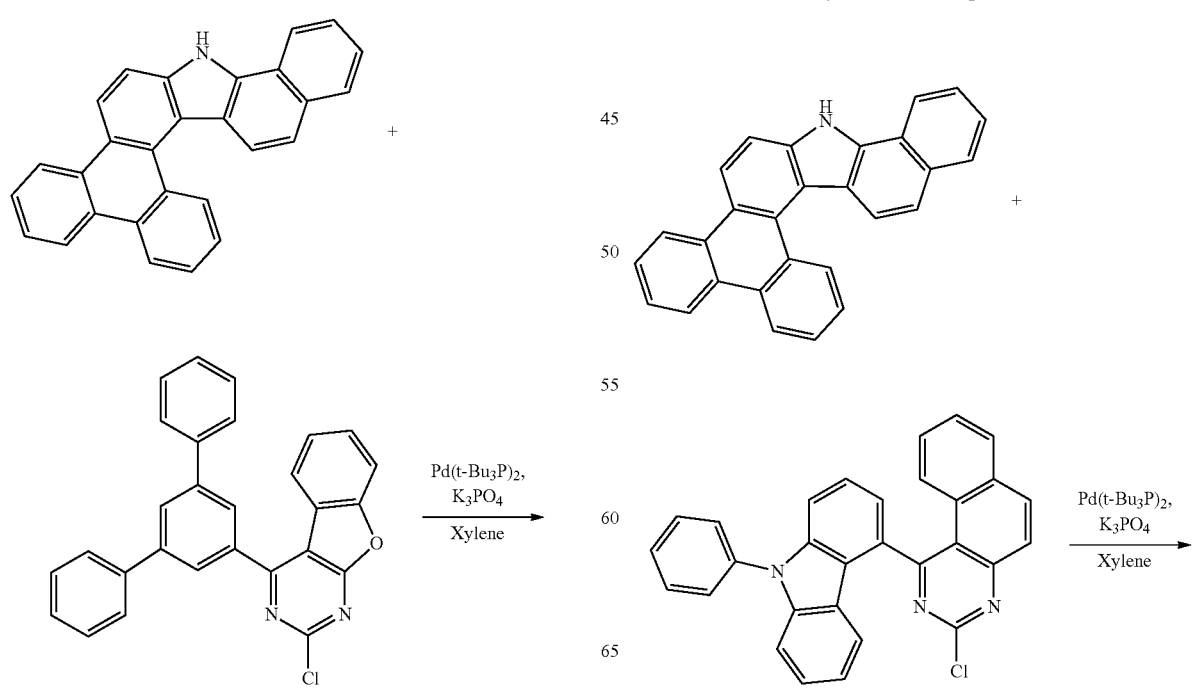

-continued

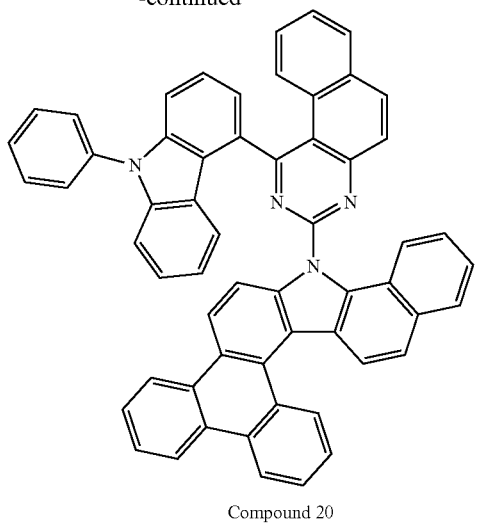

Compound 20

Compound C (10.0 g, 1.0 eq.), 3-chloro-1-(9-phenyl-9H-carbazol-4-yl)benzo[f]quinazoline (13.64 g, 1.1 eq.), Pd(t-Bu$_3$P)$_2$ (0.13 g, 0.01 eq.) and K$_3$PO$_4$ (11.55 g, 2.0 eq.) were introduced to xylene (250 ml), and the result was stirred under reflux. When the reaction was terminated after 2 hours, the result was vacuumed to remove the solvent. After that, the result was completely dissolved in CHCl$_3$, washed with water, and vacuumed again to remove approximately 50% of the solvent. Under reflux again, crystals were precipitated while adding ethyl acetate thereto, and cooled and then filtered. The result was column chromatographed to obtain Compound 20 (14.99 g, yield 70%). [M+H]=787

Experimental Example

Comparative Example 1

A glass substrate on which indium tin oxide (ITO) was coated as a thin film to a thickness of 1,000 Å was placed in distilled water in which detergent was dissolved and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum depositor.

On the transparent ITO electrode prepared as above, the following HI-1 compound was formed to a thickness of 1150 Å as a hole injection layer, and the following D-1 compound was p-doped thereto in a concentration of 1.5%. On the hole injection layer, a hole transfer layer having a film thickness of 800 Å was formed by vacuum depositing the following HT-1 compound. Subsequently, an electron blocking layer was formed to a film thickness of 150 Å on the hole transfer layer by vacuum depositing the following EB-1 compound. Then, a red light emitting layer having a thickness of 400 Å was formed on the EB-1 deposited film by vacuum depositing the following RH-1 compound and the following Dp-7 compound in a weight ratio of 98:2. On the light emitting layer, a hole blocking layer was famed to a film thickness of 30 Å by vacuum depositing the following HB-1 compound. Subsequently, an electron injection and transfer layer was formed to a thickness of 300 Å on the hole blocking layer by vacuum depositing the following ET-1 compound and the following LiQ compound in a weight ratio of 2:1. On the electron injection and transfer layer, a cathode was formed by consecutively depositing lithium fluoride (LiF) to a thickness of 12 Å and aluminum to a thickness of 1,000 Å.

In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at $2\times10^{-7}$ torr to $5\times10^{-6}$ torr to manufacture an organic light emitting device.

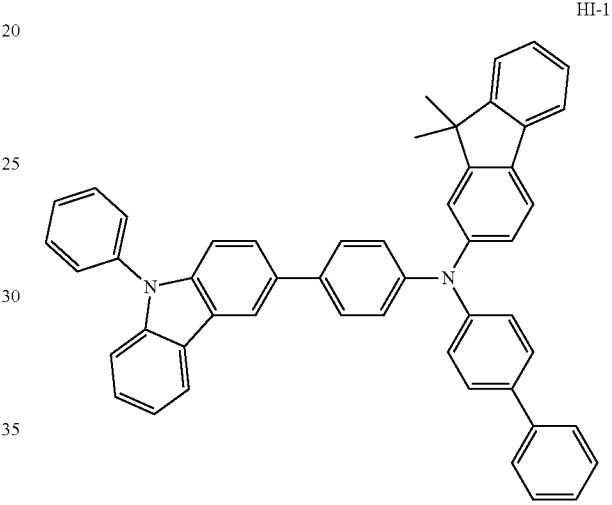

HI-1

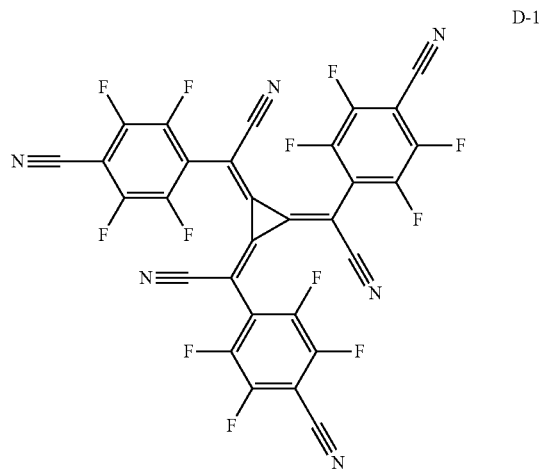

D-1

HT-1
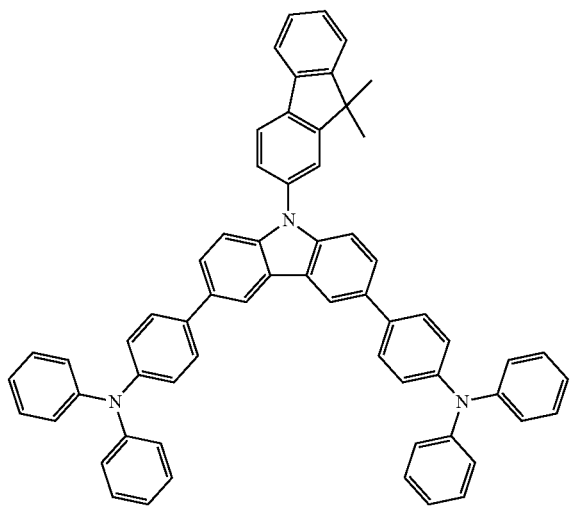
Dp-7
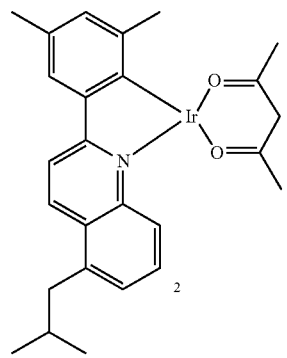
HB-1
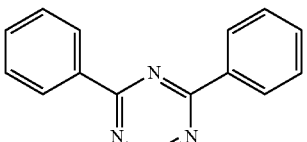
EB-1
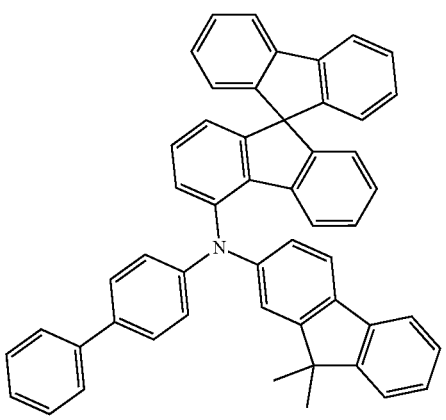
ET-1
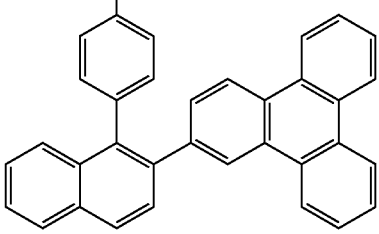
RH-1
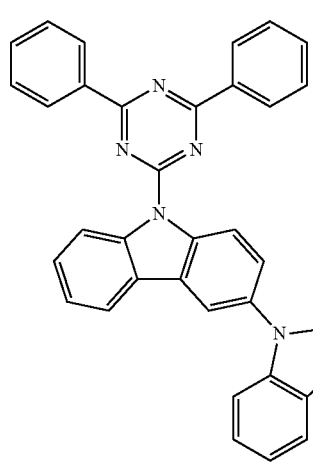
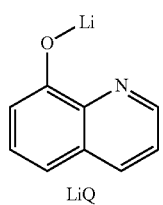
LiQ Comparative Example Compound
C-1
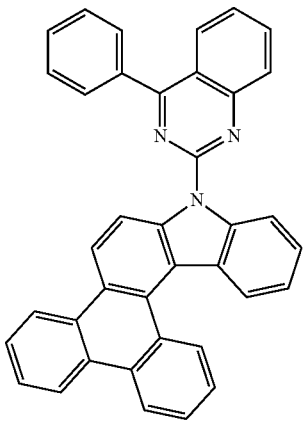
C-2
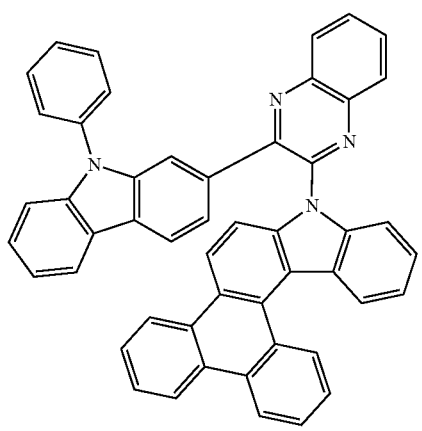
C-3
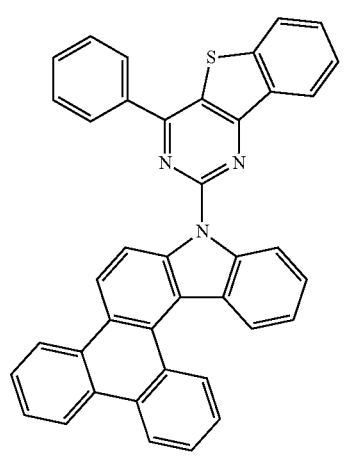
C-4
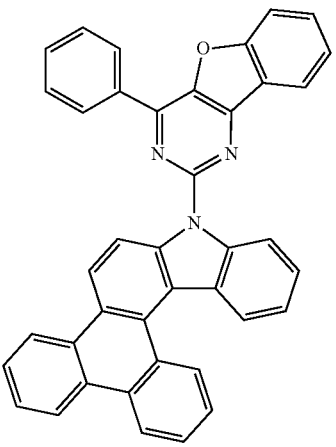
C-5
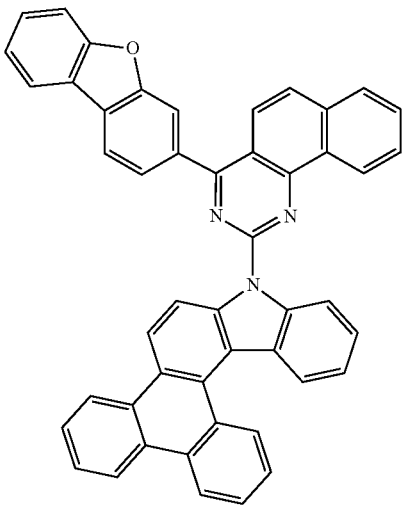
C-6
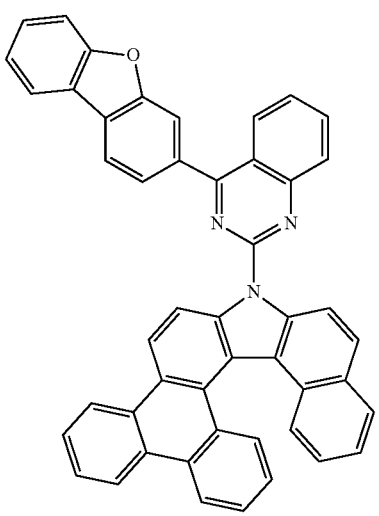

C-7
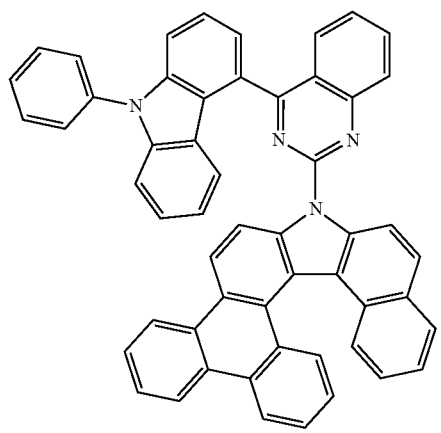
C-8
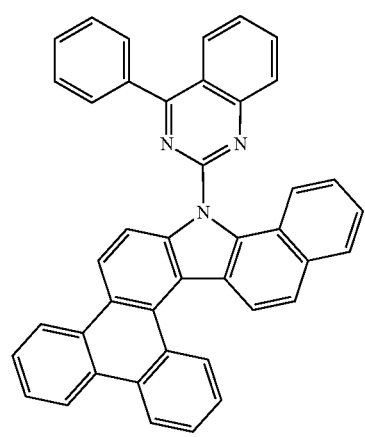
C-9
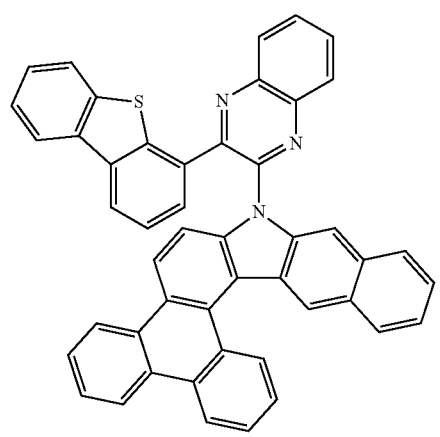
C-10
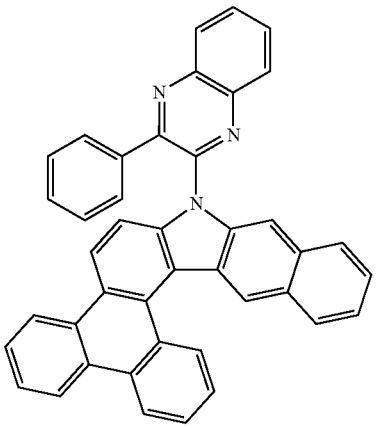
C-11
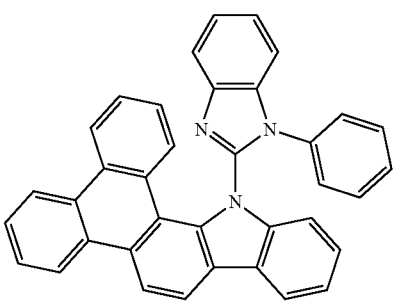
C-12
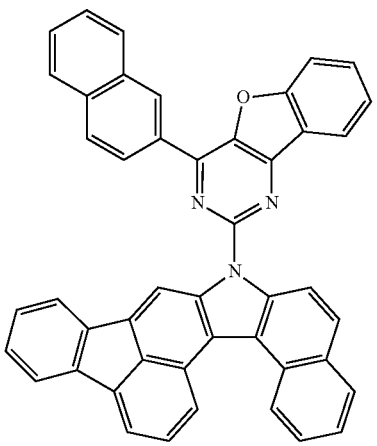
C-13
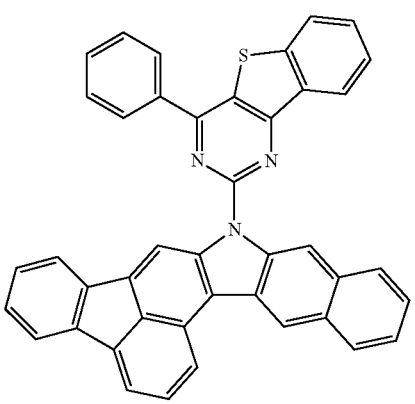

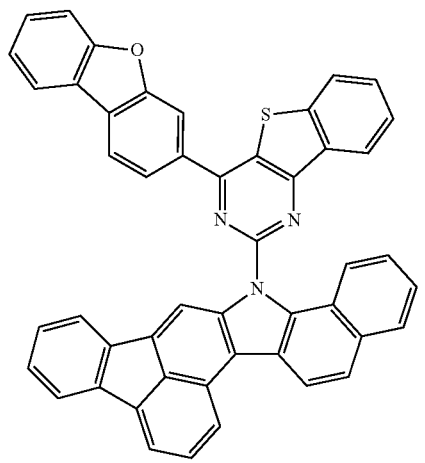

C-14

C-15

Example 1 to Example 20

Organic light emitting devices were manufactured in the same manner as in Comparative Example 1 except that compounds described in the following Table 1 were used instead of RH-1 in the organic light emitting device of Comparative Example 1.

Comparative Example 2 to Comparative Example 16

Organic light emitting devices were manufactured in the same manner as in Comparative Example 1 except that compounds described in the following Table 1 were used instead of RH-1 in the organic light emitting device of Comparative Example 1.

When applying a current to each of the organic light emitting devices manufactured in Example 1 to Example 20, and Comparative Example 1 to Comparative Example 16, voltage, efficiency and lifetime were measured, and the results are shown in the following Table 1. T95 means time taken for luminance decreasing to 95% with respect to initial luminance (10,000 nit).

TABLE 1

| Category | Material | Driving Voltage (V) | Efficiency (cd/A) | Lifetime T95 (hr) | Light Emission Color |
|---|---|---|---|---|---|
| Comparative Example 1 | RH-1 | 4.48 | 34.7 | 174 | Red |
| Example 1 | Compound 1 | 3.95 | 37.5 | 213 | Red |
| Example 2 | Compound 2 | 3.93 | 43.1 | 295 | Red |
| Example 3 | Compound 3 | 4.23 | 38.8 | 191 | Red |
| Example 4 | Compound 4 | 4.17 | 39.7 | 234 | Red |
| Example 5 | Compound 5 | 4.03 | 37.6 | 217 | Red |
| Example 6 | Compound 6 | 4.05 | 39.9 | 203 | Red |
| Example 7 | Compound 7 | 3.97 | 38.5 | 199 | Red |
| Example 8 | Compound 8 | 4.17 | 42.1 | 223 | Red |
| Example 9 | Compound 9 | 4.10 | 38.9 | 221 | Red |
| Example 10 | Compound 10 | 4.27 | 34.3 | 195 | Red |
| Example 11 | Compound 11 | 4.15 | 38.0 | 190 | Red |
| Example 12 | Compound 12 | 4.01 | 37.5 | 214 | Red |
| Example 13 | Compound 13 | 3.92 | 39.4 | 199 | Red |
| Example 14 | Compound 14 | 3.84 | 37.5 | 205 | Red |
| Example 15 | Compound 15 | 4.13 | 38.1 | 239 | Red |
| Example 16 | Compound 16 | 3.85 | 38.5 | 193 | Red |
| Example 17 | Compound 17 | 4.31 | 37.3 | 229 | Red |
| Example 18 | Compound 18 | 4.21 | 36.5 | 231 | Red |
| Example 19 | Compound 19 | 3.93 | 36.7 | 251 | Red |
| Example 20 | Compound 20 | 4.04 | 37.0 | 217 | Red |
| Comparative Example 2 | C-1 | 4.61 | 31.7 | 197 | Red |
| Comparative Example 3 | C-2 | 4.23 | 34.5 | 79 | Red |

TABLE 1-continued

| Category | Material | Driving Voltage (V) | Efficiency (cd/A) | Lifetime T95 (hr) | Light Emission Color |
|---|---|---|---|---|---|
| Comparative Example 4 | C-3 | 4.35 | 33.5 | 188 | Red |
| Comparative Example 5 | C-4 | 4.53 | 32.8 | 134 | Red |
| Comparative Example 6 | C-5 | 4.50 | 32.1 | 142 | Red |
| Comparative Example 7 | C-6 | 4.64 | 33.1 | 195 | Red |
| Comparative Example 8 | C-7 | 4.59 | 34.7 | 177 | Red |
| Comparative Example 9 | C-8 | 4.69 | 31.5 | 181 | Red |
| Comparative Example 10 | C-9 | 4.30 | 33.9 | 61 | Red |
| Comparative Example 11 | C-10 | 4.35 | 33.5 | 93 | Red |
| Comparative Example 12 | C-11 | 4.55 | 29.4 | 47 | Red |
| Comparative Example 13 | C-12 | 4.15 | 31.5 | 53 | Red |
| Comparative Example 14 | C-13 | 4.04 | 34.5 | 73 | Red |
| Comparative Example 15 | C-14 | 4.37 | 32.3 | 67 | Red |
| Comparative Example 16 | C-15 | 4.55 | 23.1 | 31 | Red |

When applying a current to each of the organic light emitting devices manufactured in Examples 1 to 20 and Comparative Examples 1 to 16, results of Table 1 were obtained. In the red organic light emitting device of Comparative Example 1, materials widely used in the art were used.

In Comparative Examples 2 to 16, organic light emitting devices were manufactured using C-1 to C-15 instead of RH-1. Based on the results of Table 1, a driving voltage decreased by up to almost 20% when using the compounds of the present disclosure as a host of a red light emitting layer compared to the materials of the comparative examples, and efficiency also increased by 20% or greater. Based on such results, it was seen that energy was favorably transferred from the host to the red dopant. In addition, it was seen that lifetime properties were significantly improved by 1.5 times or greater while maintaining high efficiency.

This can be considered to be due to the fact that the compounds of the present disclosure have higher stability for electrons and holes compared to the compounds of the comparative examples, and electron migration and hole migration are well balanced in the red OLED device. In conclusion, it was identified that using the compounds of the present disclosure as a host of a red light emitting layer was capable of improving driving voltage, light emission efficiency and lifetime properties of an organic light emitting device.

The invention claimed is:

1. A heterocyclic compound of any one of the following Chemical Formulae 1-1 to 1-3:

[Chemical Formula 1-1]

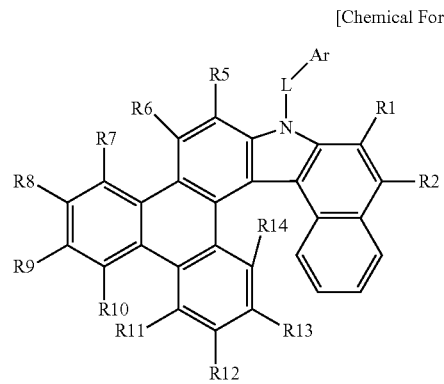

[Chemical Formula 1-2]

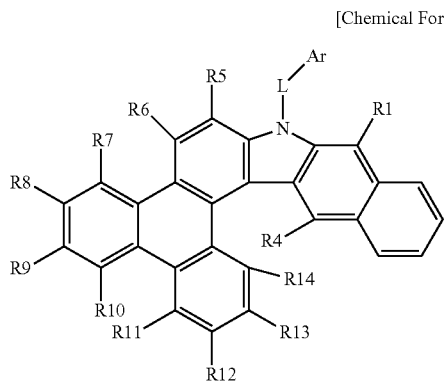

[Chemical Formula 1-3]

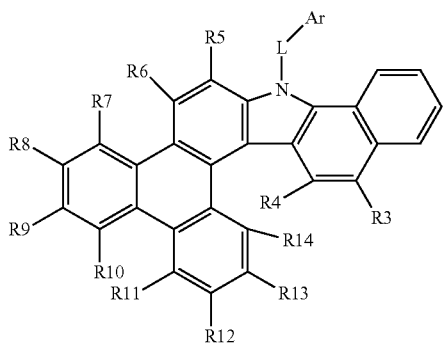

wherein in Chemical Formulae 1-1 to 1-3:
Ar is an unsubstituted alkyl group, a phenyl group, a biphenyl group, a naphthyl group, a phenanthrene group, a triphenylene group, a dibenzofuran group, a dibenzothiophene group, or a carbazole group, and the phenyl group, the biphenyl group, the naphthyl group, the phenanthrene group, the triphenylene group, the dibenzofuran group, the dibenzothiophene group, or the carbazole group is unsubstituted or substituted with an alkyl group having 1 to 10 carbon atoms, an aryl group having 6 to 20 carbon atoms, or a heteroaryl group having 3 to 30 carbon atoms;
R1 to R14 are the same as or different from each other, and each independently is hydrogen, a nitrile group, a halogen group, an unsubstituted alkyl group, an unsubstituted aryl group selected from among a phenyl group, a biphenyl group, a terphenyl group, a naphthyl group, an anthracenyl group, a phenanthryl group, a triphenylene group, a pyrenyl group, a phenalenyl group, a perylenyl group, a chrysenyl group, and a fluorenyl group, or an unsubstituted heteroaryl group selected from among a thiophene group, a furanyl group, a pyrrole group, an imidazolyl group, a triazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, and a dibenzofuranyl group; and,
L is Chemical Formula 3 or Chemical Formula 4:

[Chemical Formula 3]

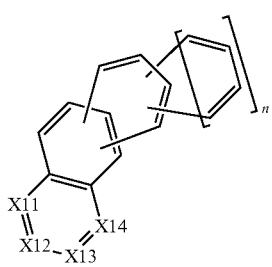

[Chemical Formula 4]

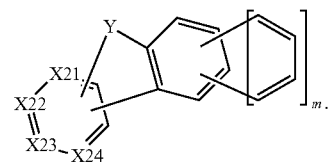

wherein in Chemical Formula 3 and 4:
X11 to X14 and X21 to X24 are the same as or different from each other, and are each N or C;
one of X11 to X14 bonds to N of any one of Chemical Formulae 1-1 to 1-3, or one of X21 to X24 bonds to N of any one of Chemical Formulae 1-1 to 1-3;
two of X11 to X14 are N, or two of X21 to X24 are N;
one of X11 to X14 is C that bonds to Ar of any one of Chemical Formulae 1-1 to 1-3, or one of X21 to X24 is C that bonds to Ar of any one of Chemical Formulae 1-1 to 1-3;
Y is O, S or $C(CH_3)_2$; and
n and m are 0 or 1.

2. A heterocyclic compound that is any one compound selected from among the following compounds:

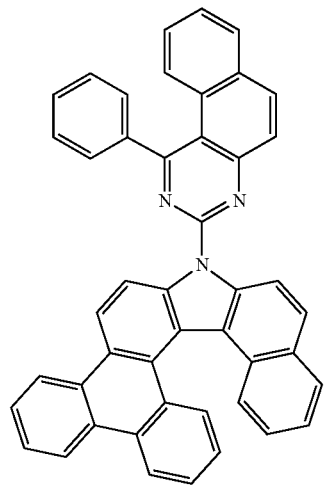

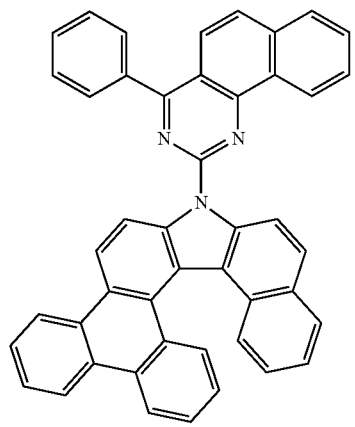

241
-continued
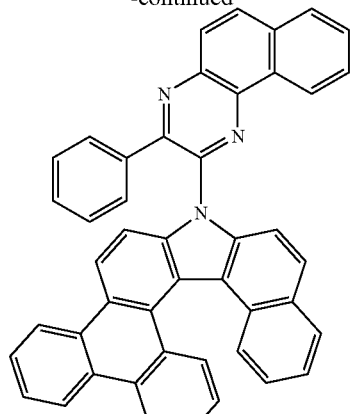
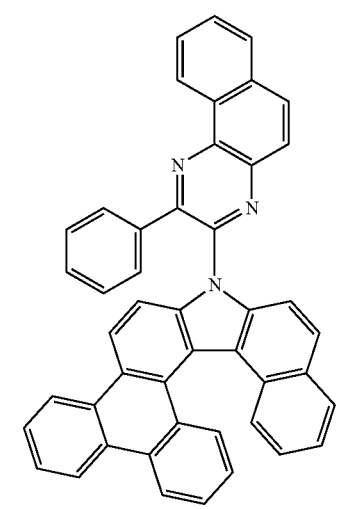
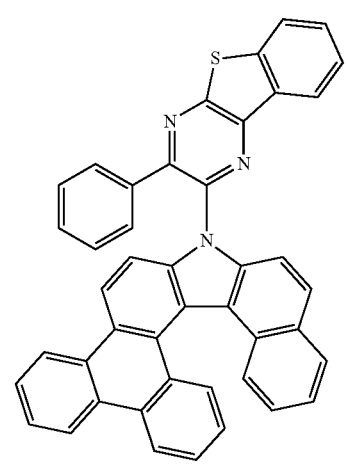
242
-continued
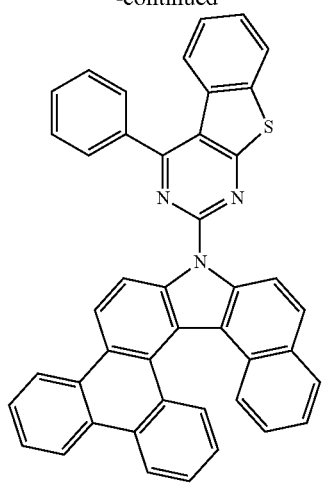
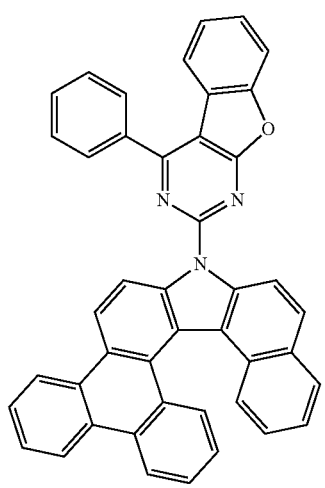
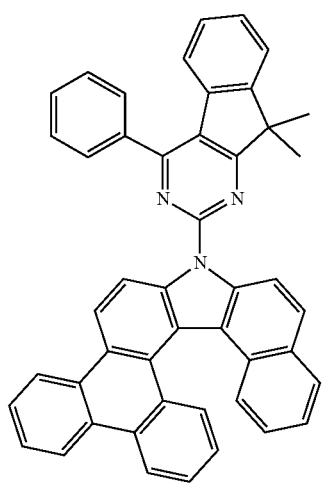

243
-continued
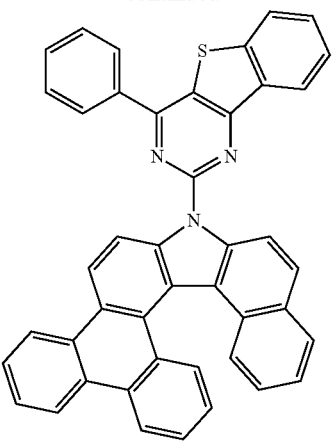
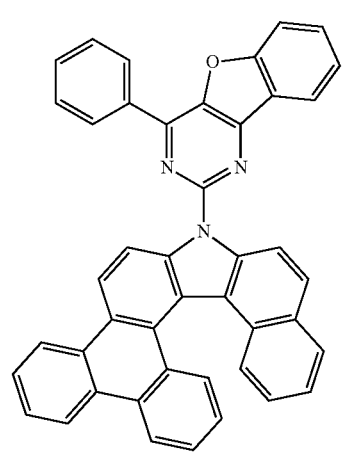
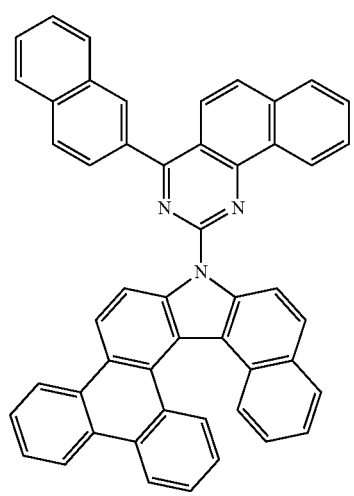
244
-continued
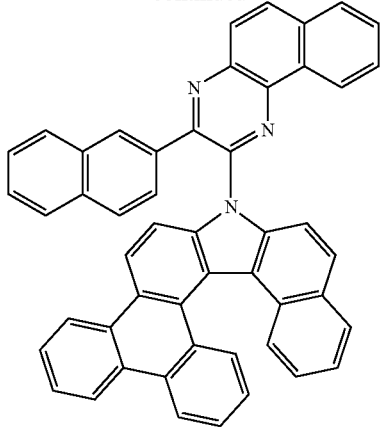
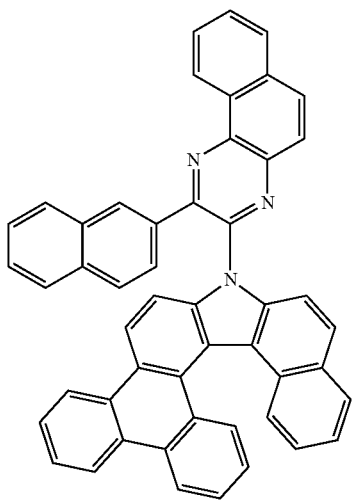
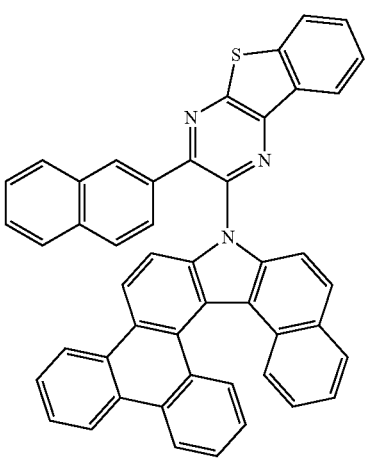

245
-continued
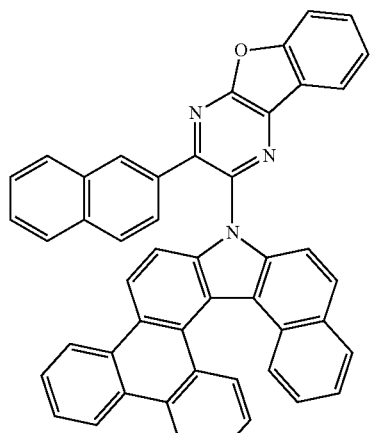
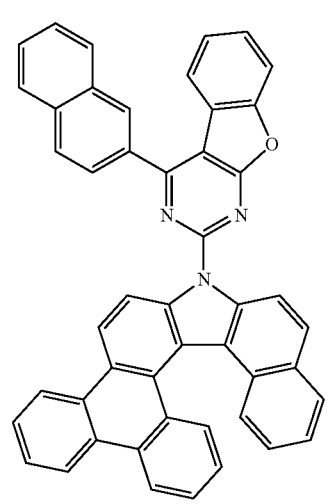
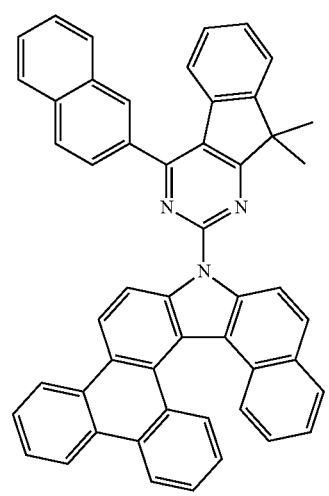
246
-continued
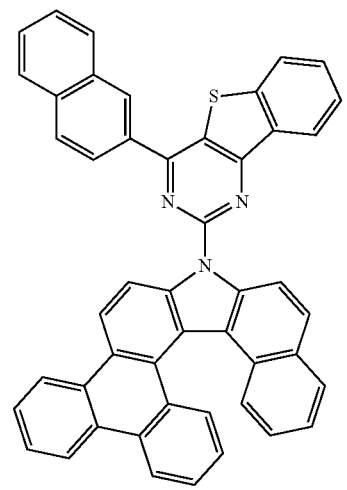
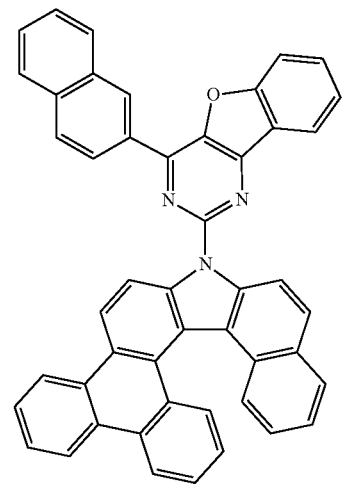
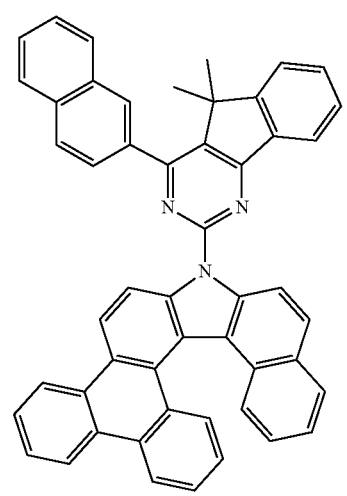

247
-continued
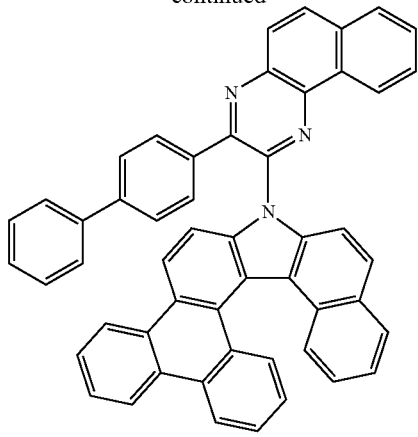
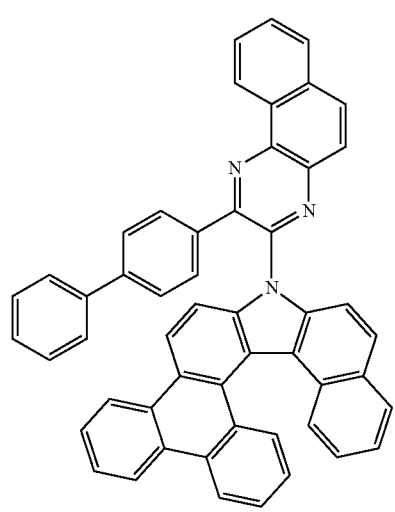
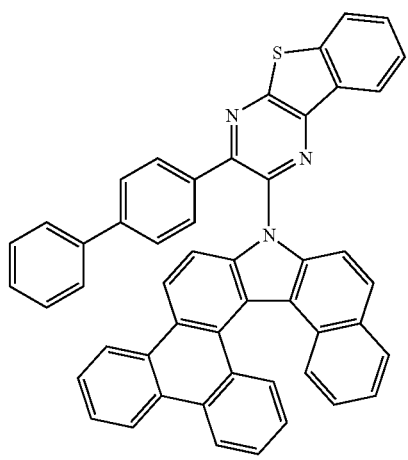
248
-continued
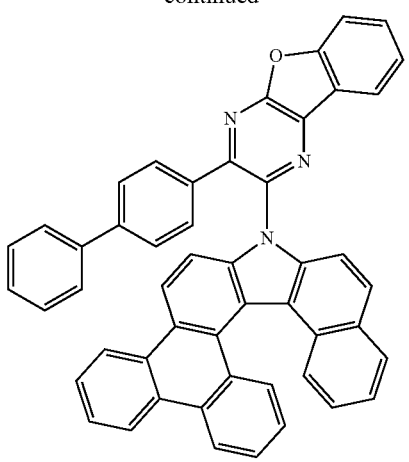
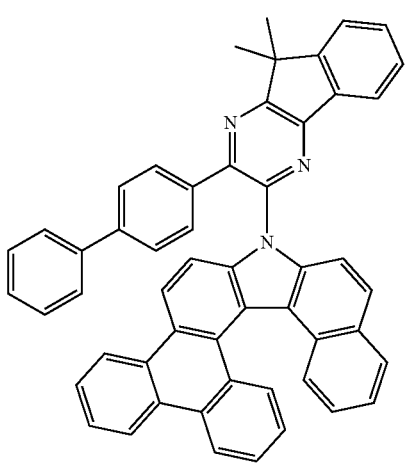
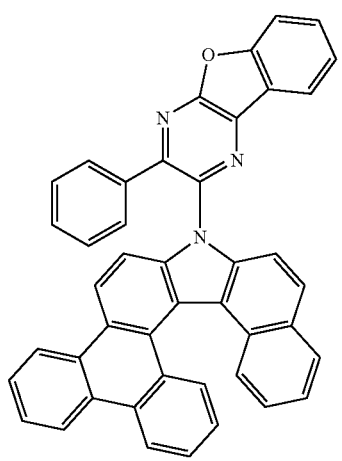

249
-continued
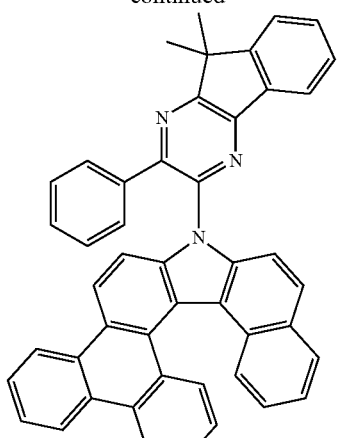
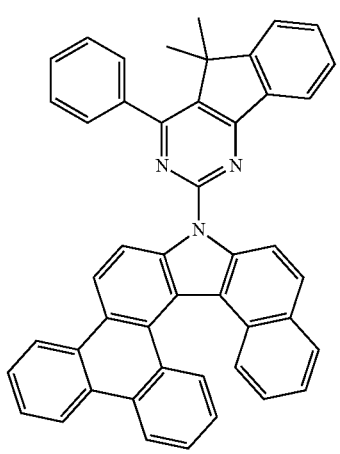
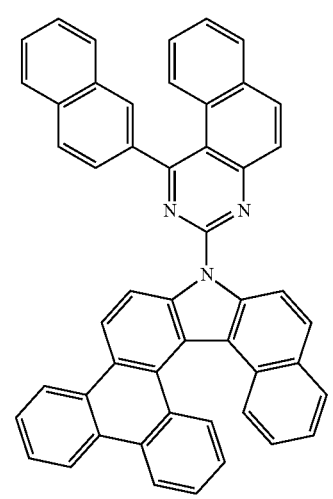
250
-continued
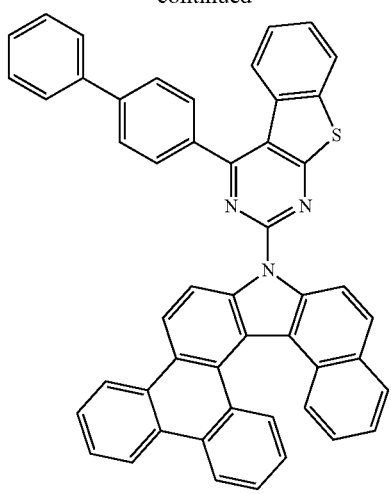
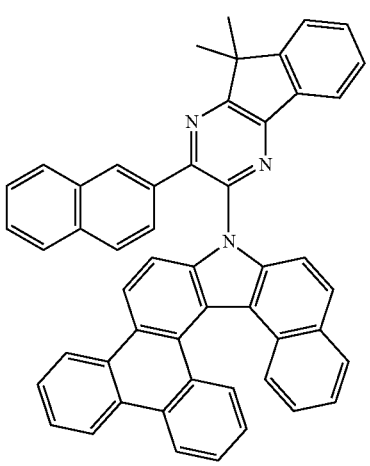
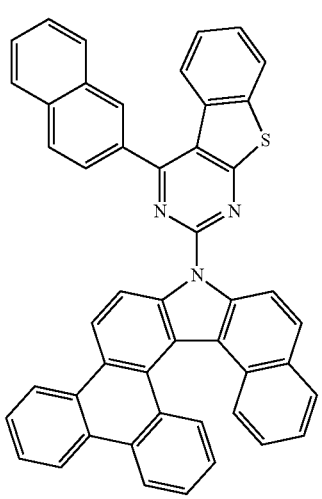

251
-continued
252
-continued
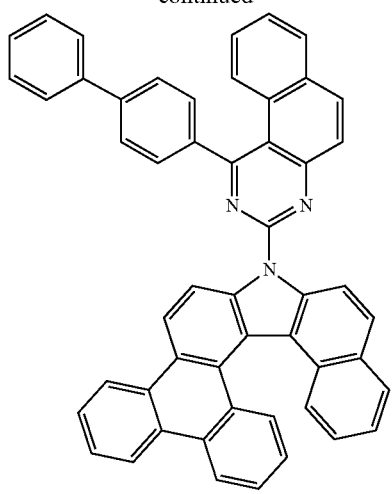
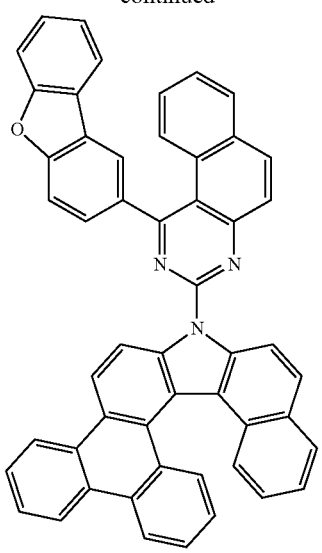
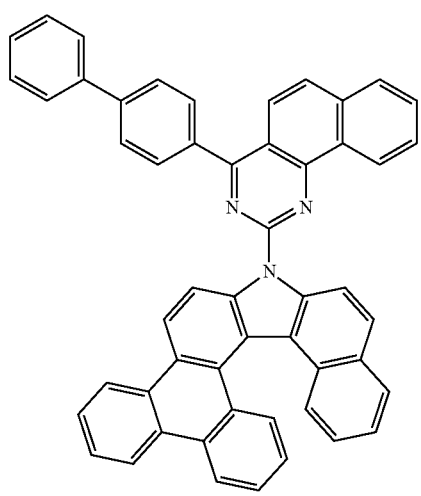
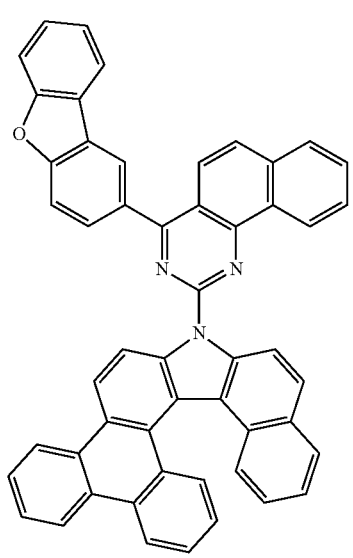
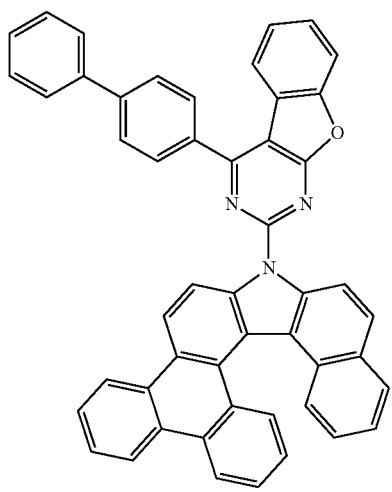
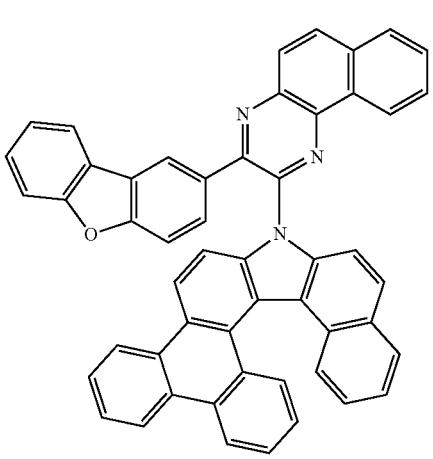

253
-continued
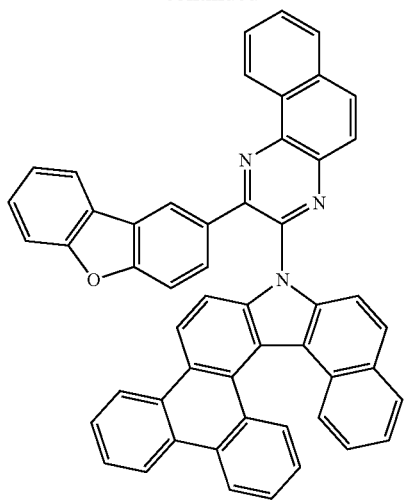
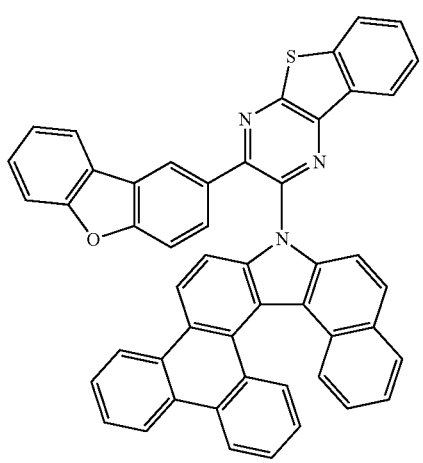
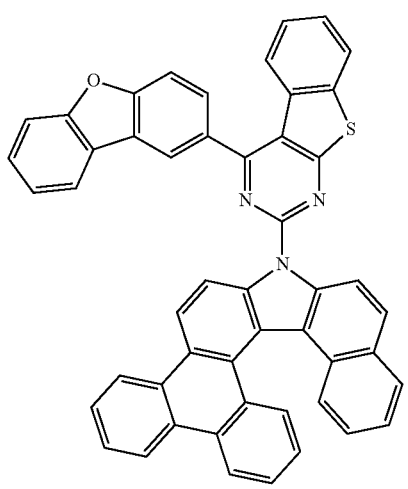
254
-continued
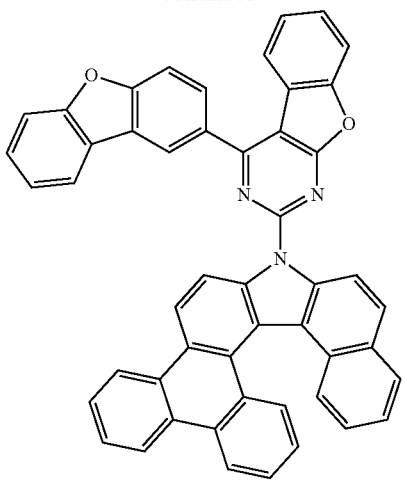
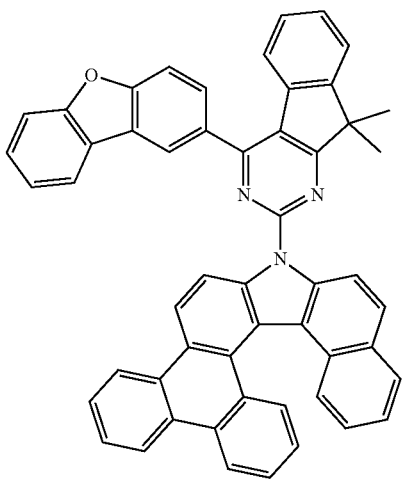
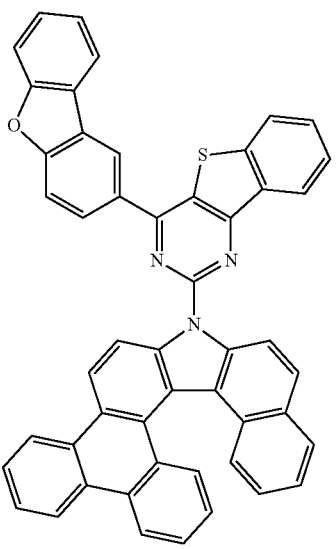

255
-continued
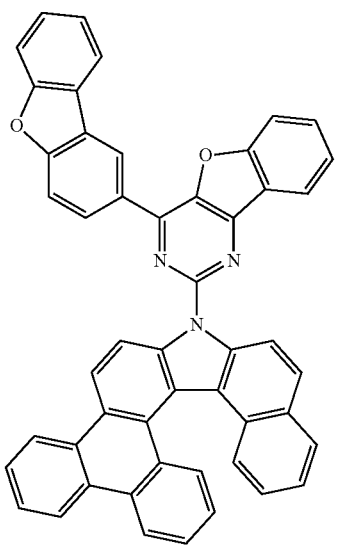
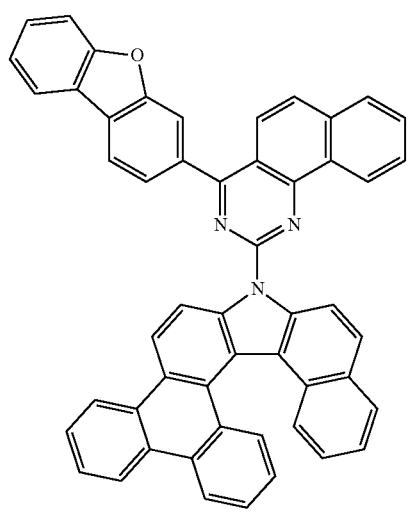
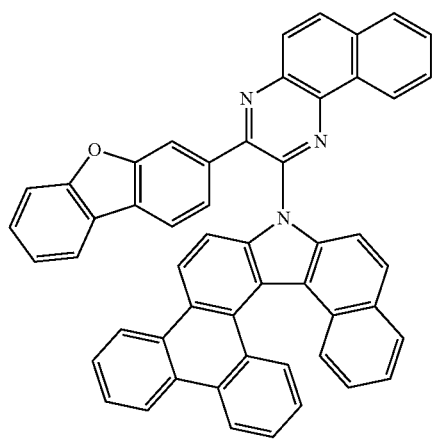
256
-continued
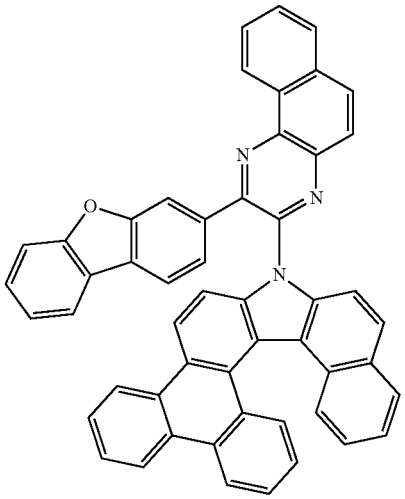
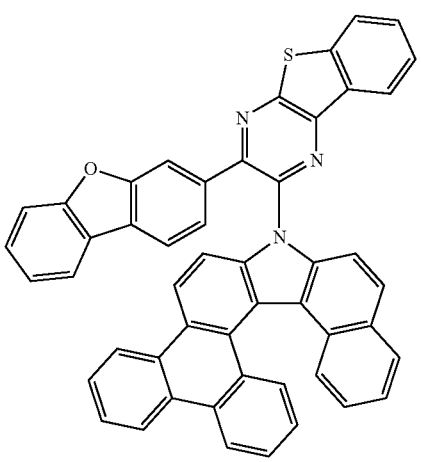
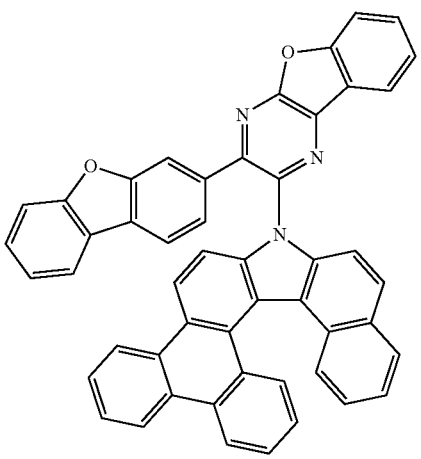

257
-continued
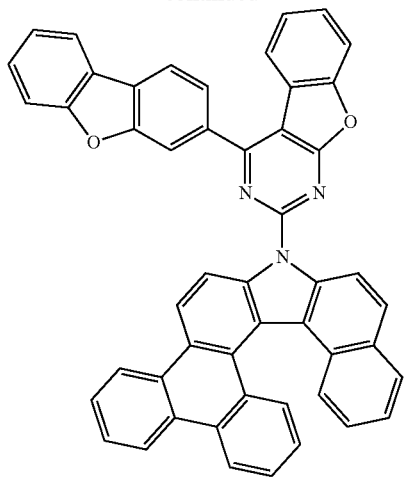
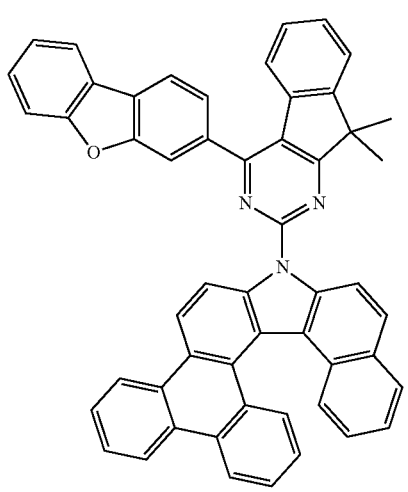
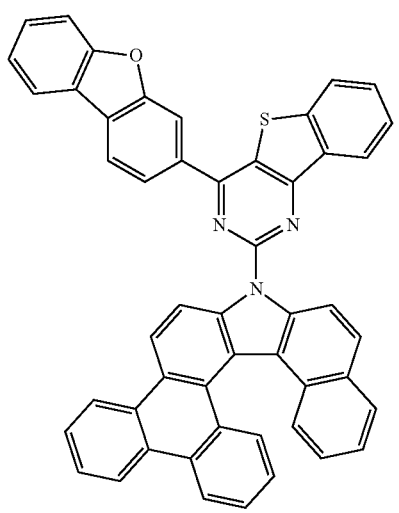
258
-continued
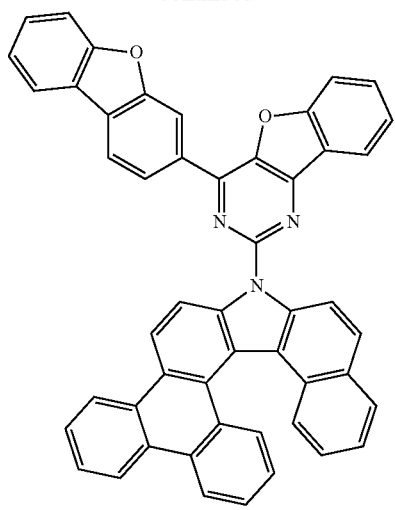
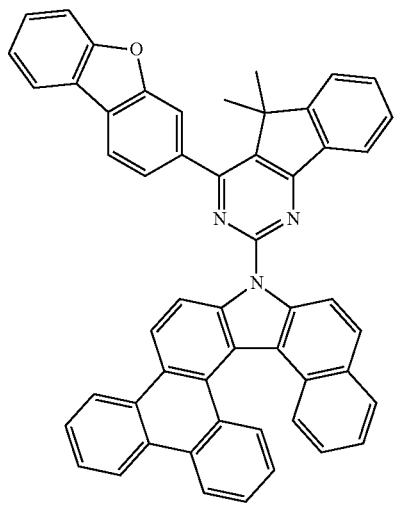
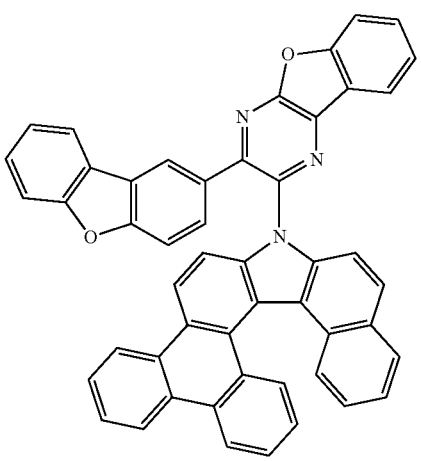

259
-continued
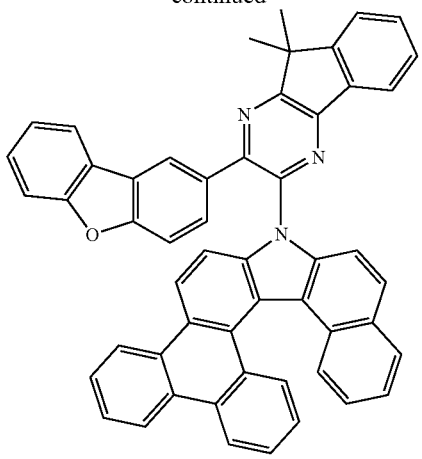
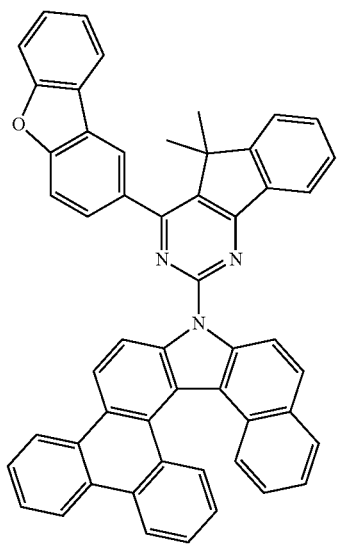
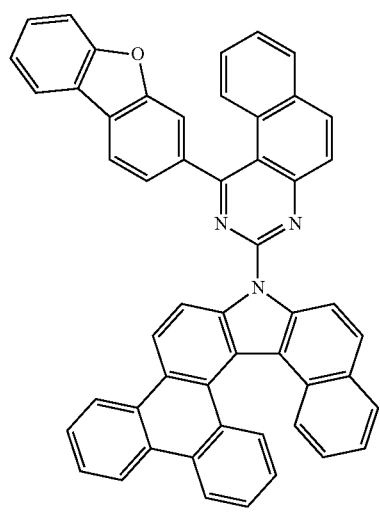
260
-continued
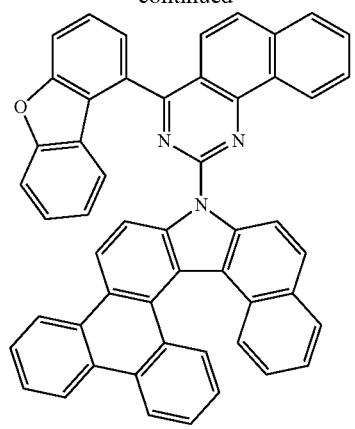
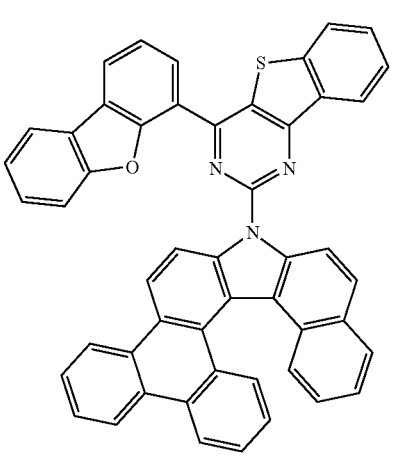
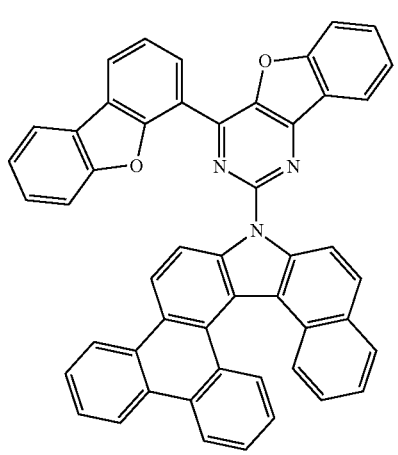

261
-continued
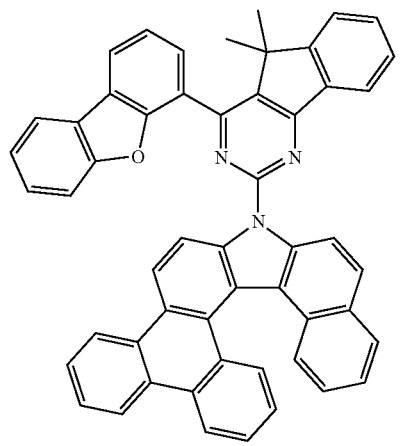
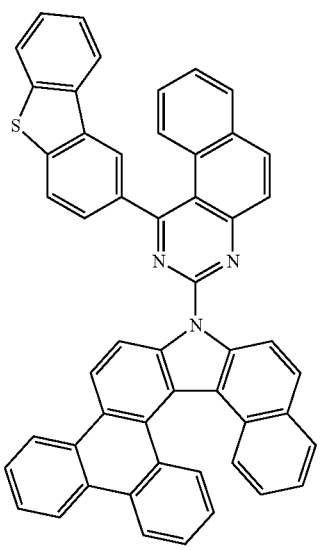
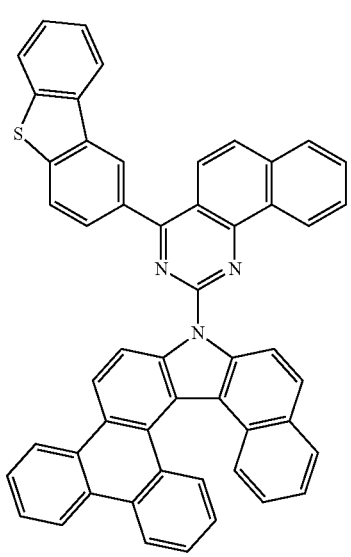
262
-continued
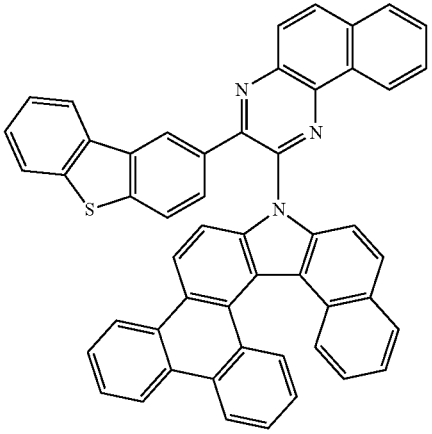
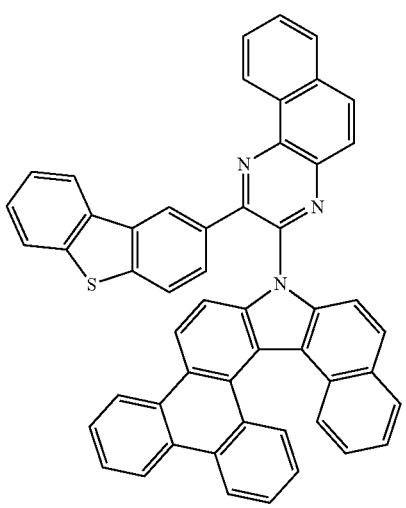
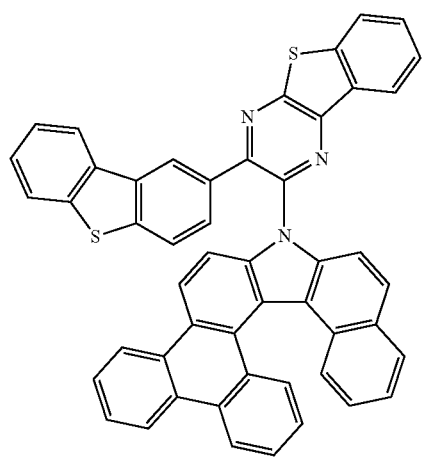

263
-continued
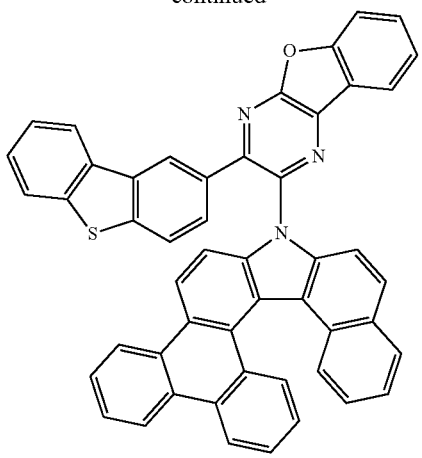
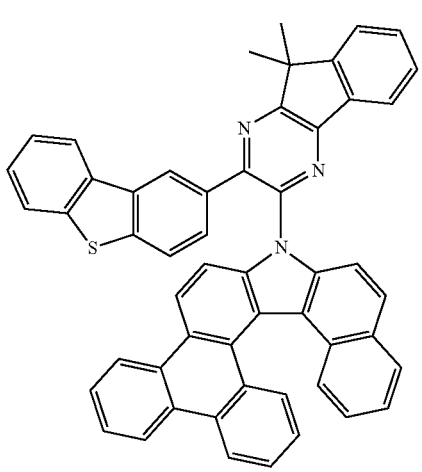
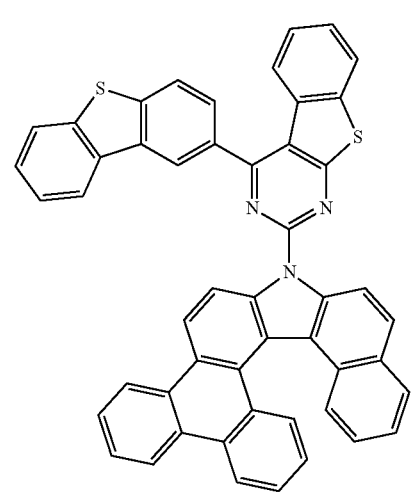
264
-continued
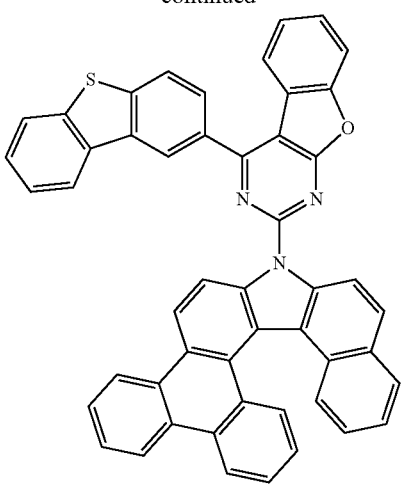
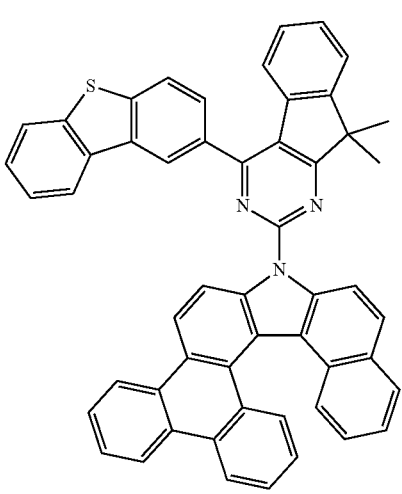
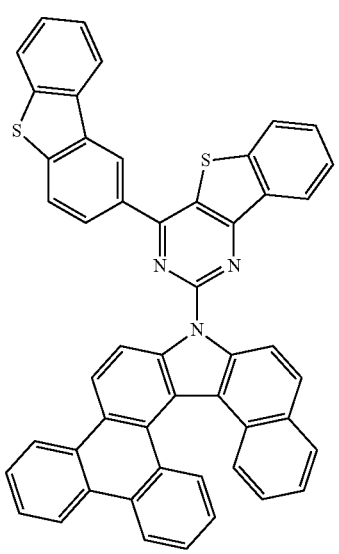

265
-continued
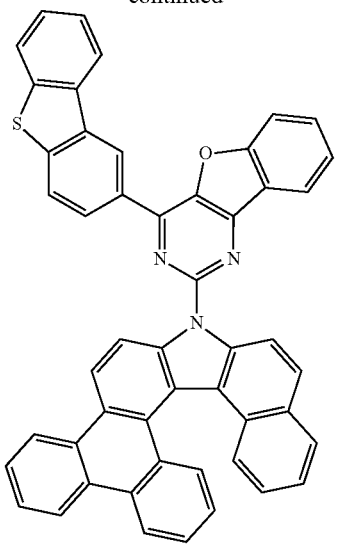
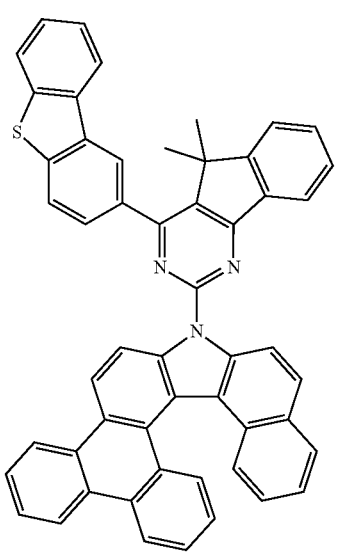
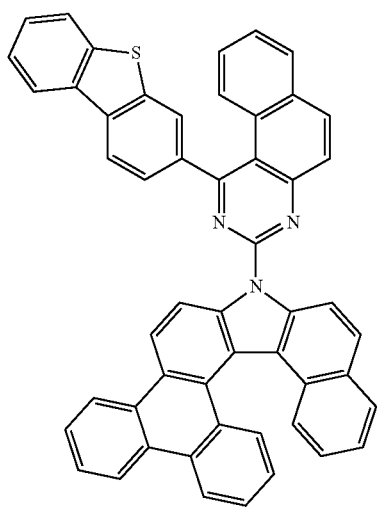
266
-continued
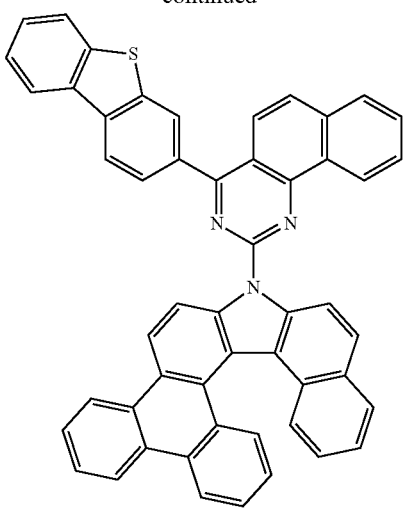
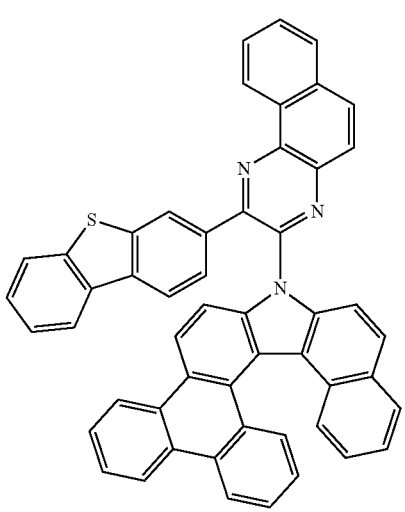

267
-continued
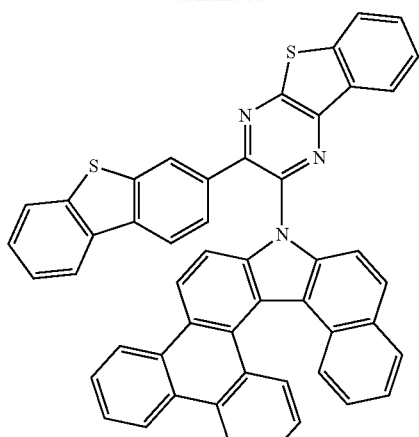
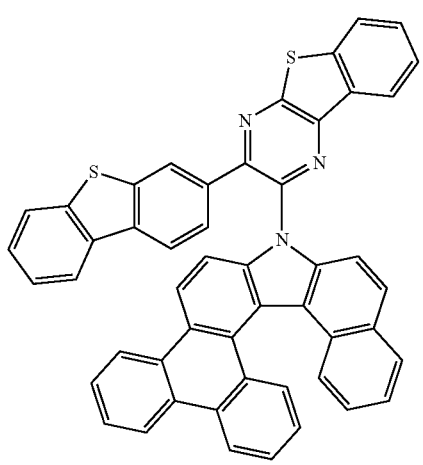
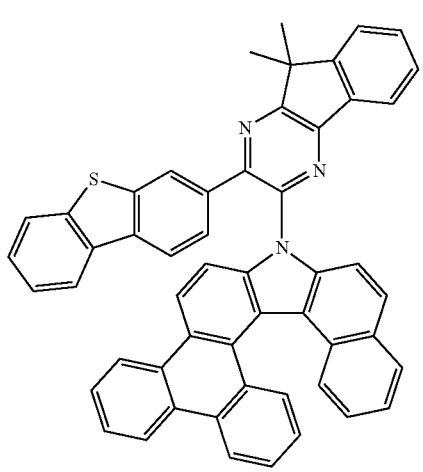
268
-continued
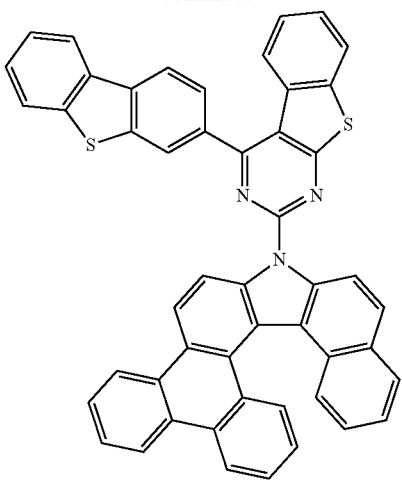
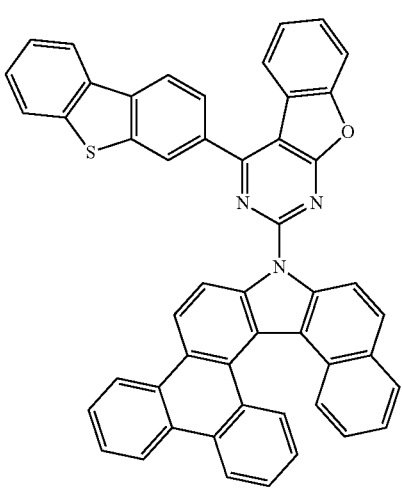
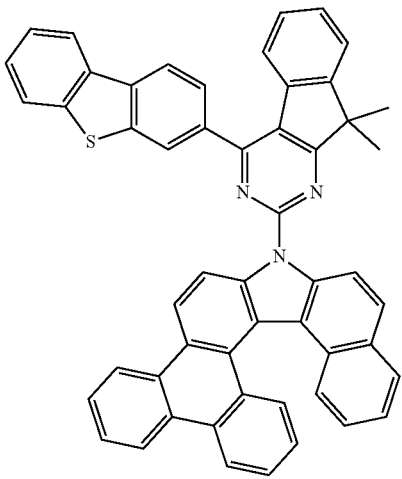

269
-continued
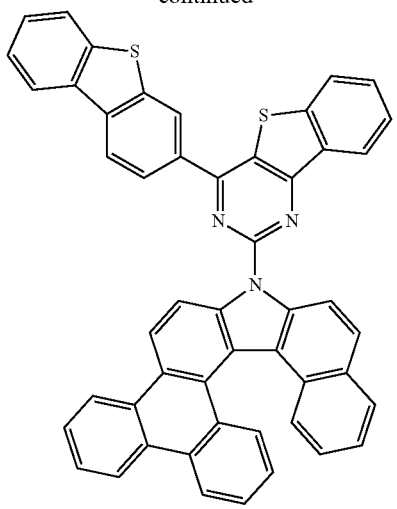
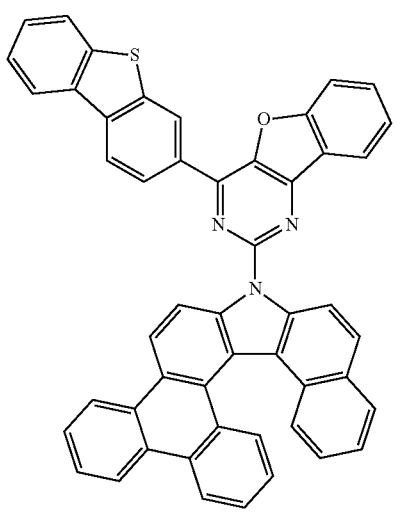
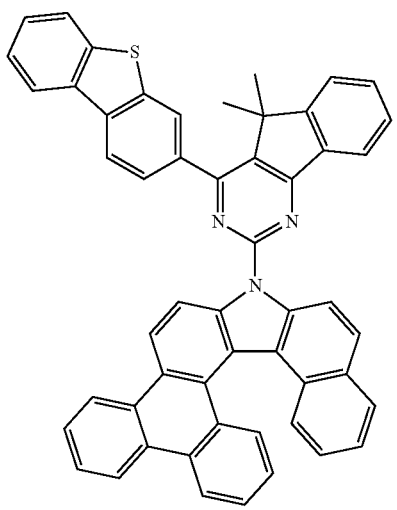
270
-continued
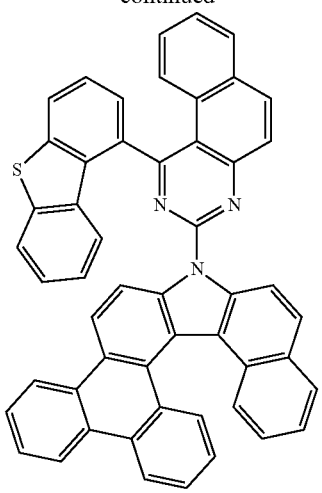
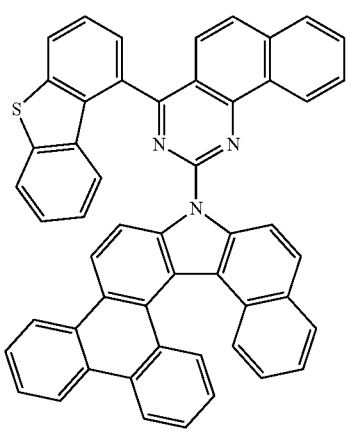
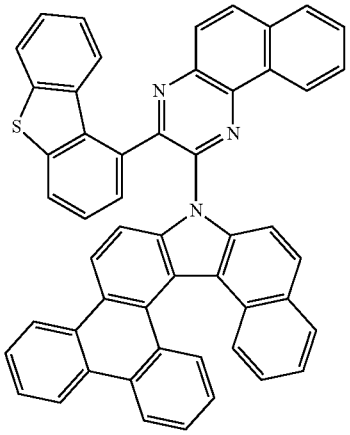

271
-continued
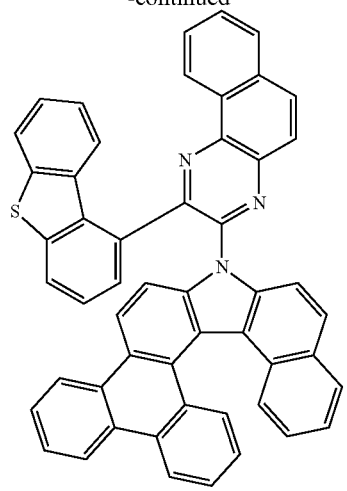
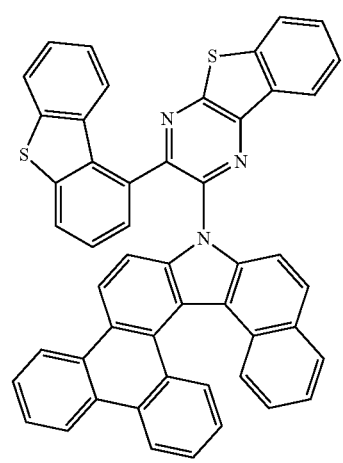
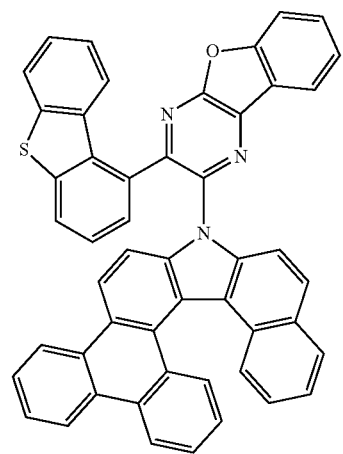
272
-continued
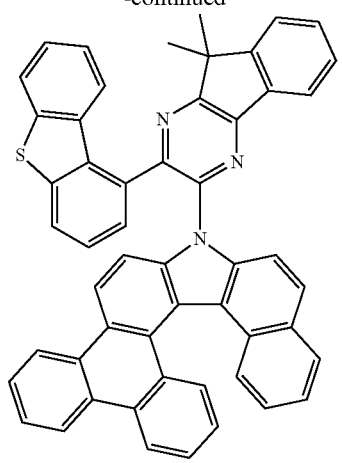
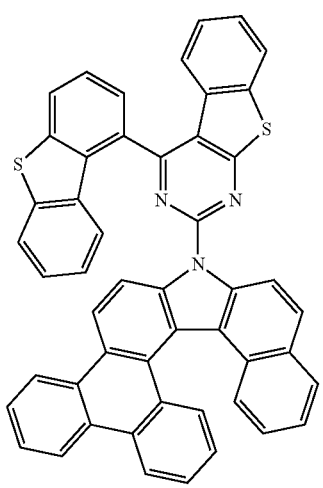
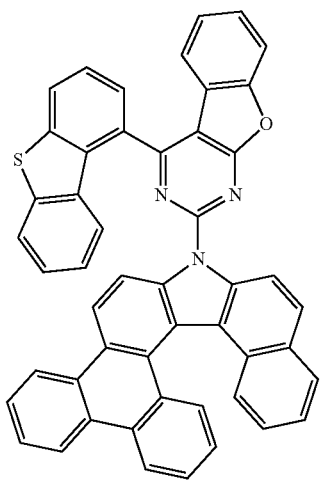

273
-continued
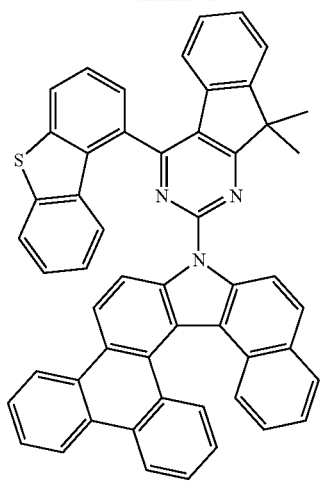
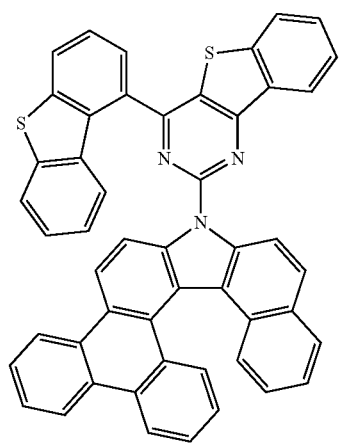
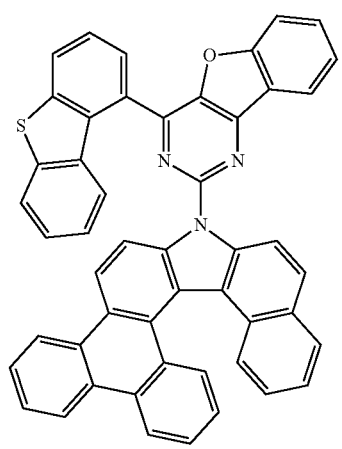
274
-continued
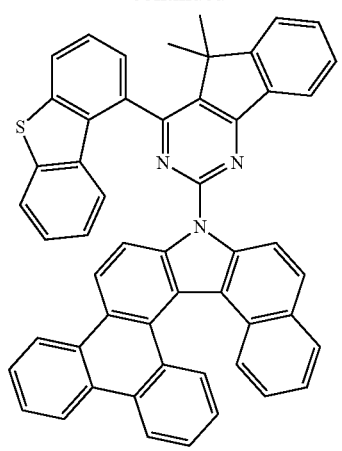
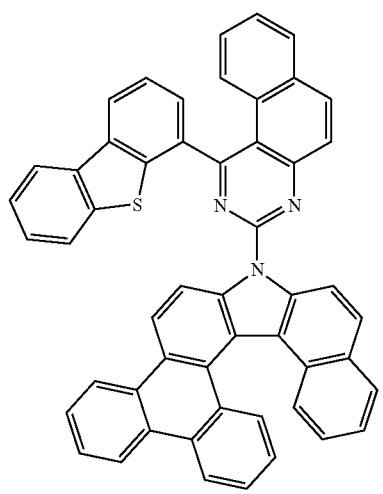
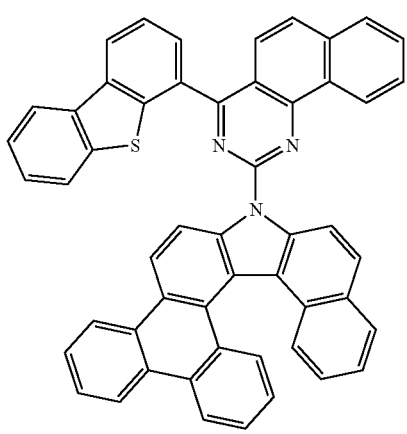

275
-continued
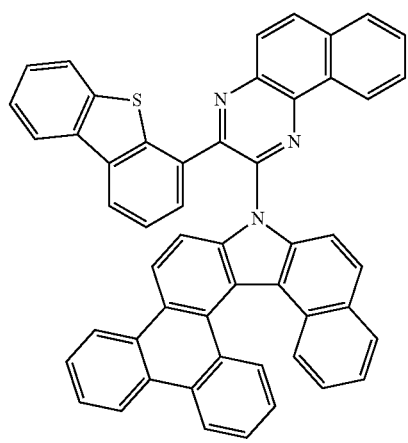
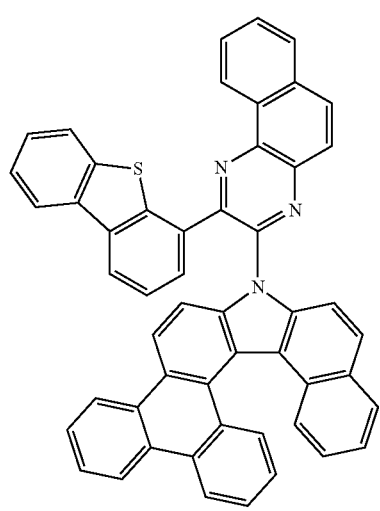
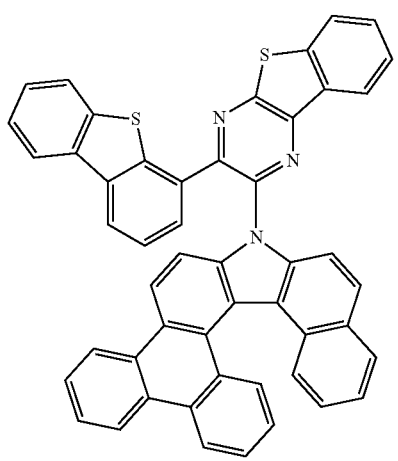
276
-continued
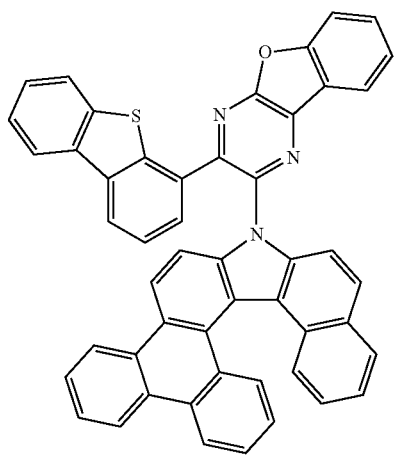
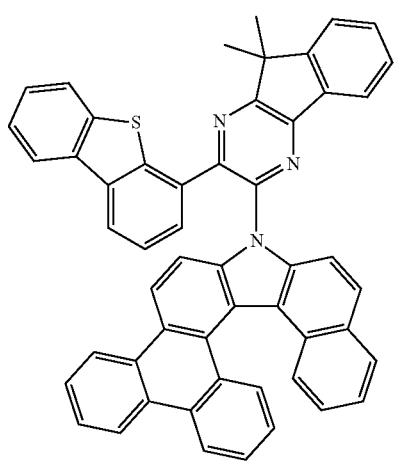
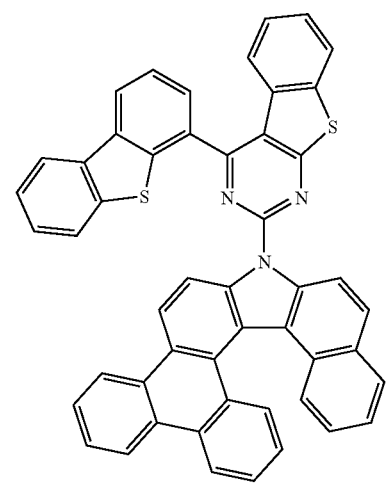

277
-continued
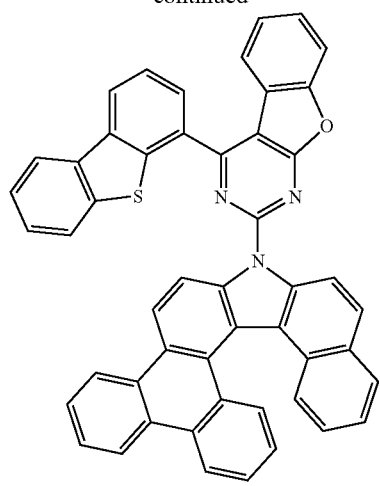
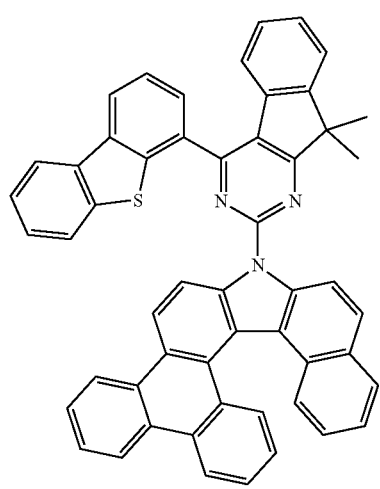
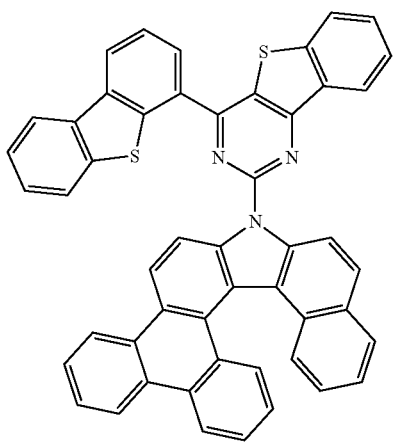
278
-continued
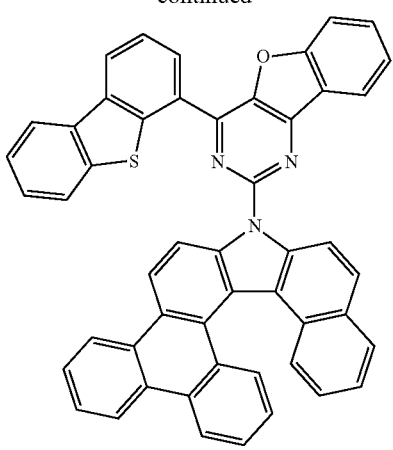
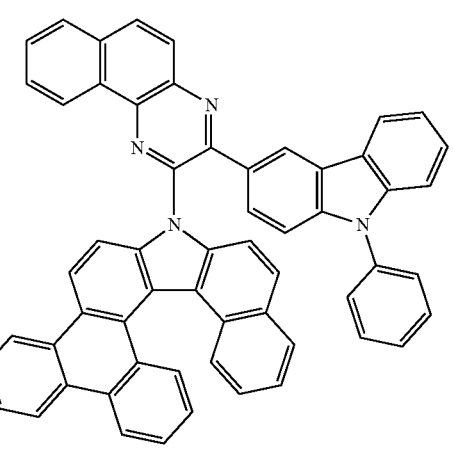
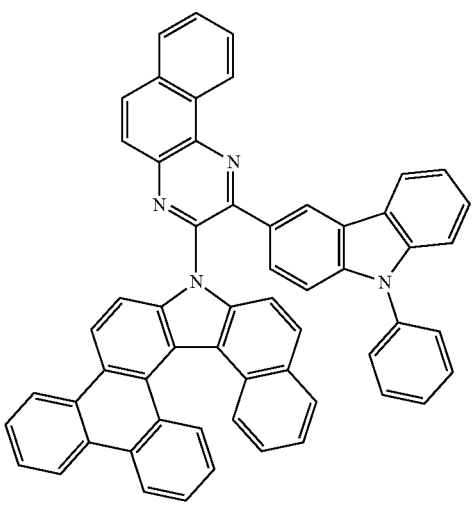

279
-continued
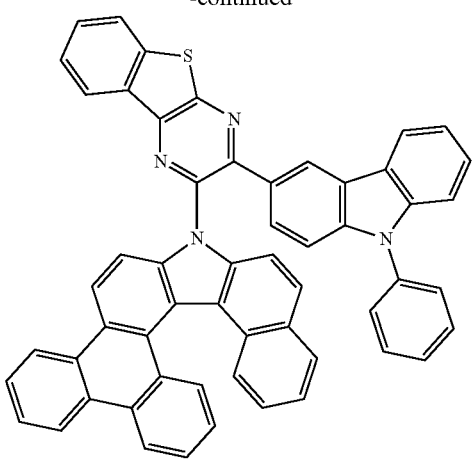
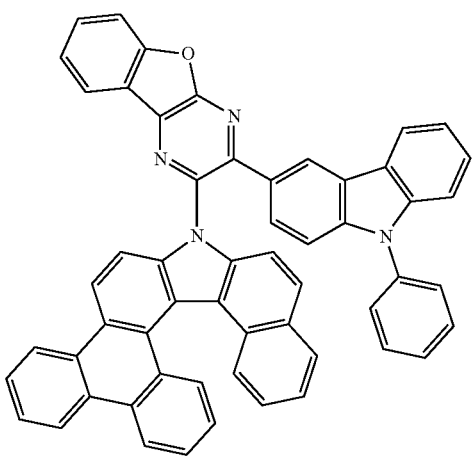
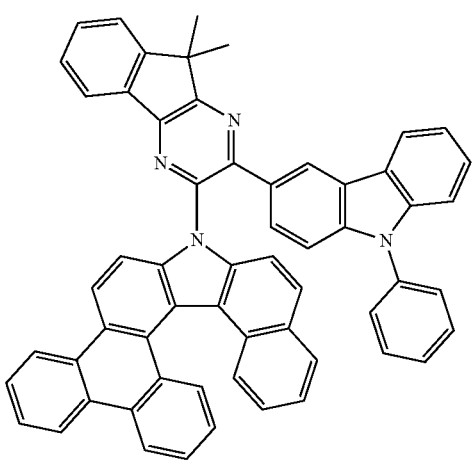
280
-continued
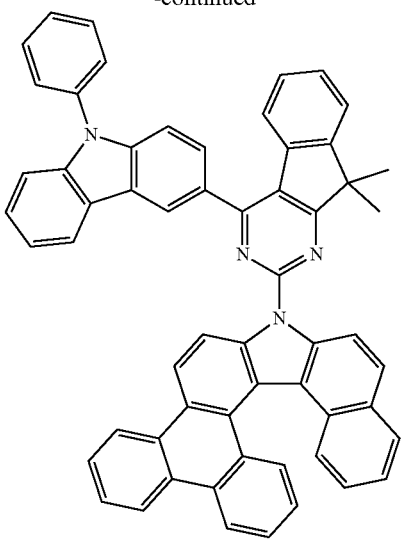
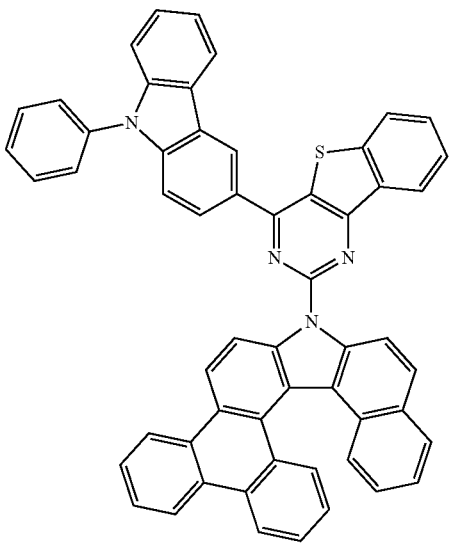
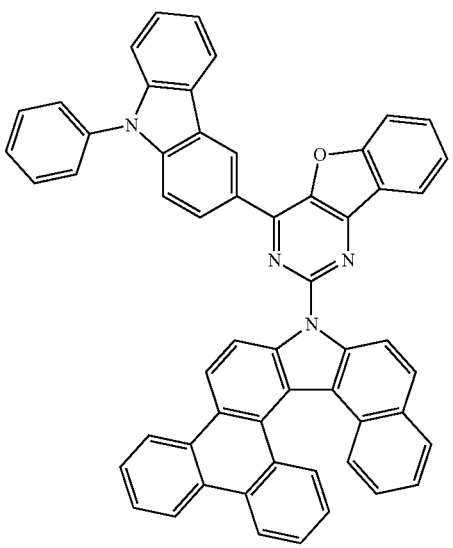

-continued
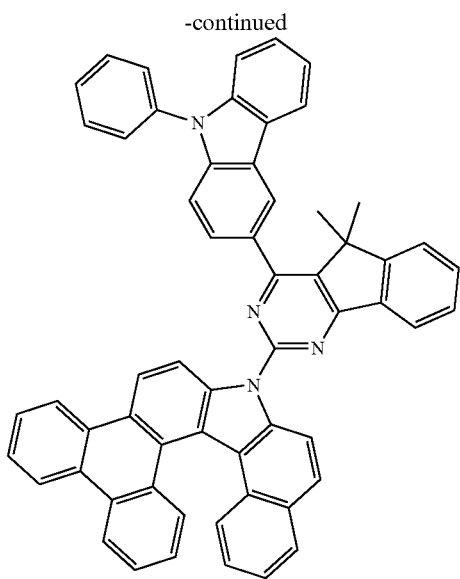
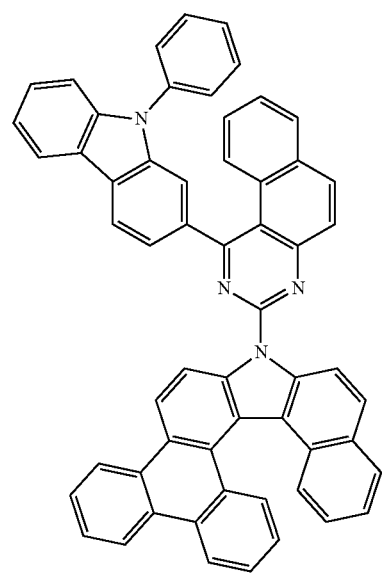
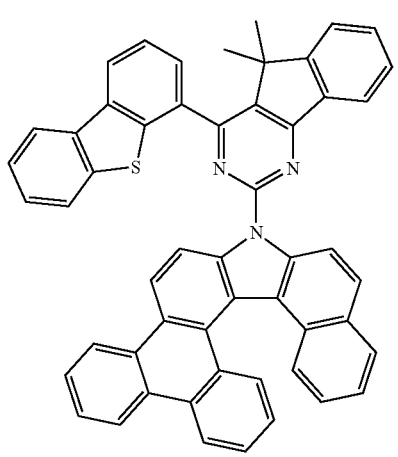
-continued
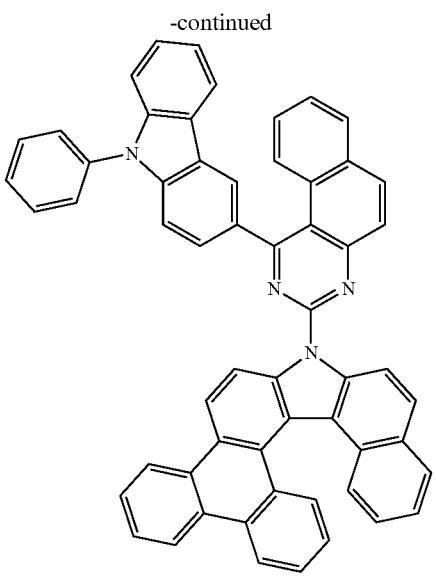
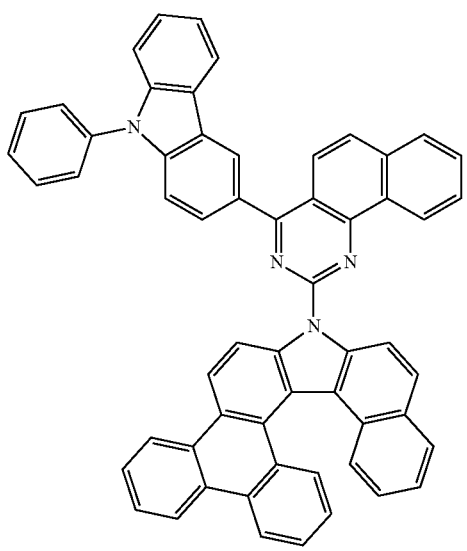
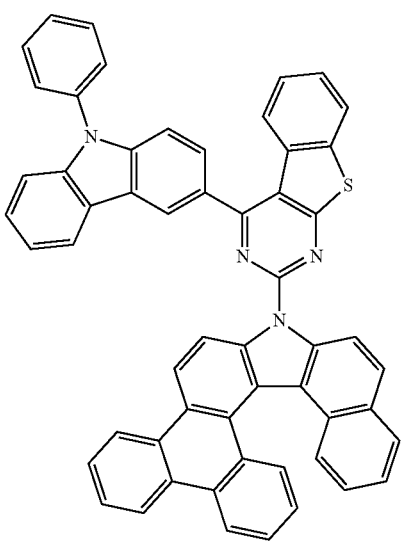

283
-continued
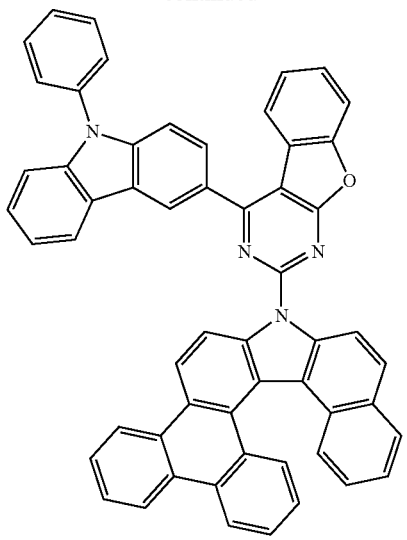
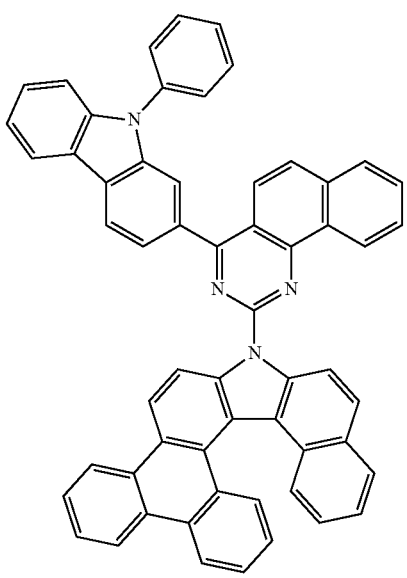
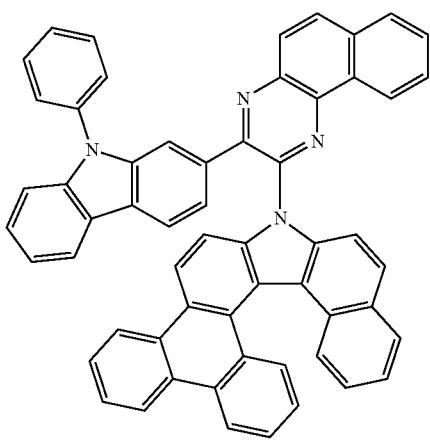
284
-continued
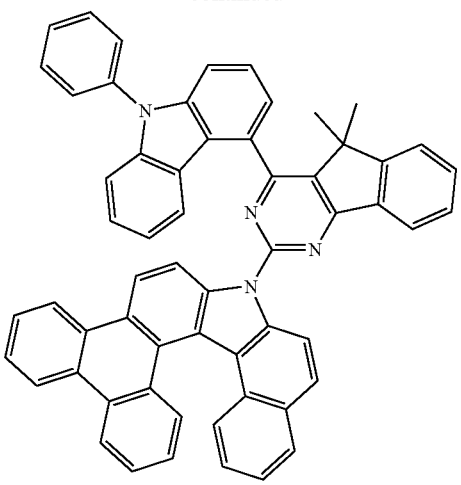
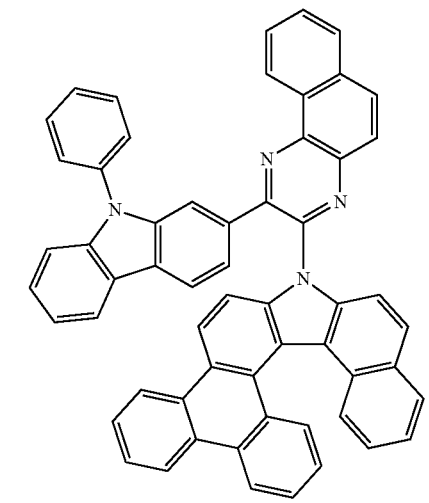
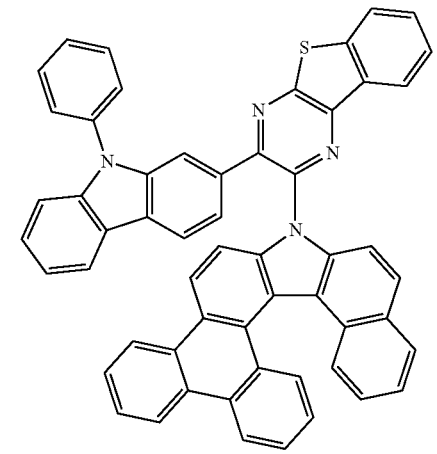

285
-continued
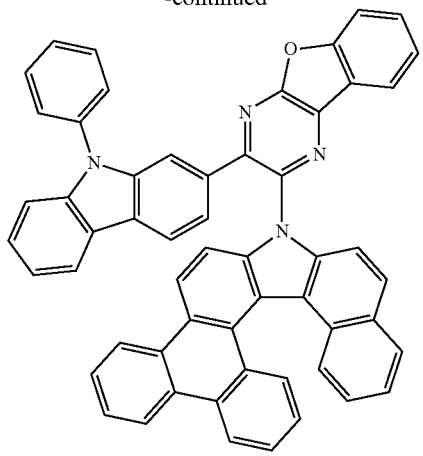
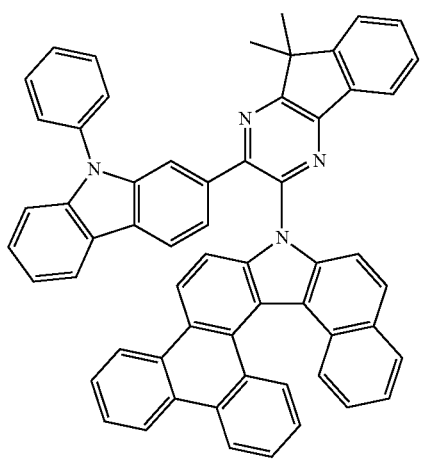
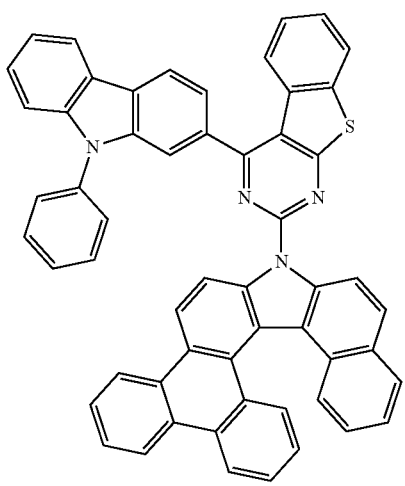
286
-continued
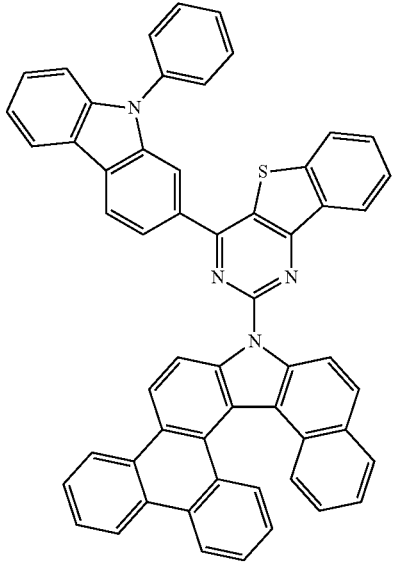
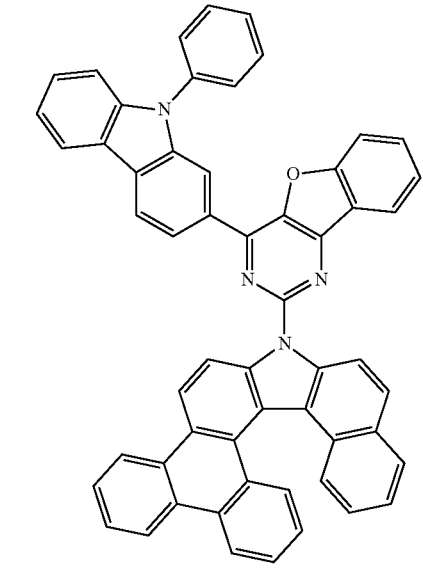
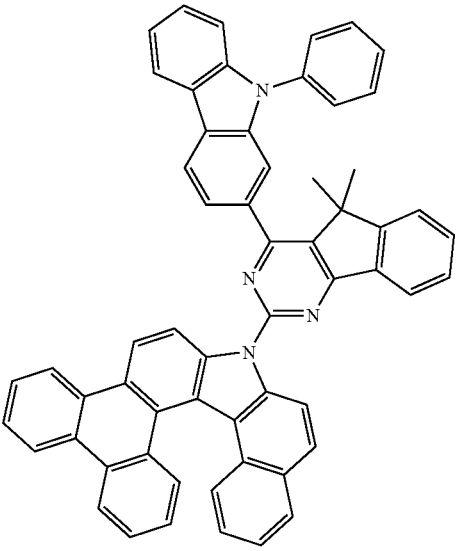

287
-continued
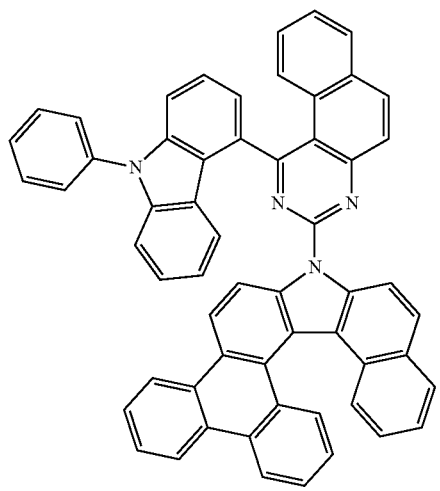
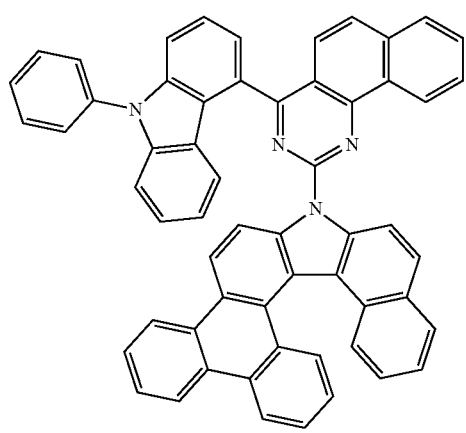
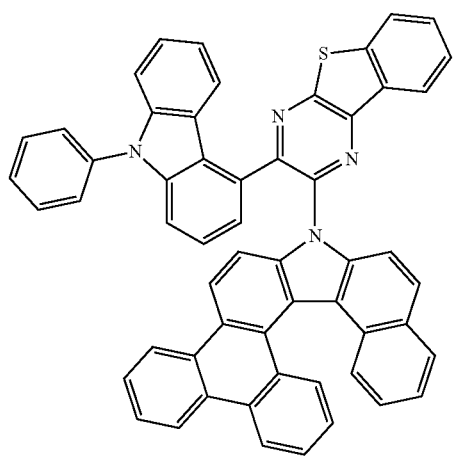
288
-continued
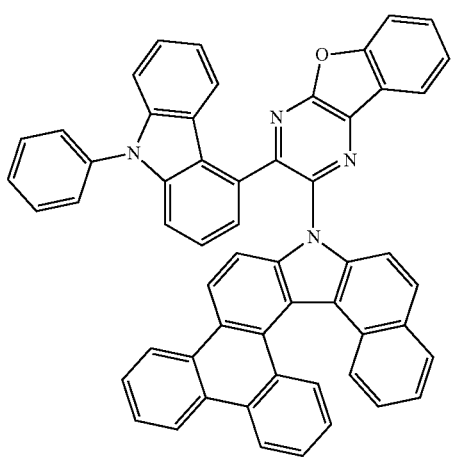
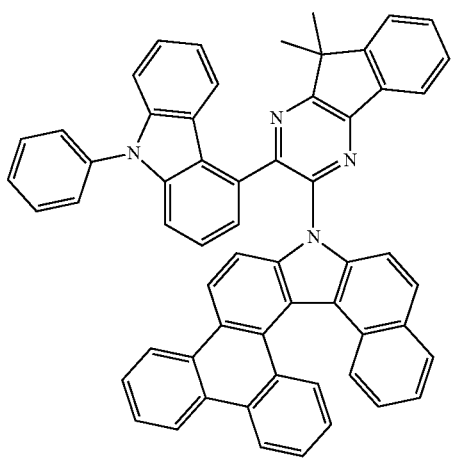
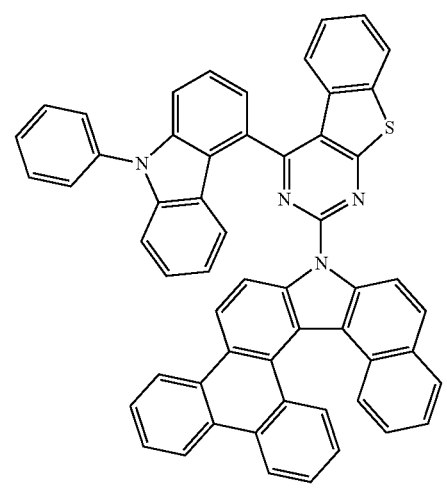

289
-continued
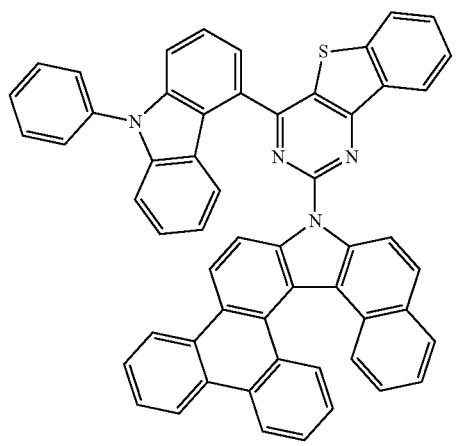
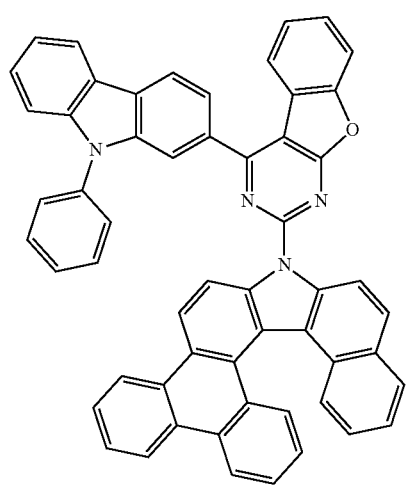
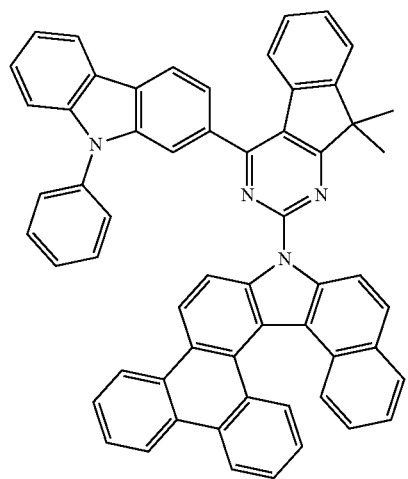
290
-continued
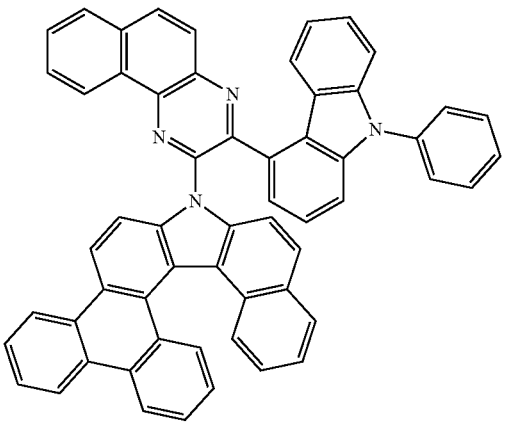
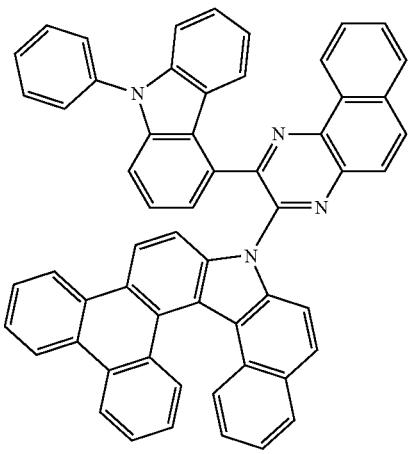
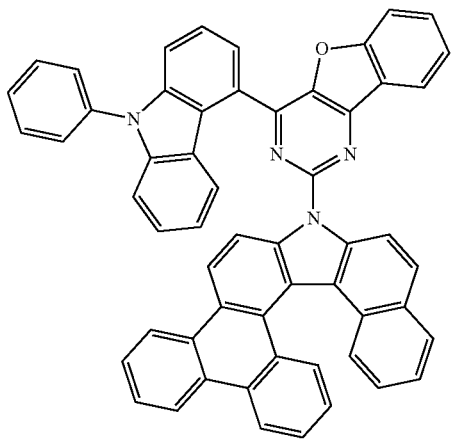

291
-continued
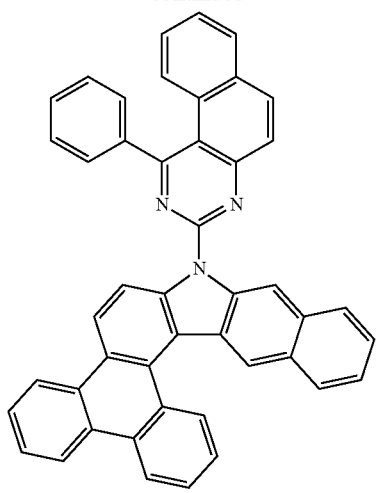
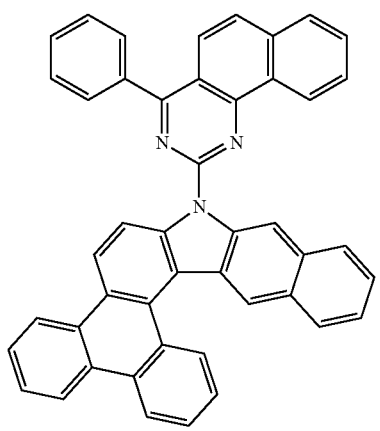
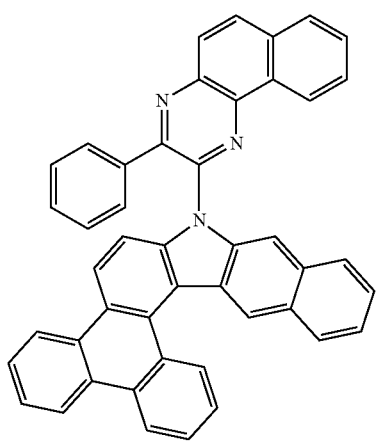
292
-continued
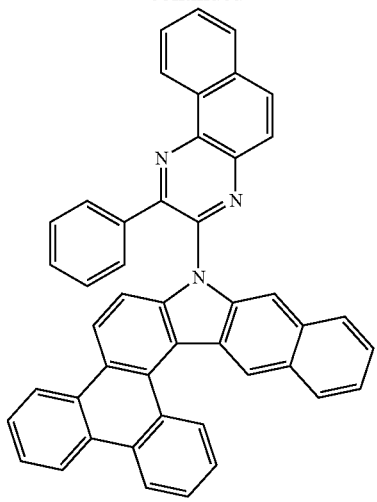
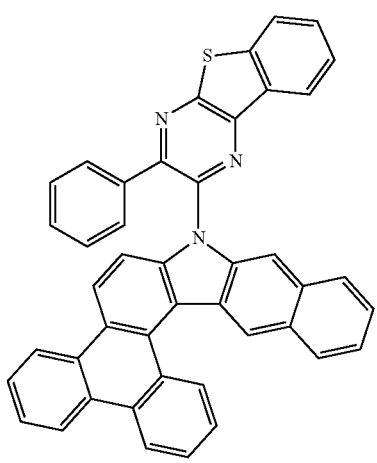
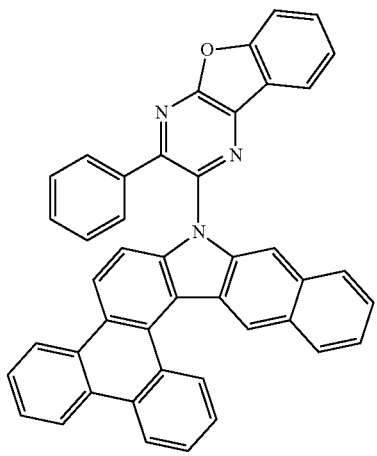

293
-continued
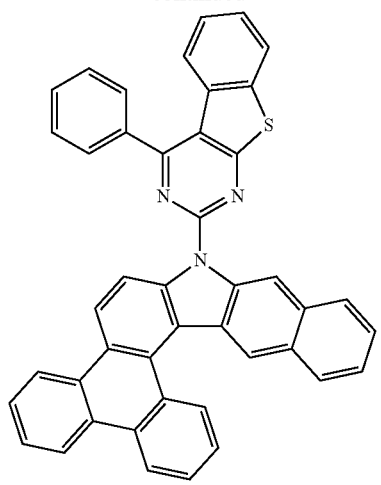
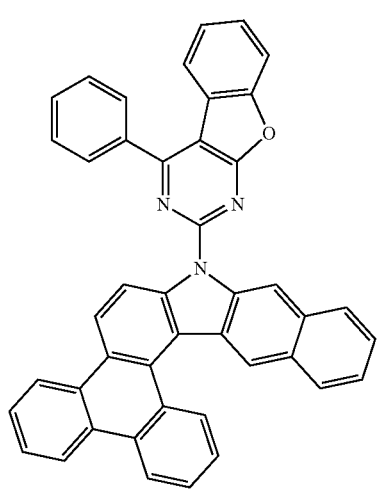
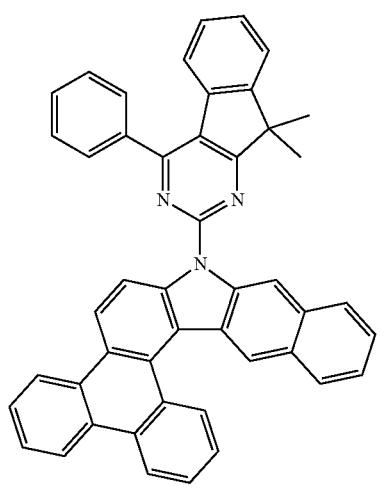
294
-continued
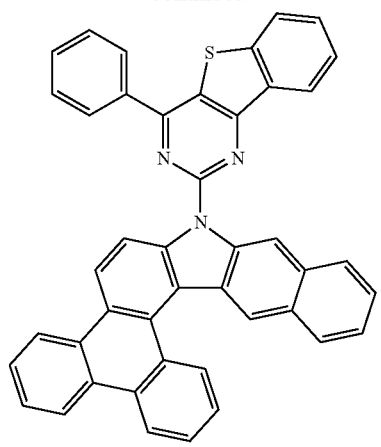
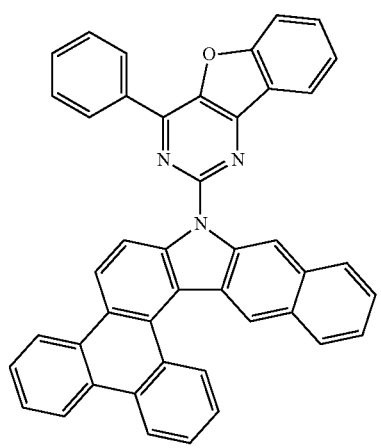
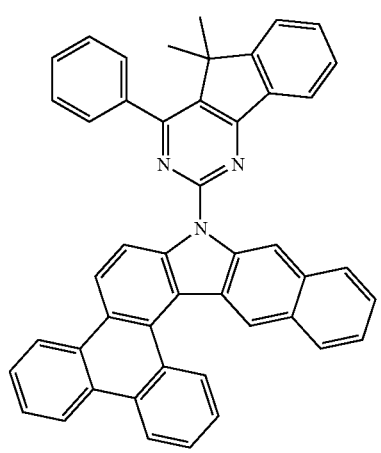

295
-continued
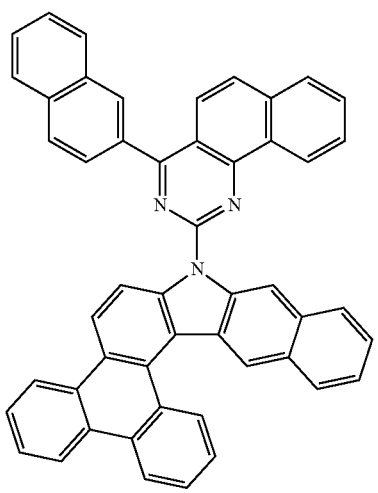
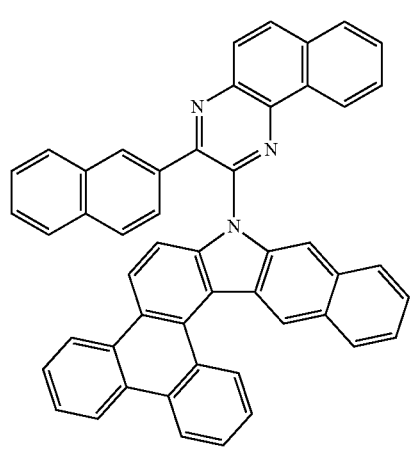
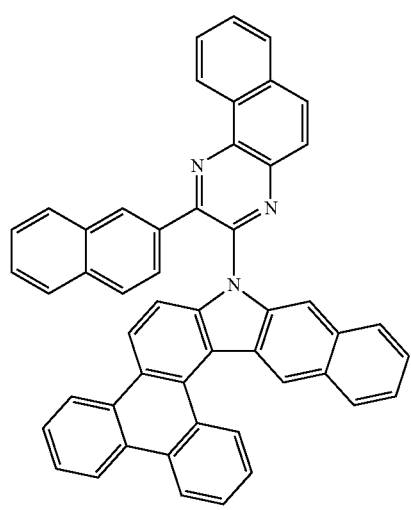
296
-continued
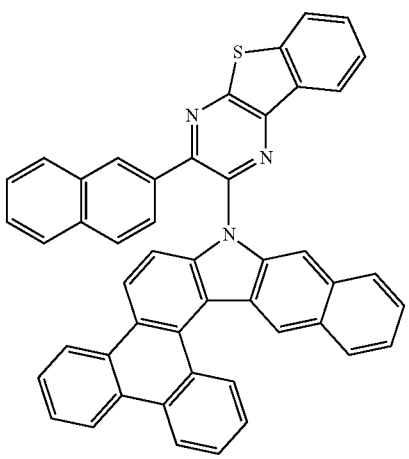
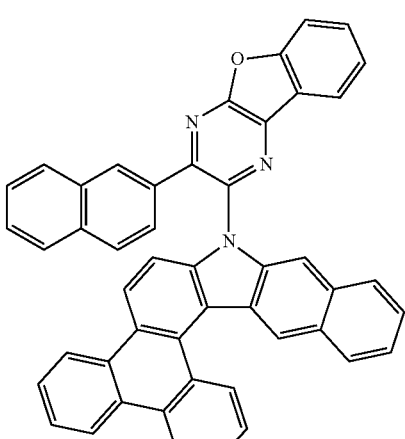
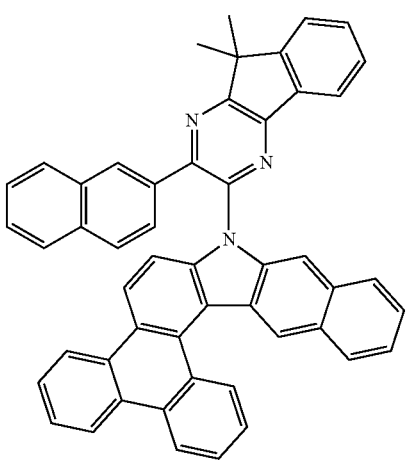

297
-continued
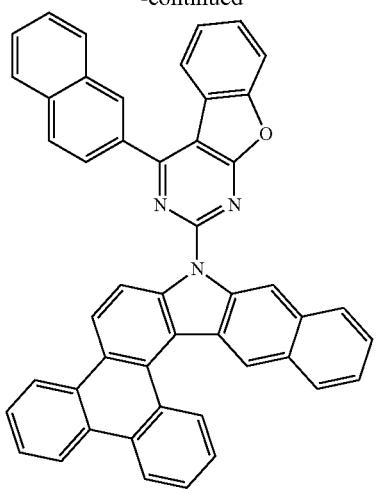
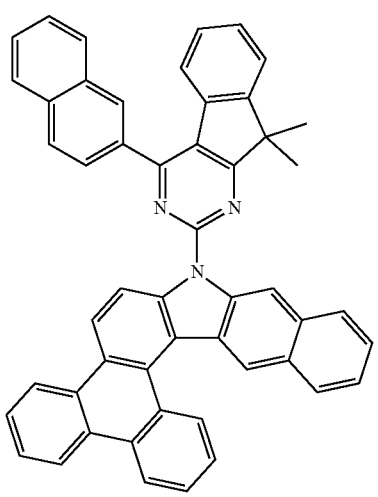
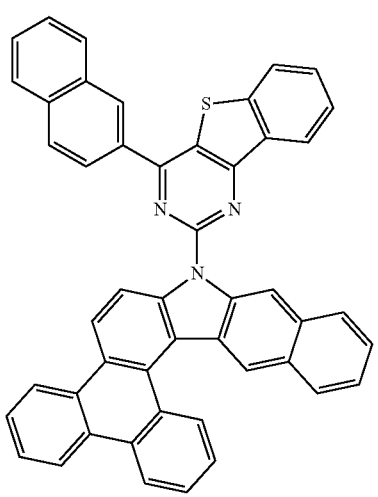
298
-continued
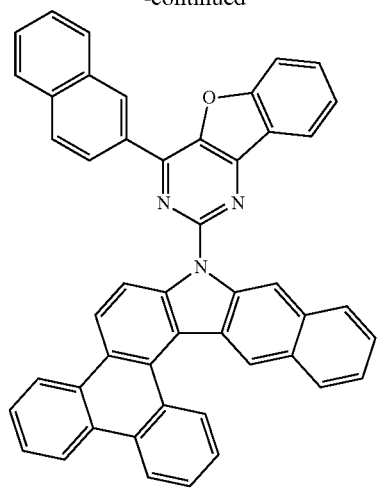
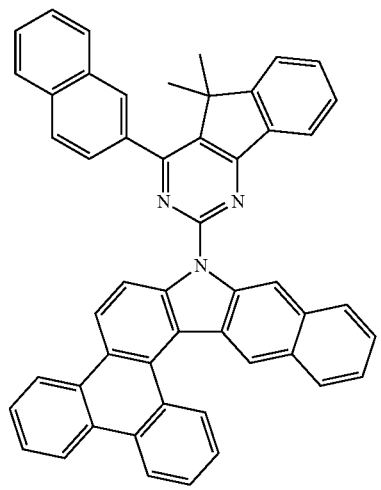
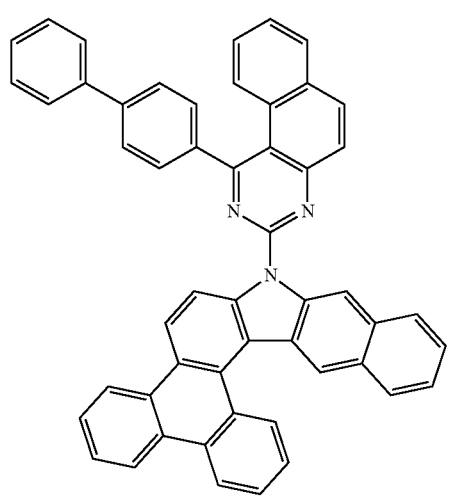

299
-continued
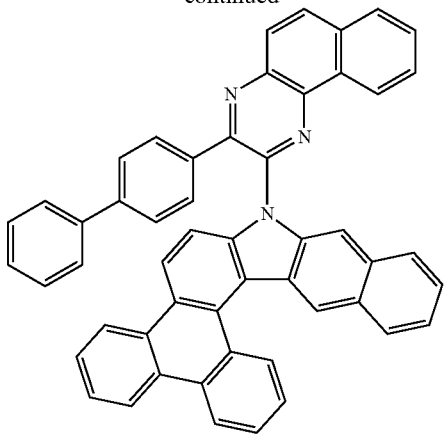
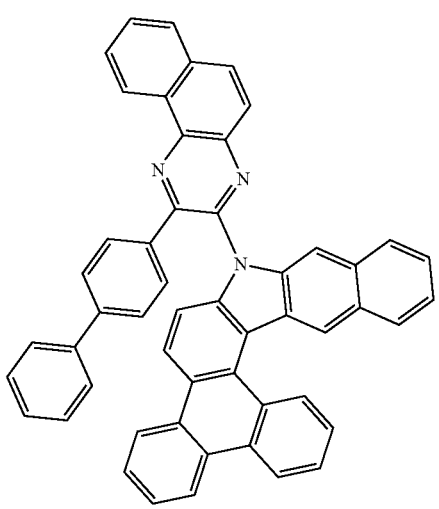
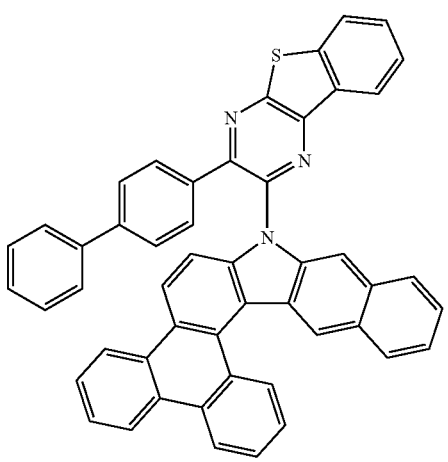
300
-continued
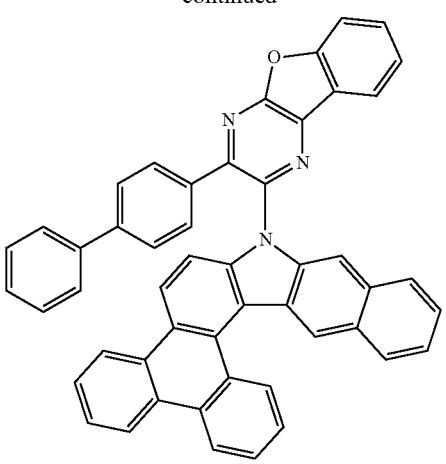
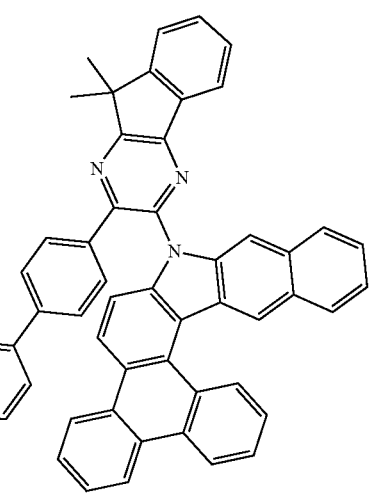
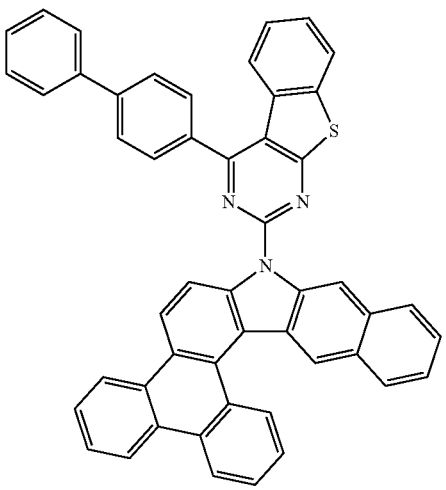

| 301 -continued | 302 -continued |
|---|---|
| 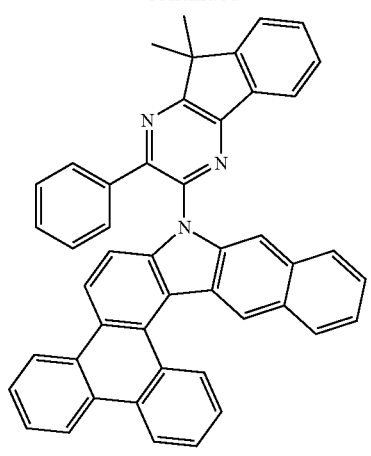 | 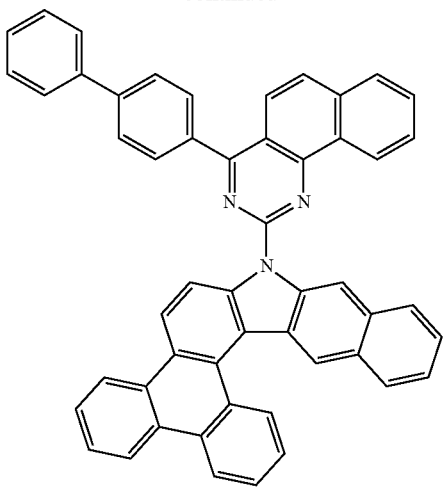 |
| 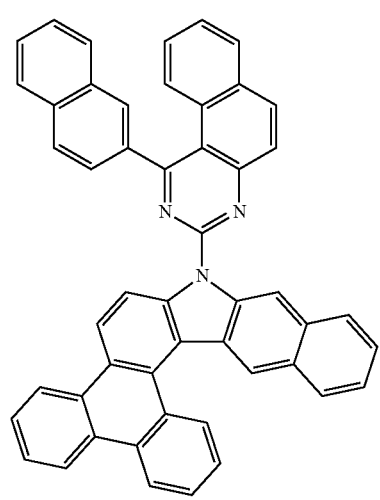 | 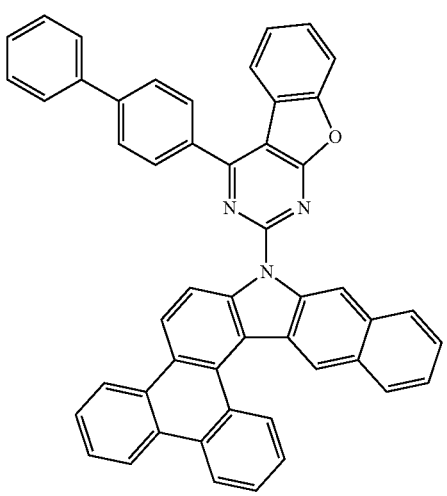 |
| 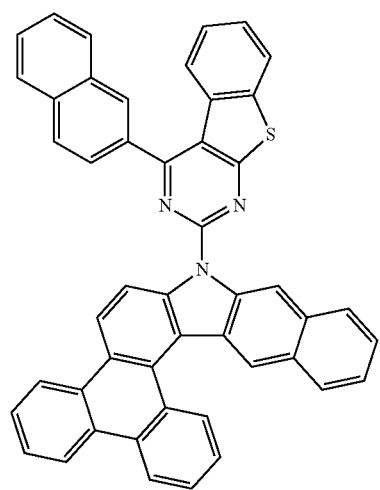 | 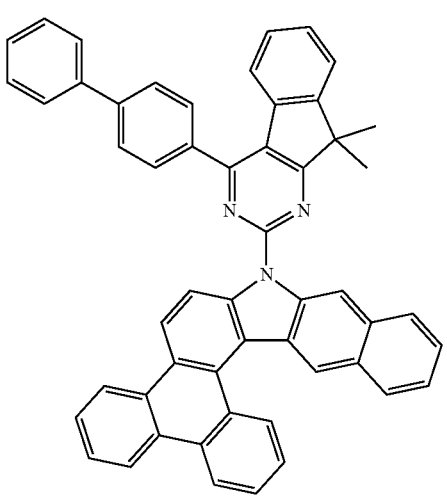 |

303
-continued
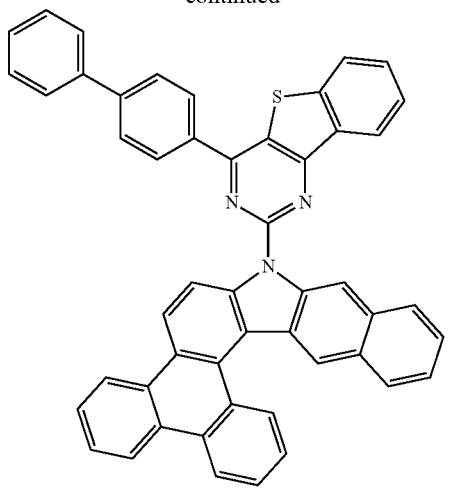
304
-continued
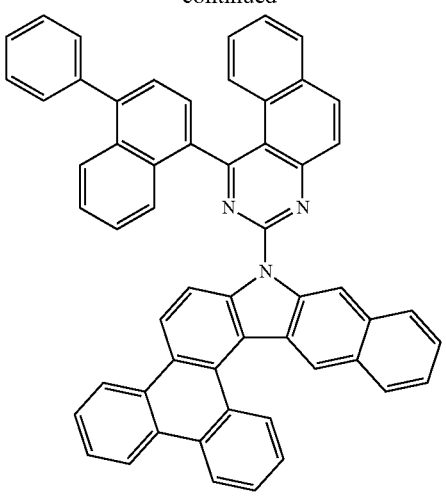
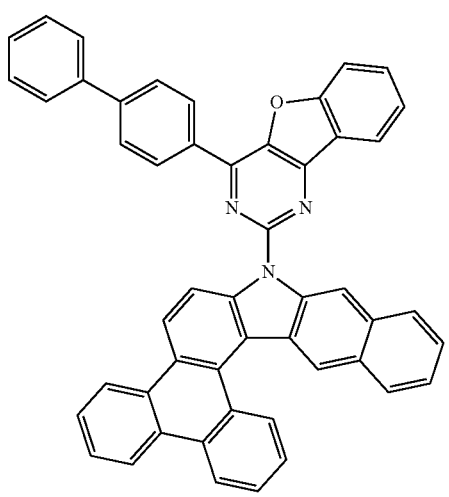
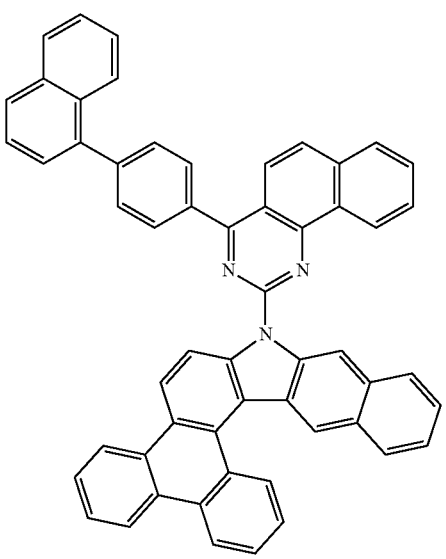
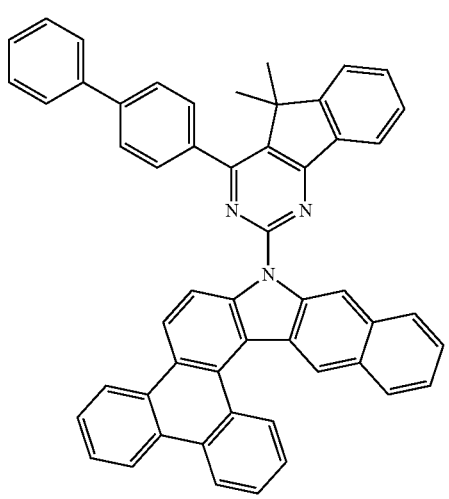
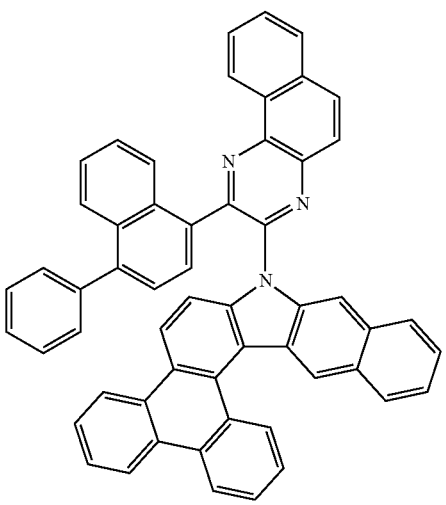

305
-continued
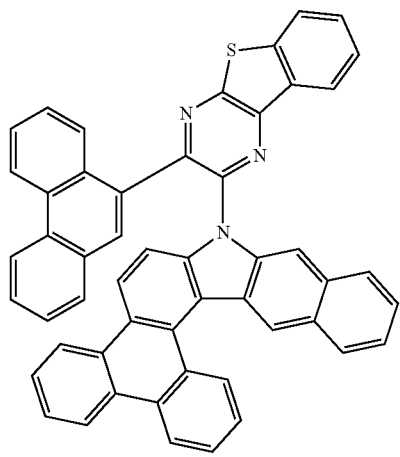
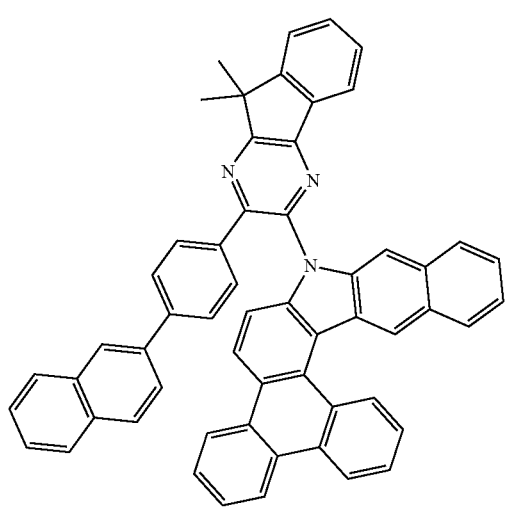
306
-continued
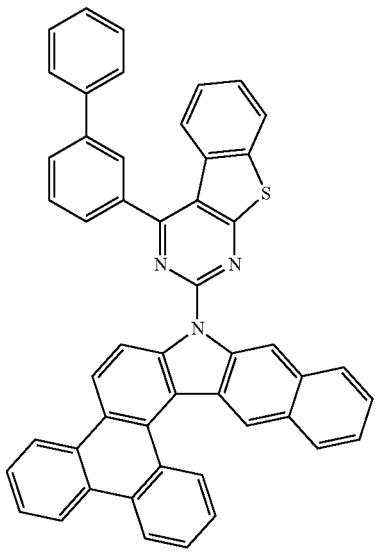
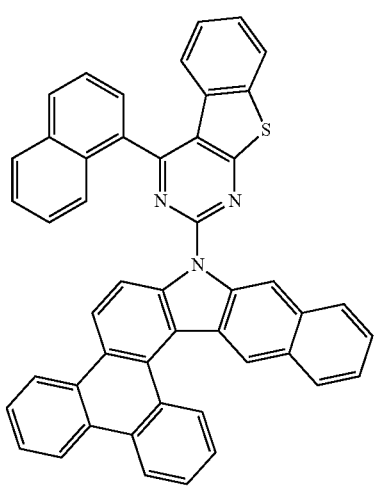
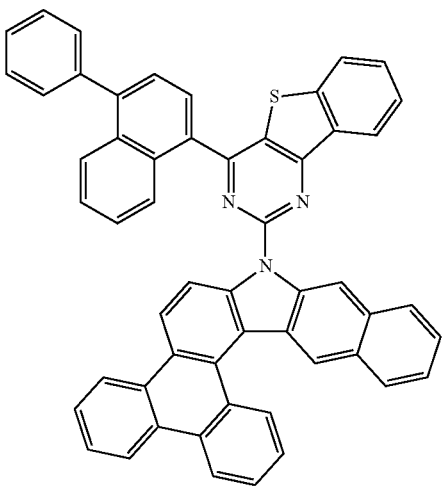

307
-continued
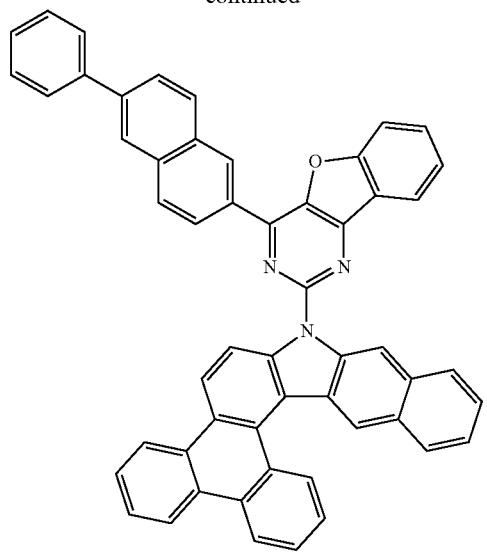
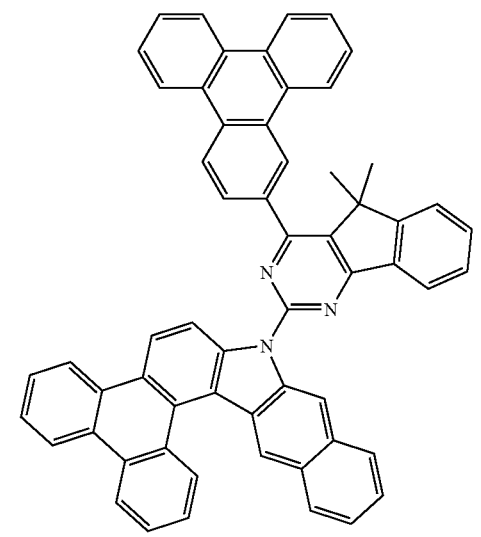
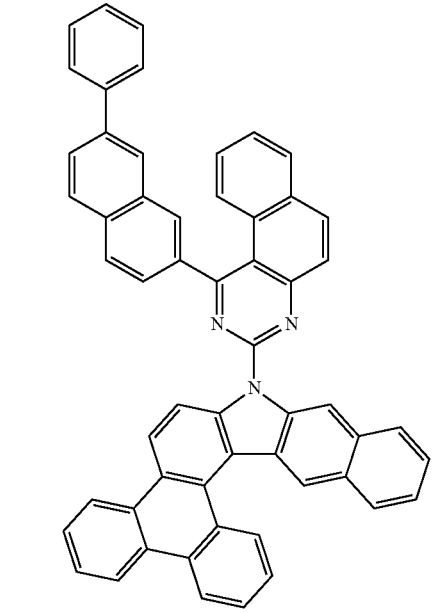
308
-continued
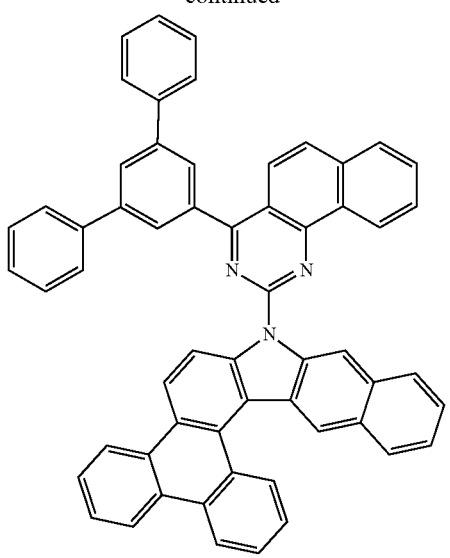
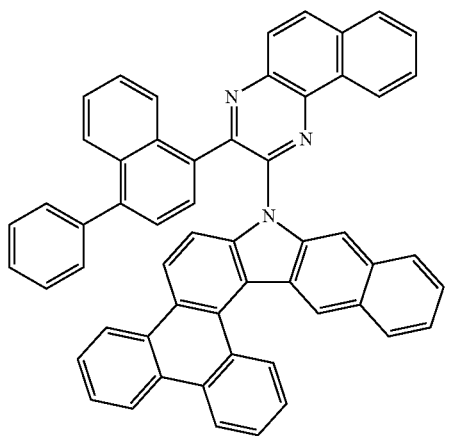
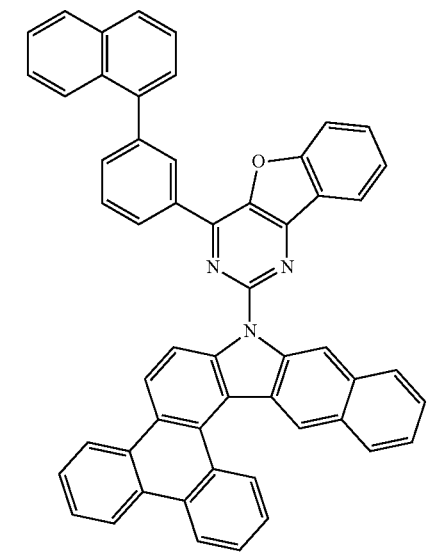

309
-continued
310
-continued
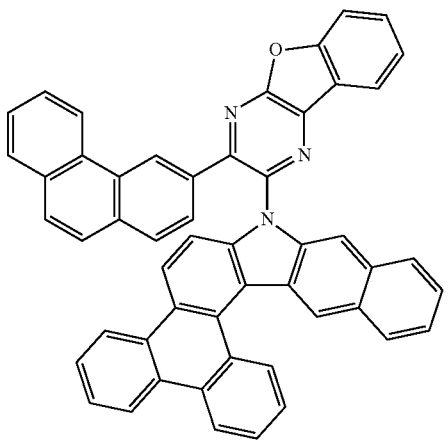
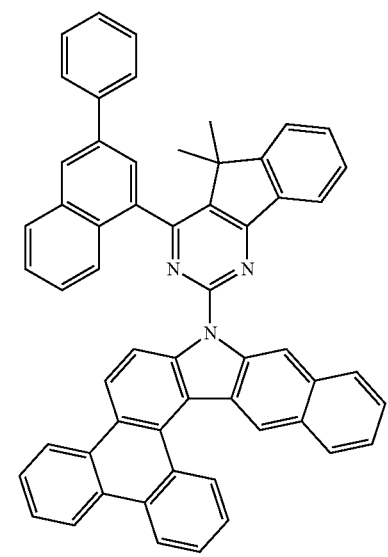
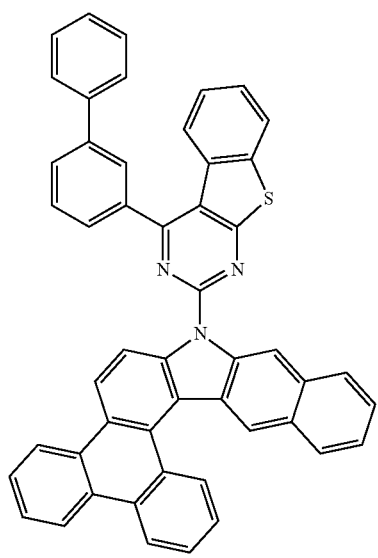
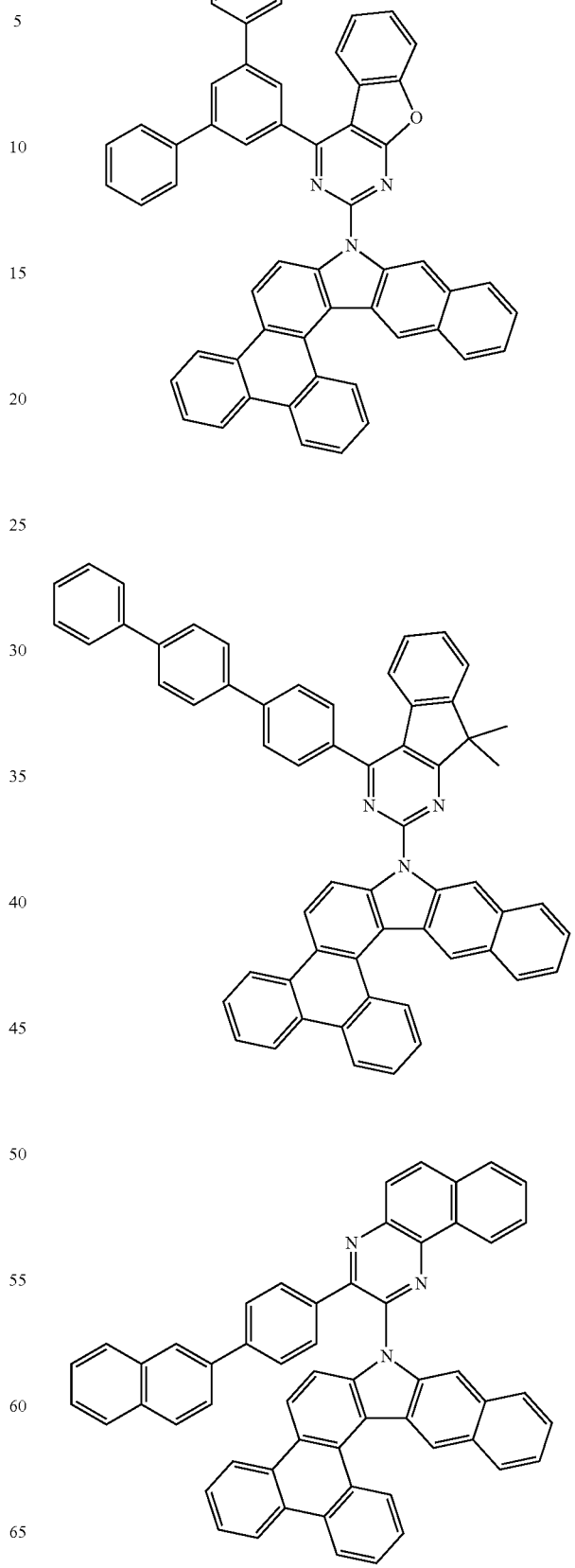

| 311 -continued | 312 -continued |
|---|---|
| 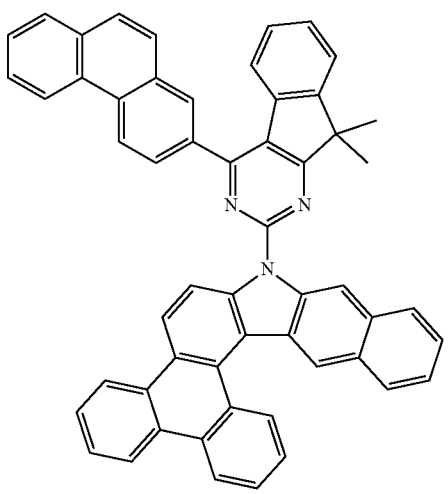 | 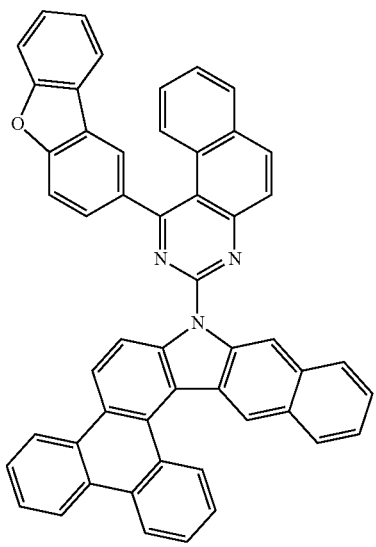 |
| 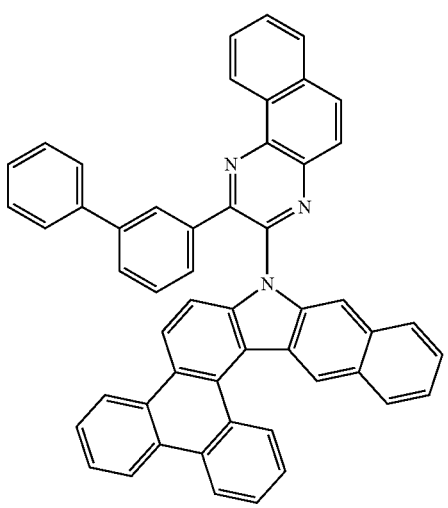 | 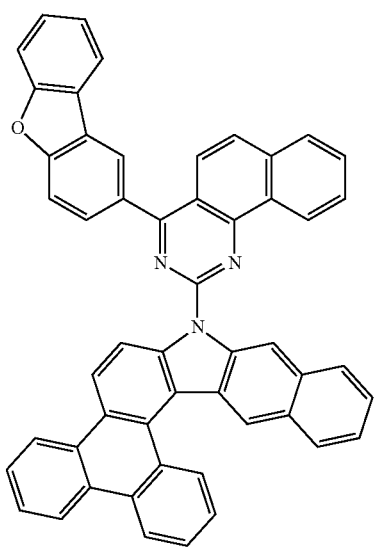 |
| 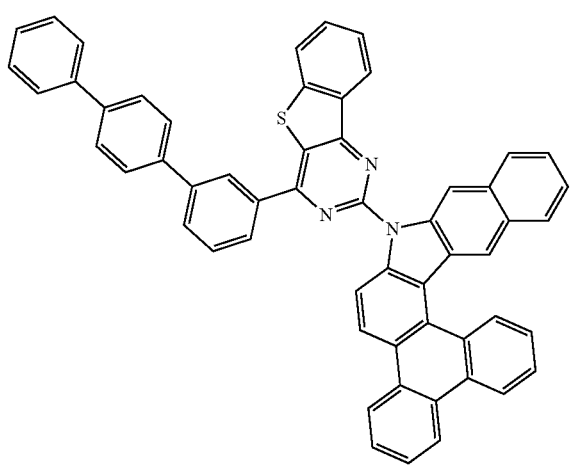 | 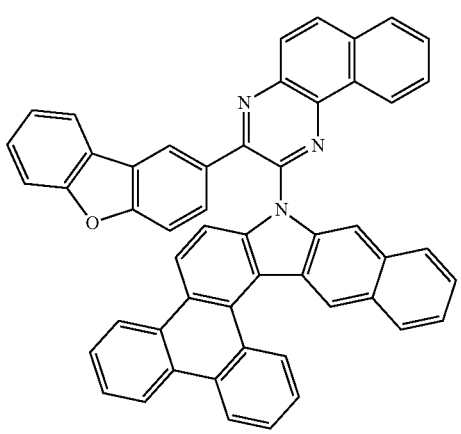 |

313
-continued
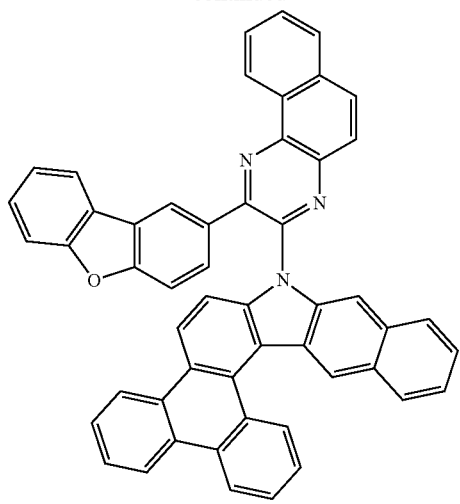
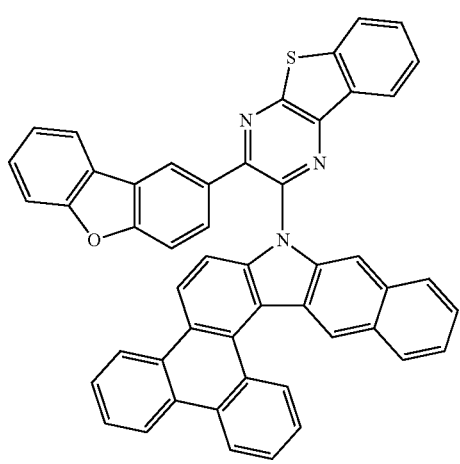
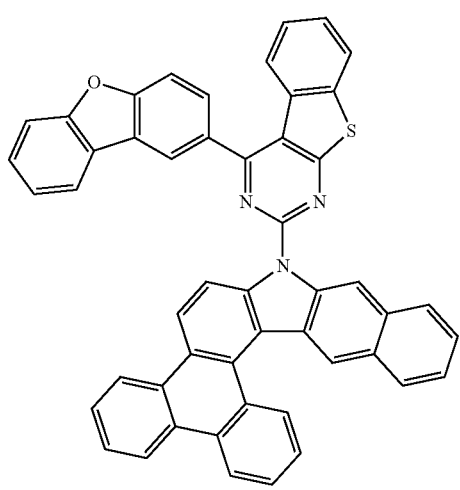
314
-continued
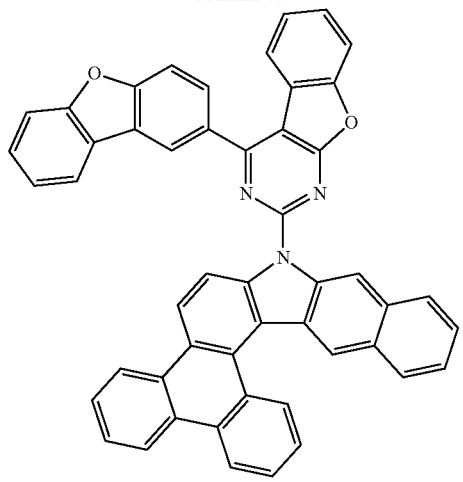
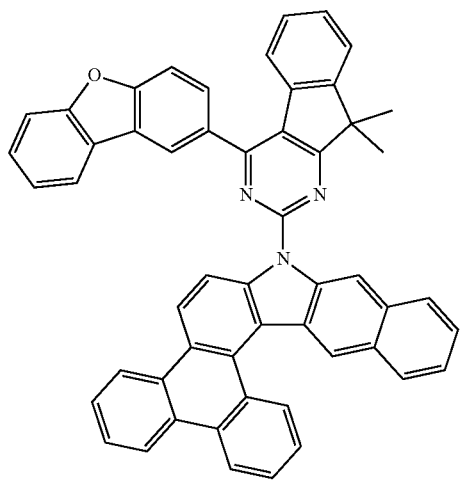
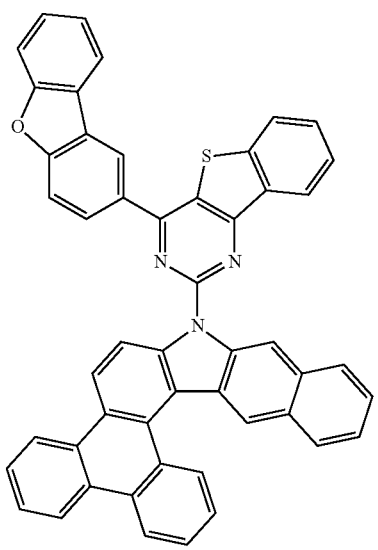

315
-continued
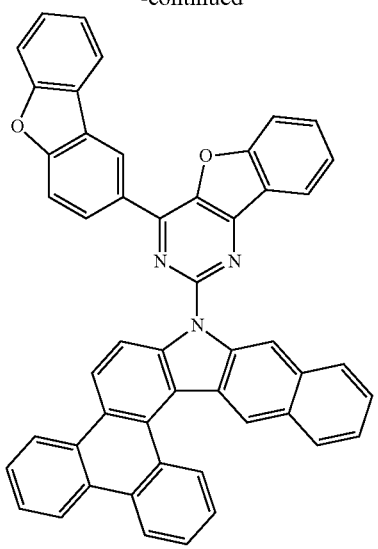
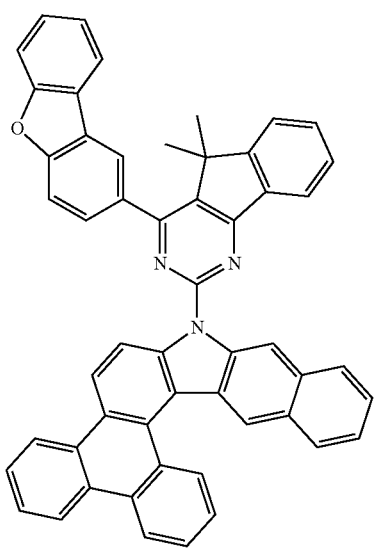
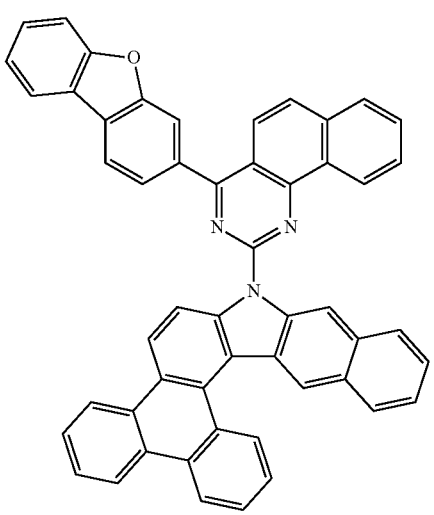
316
-continued
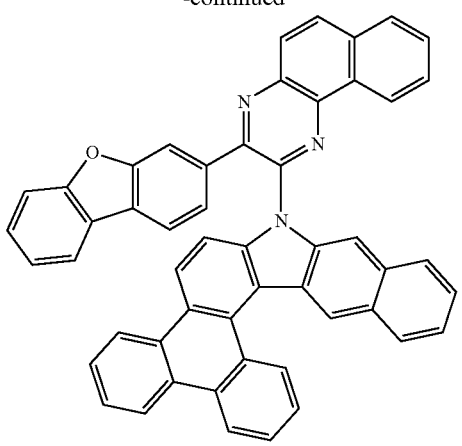
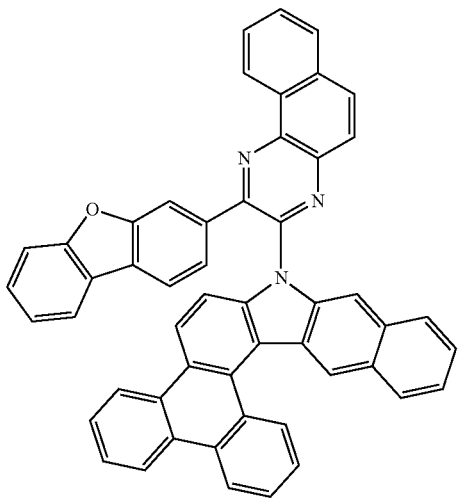
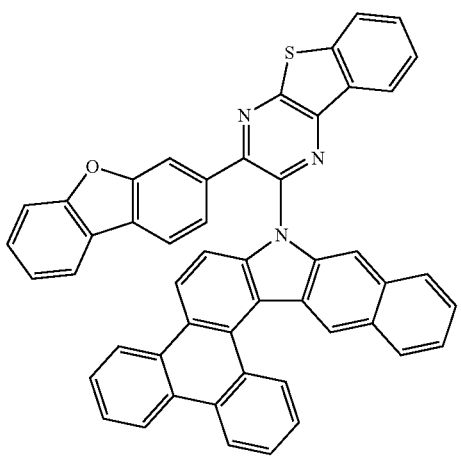

317
-continued
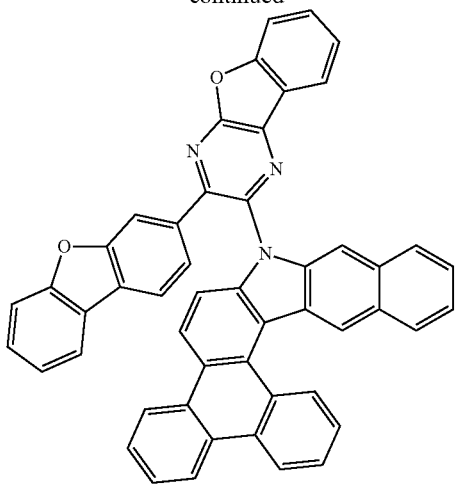
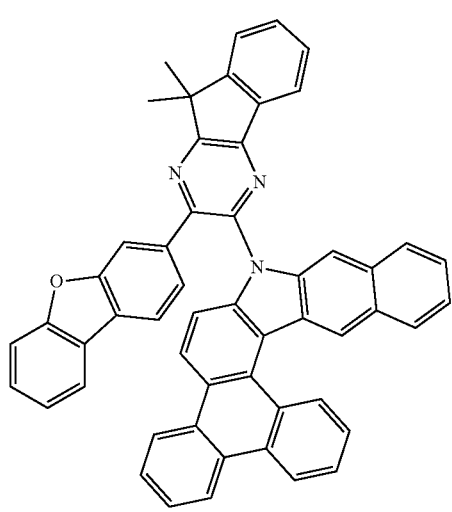
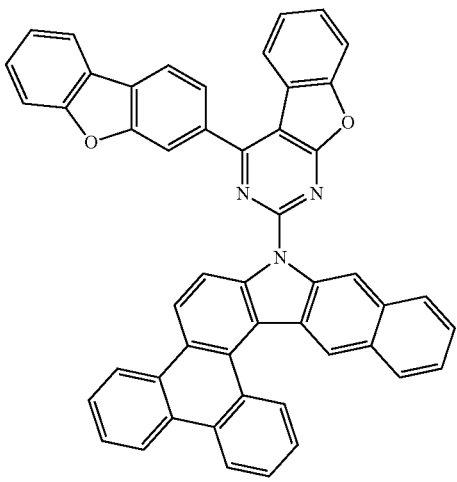
318
-continued
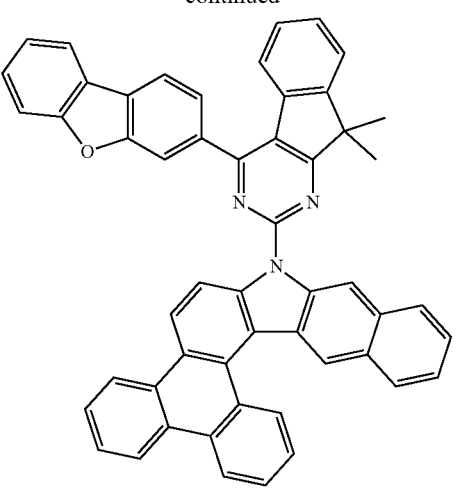
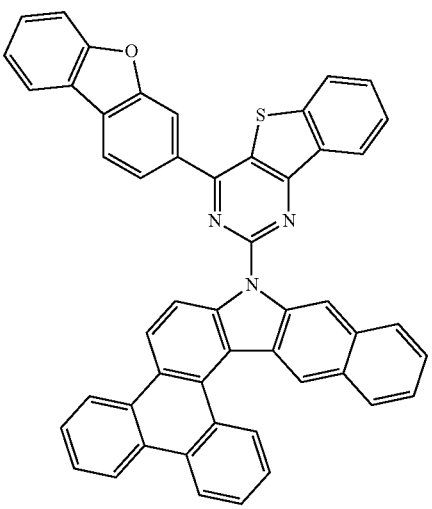
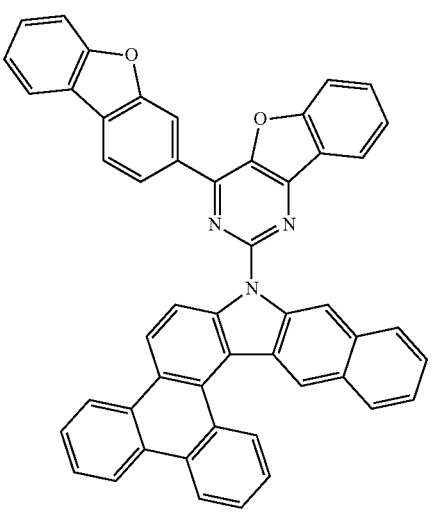

319
-continued
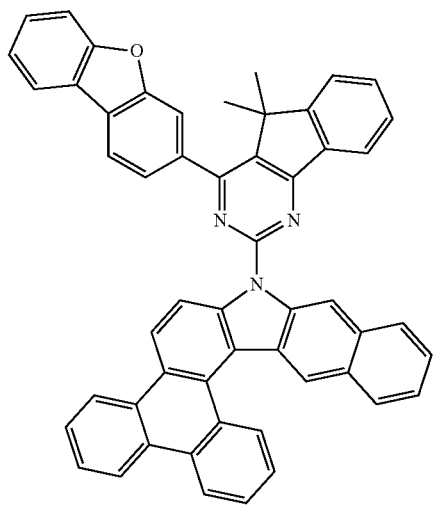
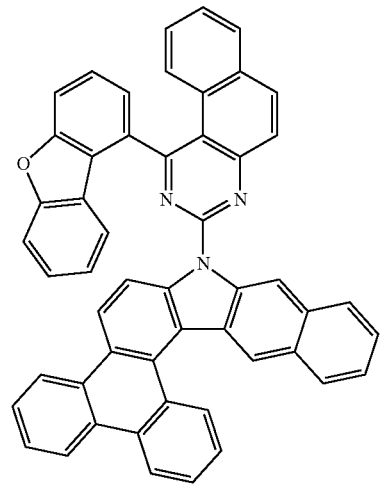
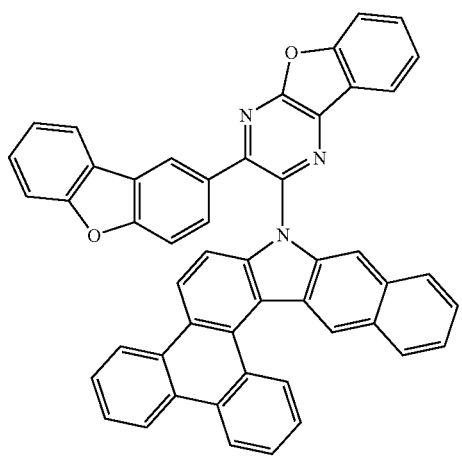
320
-continued
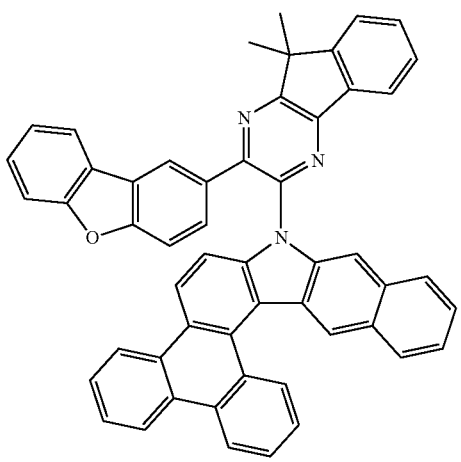
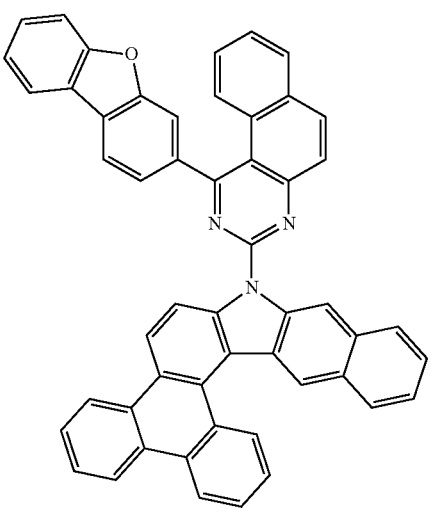
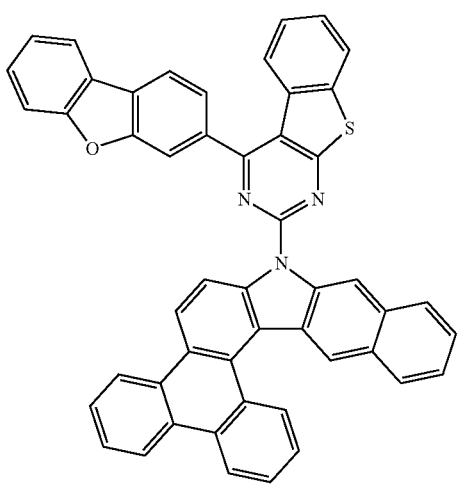

321
-continued
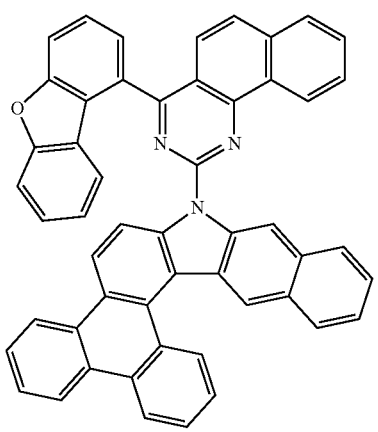
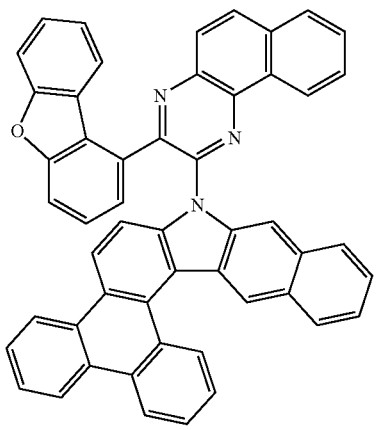
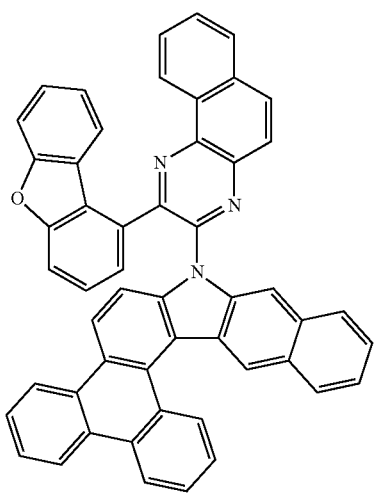
322
-continued
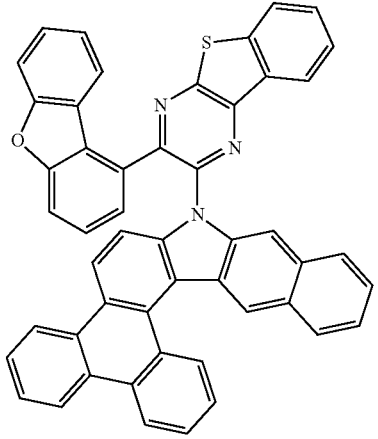
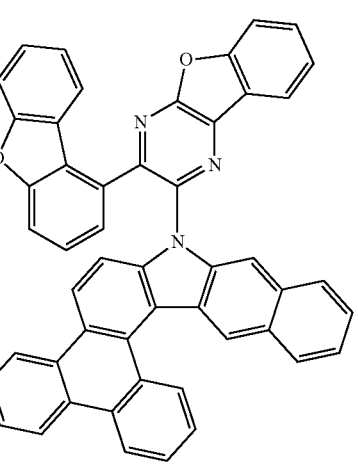
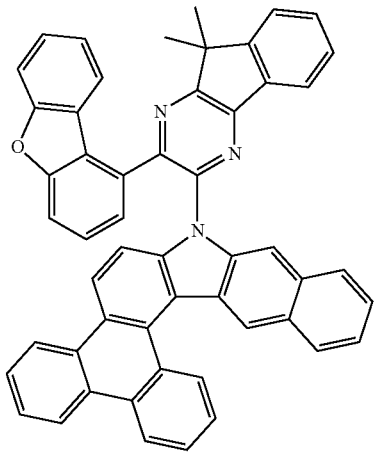

323
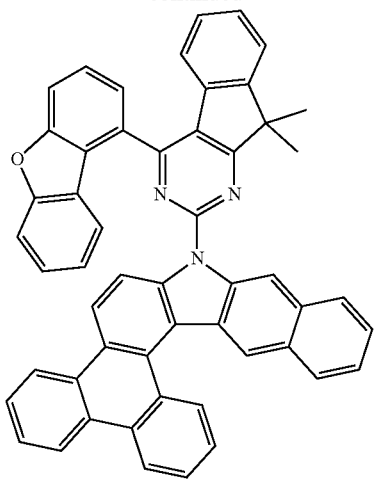
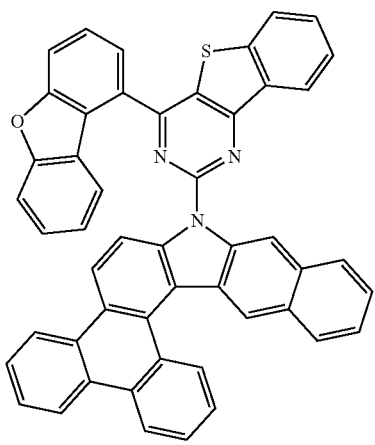
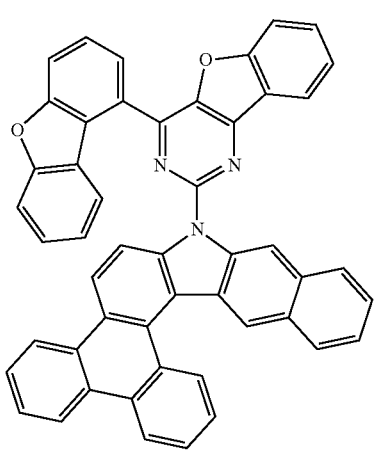
324
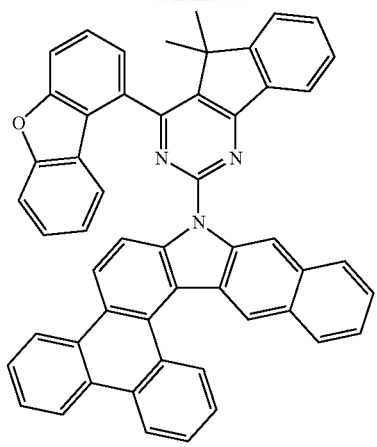
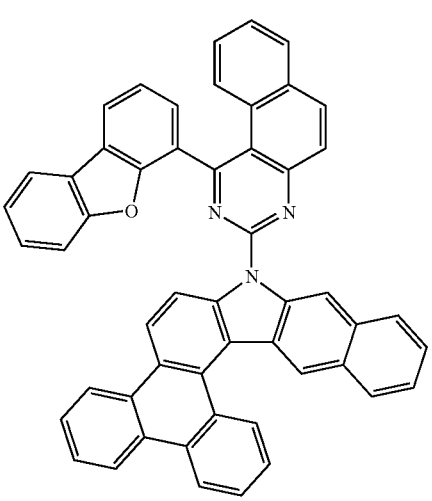
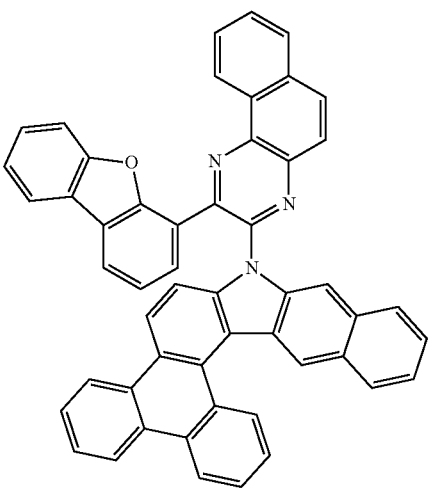

325
-continued
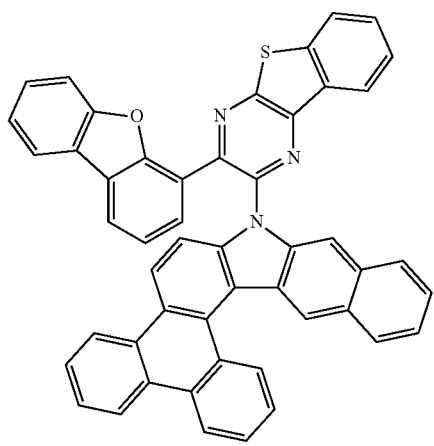
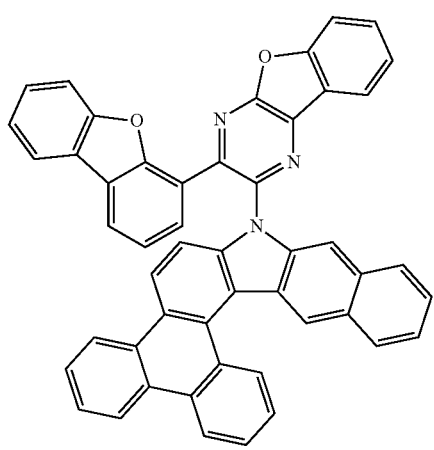
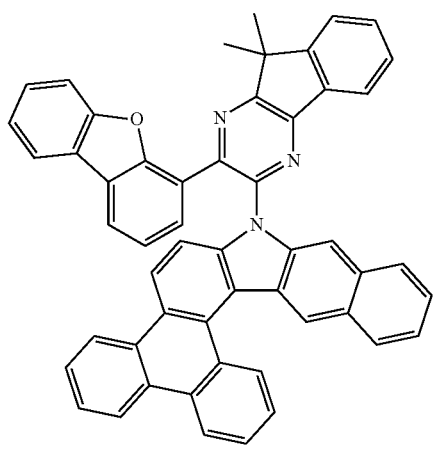
326
-continued
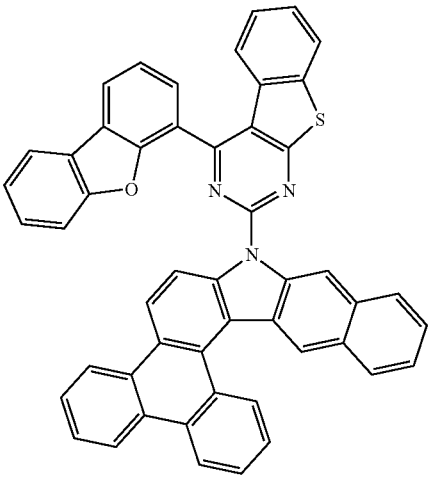
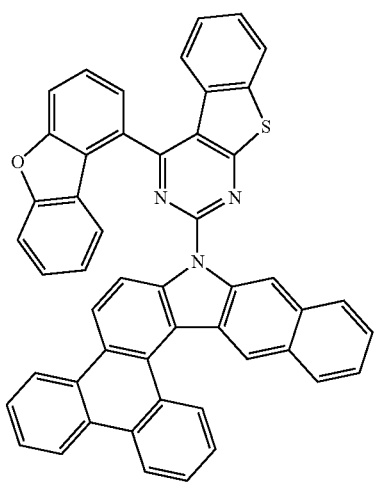
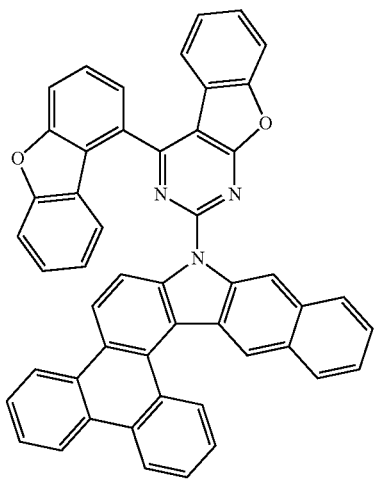

327
-continued
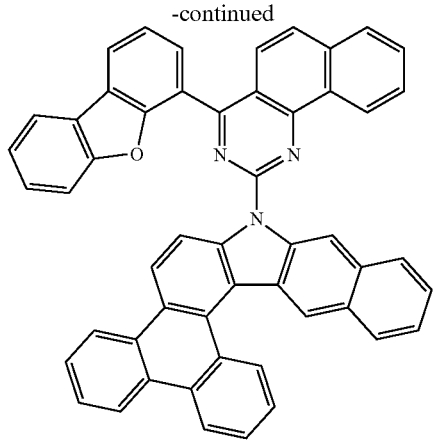
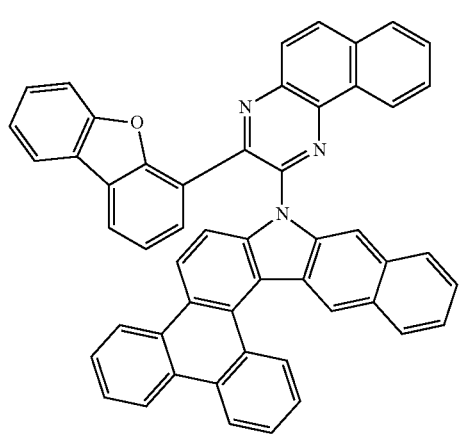
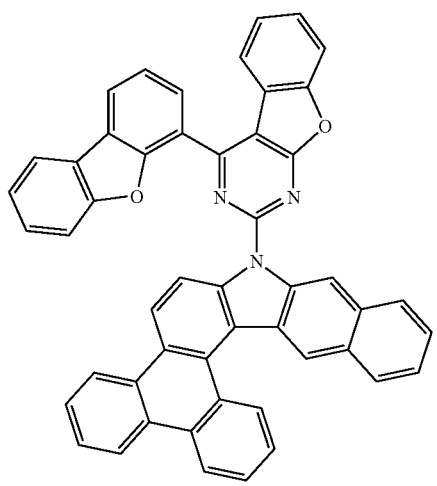
328
-continued
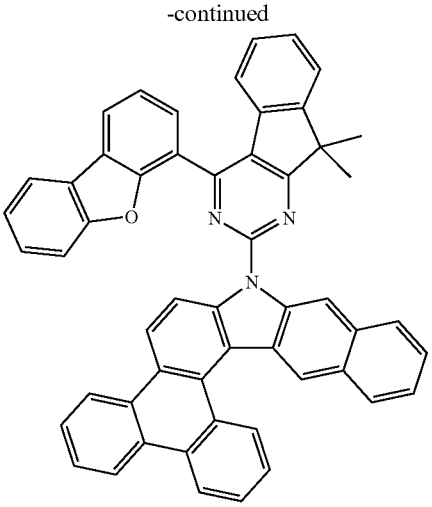
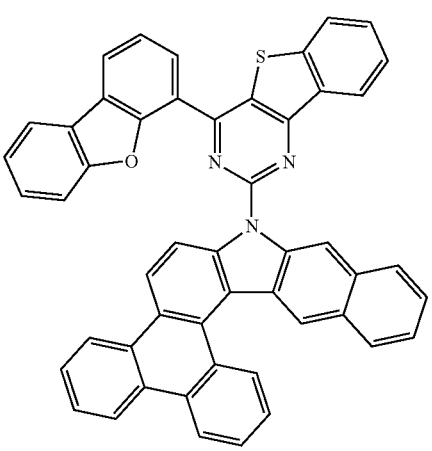
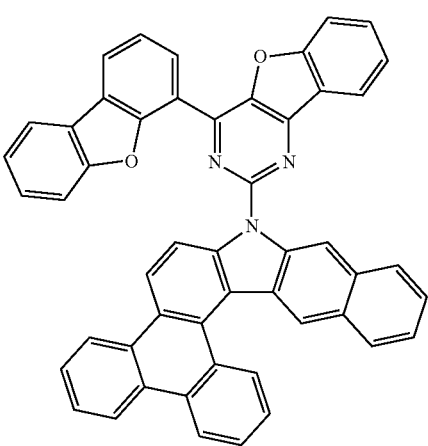

329
-continued
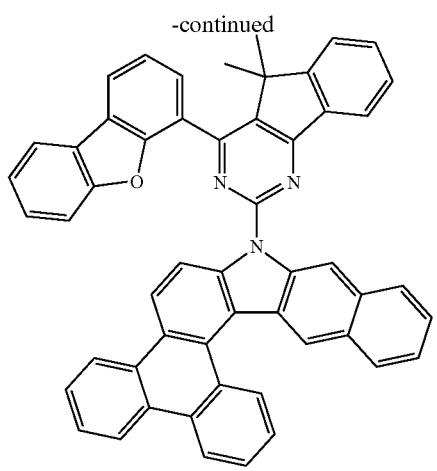
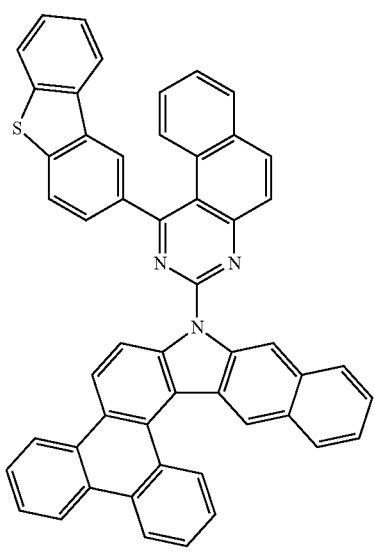
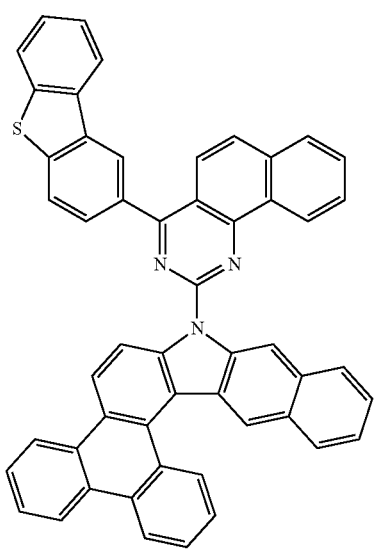
330
-continued
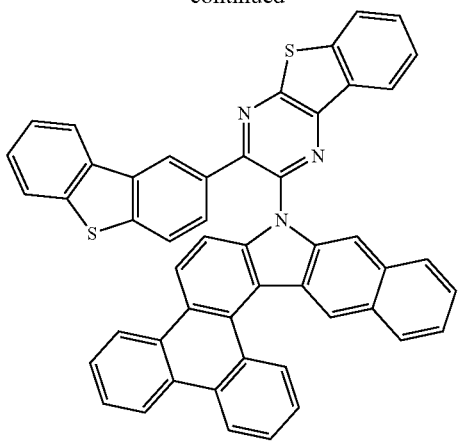
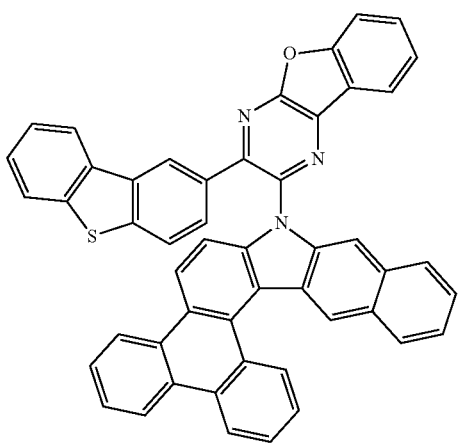
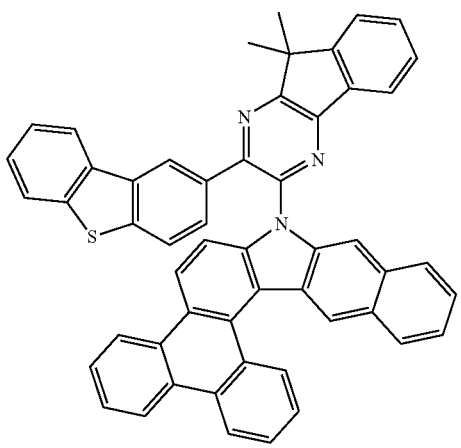

331
-continued
332
-continued
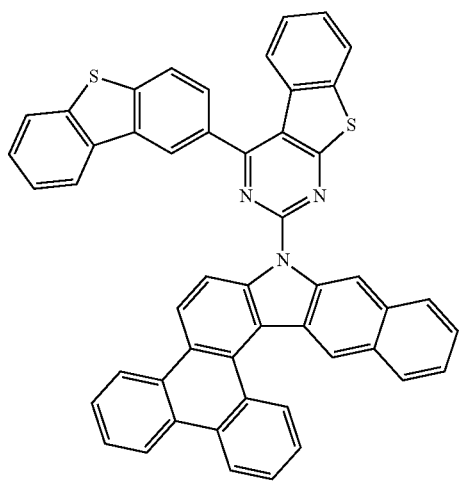
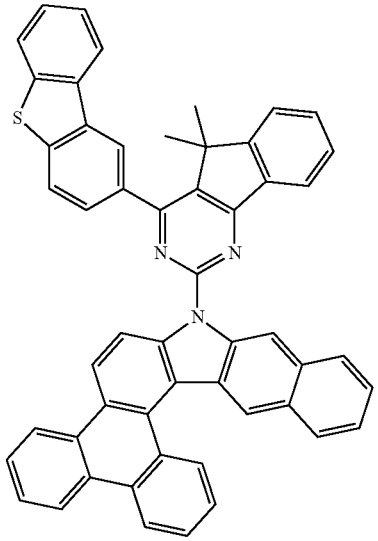
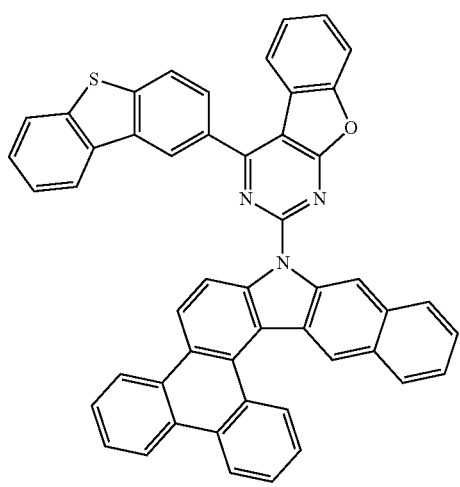
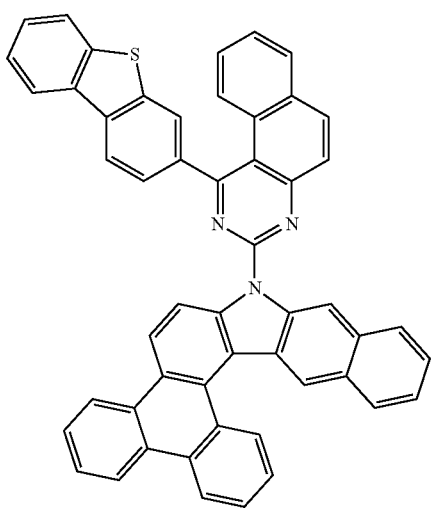
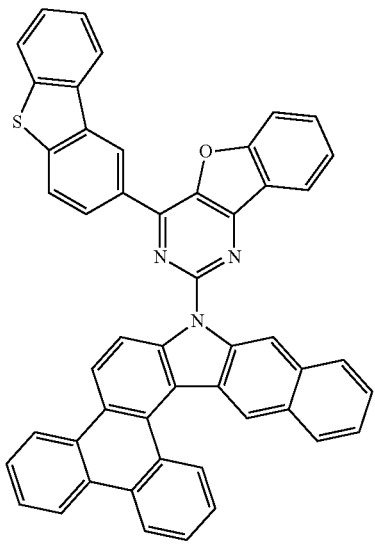
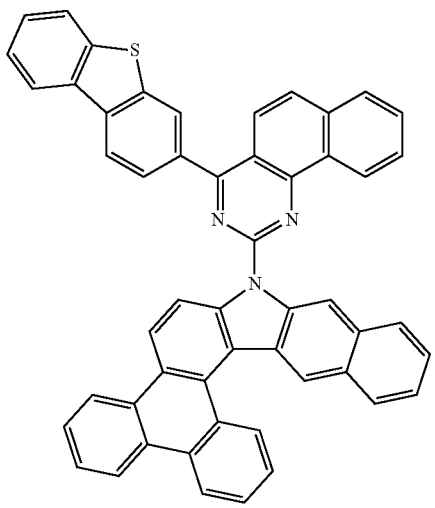

333
-continued
334
-continued
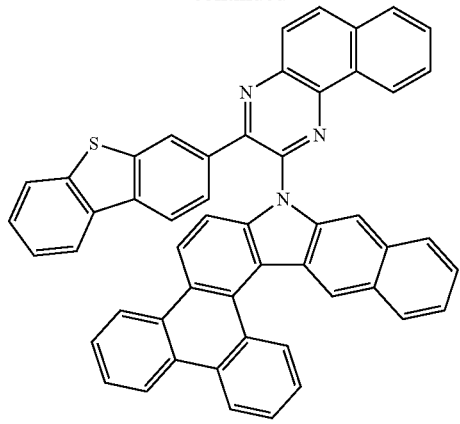
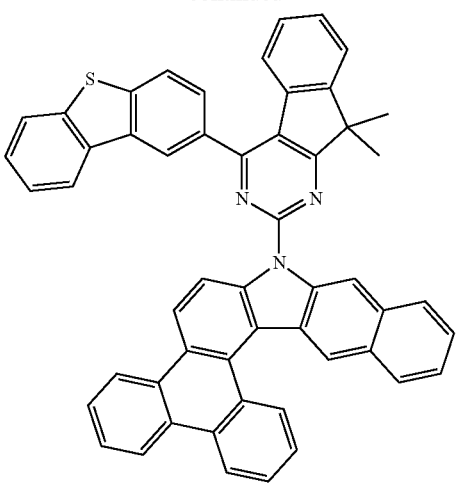
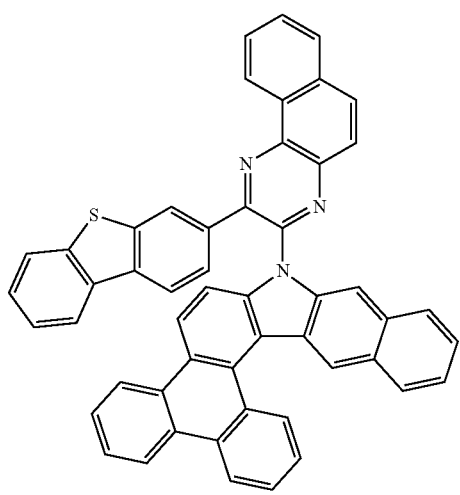
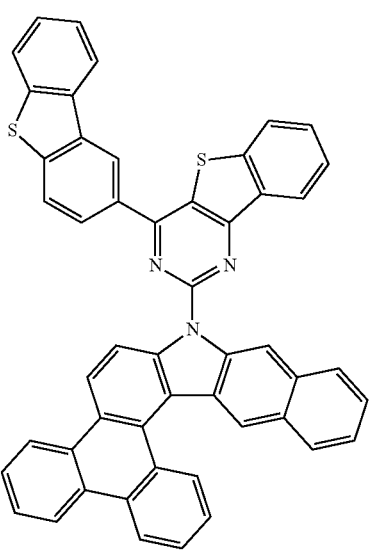
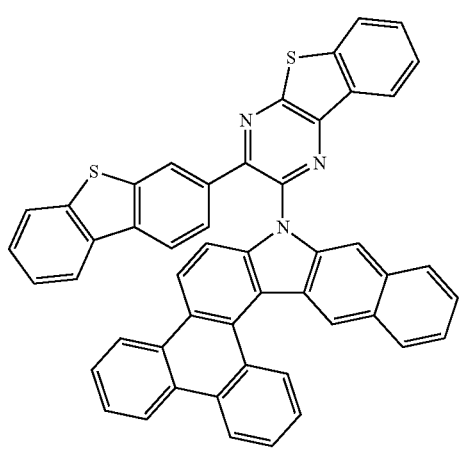
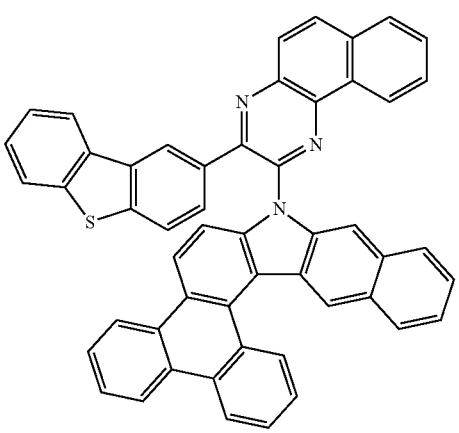

335
-continued
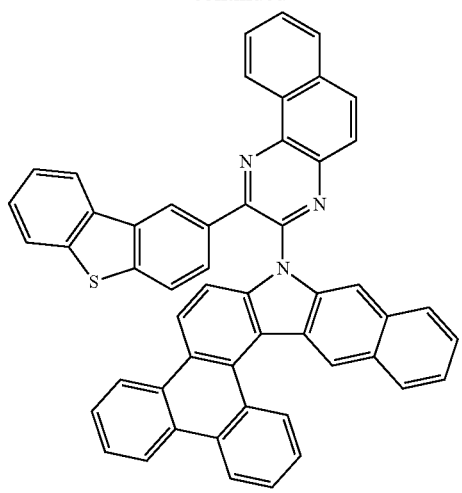
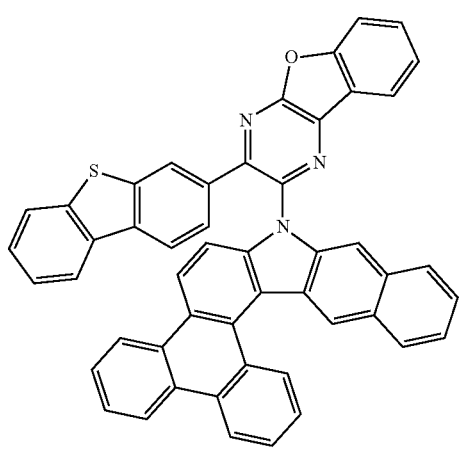
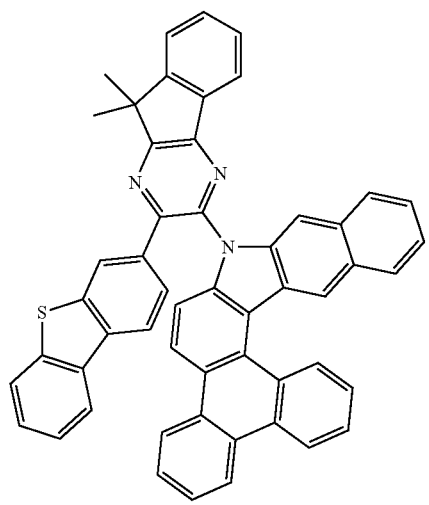
336
-continued
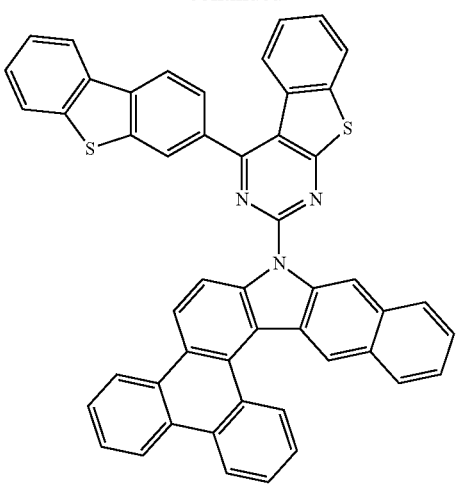

337
-continued
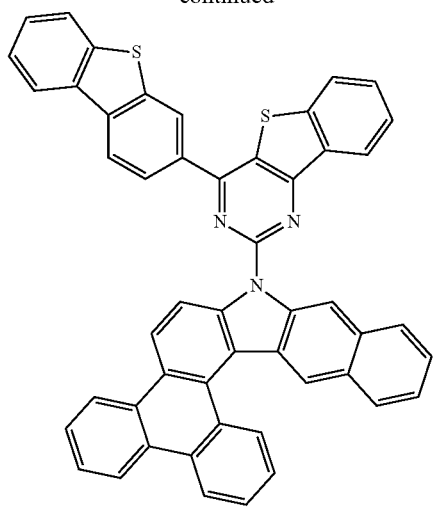
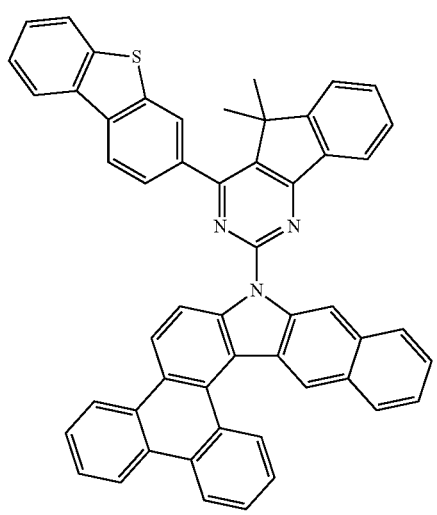
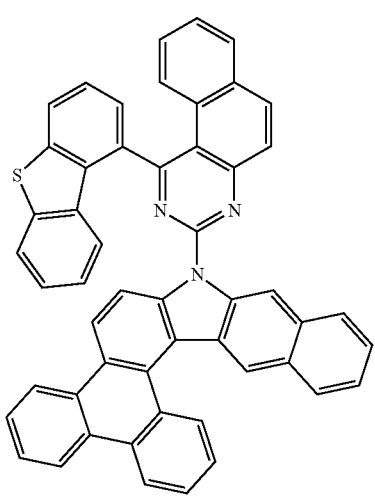
338
-continued
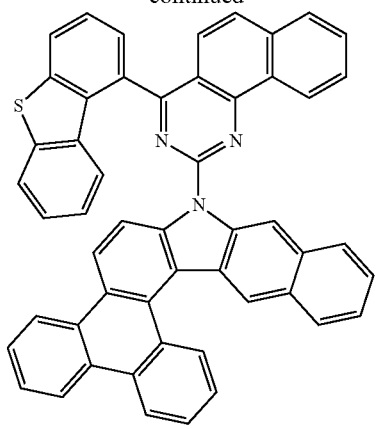
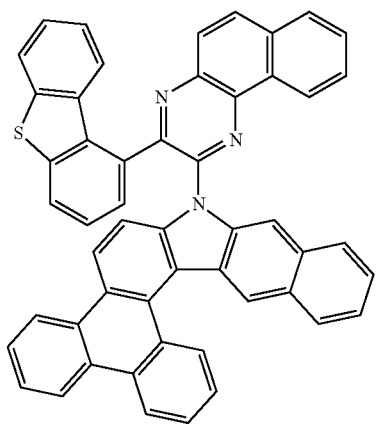
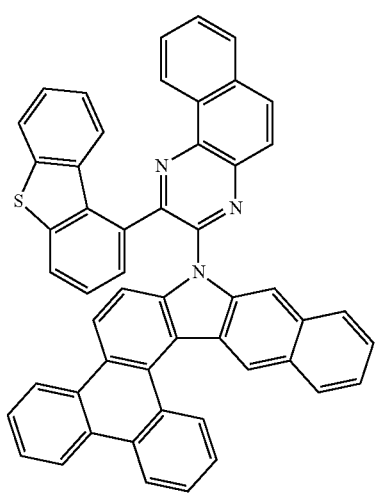

339
-continued
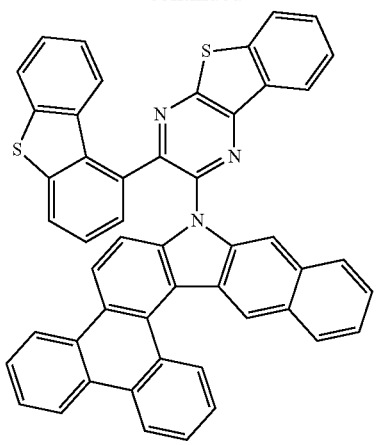
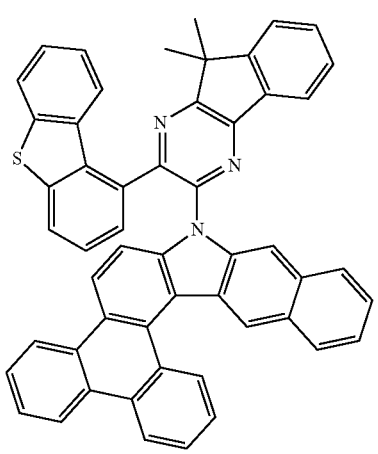
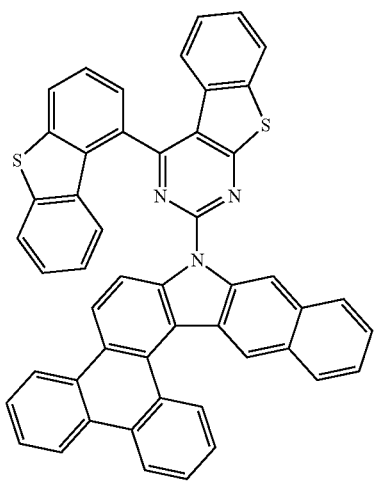
340
-continued
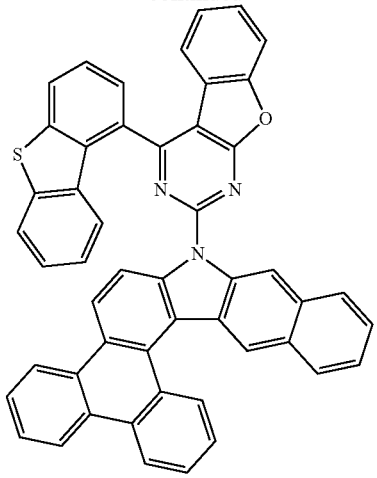
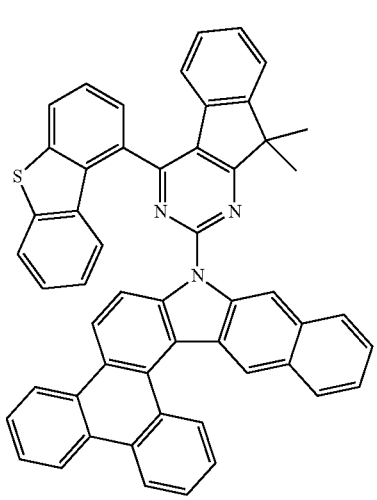
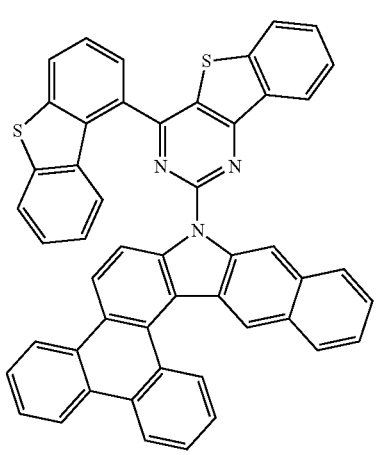

341
-continued
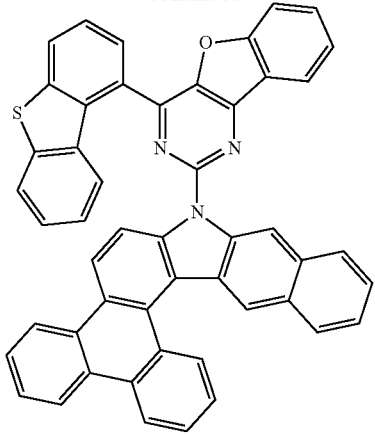
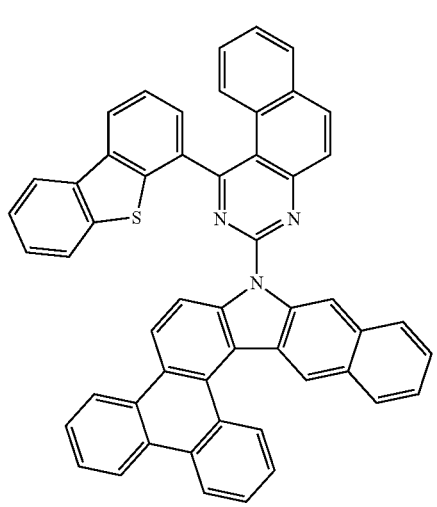
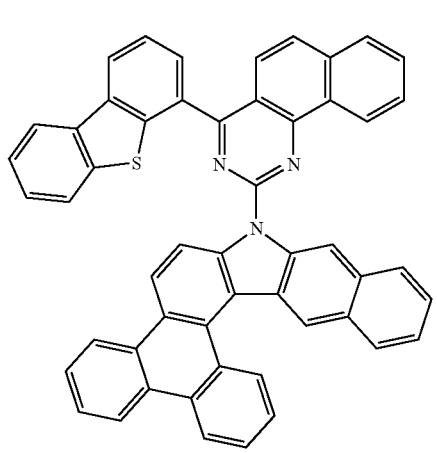
342
-continued
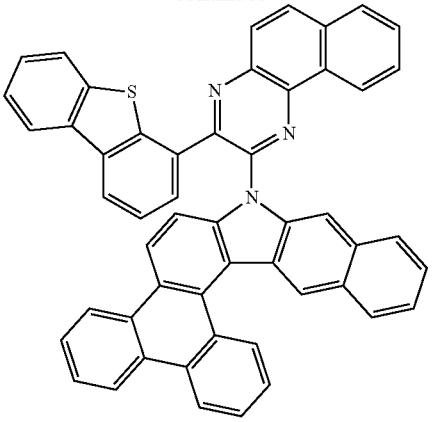
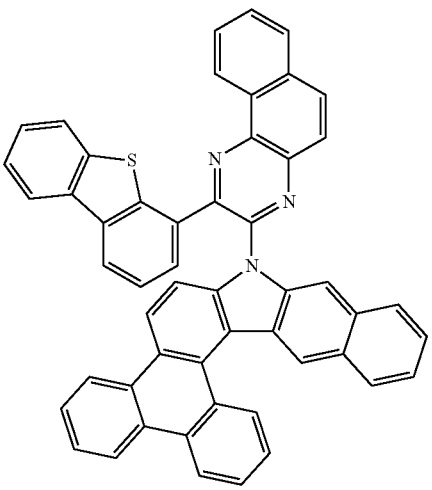
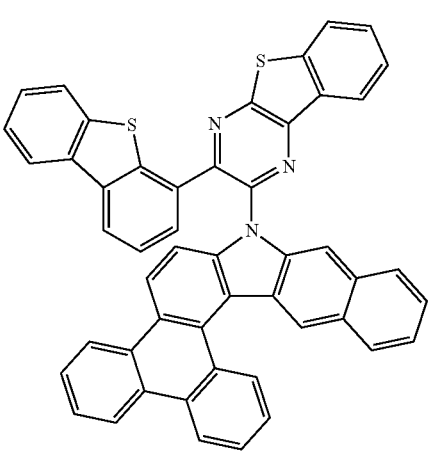

343
-continued
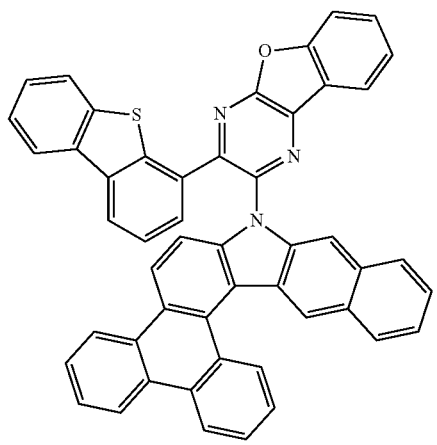
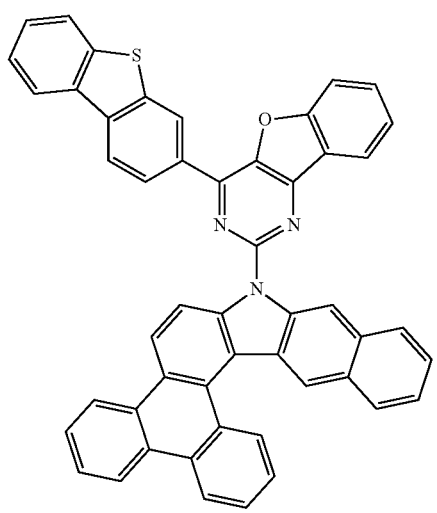
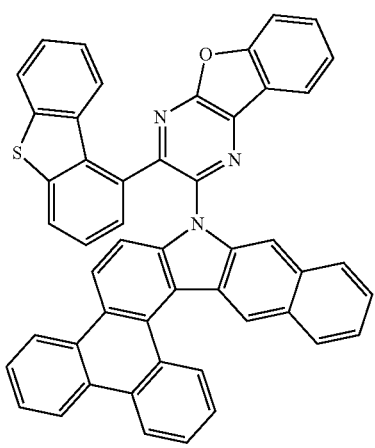
344
-continued
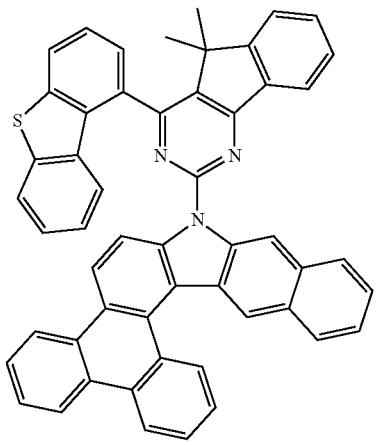
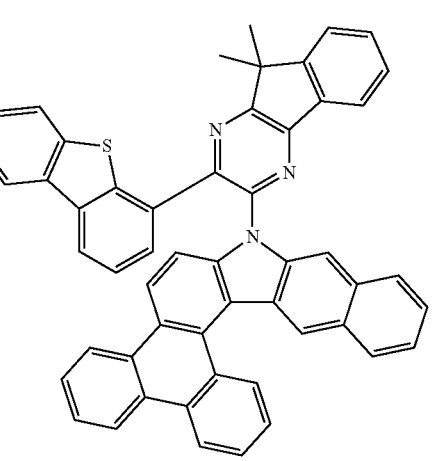
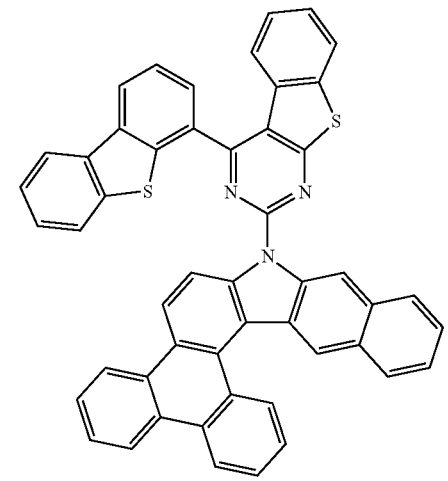

345
-continued
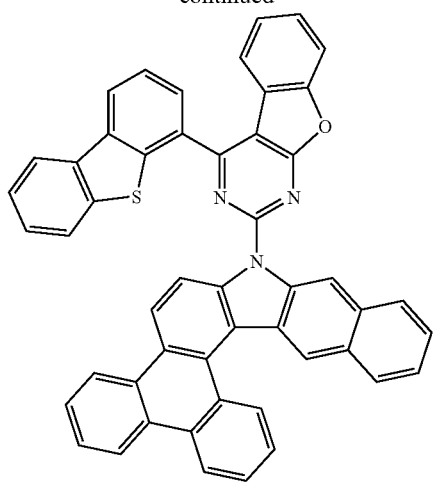
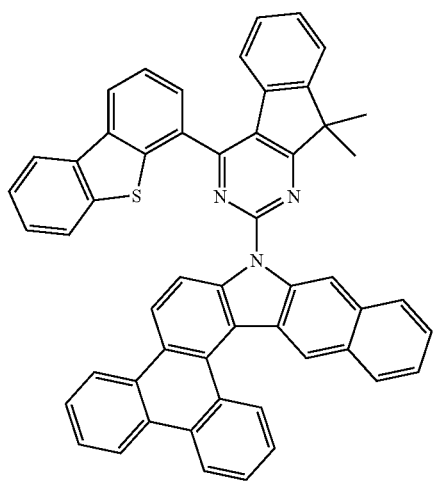
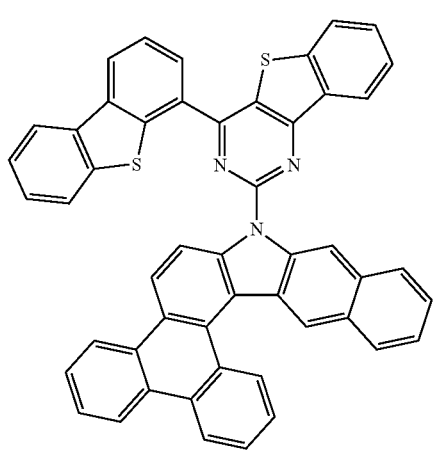
346
-continued
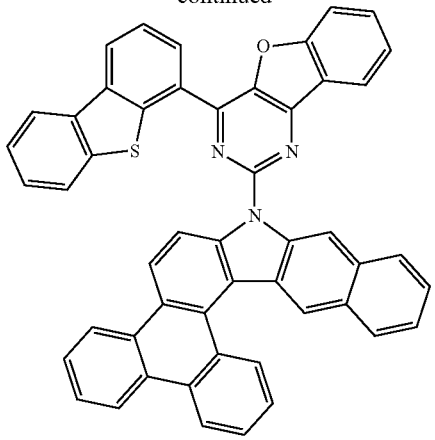
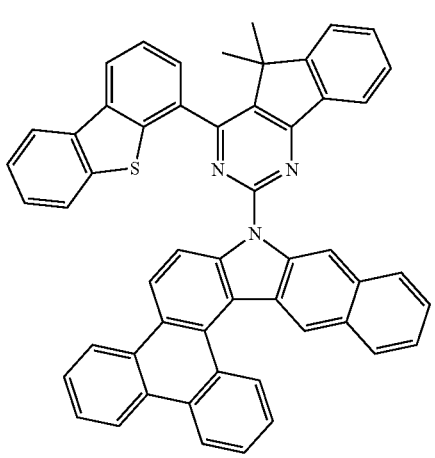
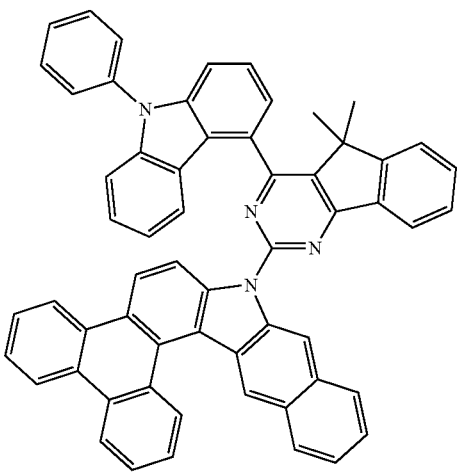 [SMILES: CC1(C)c2ccccc2-c2nc(-n3c4cc5ccccc5cc4c4c5c6ccccc6c6ccccc6c5ccc43)nc(-c3cccc4c3c3ccccc3n4-c3ccccc3)c21]

347
-continued
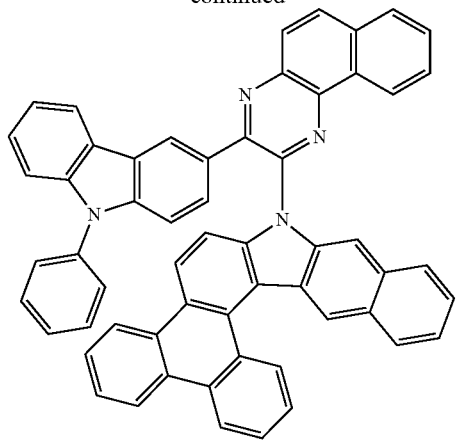
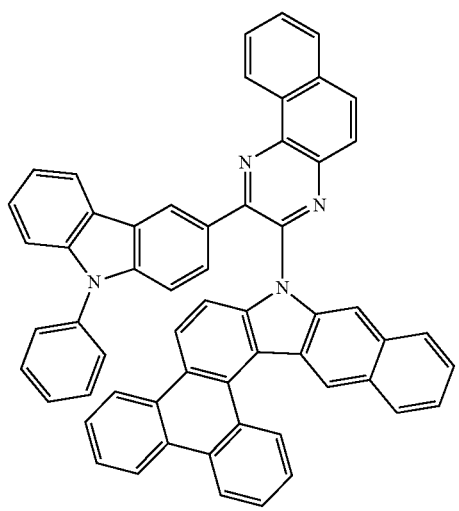
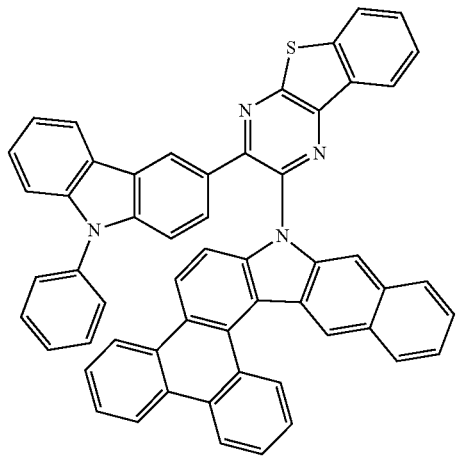
348
-continued
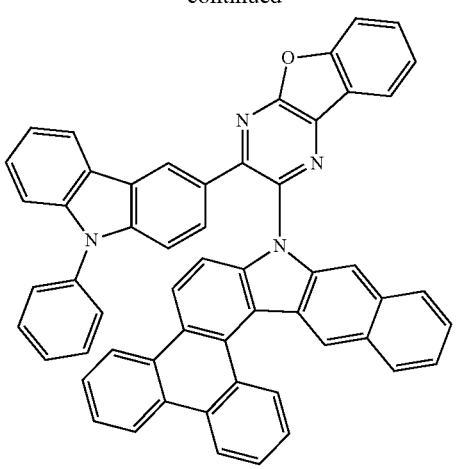
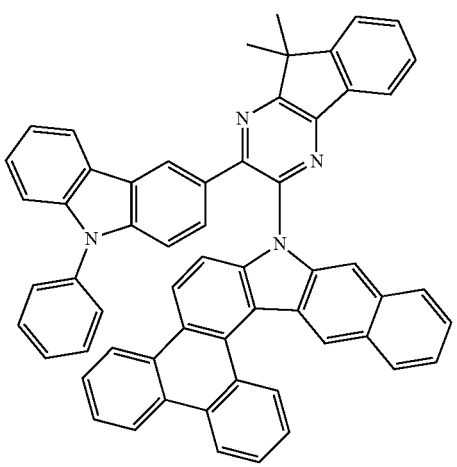
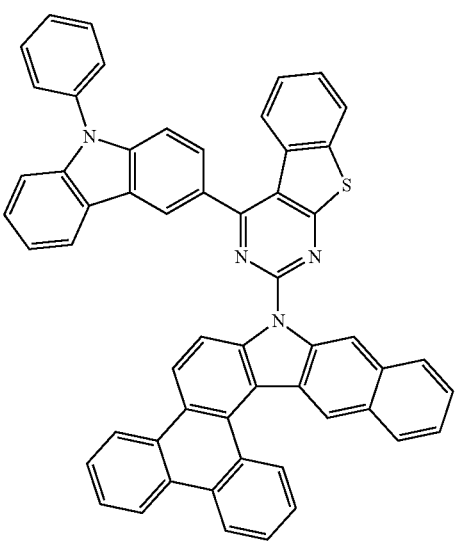

349
-continued
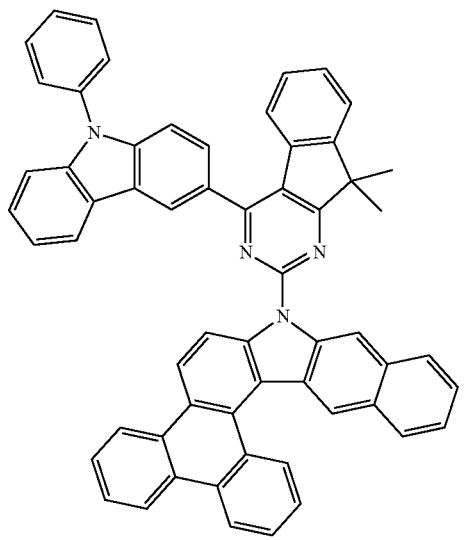
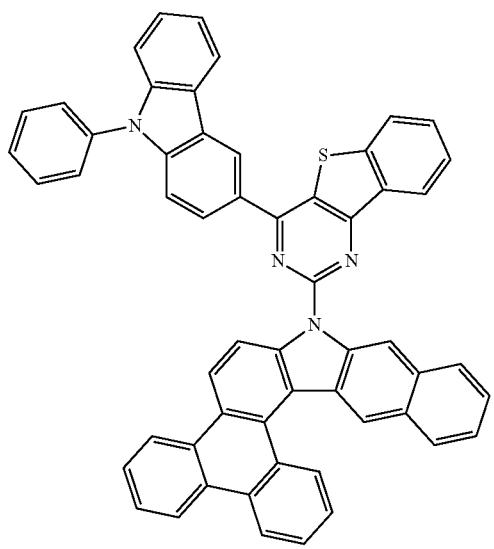
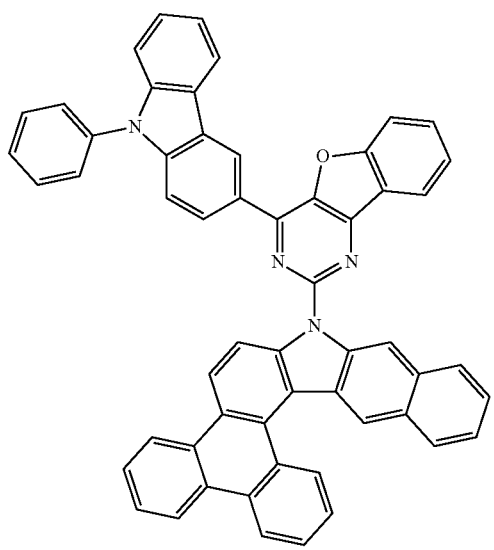
350
-continued
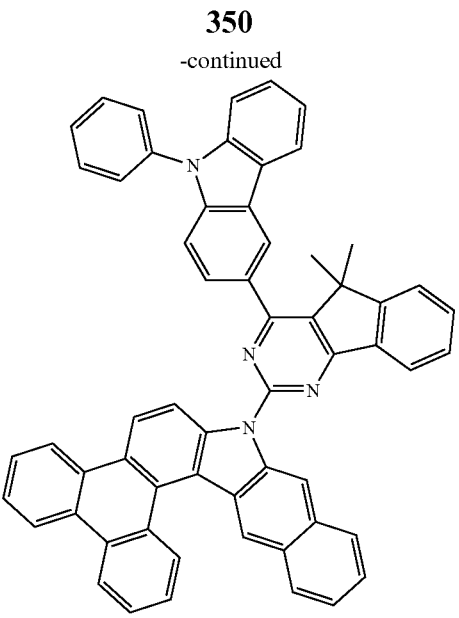
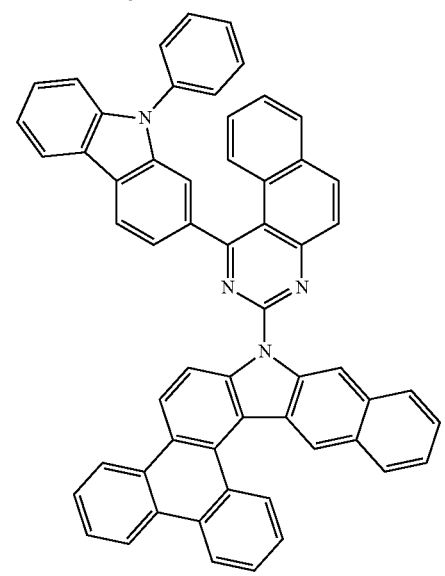
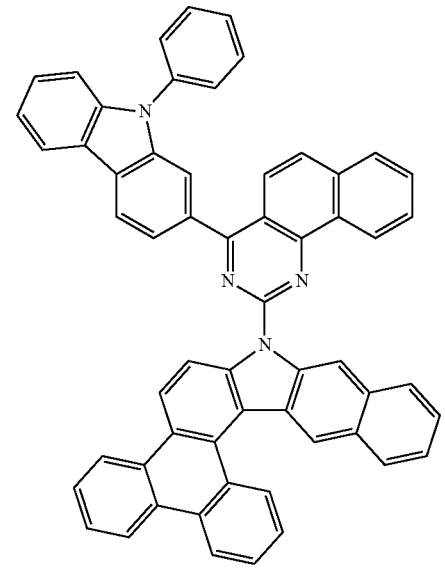

351
-continued
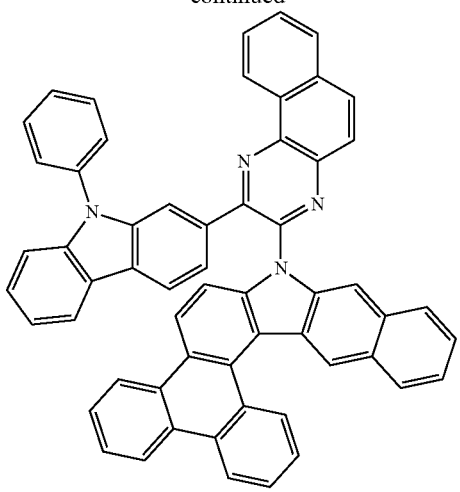
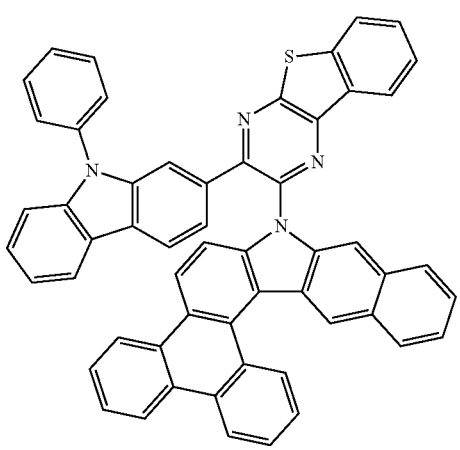
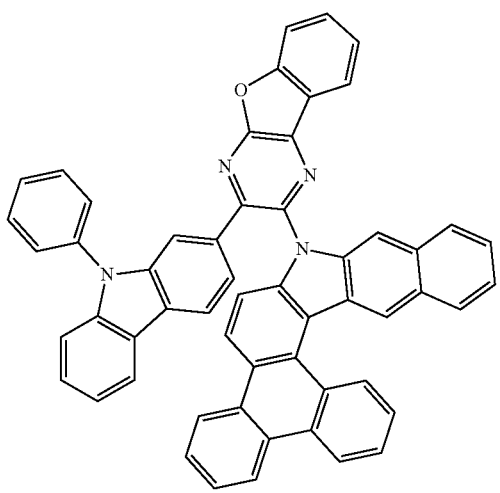
352
-continued
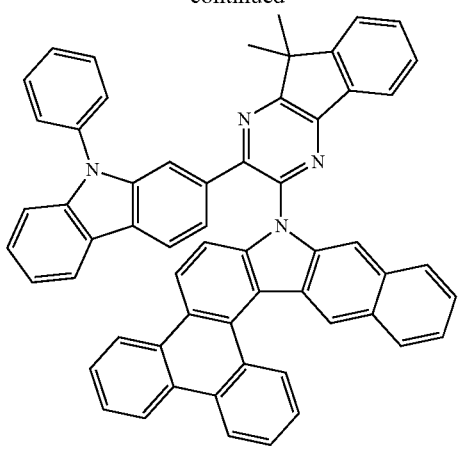
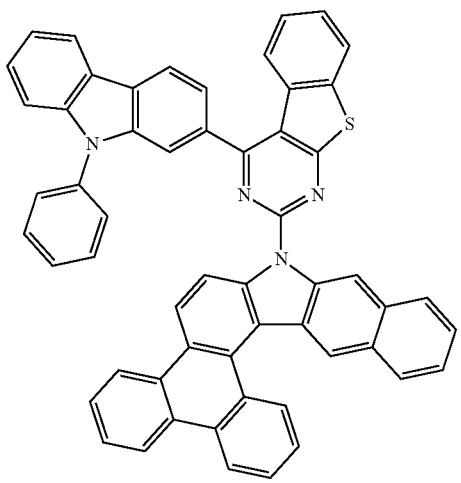
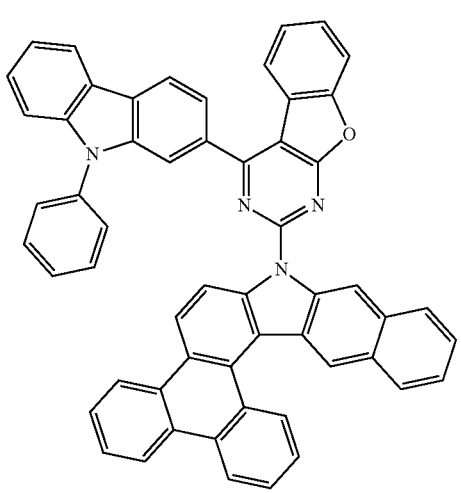

353
-continued
354
-continued
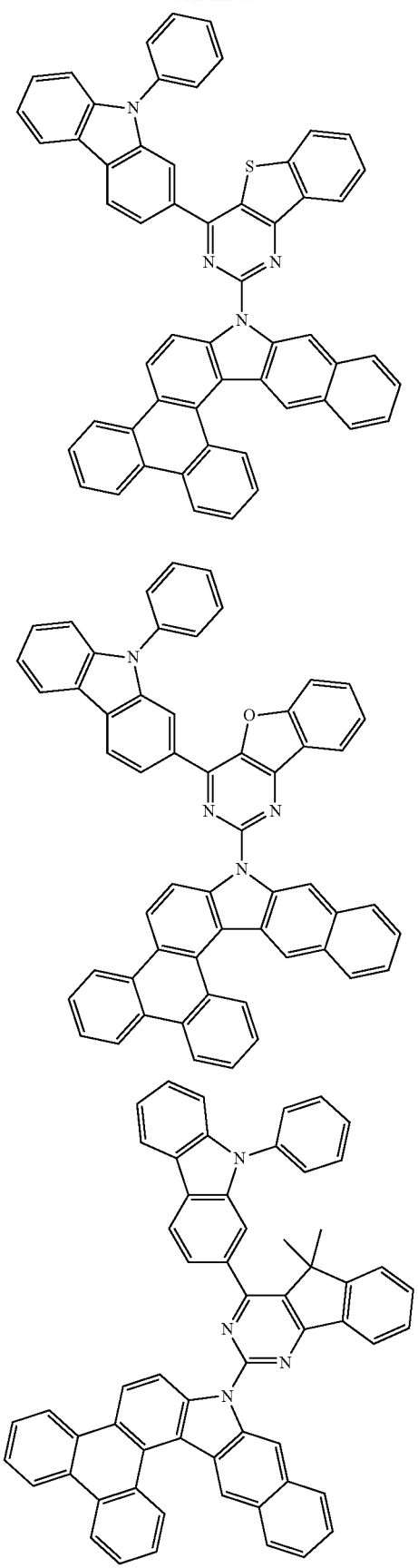
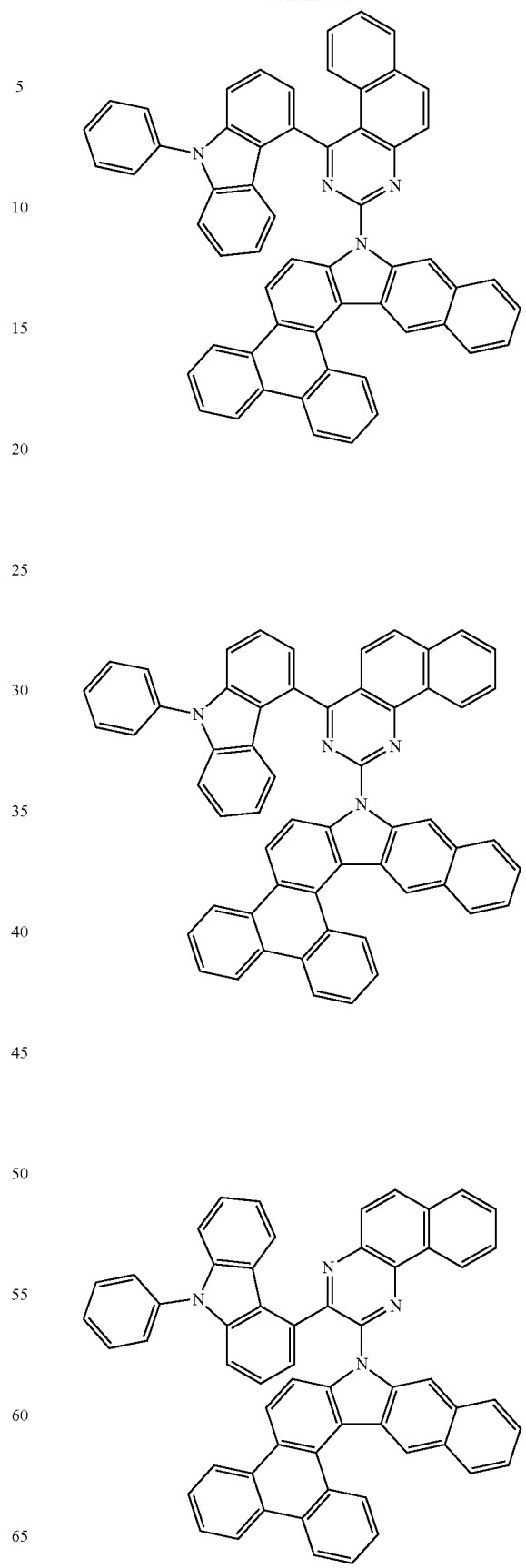

355
-continued
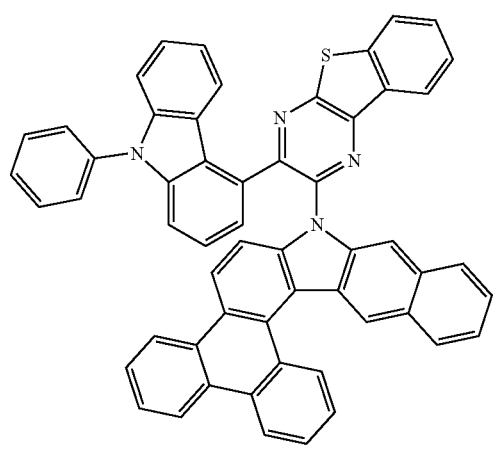
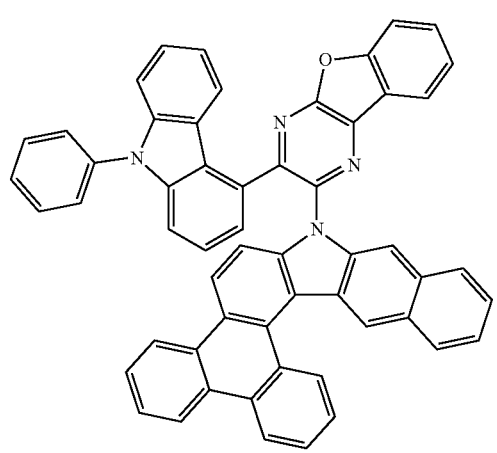
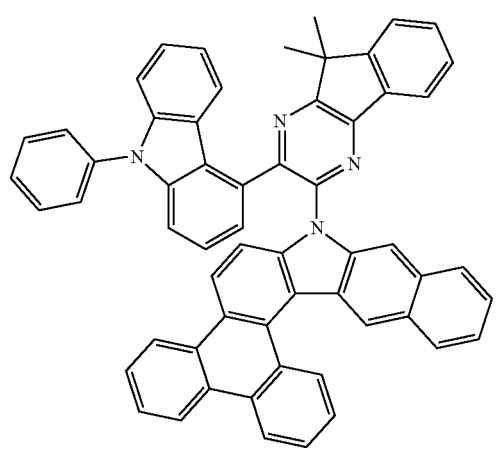
356
-continued
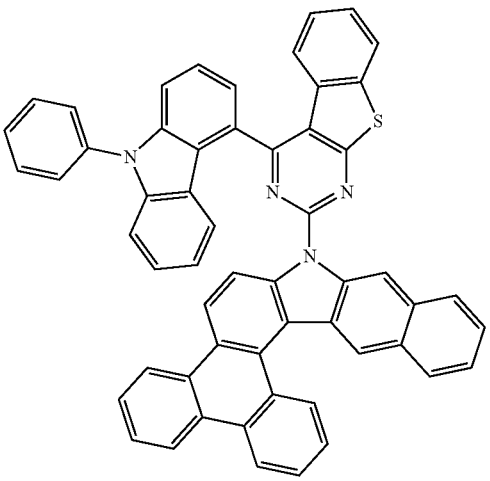
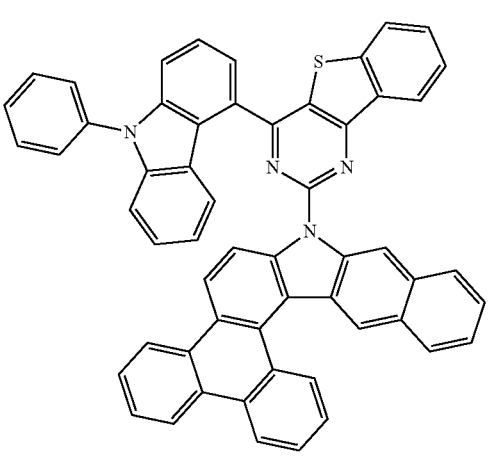
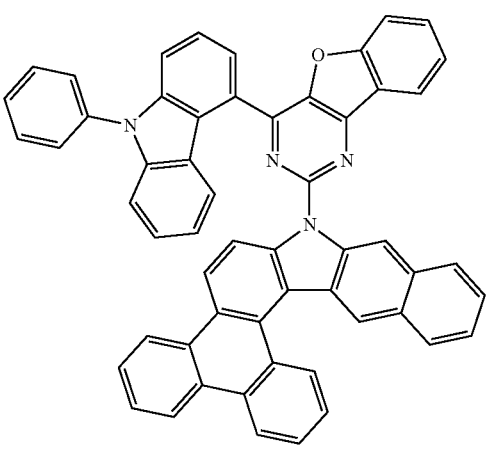

357
-continued
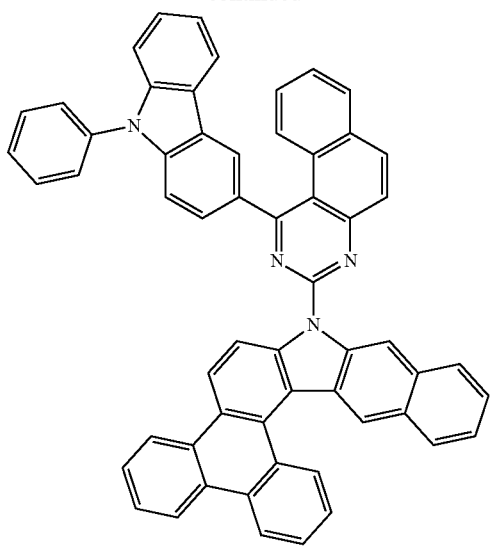
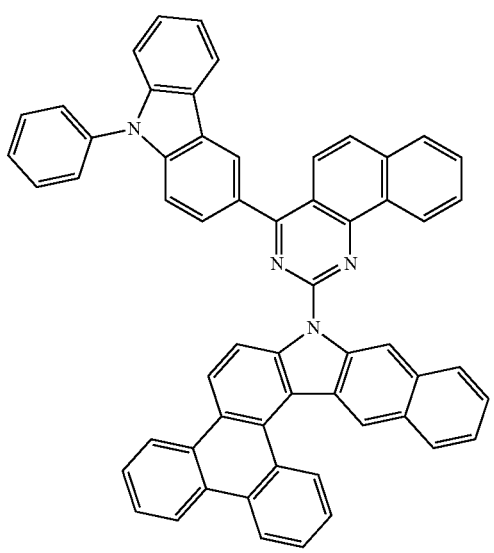
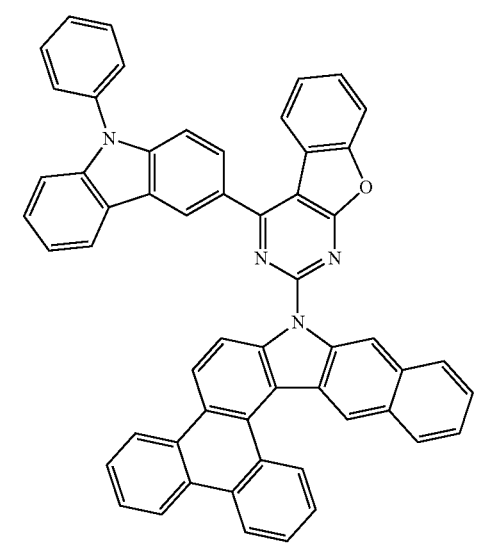
358
-continued
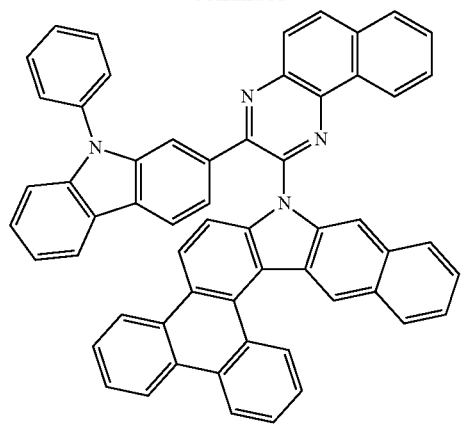
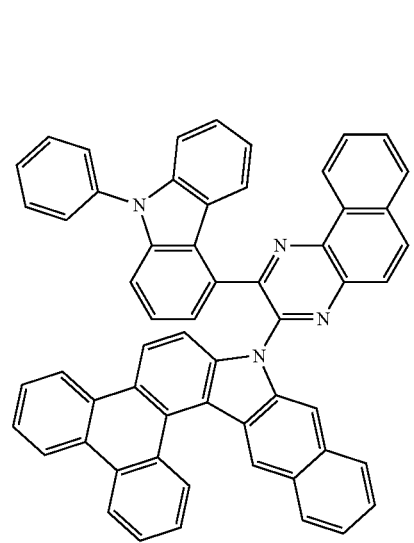

359
-continued
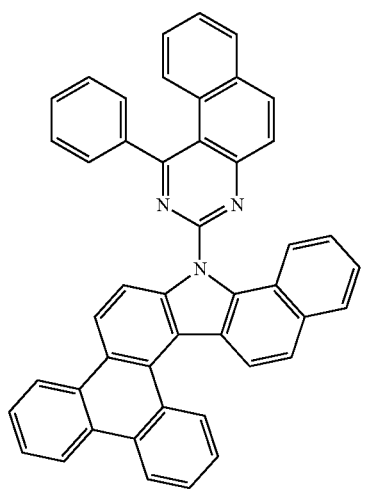
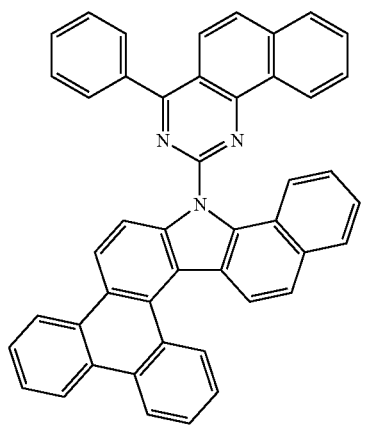
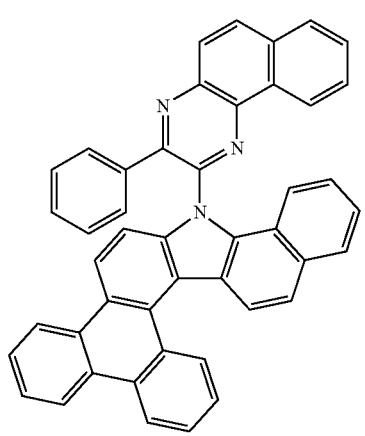
360
-continued
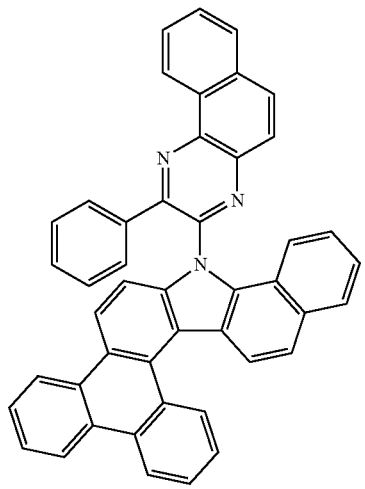
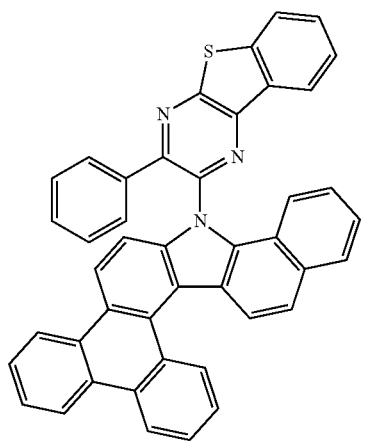
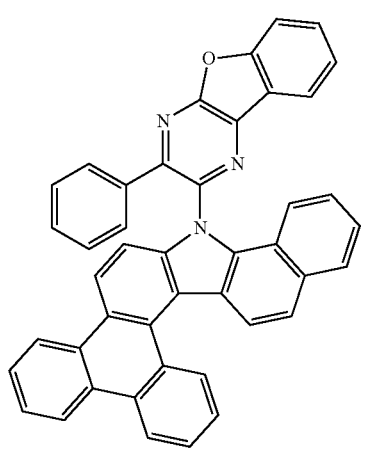

361
-continued
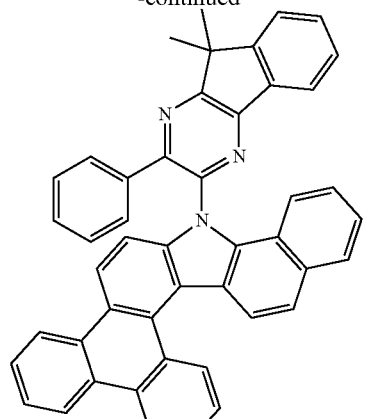
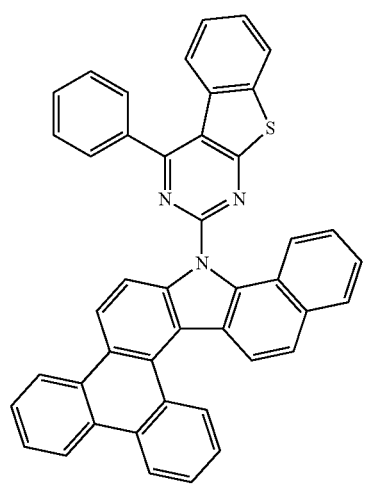
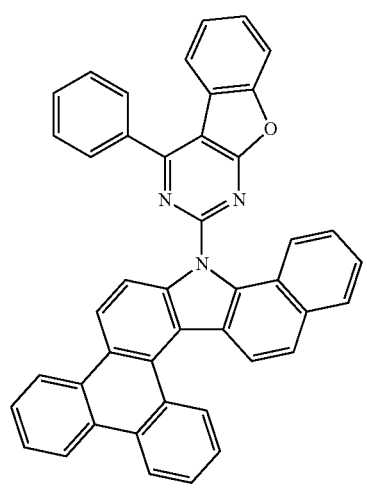
362
-continued
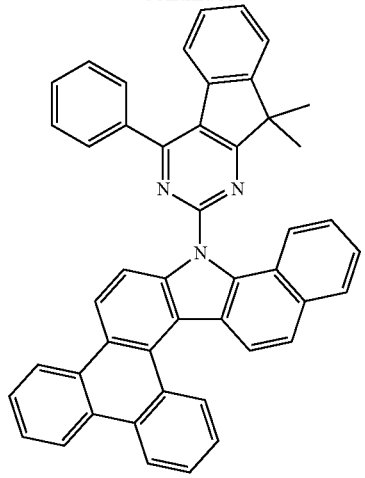
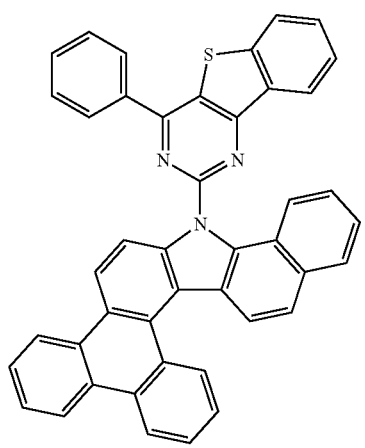
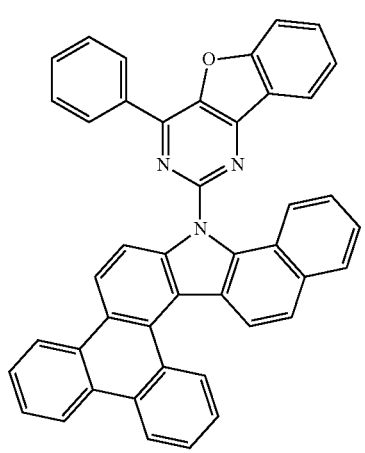

363
-continued
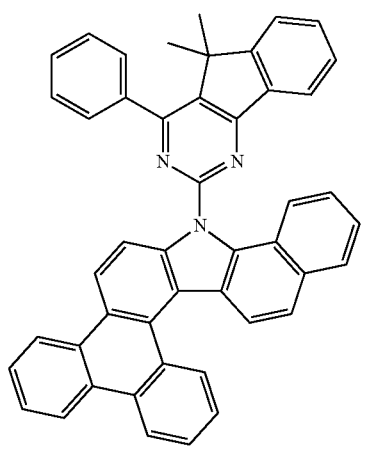
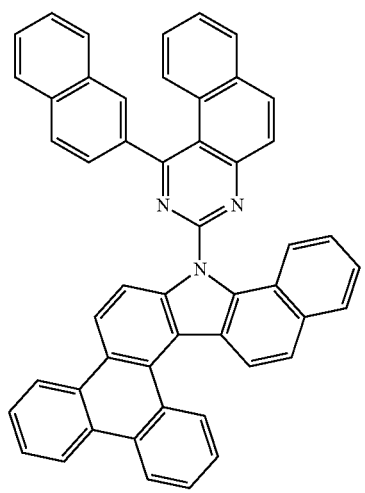
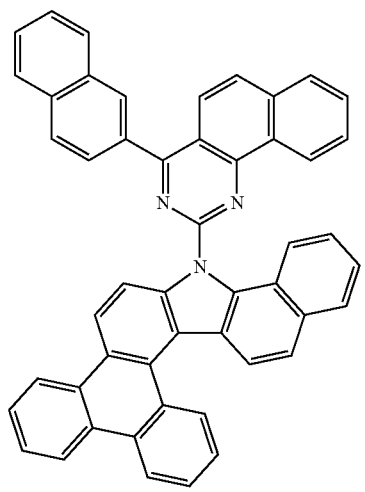
364
-continued
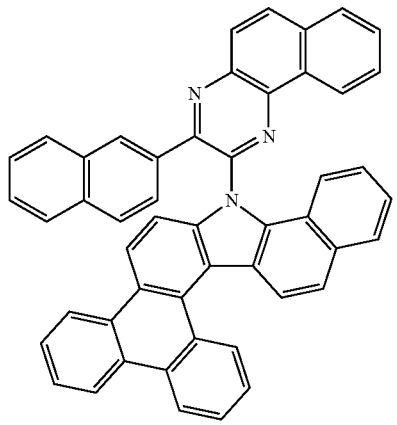
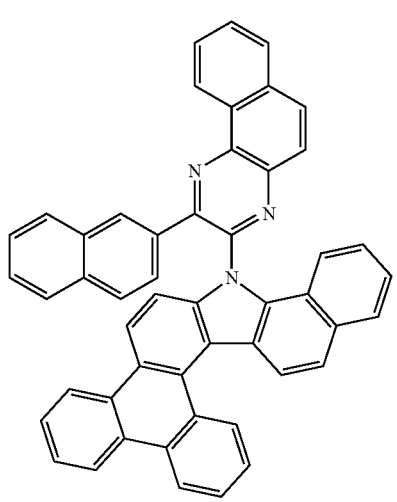
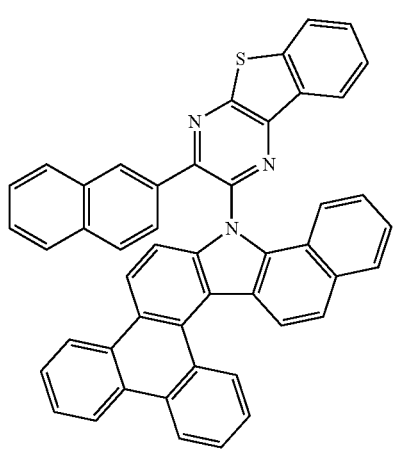

365
-continued
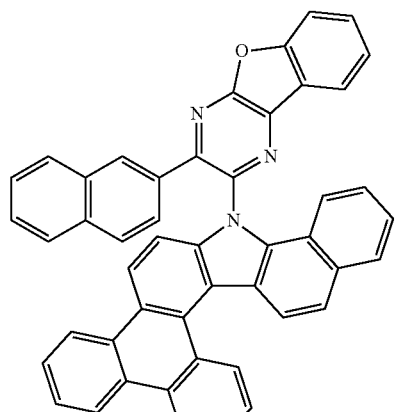
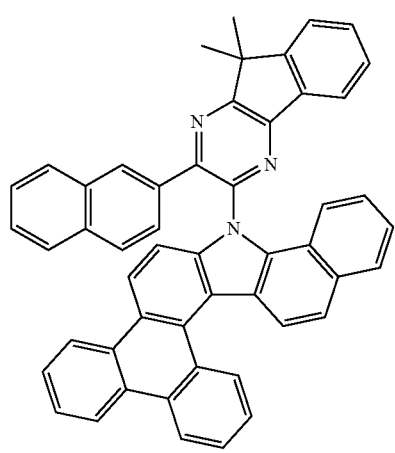
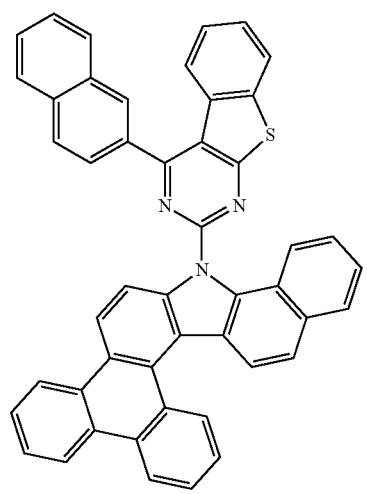
366
-continued
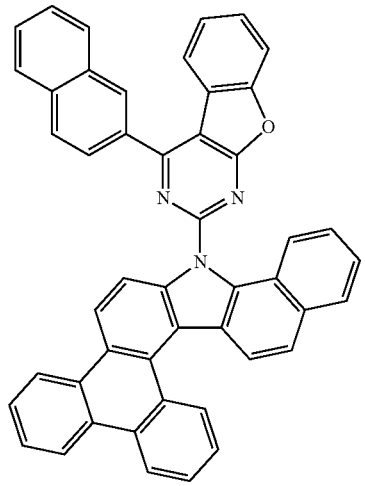
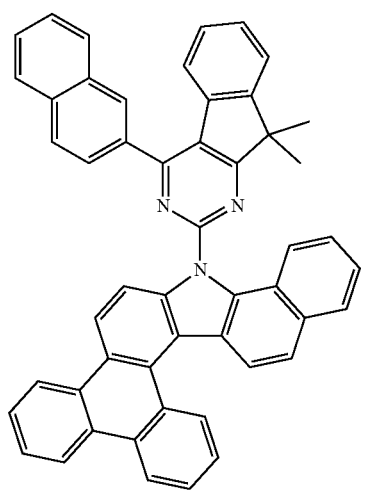
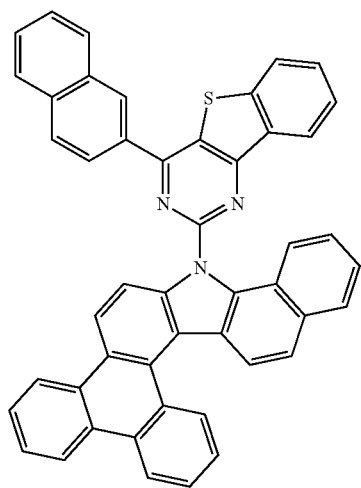

367
-continued
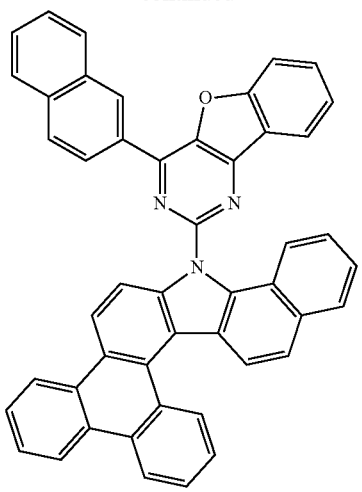
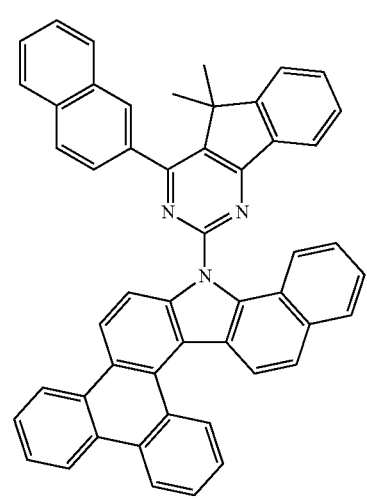
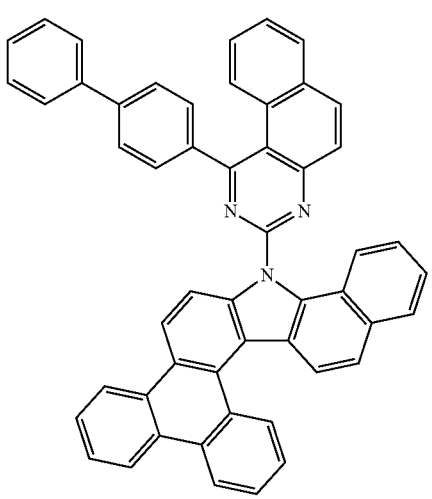
368
-continued
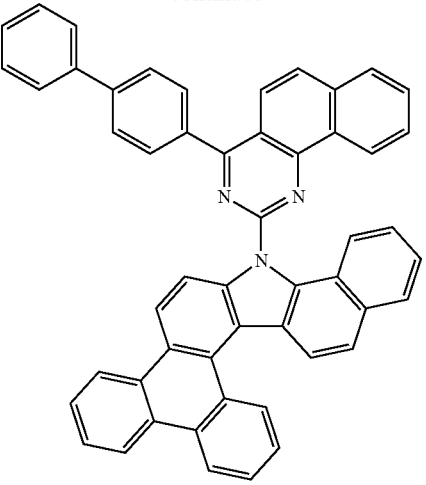
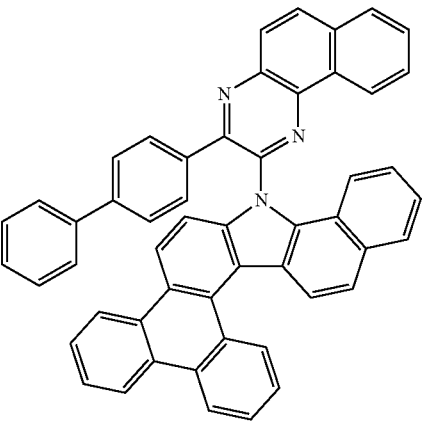
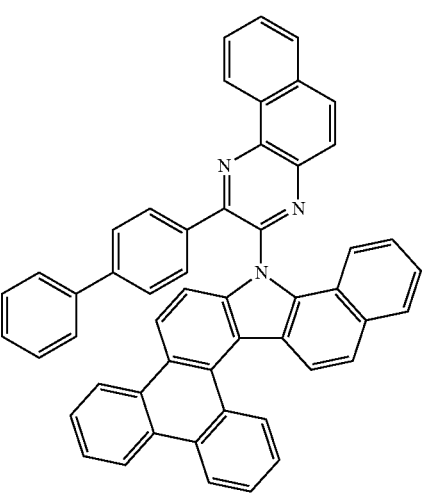

369
-continued
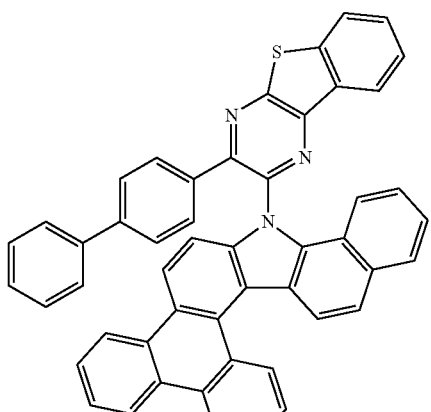
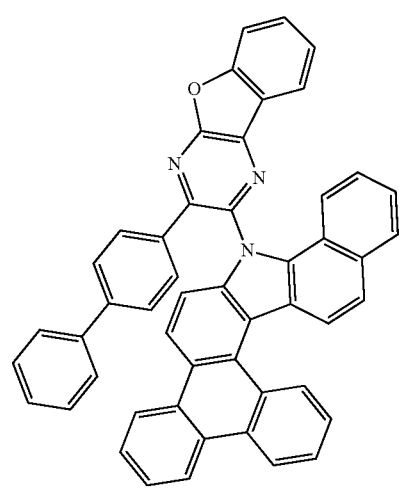
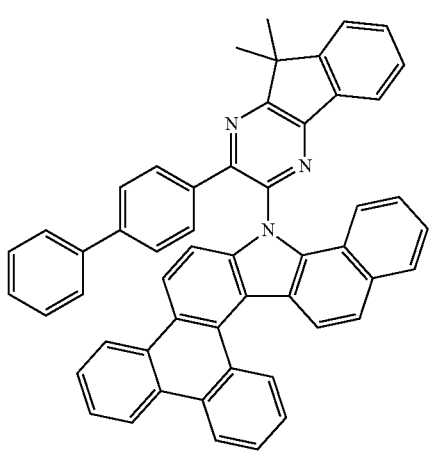
370
-continued
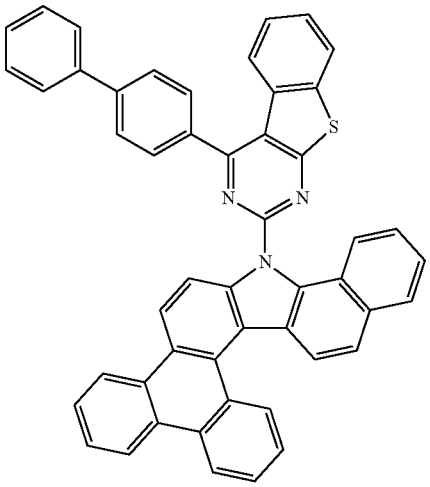
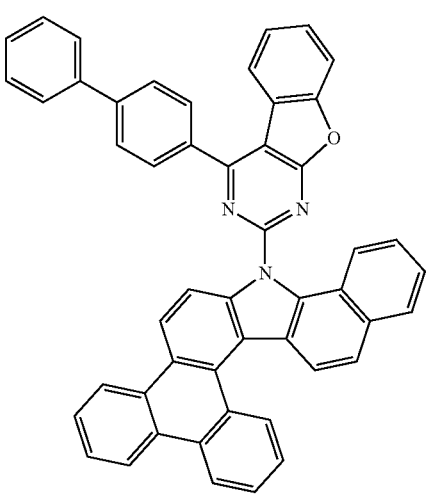
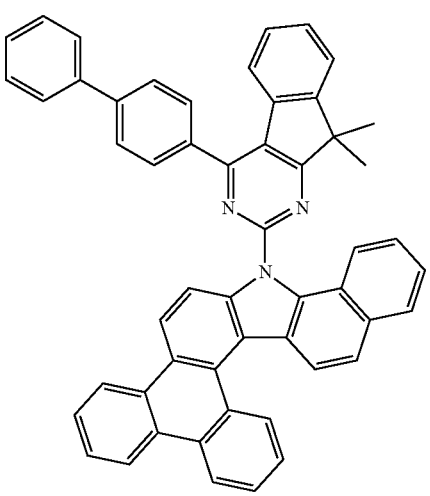

371
-continued
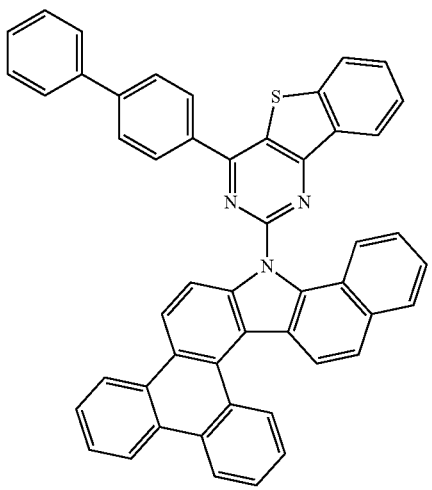
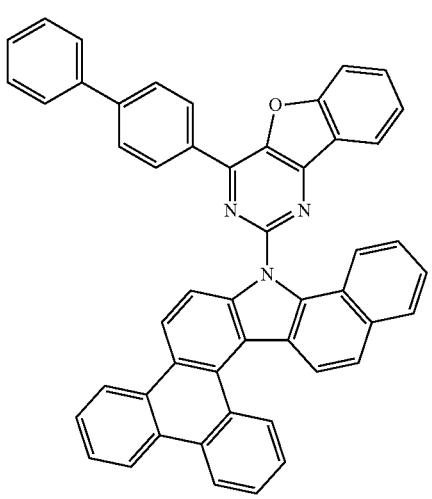
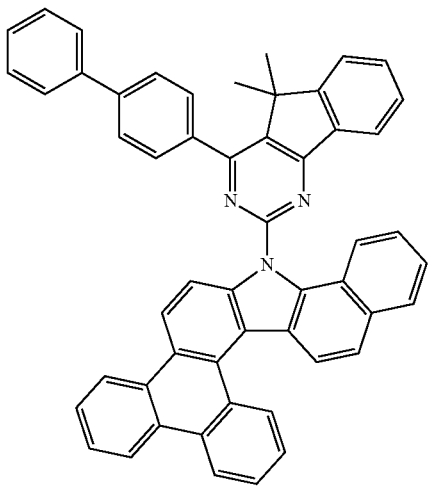
372
-continued
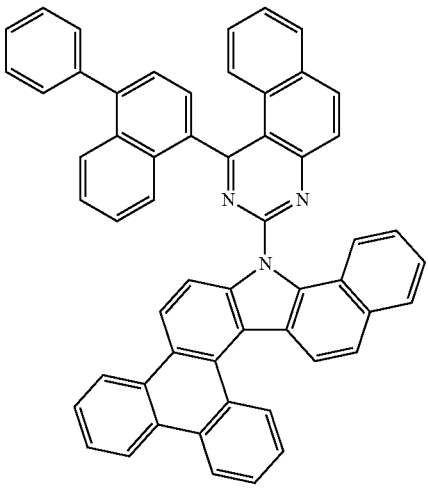
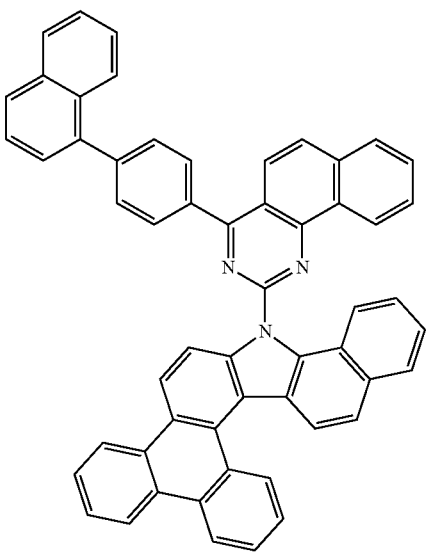
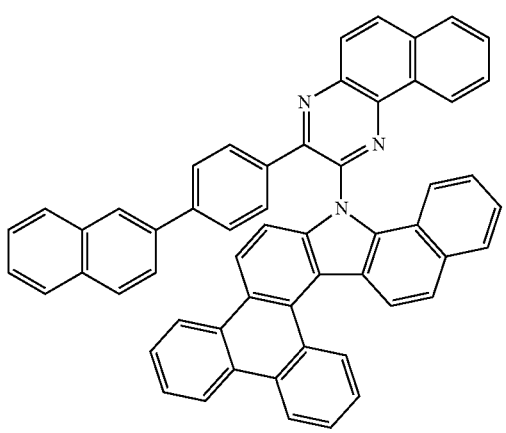

US 11,858,947 B2
373
-continued
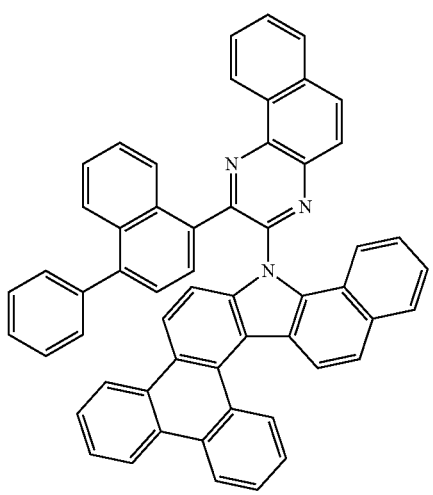
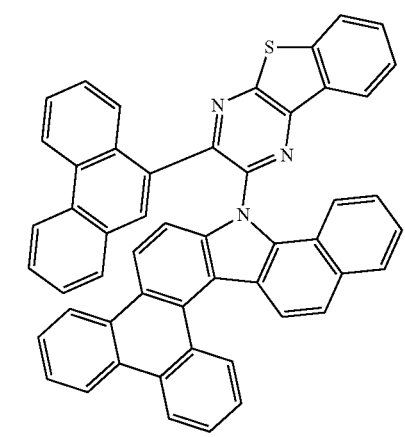
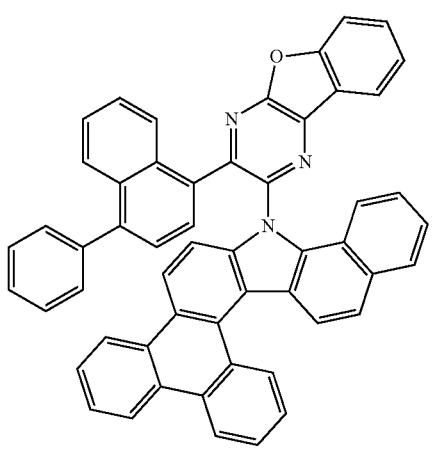
374
-continued
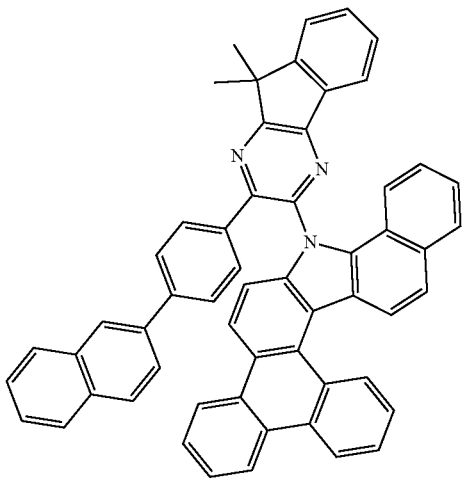
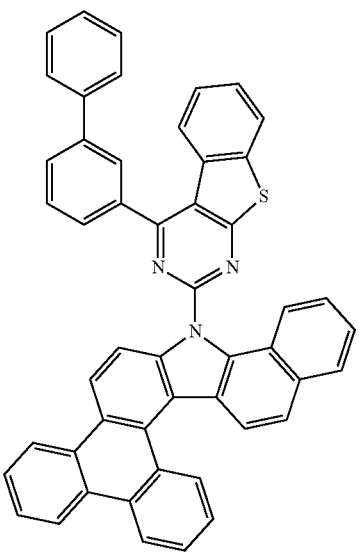
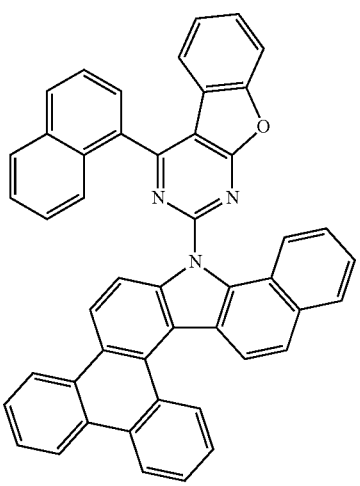

375
-continued
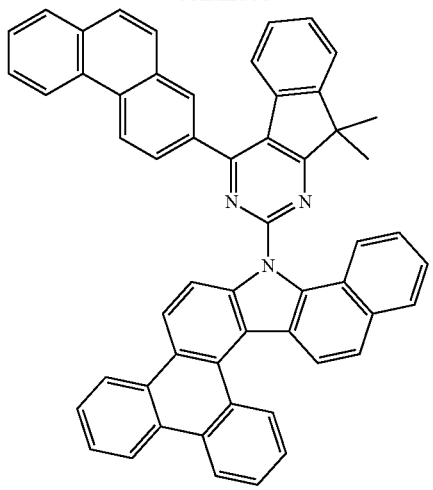
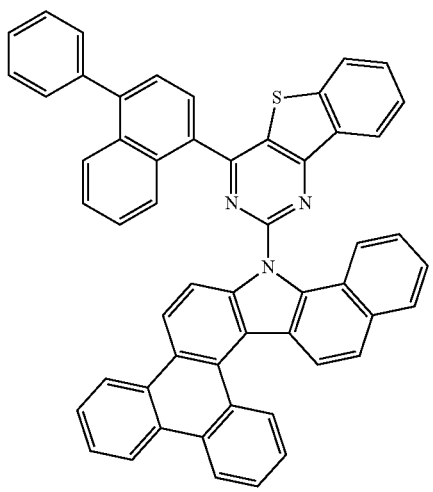
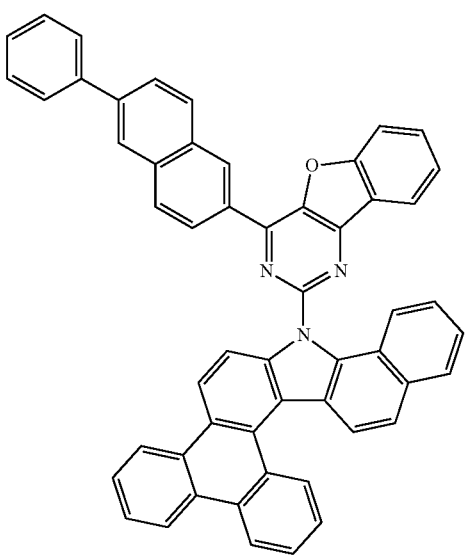
376
-continued
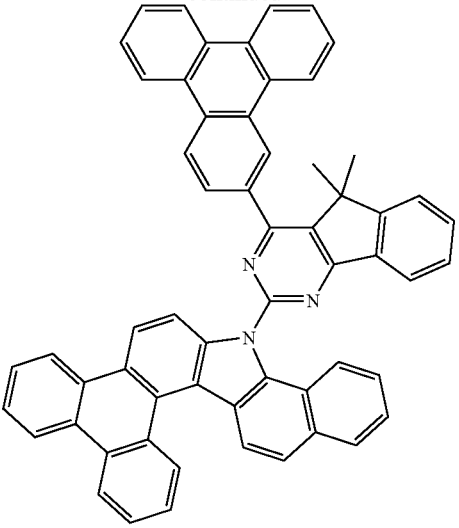
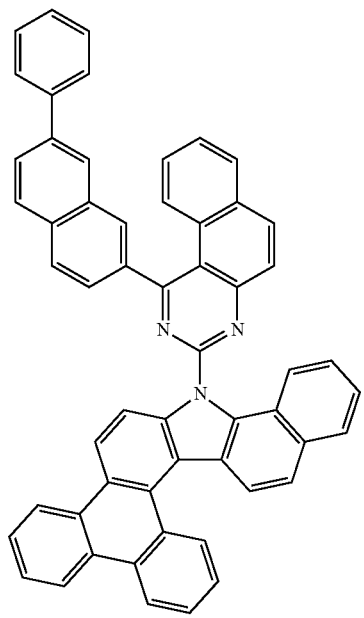
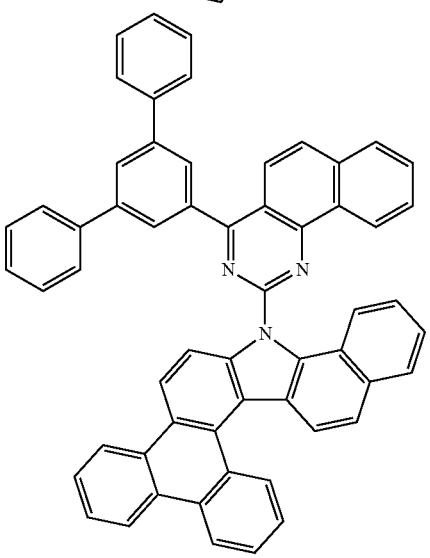

377
-continued
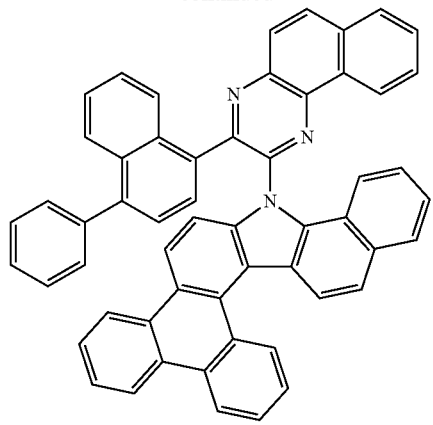
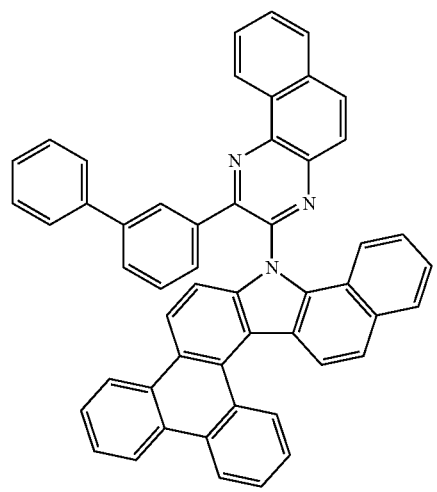
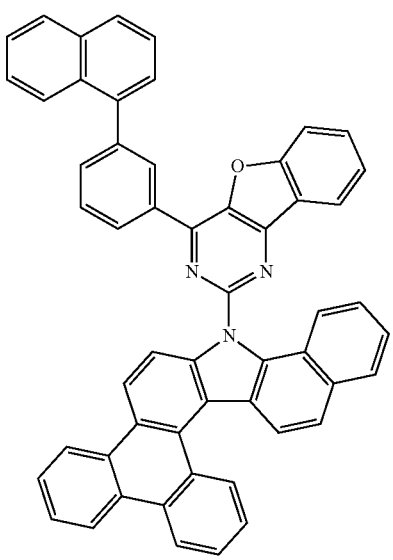
378
-continued
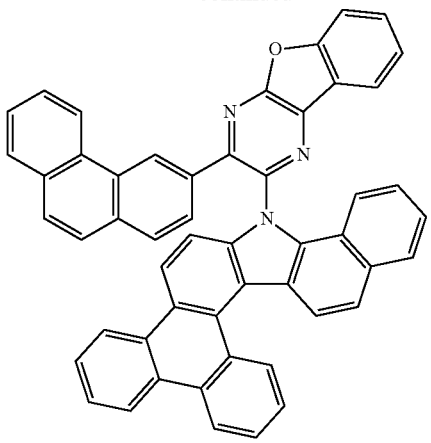
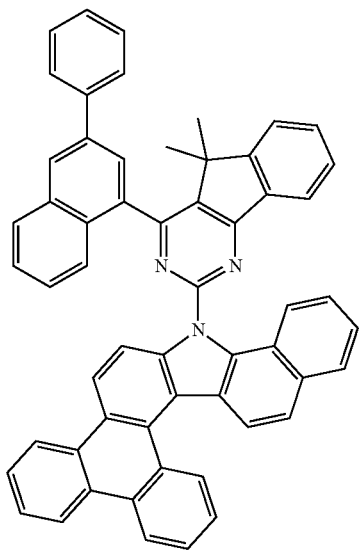
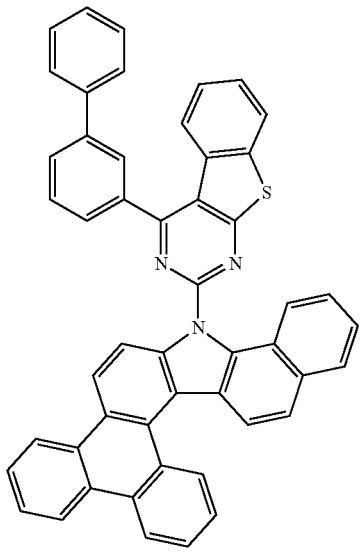

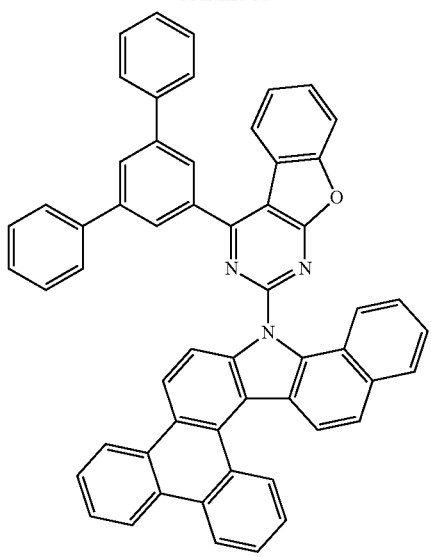
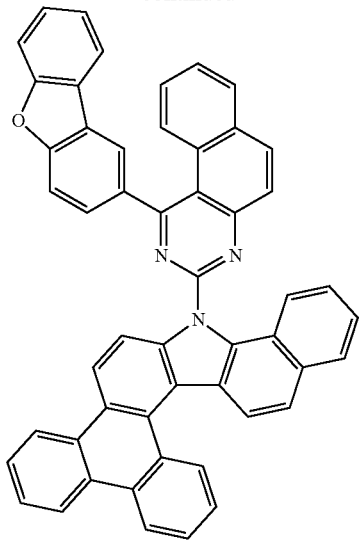
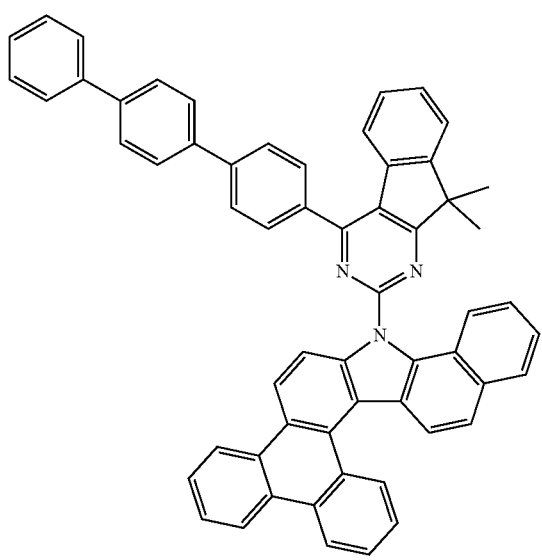
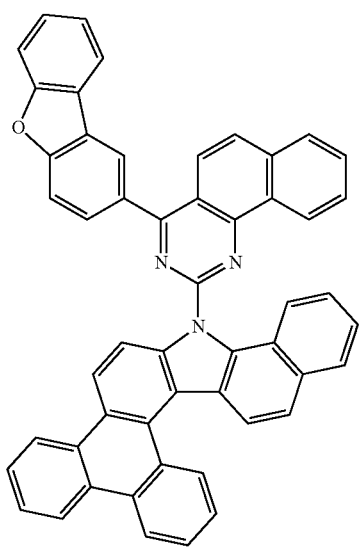
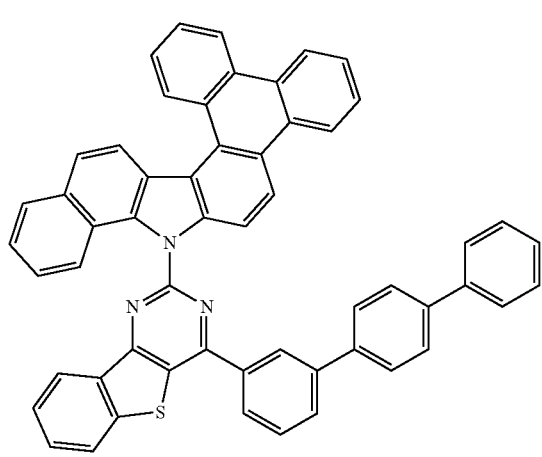
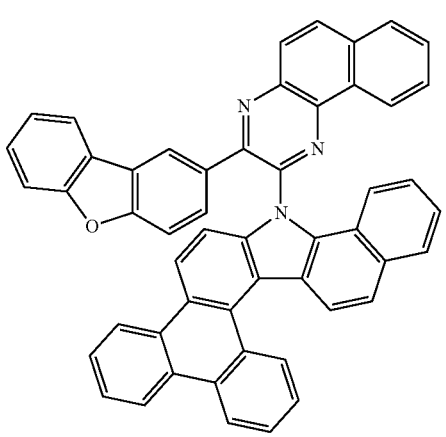

381
-continued
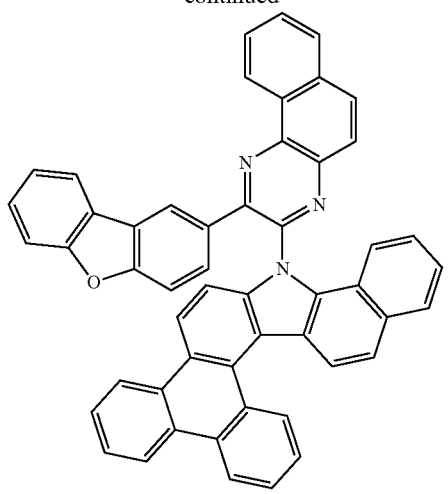
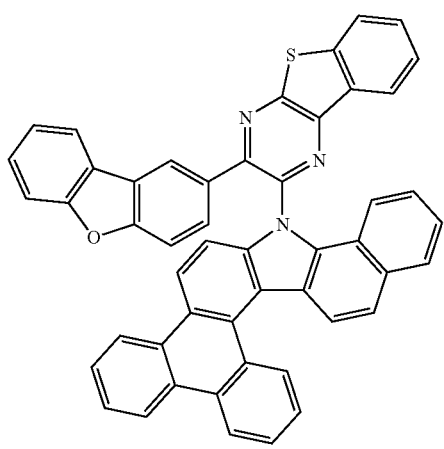
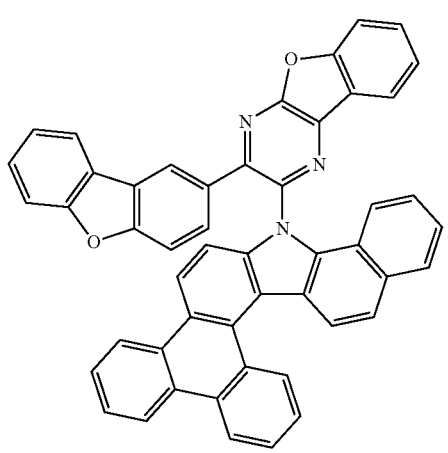
382
-continued
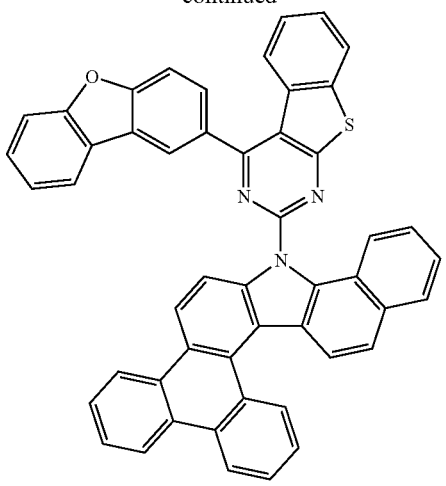
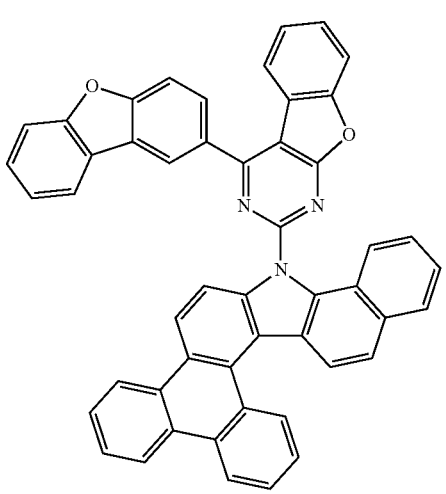
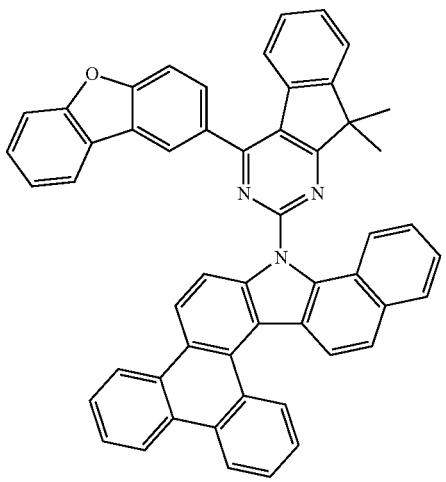

383
-continued
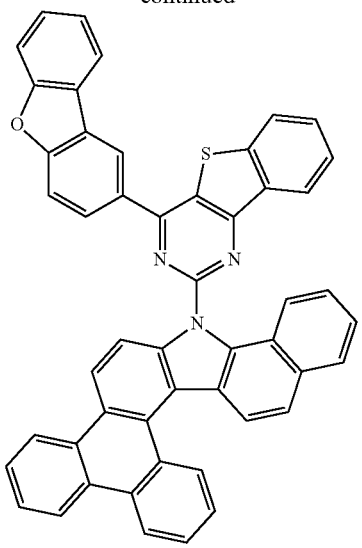
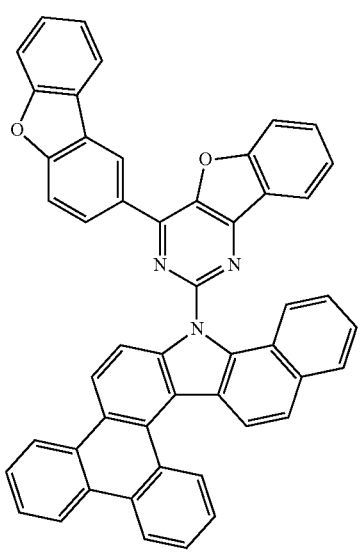
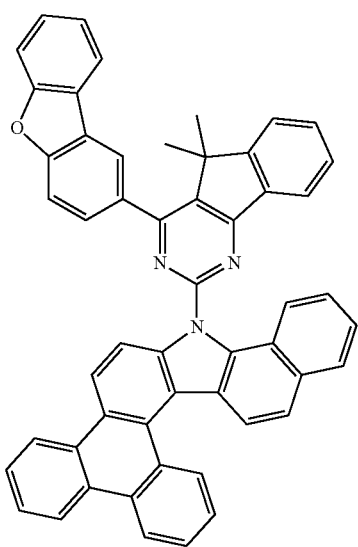
384
-continued
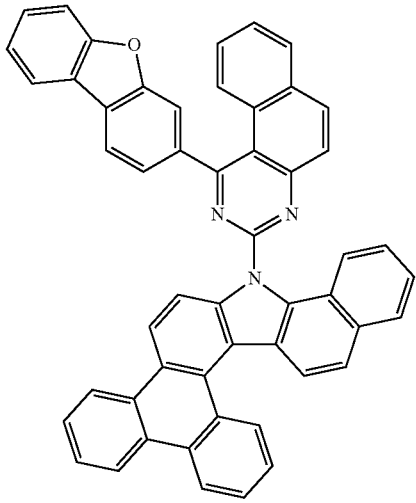
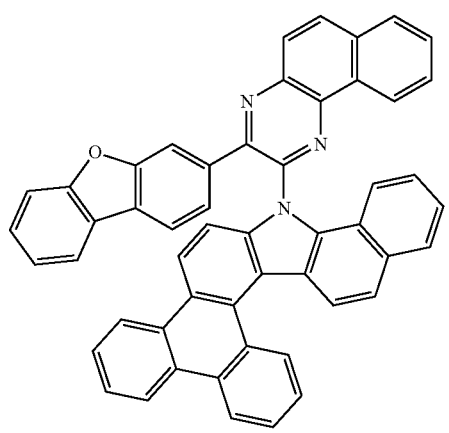

385
-continued
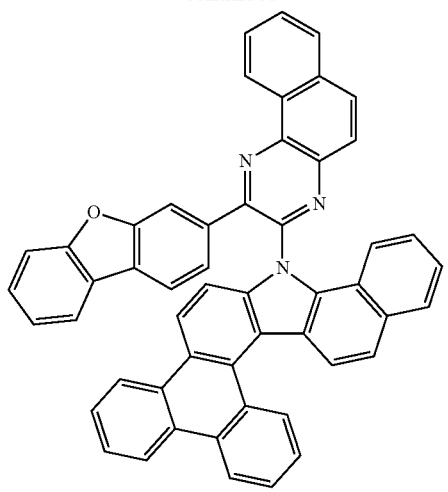
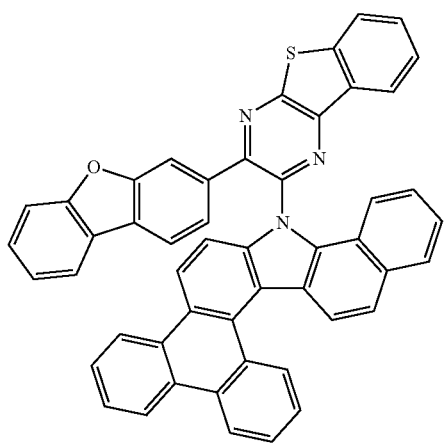
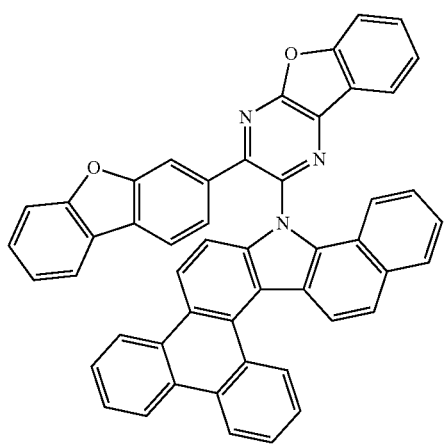
386
-continued
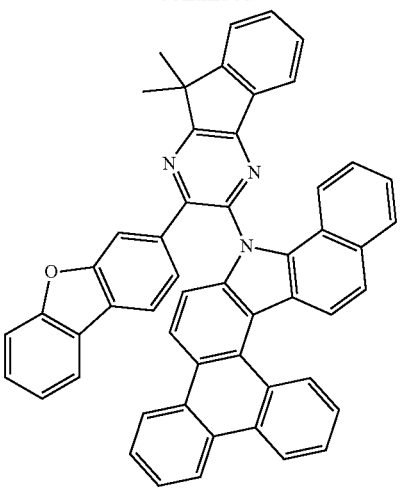
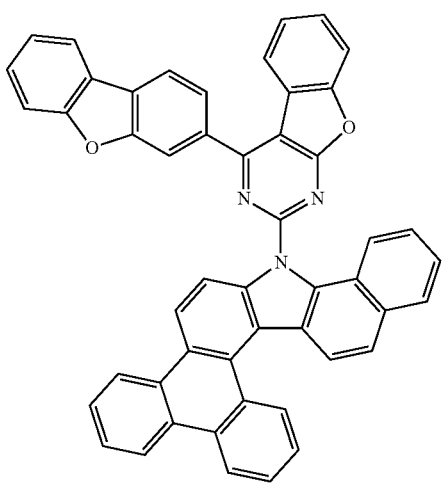
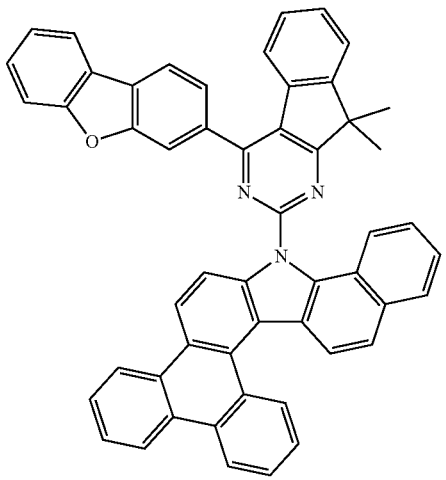

387
-continued
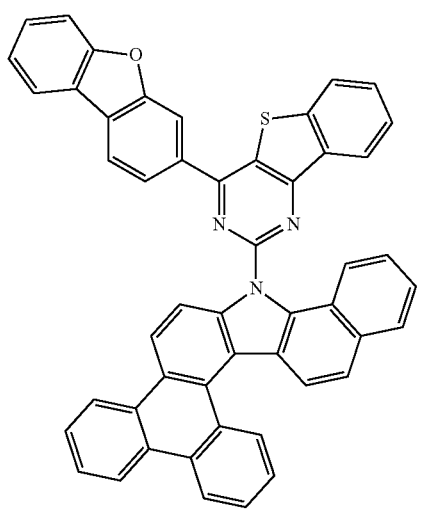
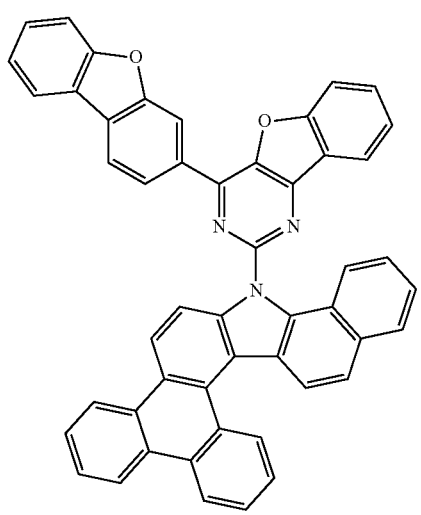
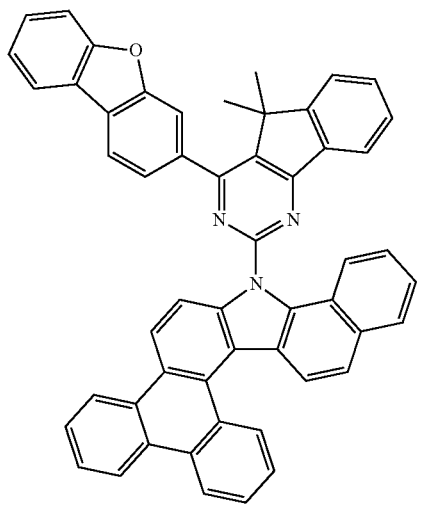
388
-continued
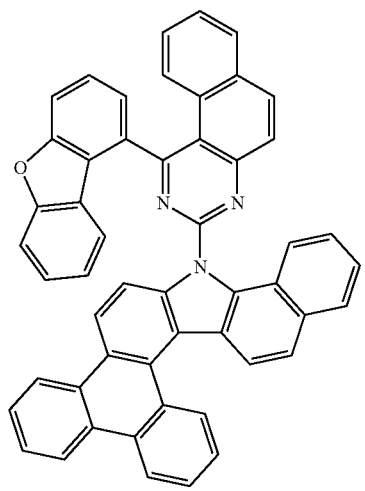
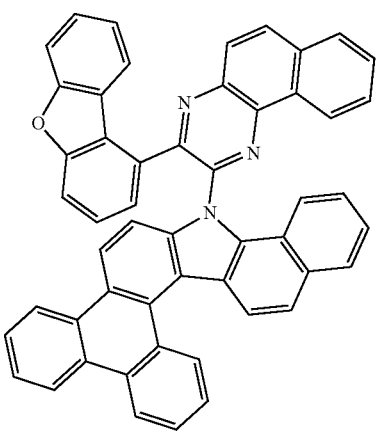
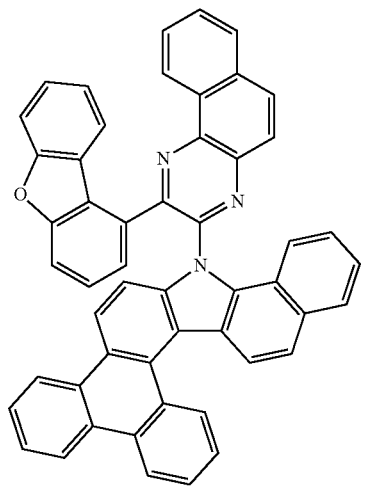

389
-continued
390
-continued
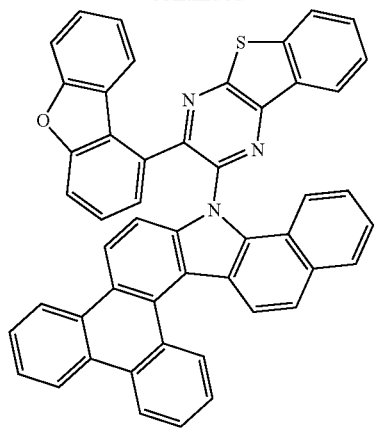
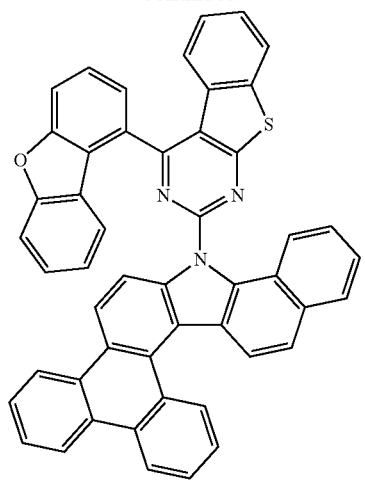
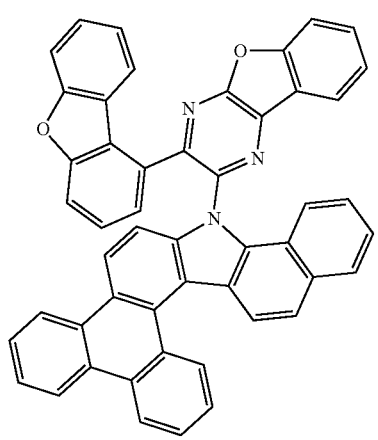
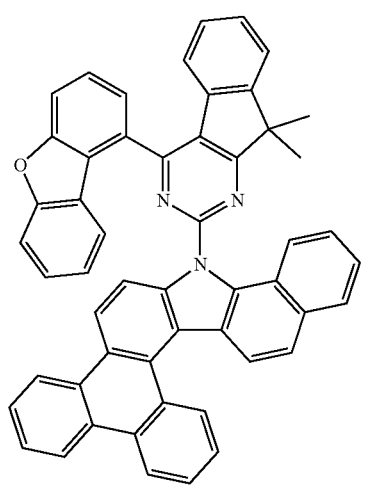
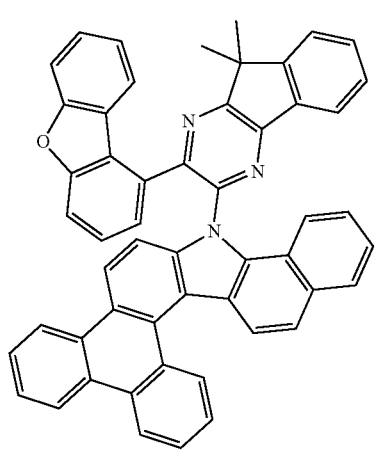
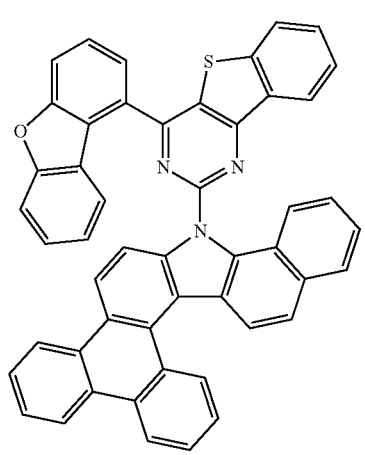

391
-continued
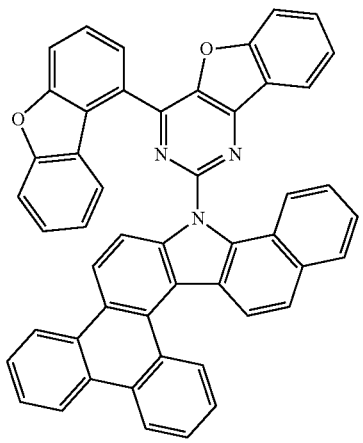
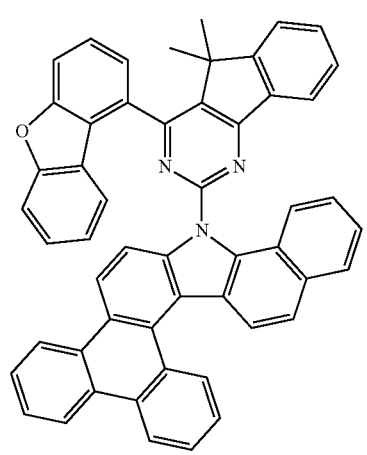
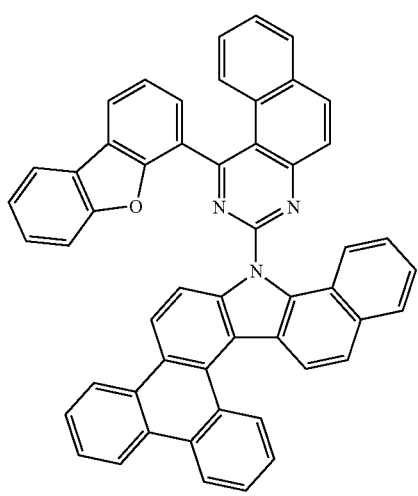
392
-continued
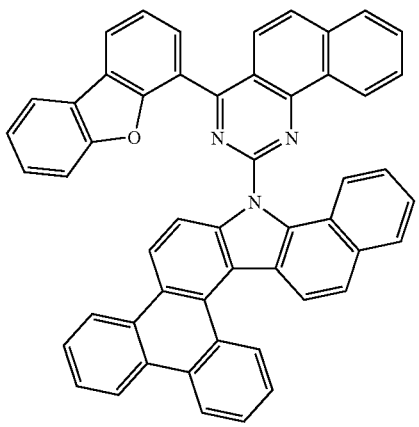
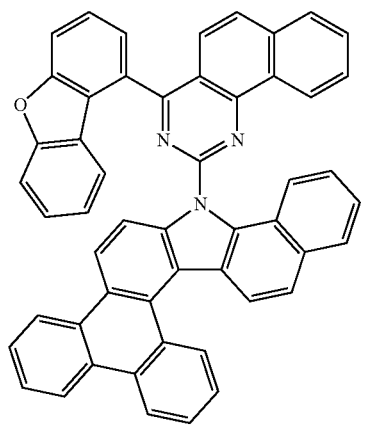
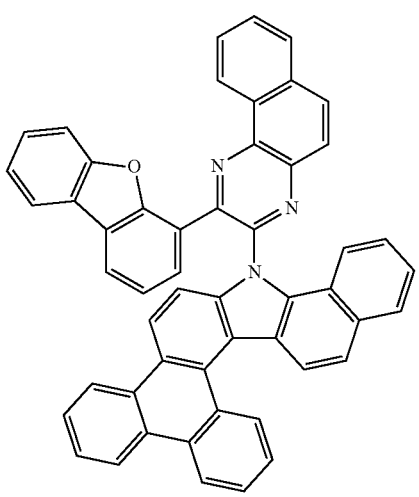

393
-continued
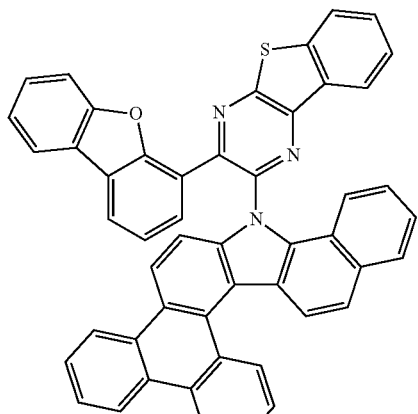
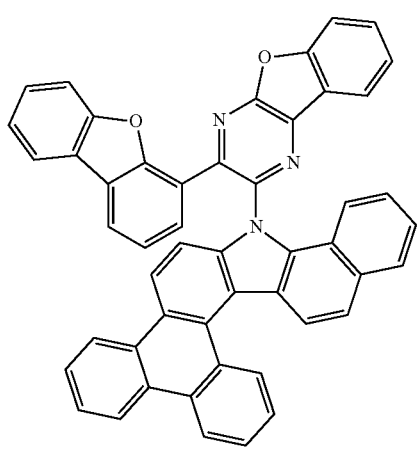
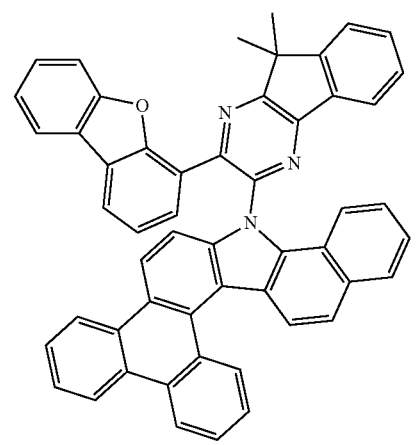
394
-continued
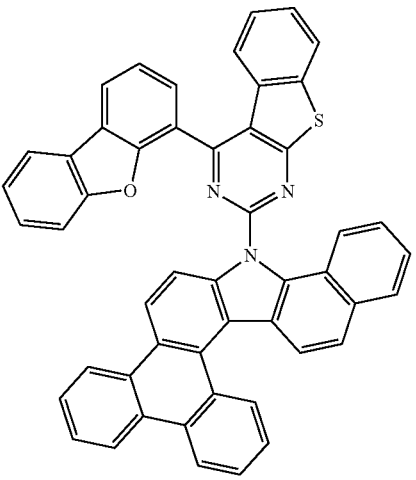
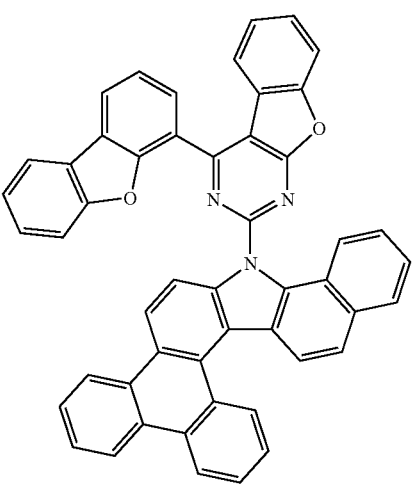
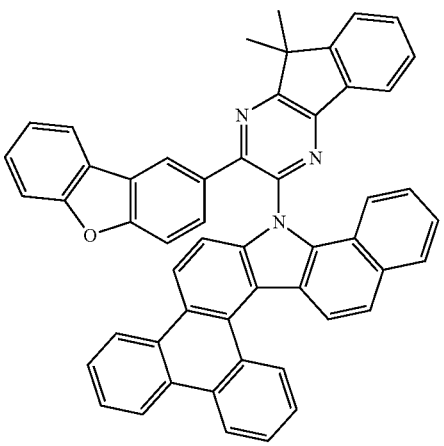

395
-continued
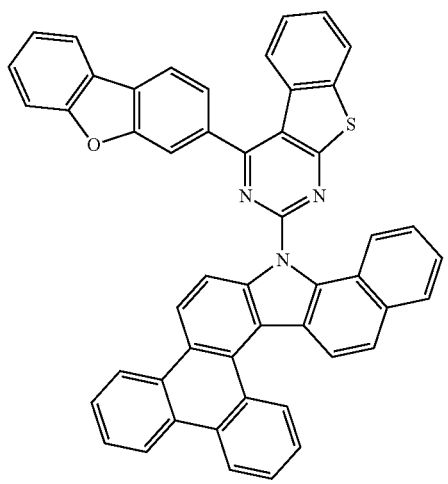
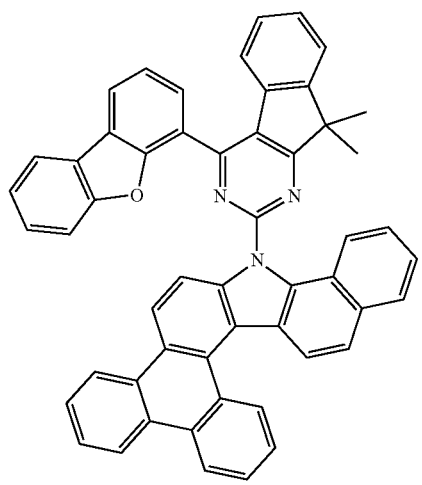
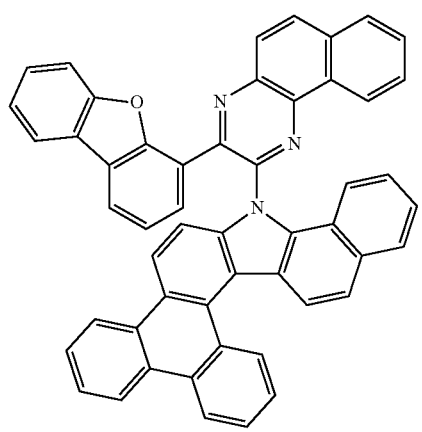
396
-continued
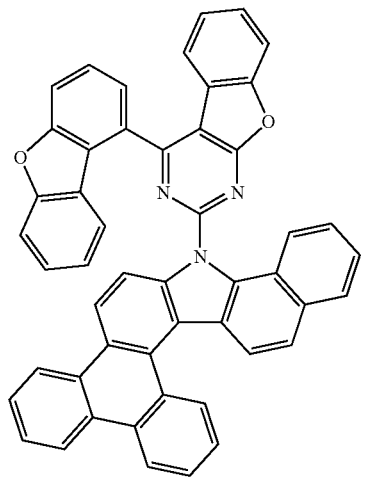
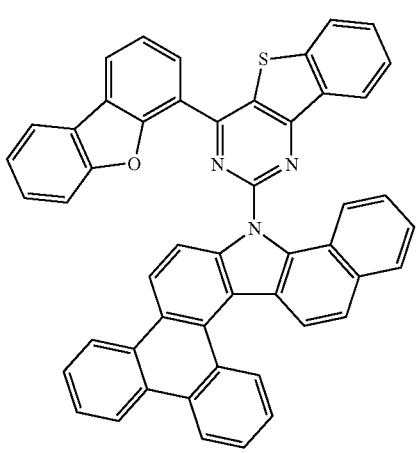
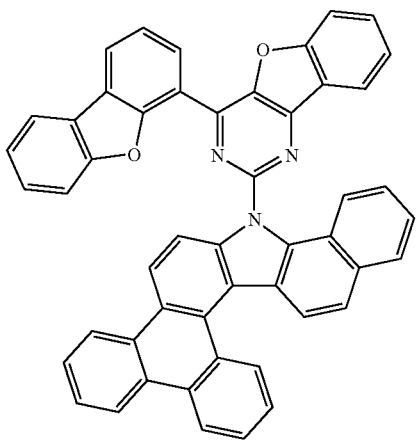

397
-continued
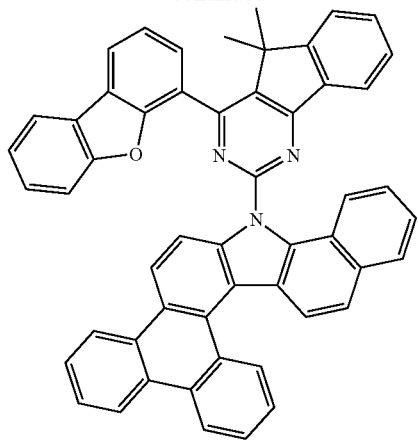
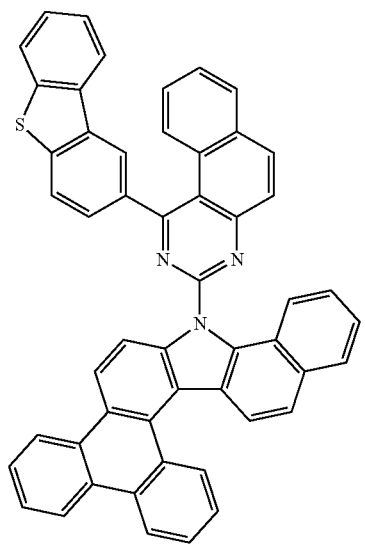
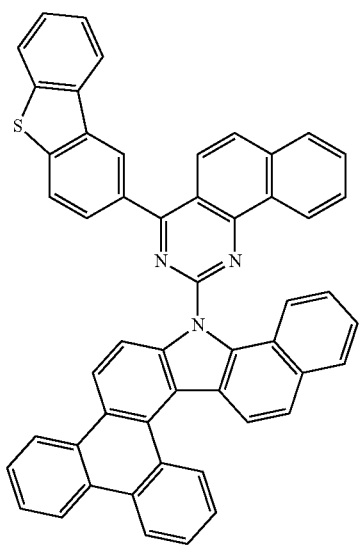
398
-continued
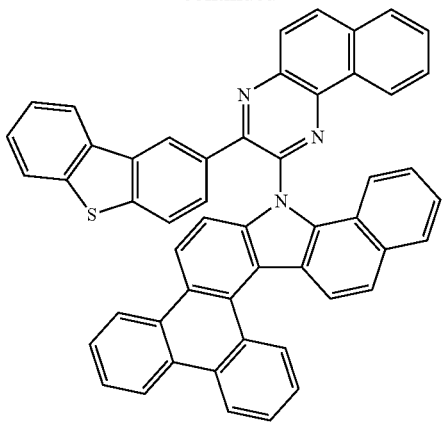
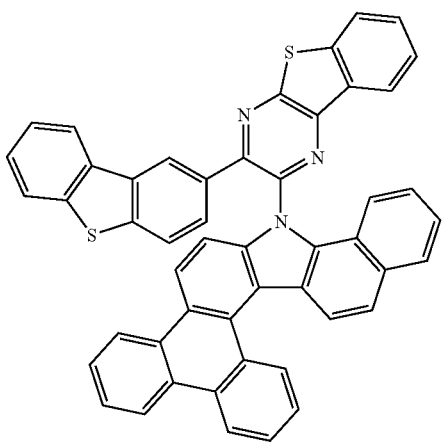
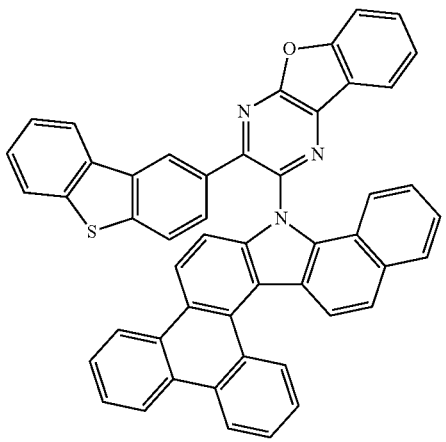

399
-continued

400
-continued

401
-continued
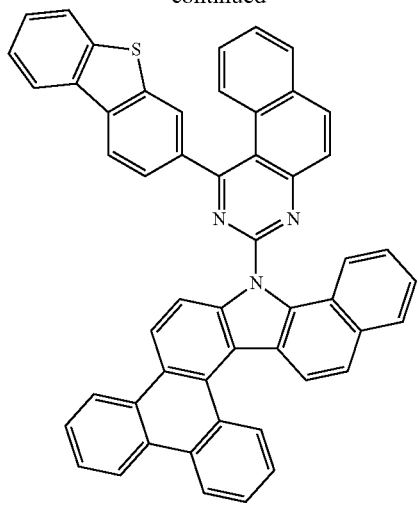
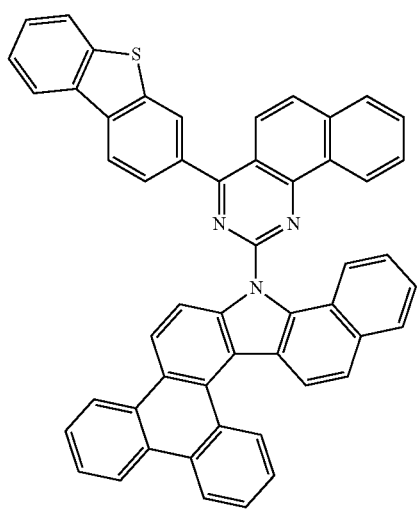
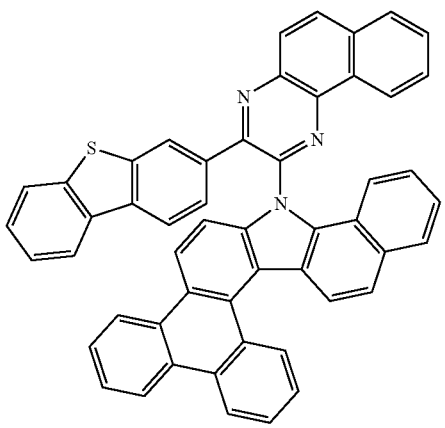
402
-continued
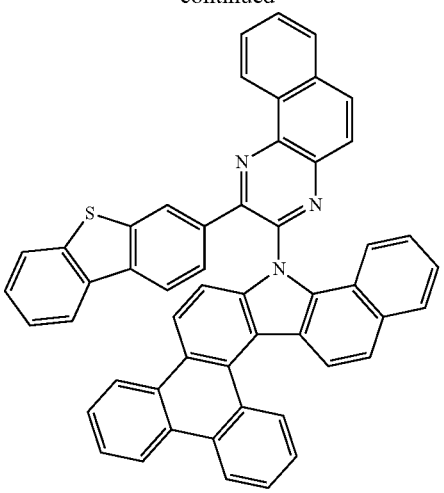
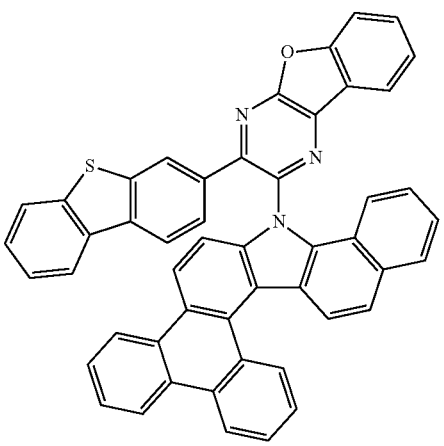
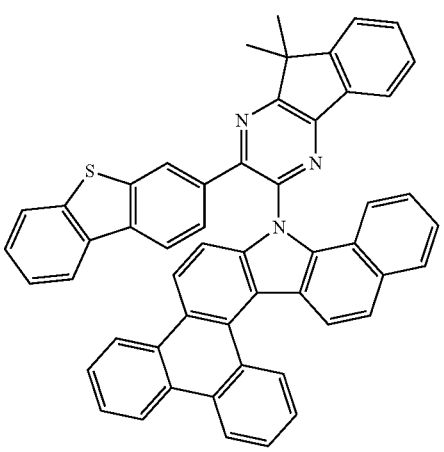

403
-continued
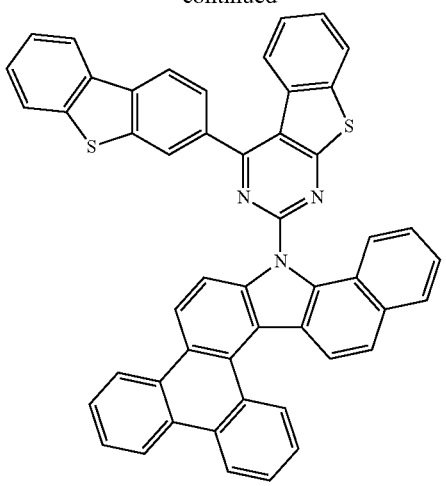
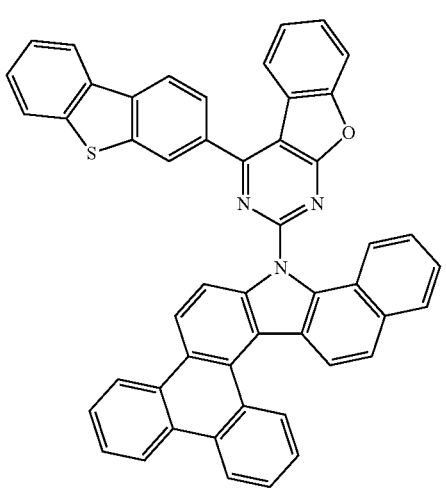
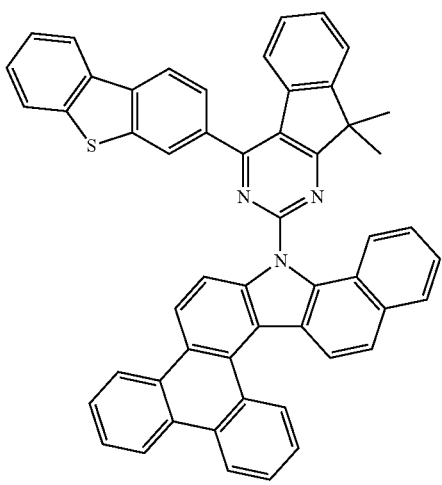
404
-continued
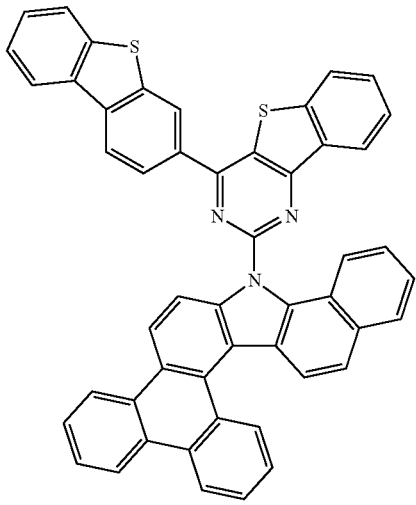
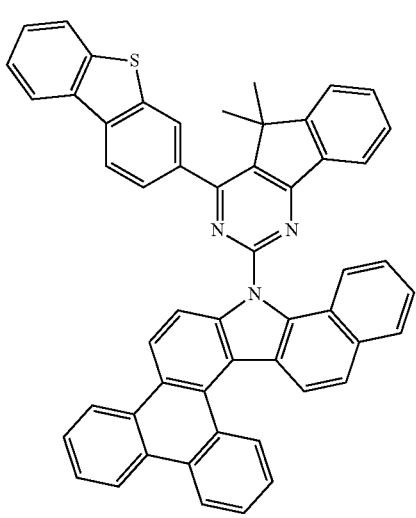
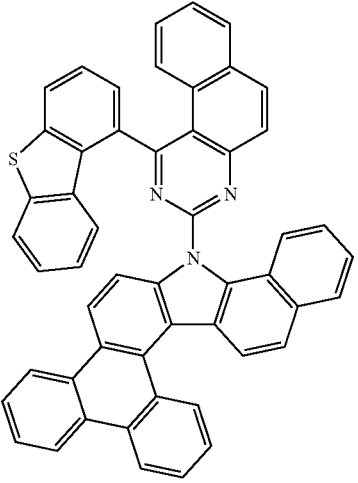

405
-continued
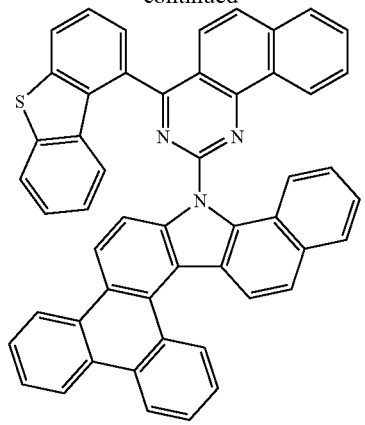
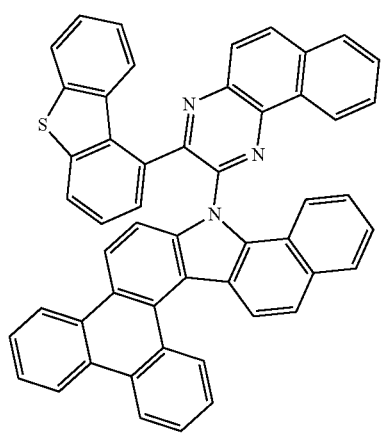
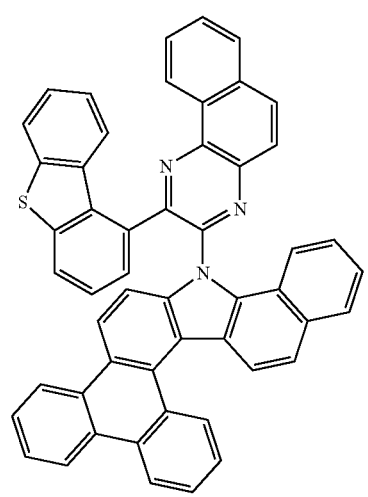
406
-continued
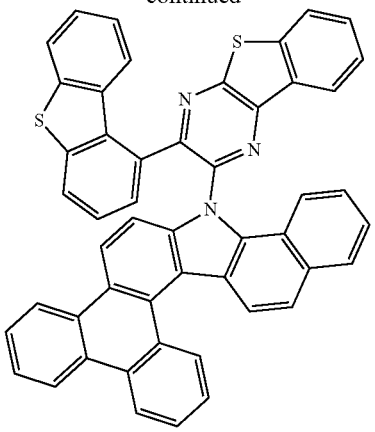
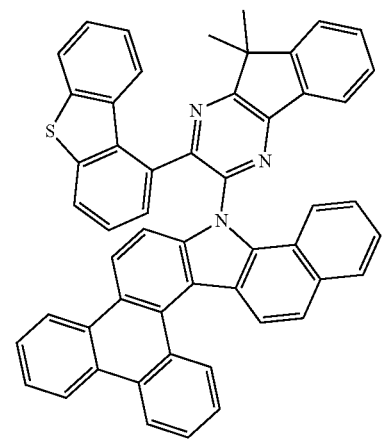
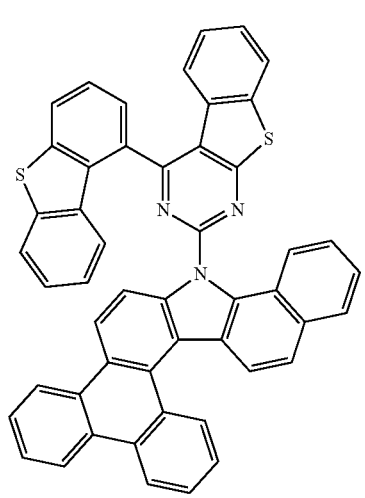

407
-continued
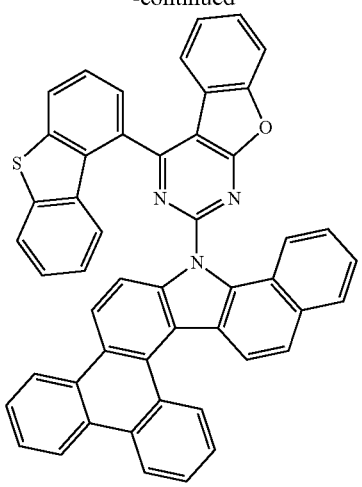
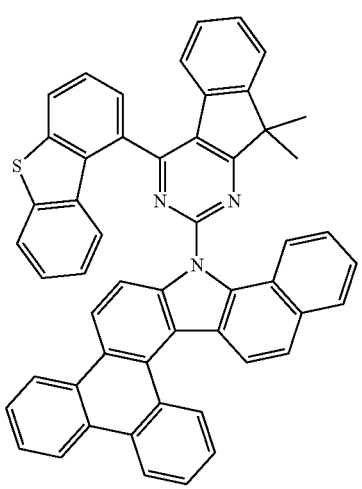
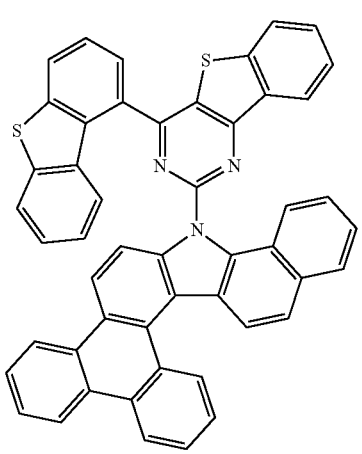
408
-continued
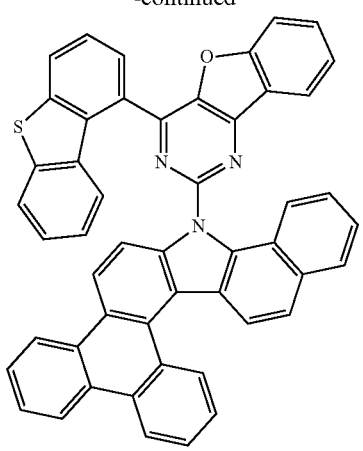
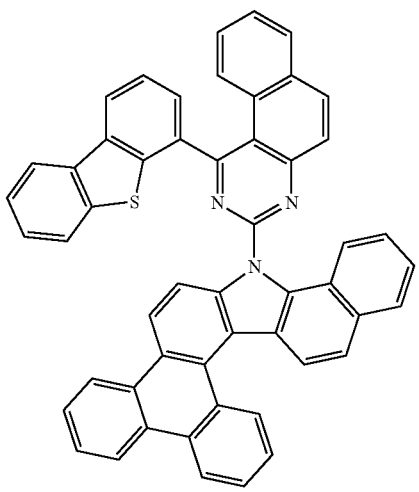
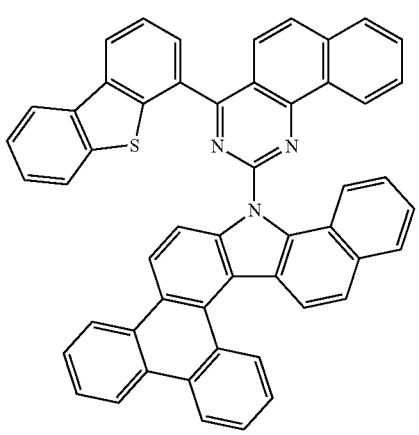

409
-continued
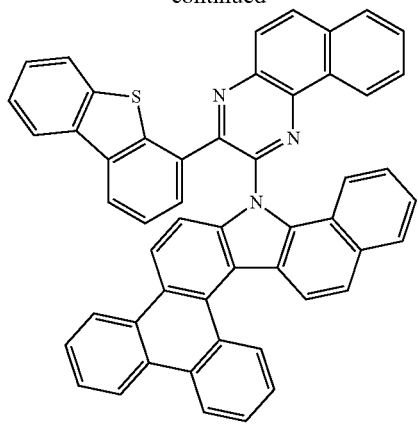
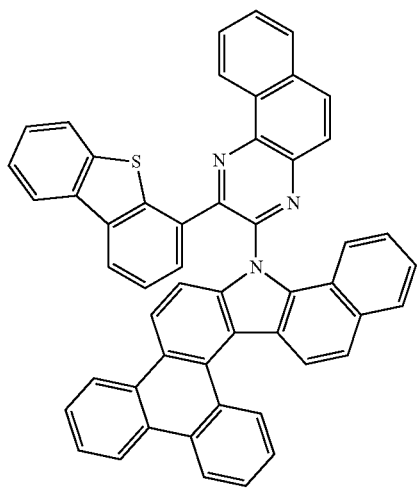
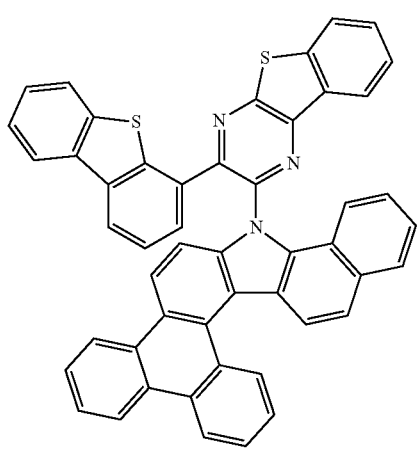
410
-continued
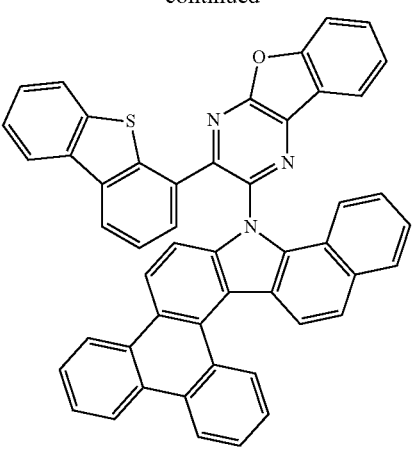
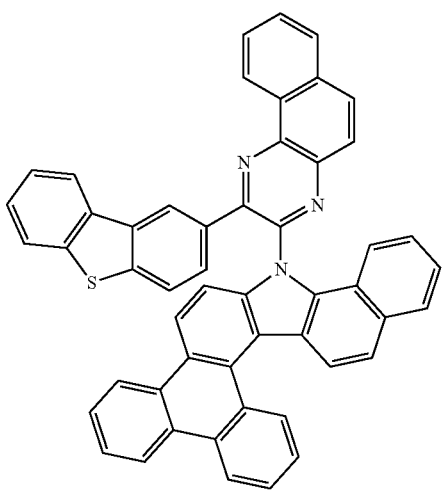
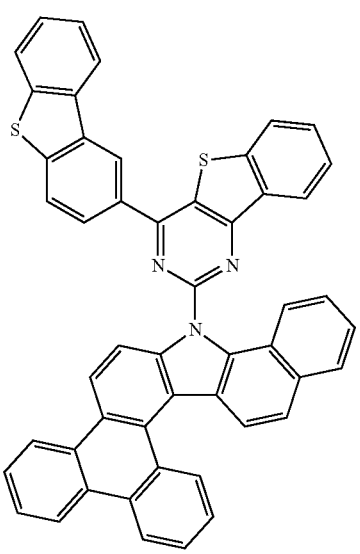

| 411 | 412 |
|---|---|
| -continued | -continued |
| 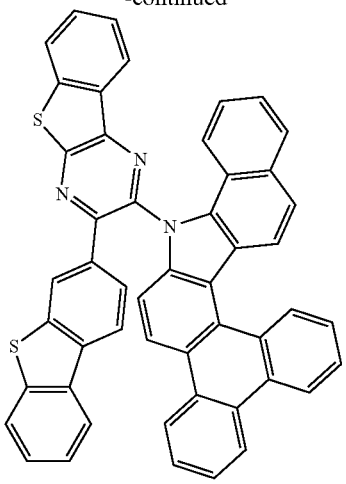 | 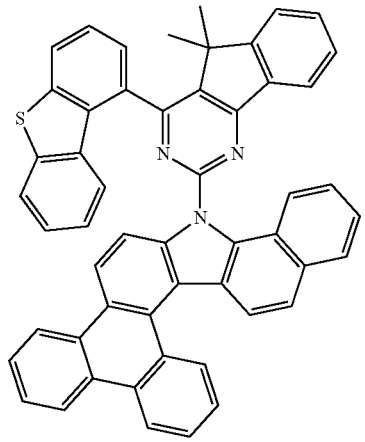 |
| 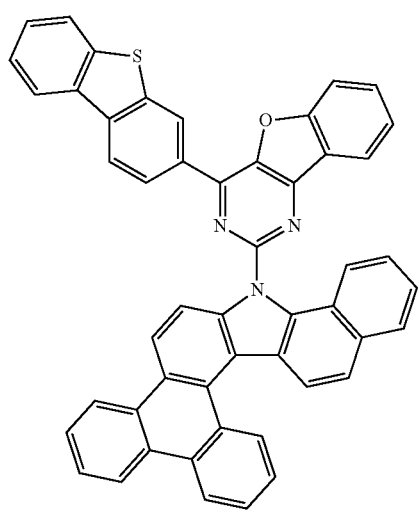 | 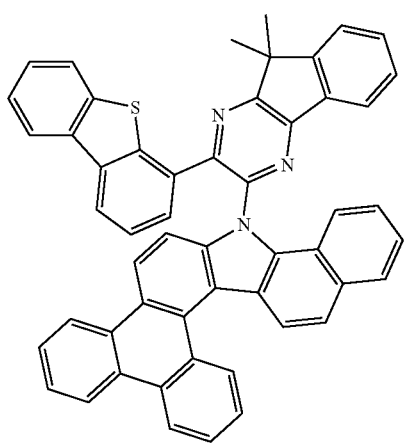 |
| 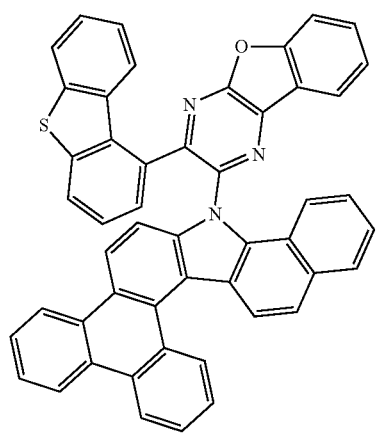 | 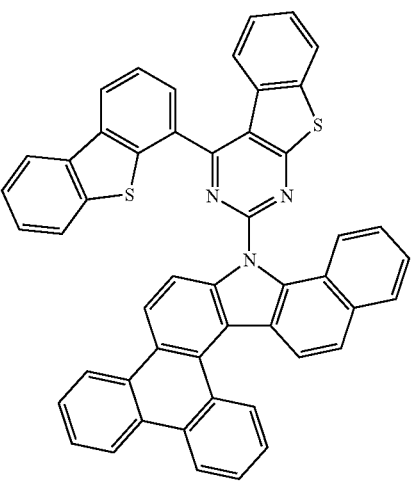 |

413
-continued
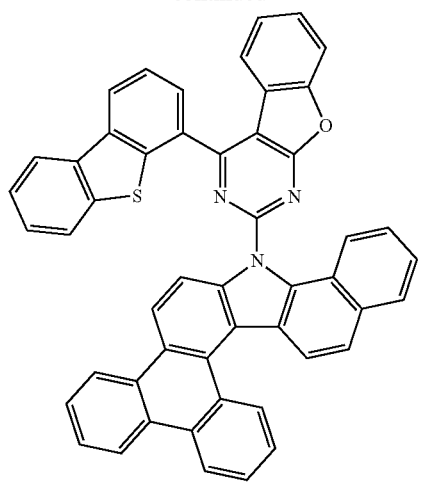
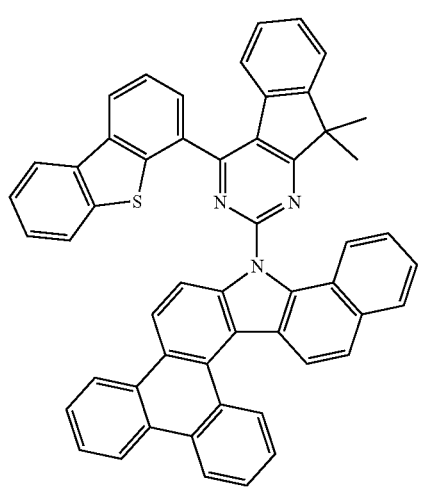
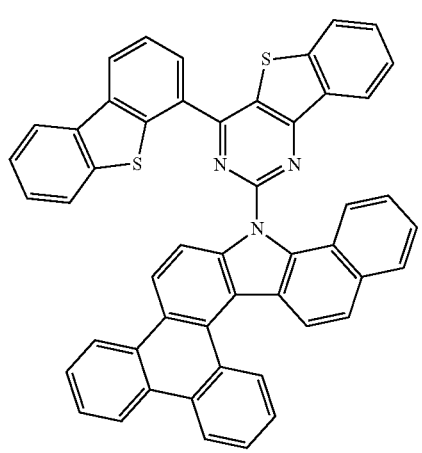
414
-continued
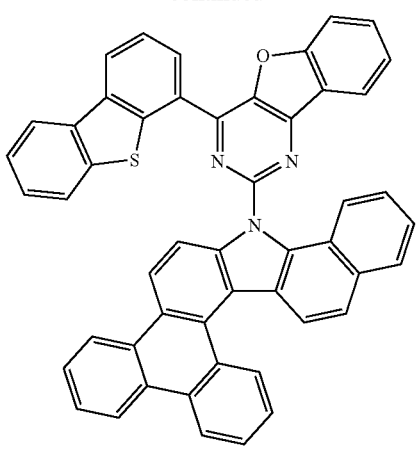
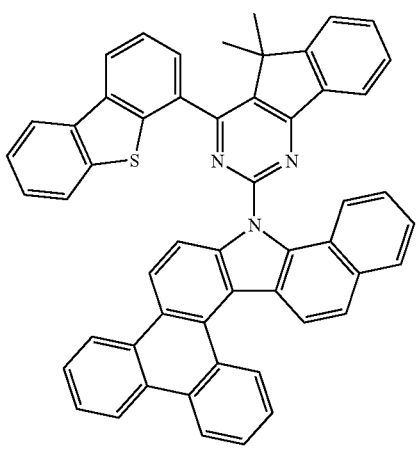
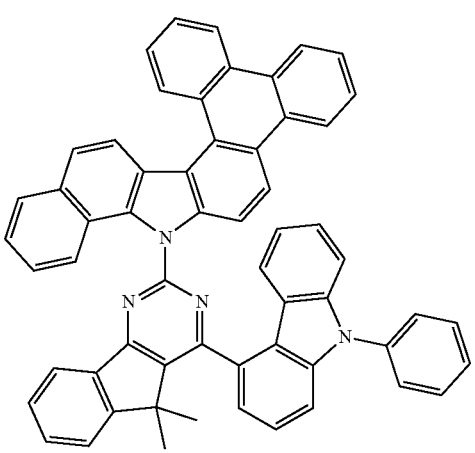

415
-continued
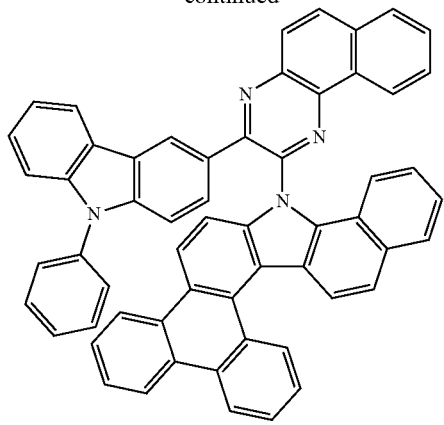
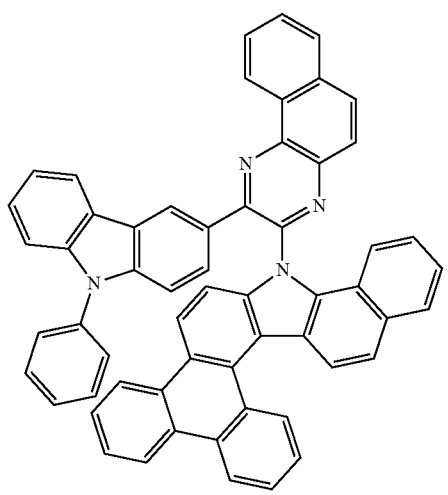
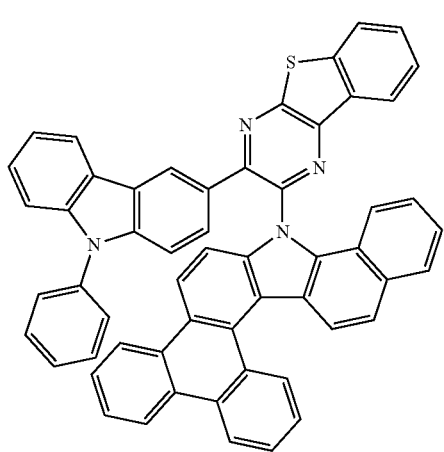
416
-continued
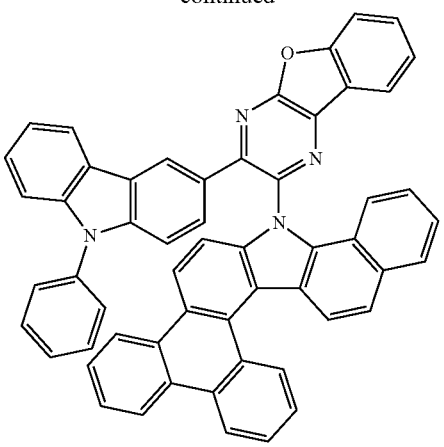
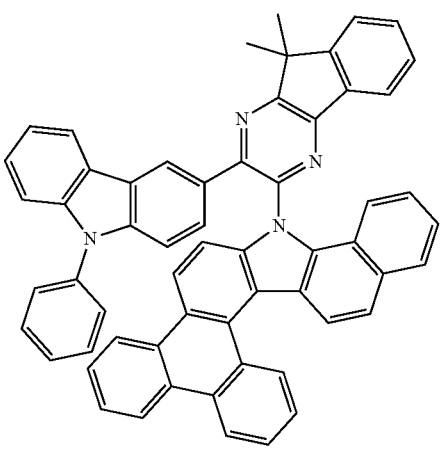
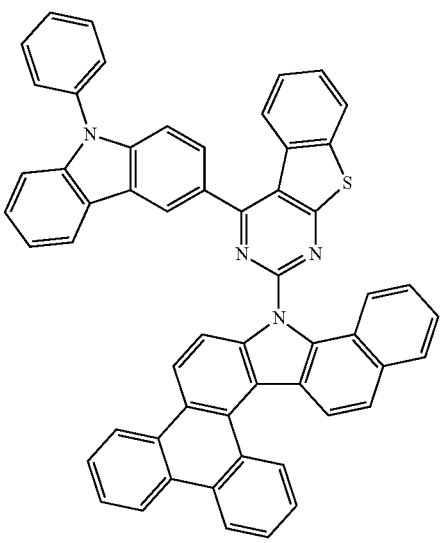

417
-continued
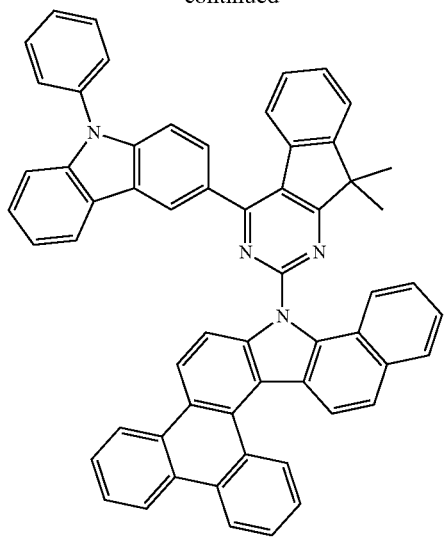
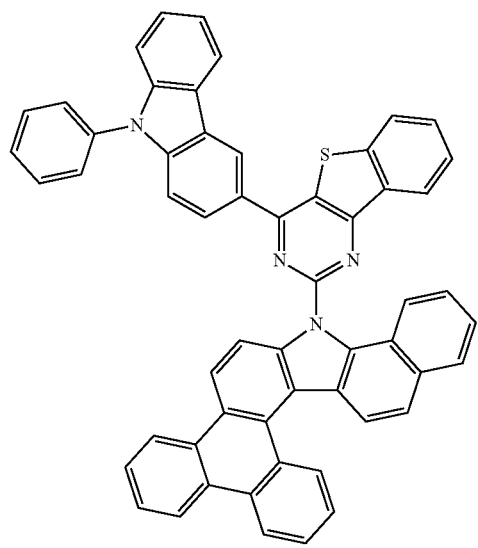
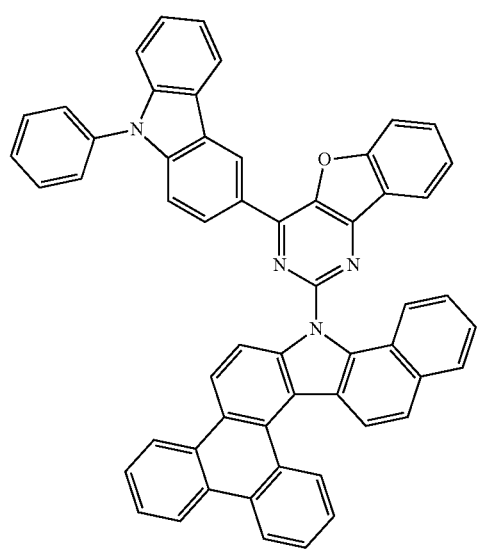
418
-continued
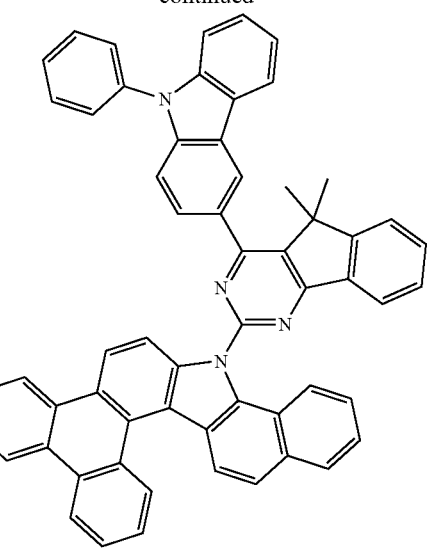
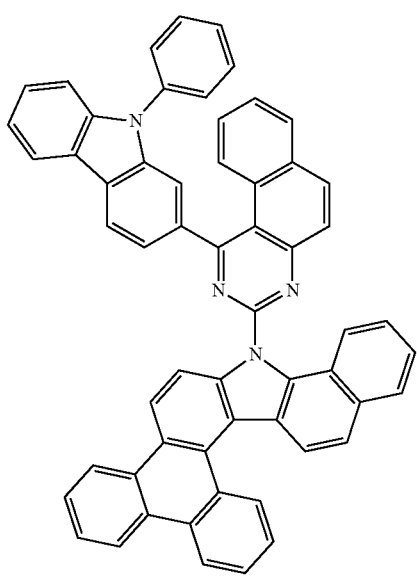
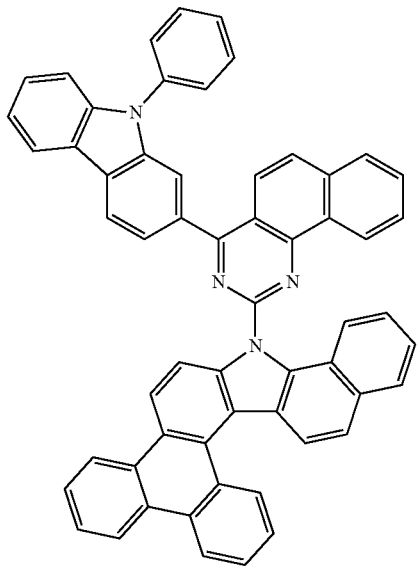

419
-continued
420
-continued
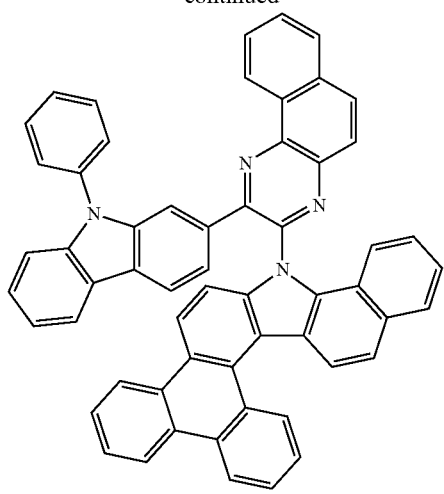
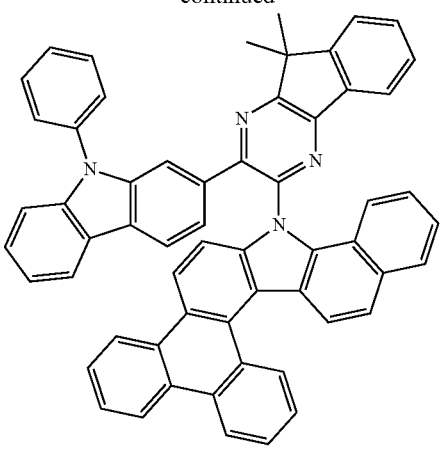
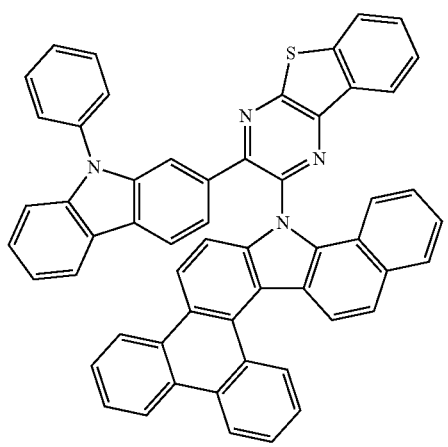
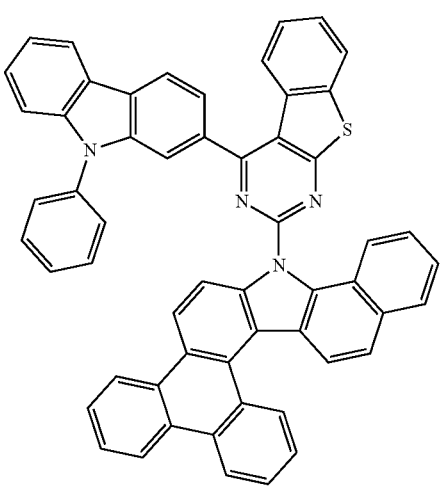
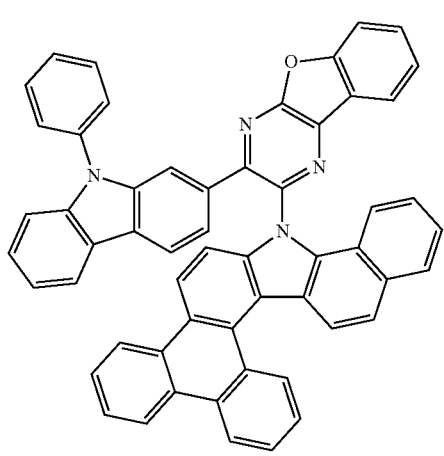
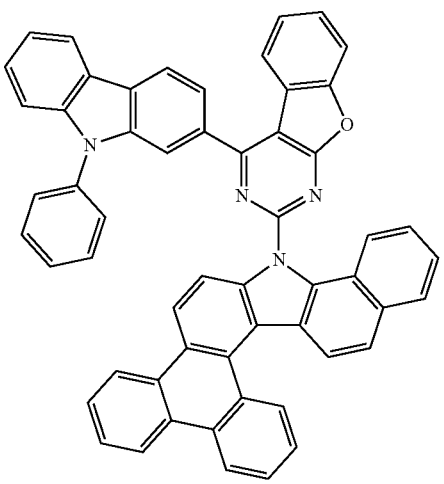

421
-continued
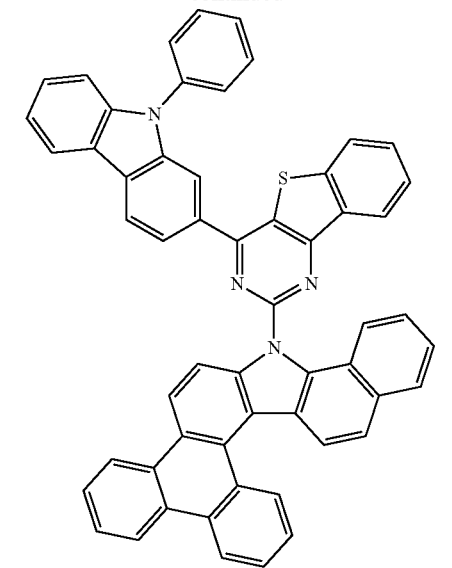
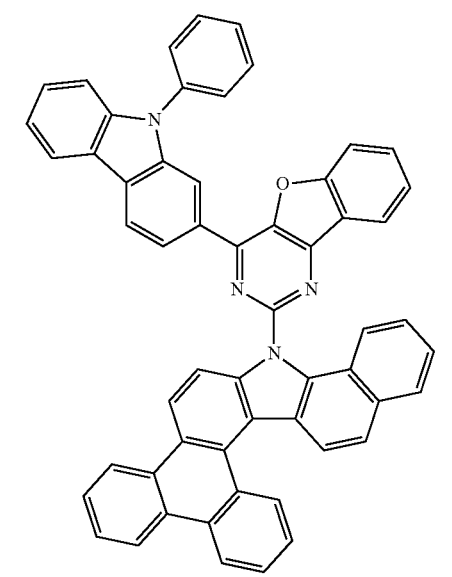
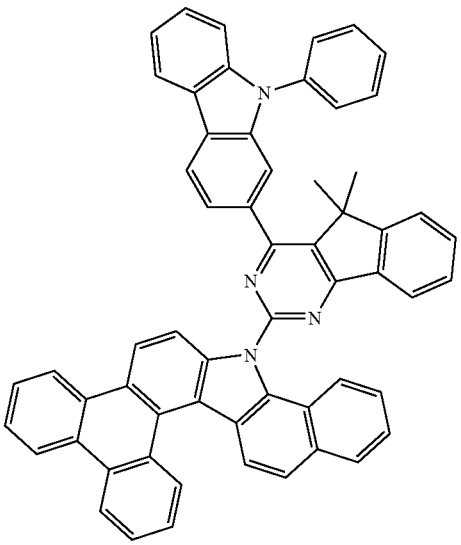
422
-continued
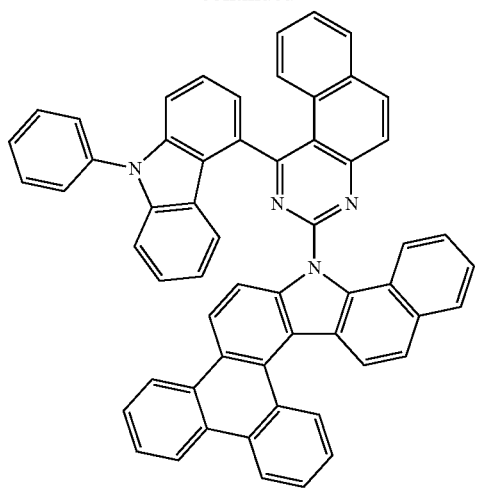
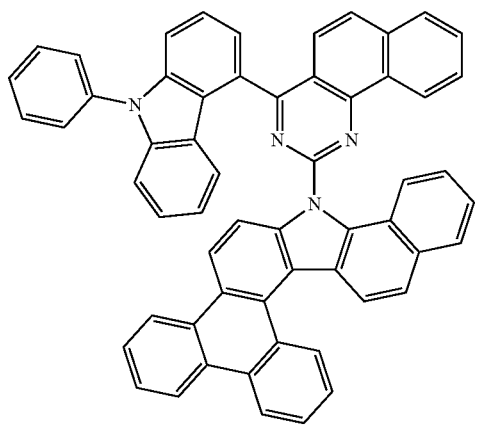
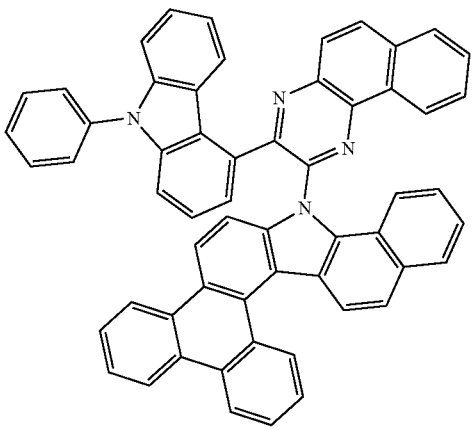

423
-continued
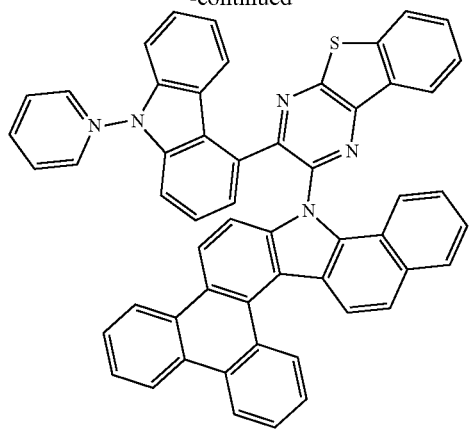
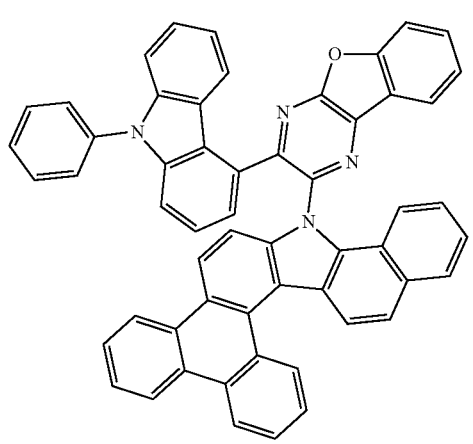
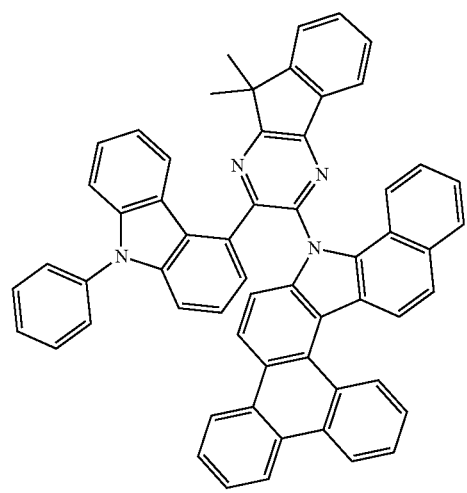
424
-continued
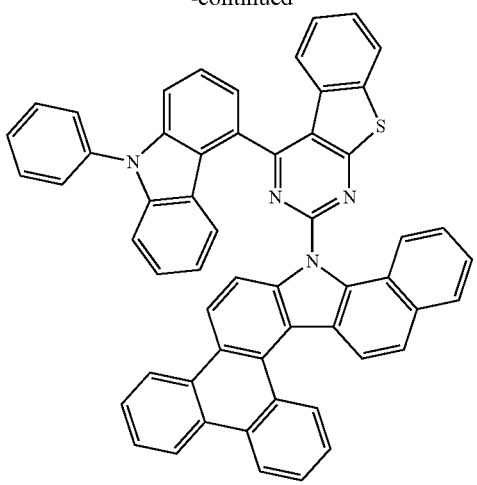
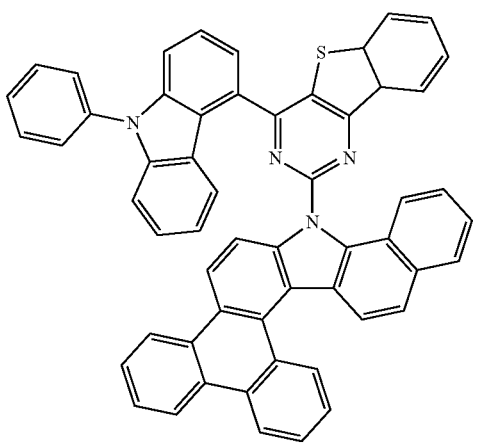
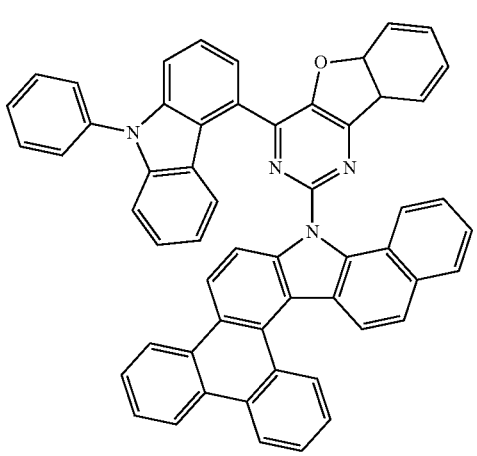

425
-continued

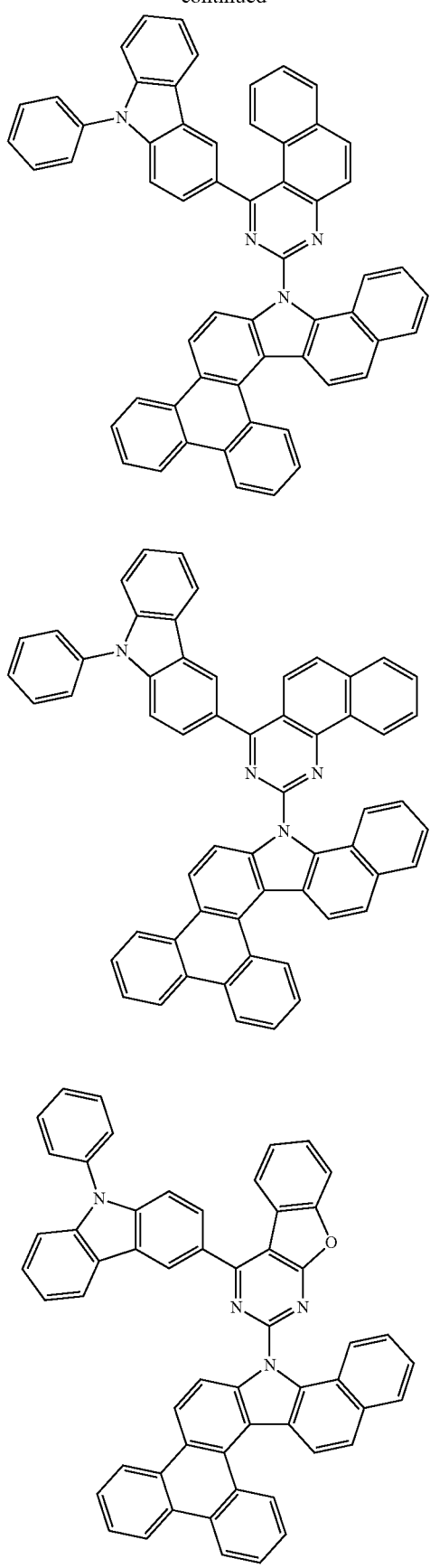

426
-continued

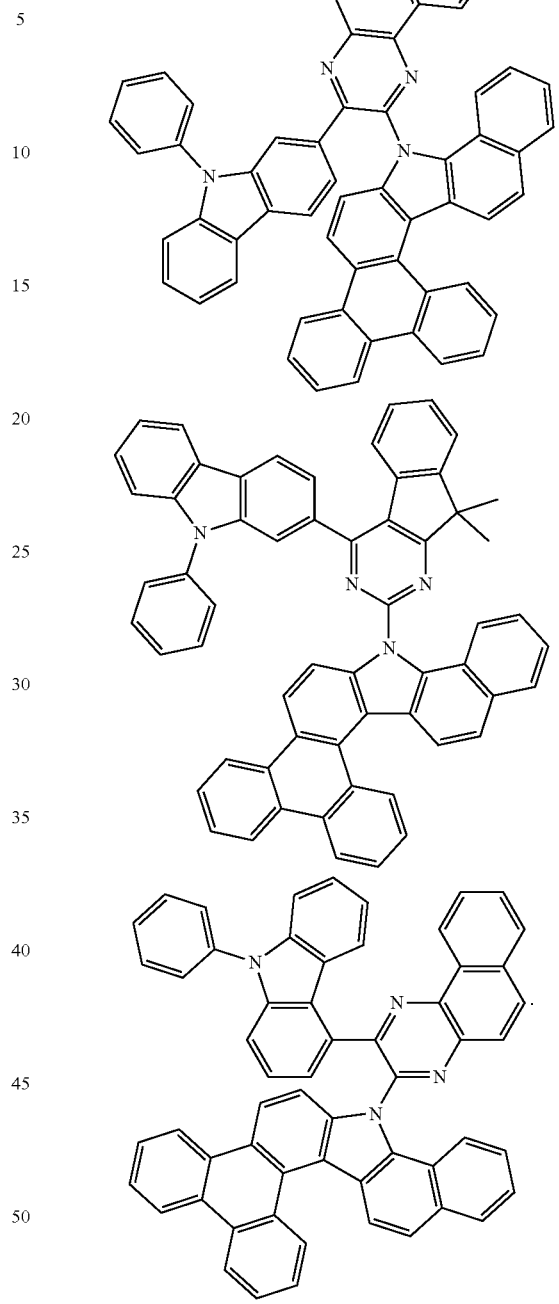

3. An organic light emitting device comprising:
a first electrode;
a second electrode provided opposite to the first electrode; and
one, two or more organic material layers provided between the first electrode and the second electrode,
wherein one or more layers of the organic material layers include the heterocyclic compound of claim 1.

4. The organic light emitting device of claim 3, wherein the organic material layer includes a light emitting layer, and the light emitting layer includes the heterocyclic compound.

5. The organic light emitting device of claim 3, wherein the organic material layer includes a light emitting layer, and the light emitting layer includes the heterocyclic compound as a host.

6. An organic light emitting device comprising:
a first electrode;
a second electrode provided opposite to the first electrode; and
one, two or more organic material layers provided between the first electrode and the second electrode,
wherein one or more layers of the organic material layers include the heterocyclic compound of claim 2.

7. The heterocyclic compound of claim 1, wherein Ar is a phenyl group, a biphenyl group, a naphthyl group, a phenanthrene group, a triphenylene group, a dibenzofuran group, a dibenzothiophene group, or a carbazole group, and the phenyl group, the biphenyl group, the naphthyl group, the phenanthrene group, the triphenylene group, the dibenzofuran group, the dibenzothiophene group, or the carbazole group is unsubstituted or substituted with a phenyl group or a naphthyl group.

8. The heterocyclic compound of claim 1, wherein Chemical Formula 3 is any one of the following Chemical Formula 3-1 to Chemical Formula 3-4:

[Chemical Formula 3-1]
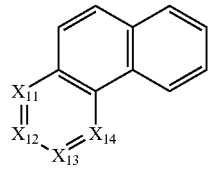

[Chemical Formula 3-2]
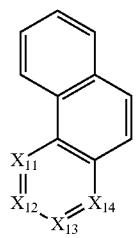

[Chemical Formula 3-3]
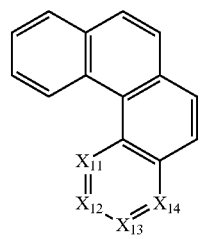

[Chemical Formula 3-4]
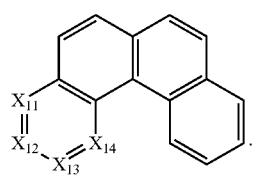

wherein X11 to X14 have the same definitions as in Chemical Formula 3.

9. The heterocyclic compound of claim 1, wherein Chemical Formula 4 is any one of the following Chemical Formula 4-1 or Chemical Formula 4-2:

[Chemical Formula 4-1]
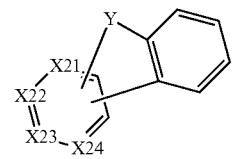

[Chemical Formula 4-2]
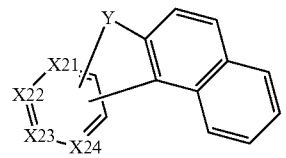

wherein X21 to X24 and Y have the same definitions as in Chemical Formula 4.

10. The heterocyclic compound of claim 1, wherein Chemical Formula 4 is any one selected from among the following substituents:

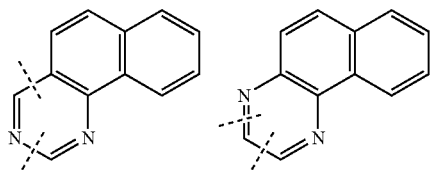
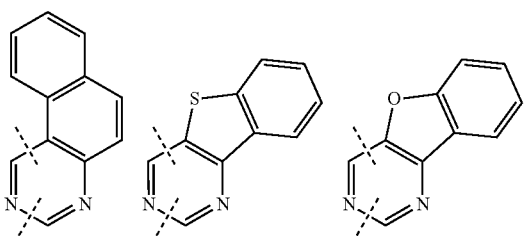
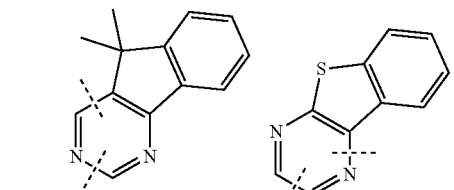
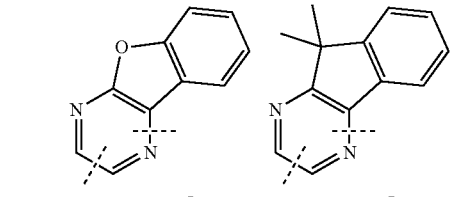
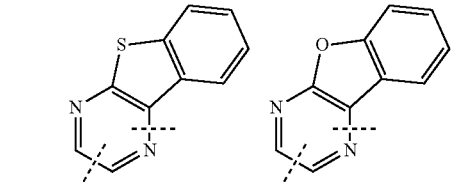

-continued
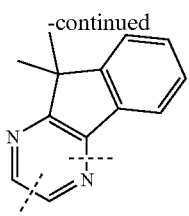
wherein one of the dotted lines bonds to N of any one of Chemical Formulae 1-1 to 1-3, and the other dotted line bonds to Ar.
* * * * *